(12) United States Patent
Slusher et al.

(10) Patent No.: US 11,866,394 B2
(45) Date of Patent: Jan. 9, 2024

(54) PRODRUGS OF HYDROXAMATE-BASED GCPII INHIBITORS

(71) Applicants: The Johns Hopkins University, Baltimore, MD (US); Institute of Organic Chemistry and Biochemistry AS CR v.v.i., Prague (CZ)

(72) Inventors: Barbara Slusher, Kingsville, MD (US); Rana Rais, West Friendship, MD (US); Jan Vavra, Prague (CZ); Tomas Tichy, Prague (CZ); Pavel Majer, Sykesville, MD (US); Andrej Jancarik, Koprivnice (CZ); Lukas Tenora, Kretin (CZ)

(73) Assignees: THE JOHNS HOPKINS UNIVERSTY, Baltimore, MD (US); INSTITUTE OF ORGANIC CHEMISTRY AND BIOCHEMISTRY AS CR V.V.I., Prague (CZ)

( * ) Notice: Subject to any disclaimer, the term of this patent is extended or adjusted under 35 U.S.C. 154(b) by 0 days.

(21) Appl. No.: 17/372,899

(22) Filed: Jul. 12, 2021

(65) Prior Publication Data
US 2021/0355079 A1 Nov. 18, 2021

Related U.S. Application Data

(62) Division of application No. 16/461,630, filed as application No. PCT/US2017/062565 on Nov. 20, 2017, now Pat. No. 11,059,775.

(60) Provisional application No. 62/423,839, filed on Nov. 18, 2016.

(51) Int. Cl.
| C07C 259/06 | (2006.01) |
| A61P 25/02 | (2006.01) |
| C07C 259/08 | (2006.01) |
| C07D 317/38 | (2006.01) |

(52) U.S. Cl.
CPC ............ *C07C 259/06* (2013.01); *A61P 25/02* (2018.01); *C07C 259/08* (2013.01); *C07D 317/38* (2013.01)

(58) Field of Classification Search
CPC .................................................. C07C 259/06
See application file for complete search history.

(56) References Cited

U.S. PATENT DOCUMENTS

| 3,819,600 | A | 6/1974 | Hamanaka |
| 5,646,167 | A | 7/1997 | MacPherson et al. |
| 6,884,907 | B2 | 4/2005 | Tsukamoto et al. |
| 7,220,780 | B2 | 5/2007 | Slusher et al. |
| 9,636,298 | B2 | 5/2017 | Ajamian et al. |
| 11,059,775 | B2 * | 7/2021 | Slusher .................. A61P 25/18 |
| 2003/0036534 | A1 | 2/2003 | Slusher et al. |
| 2003/0087897 | A1 | 5/2003 | Tsukamoto et al. |
| 2004/0186081 | A1 | 9/2004 | Slusher et al. |
| 2015/0203517 | A1 | 7/2015 | Ajamian et al. |
| 2019/0352255 | A1 | 11/2019 | Slusher et al. |

FOREIGN PATENT DOCUMENTS

DE 2262001 8/1973

OTHER PUBLICATIONS

McDonnell, Bioorg Med Chem. Sep. 15, 2012; 20(18): 5642-5648.*
Attal, et al., Further evidence for 'painrelated' behaviours in a model of unilateral peripheral mononeuropathy. Pain 1990, 41, 235-251.
Barinka, et al., Glutamate carboxypeptidase II in diagnosis and treatment of neurologic disorders and prostate cancer. Curr. Med. Chem. 2012, 19, 856-870.
Bennett, et al., A peripheral mononeuropathy in rat that produces disorders of pain sensation like those seen in man. Pain 1988, 33, 87-107.
Cannon, Chapter 19 in Burger's Medicinal Chemistry and Drug Discovery, Fifth Edition, vol. I: Principles and Practice, Wiley-Interscience 1995, pp. 783-802.
Ferraris, et al., δ-Thiolactones as Prodrugs of Thiol-Based Glutamate Carboxypeptidase II (GCPII) Inhibitors. J Med Chem. 2014, 57, 243-247.
Flipo, et al., Hydroxamates: relationships between structure and plasma stability. J. Med. Chem 2009, 52, 6790-802.
Hargreaves, et al., A new and sensitive method for measuring thermal nociception in cutaneous hyperalgesia. Pain 1988, 32, 77-88.
Jackson, et al., Design, synthesis, and biological activity of a potent inhibitor of the neuropeptidase N-acetylated alpha-linked acidic dipeptidase. J. Med. Chem. 1996, 39, 619-622.
Jackson, et al., Design and pharmacological activity of phosphinic acid based NAALADase inhibitors. J. Med. Chem. 2001, 44, 4170-4175.
Kozikowski, et al., Design of remarkably simple, yet potent urea-based inhibitors of glutamate carboxypeptidase II (NAALADase). J. Med. Chem. 2001, 44, 298-301.
Linenberger et al., Biochemistry students' ideas about shape and charge in enzyme-substrate interactions. Biochem Mol Biol Educ. May-Jun. 2014;42(3):203-12.
Majer, et al., Synthesis and biological evaluation of thiol-based inhibitors of glutamate carboxypeptidase II: discovery of an orally active GCP II inhibitor. J. Med. Chem. 2003, 46, 1989-1996.
Majer, et al., Discovery of orally available prodrugs of the Glutamate Carboxypeptidase II (GCPII) inhibitor 2-Phosphonomethylpentanedioic Acid (2-PMPA). J. Med. Chem. 2016, 59, 2810-2819.
Nishimura et al., KY-109, a new bifunctional prodrug of cephalosporin. II. Mechanism of oral absorption. Chem Pharm Bull (Tokyo). Jun. 1988;36(6):2128-34.
Novakova, et al., Unprecedented binding mode of hydroxamate-based inhibitors of Glutamate Carboxypeptidase II: Structural characterization and biological activity. J. Med. Chem. 2016, 59, 4539-4550.

(Continued)

*Primary Examiner* — Nizal S Chandrakumar
(74) *Attorney, Agent, or Firm* — Casimir Jones, SC; Jeffrey W. Childers

(57) ABSTRACT

Prodrugs of hydroxamate-based GCPII inhibitors and methods of their use for treating a disease or condition are disclosed.

3 Claims, 22 Drawing Sheets

(56) References Cited

OTHER PUBLICATIONS

Rais, et al., Discovery of a para-Acetoxy-benzyl Ester Prodrug of a Hydroxamate-Based Glutamate Carboxypeptidase II Inhibitor as Oral Therapy for Neuropathic Pain. J. Med. Chem. 2017, 60, 7799-7809.

Raji, et al., Design, synthesis and evaluation of antiproliferative activity of melanoma-targeted histone deacetylase inhibitors. Bioorg. Med. Chem. Lett. 2017, 27, 744-749.

Schlimme, et al., Carbamate prodrug concept for hydroxamate HDAC inhibitors. Chem Med Chem 2011, 6, 1193-1198.

Silhar, et al., Targeting botulinum A cellular toxicity: a prodrug approach. J. Med. Chem. 2013, 56, 7870-7879.
Venkatesh et al., Role of the development scientist in compound lead selection and optimization. J Pharm Sci. Feb. 2000;89(2):145-54.
Vornov, et al., Still NAAG'ing after all these years: The continuing pursuit of GCPII inhibitors. Adv. Pharmacol. 2016, 76, 215-255.
Vornov, et al., Pharmacokinetics and pharmacodynamics of the glutamate carboxypeptidase II inhibitor 2-MPP A show prolonged alleviation of neuropathic pain through an indirect mechanism. J. Pharmacol. Exp. Ther. 2013, 346, 406-413.
Wiemer, et al., Prodrugs of phosphonates and phosphates:crossing the membrane barrier. Top. Curr. Chem. 2015, 360, 115-160.
Wolf, Burger's Medicinal Chemistry and Drug Discovery, vol. 1, Principles and Practice, John Wiley & Sones, New York, 1997.
Yamamoto, et al., Spinal N-acetyl-alphalinked acidic dipeptidase (NAALADase) inhibition attenuates mechanical allodynia induced by paw carrageenan injection in the rat. Brain Res. 2001, 909, 138-144.
Yamamoto, et al., Inhibition of spinal Nacetylated-alpha-linked acidic dipeptidase produces an antinociceptive effect in the rat formalin test. Neuroscience 2001, 102, 473-479.
International Search Report and Written Opinion for PCT/US2017/062565, dated Mar. 8, 2018, 13 pages.

* cited by examiner

50 (JHU 241; parent)

12 (JV2855)

17 (JV2925)

41 (JV2928)

25 (JV2946)

23 (JV2956)

42 (JV2947)

7 (TT171214)

PRODRUGS OF HYDROXAMATE-BASED GCPII INHIBITORS

CROSS-REFERENCE TO RELATED APPLICATIONS

This application is a divisional of U.S. patent application Ser. No. 16/461,630, filed May 16, 2019, now U.S. Pat. No. 11,059,775, which is a U.S. National Entry Application under § 371 of International Patent Application PCT/US2017/062565, filed Nov. 20, 2017, which claims the benefit of U.S. Provisional Application No. 62/423,839, filed Nov. 18, 2016, each of which is incorporated herein by reference in its entirety.

FEDERALLY SPONSORED RESEARCH OR DEVELOPMENT

This invention was made with government support under CA161056, awarded by the National Institutes of Health. The government has certain rights in the invention.

BACKGROUND

The prodrug approach is a well-established strategy to improve physicochemical, biopharmaceutic and pharmacokinetic properties of potential drug molecules. Approximately 5-7% of drugs approved worldwide are prodrugs with annual sales in 2013 of $11.2 billion. Most prodrugs are simple chemical derivatives of the parent drug molecule. Ester prodrugs, the most common prodrugs, constitute 49% of all marketed prodrugs. Reasons for the popularity of ester prodrugs include their generally straight forward synthesis, their improved lipophilicity and membrane permeability, and the ubiquitousness of estereases. An example of an approach to make an ester prodrug is capping the acidic moiety(ies) of the parent drug molecule with lipophilic alkyl or alkyloxymethyl esters (i.e., pivaloyloxymethyl (POM) or propyloxycarbonyloxymethyl (POC); e.g., Enalapril, Adefovir). Another approach is to cap the acidic moiety(ies) of the parent drug molecule with amino acids to make amides that are recognizable by transporters, such as Peptide transporter 1 (PEPT1) (e.g., Pomaglumetad methionil, Valacyclovir).

Glutamate carboxypeptidase II (GCPII) is a zinc metalloenzyme that catalyzes the hydrolysis of N-acetylated aspartate-glutamate (NAAG) to N-acetyl aspartate (NAA) and glutamate and cleaves terminal glutamate moieties sequentially from folate polyglutamate (Ristau et al., 2013; Mesters et al., 2006; Slusher et al., 2013). Glutamate carboxypeptidase II also is referred to as N-acetyl-L-aspartyl-L-glutamate peptidase I (NAALADase I), NAAG peptidase, or prostate-specific membrane antigen (PSMA). GCPII is mainly expressed in the prostate epithelium, the proximal tubules of the kidney, the jejunal brush border of the small intestine, and glial cells in the peripheral and central nervous system.

Inhibition of GCPII is effective in diseases associated with a pathological increase of glutamate concentration or an excessive activation of glutamatergic systems, leading to excito-toxic effects and neuronal death. The utility of GCPII inhibitors has been demonstrated by multiple independent laboratories in animal models of disease where excess glutamate transmission is thought to be pathogenic. These models include inflammatory and neuropathic pain, brain ischemia, stroke, motoneuron disease, spinal cord and traumatic brain injury (TBI), cognition, peripheral neuropathy, epilepsy, drug addiction/tolerance, schizophrenia, amyotrophic lateral sclerosis (ALS), and multiple sclerosis. Recent data also shows utility in angiogenesis, prostate cancer, and inflammatory bowel disease (IBD).

One promising class of GCPII inhibitors, the hydroxamate-based GCPII inhibitors, however, are polar compounds having multiple carboxylate groups and with limited oral availability. Therefore, in most cases, they must be dosed systemically or locally to achieve the desired effects. This characteristic limits their potential use as a drug since most of the above disorders require long term dosing for which the oral route is strongly preferred.

SUMMARY

In some aspects, a prodrug strategy has been utilized to mask the polar groups of hydroxamate-based GCPII inhibitors using hydrophobic moieties for enhanced permeation.

In particular aspects, the presently disclosed subject matter provides a compound of formula (I):

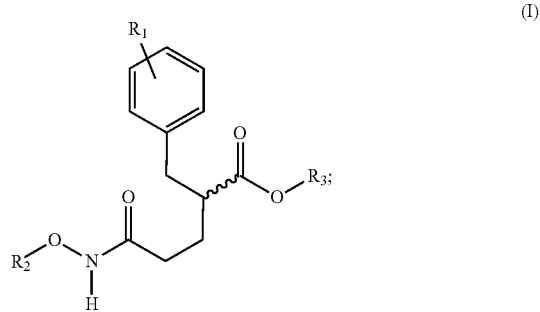

(I)

wherein: $R_1$ is selected from the group consisting of —C(=O)—O—$R_4$ and —Ar—C(=O)—O—$R_4$; $R_2$ is selected from the group consisting of substituted and unsubstituted $C_1$-$C_6$ alkyl, substituted and unsubstituted $C_3$-$C_8$ cycloalkyl, substituted and unsubstituted $C_6$-$C_{12}$ aryl, substituted and unsubstituted $C_6$-$C_{12}$ heteroaryl, —$(CR_5R_6)_n$—$R_7$, —C(=O)—O—$R_7$, —C(=O)—$R_7$, —C(=O)—$NR_7R_8$, —$(CR_5R_6)_n$—O—C(=O)—O—$R_7$, —$(CR_5R_6)_n$—Ar—O—C(=O)—$R_7$; $R_3$ is selected from the group consisting of H, substituted and unsubstituted $C_1$-$C_6$ alkyl, substituted and unsubstituted $C_3$-$C_{12}$ cycloalkyl, substituted and unsubstituted $C_6$-$C_{12}$ aryl, substituted and unsubstituted $C_5$-$C_{12}$ heteroaryl; $R_4$ is selected from the group consisting of H, substituted and unsubstituted $C_1$-$C_6$ alkyl, substituted and unsubstituted $C_3$-$C_{12}$ cycloalkyl, substituted and unsubstituted $C_6$-$C_{12}$ aryl, substituted and unsubstituted $C_5$-$C_{12}$ heteroaryl, —$(CR_5R_6)_n$—O—C(=O)—O—$R_9$, and —$(CR_5R_6)_n$—Ar—O—C(=O)—$R_9$; each $R_5$ and $R_6$ is independently selected from the group consisting of H, $C_1$-$C_{10}$ alkyl, and $C_6$-$C_{12}$ aralkyl; $R_7$ is selected from the group consisting of H, and substituted and unsubstituted $C_1$-$C_{10}$ alkyl, substituted and unsubstituted $C_1$-$C_{10}$ heteroalkyl, substituted and unsubstituted $C_3$-$C_{16}$ cycloalkyl, substituted and unsubstituted $C_3$-$C_{12}$ cycloheteroalkyl, substituted and unsubstituted $C_3$-$C_{12}$ cycloheteroalkenyl, substituted and unsubstituted $C_6$-$C_{12}$ aryl, substituted and unsubstituted $C_6$-$C_{12}$ heteroaryl, and substituted and unsubstituted $C_6$-$C_{12}$ aralkyl; $R_8$ is selected from the group consisting of H, and substituted and unsubstituted $C_1$-$C_6$ alkyl; $R_9$ is selected from the group consisting of H, and substituted and unsubstituted $C_1$-$C_6$ alkyl; n is an integer selected from the group consisting of 0, 1, 2, 3, 4, 5, and 6; Ar is selected from the group consisting of substituted and unsubstituted $C_6$-$C_{12}$ aryl, and substituted and unsubstituted $C_6$-$C_{12}$ heteroaryl; and stereoisomers and pharmaceutically acceptable salts thereof.

In other aspects, the presently disclosed subject matter provides a method for treating a disease or a condition, the method comprising administering to a subject in need of treatment thereof, a compound of formula (I), or a pharmaceutical composition thereof, in an amount effective for treating the disease or condition.

In certain aspects, the disease or condition is selected from the group consisting of a neurodegenerative disease, cancer, angiogenesis, and inflammatory bowel disease.

In yet more certain aspects, the neurodegenerative disease is selected from the group consisting of amyotrophic lateral sclerosis (ALS), Parkinson's disease (PD), Alzheimer's disease (AD), Huntington's disease, dementia with Lewy Bodies (DLB), schizophrenia, inflammatory and neuropathic pain, peripheral neuropathy, epilepsy, brain ischemia, stroke, spinal cord and traumatic brain injury (TBI), cognition, motoneuron disease, drug addiction/tolerance, and multiple sclerosis (MS).

In particular aspects, the disease or condition results in excess PSMA activity. In such aspects, the method further comprises inhibiting the excess PSMA activity when the compound of formula (I), or a pharmaceutical composition thereof, is administered.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1A:
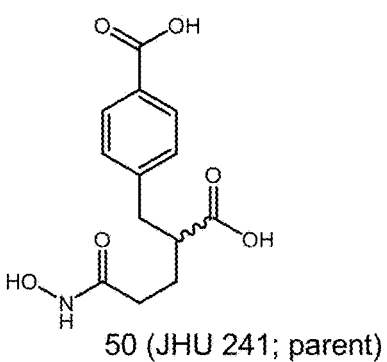
Figure 1A:
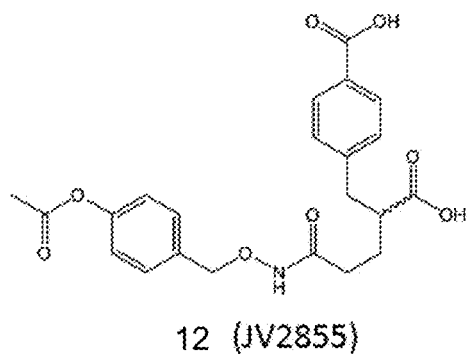
Figure 1A:
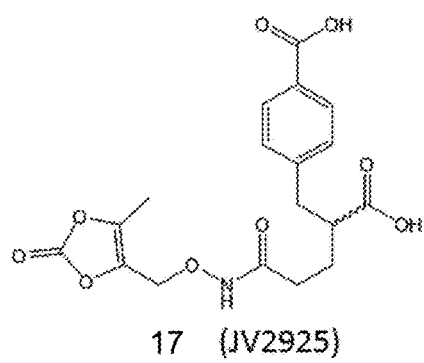
Figure 1A:
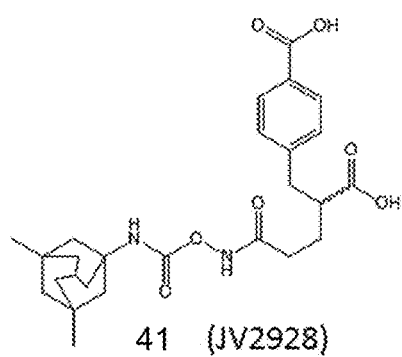
Figure 1A:
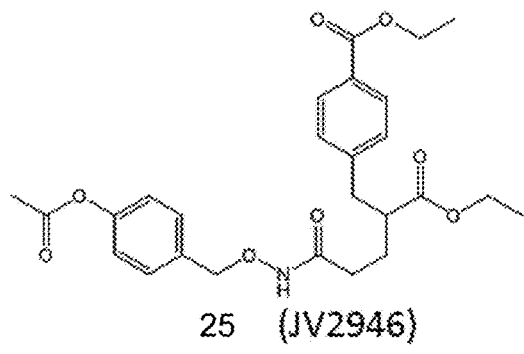
Figure 1A:
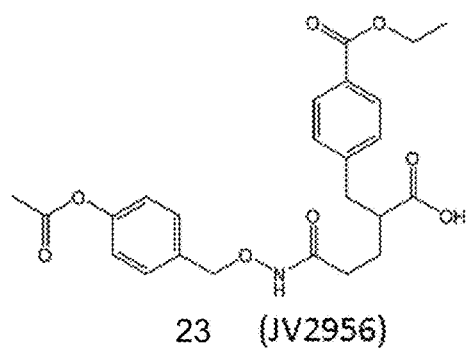
Figure 1A:
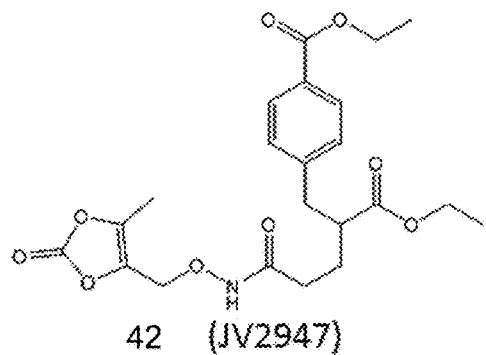
Figure 1A:
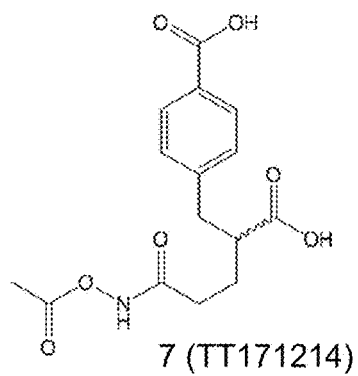
Figure 1B:
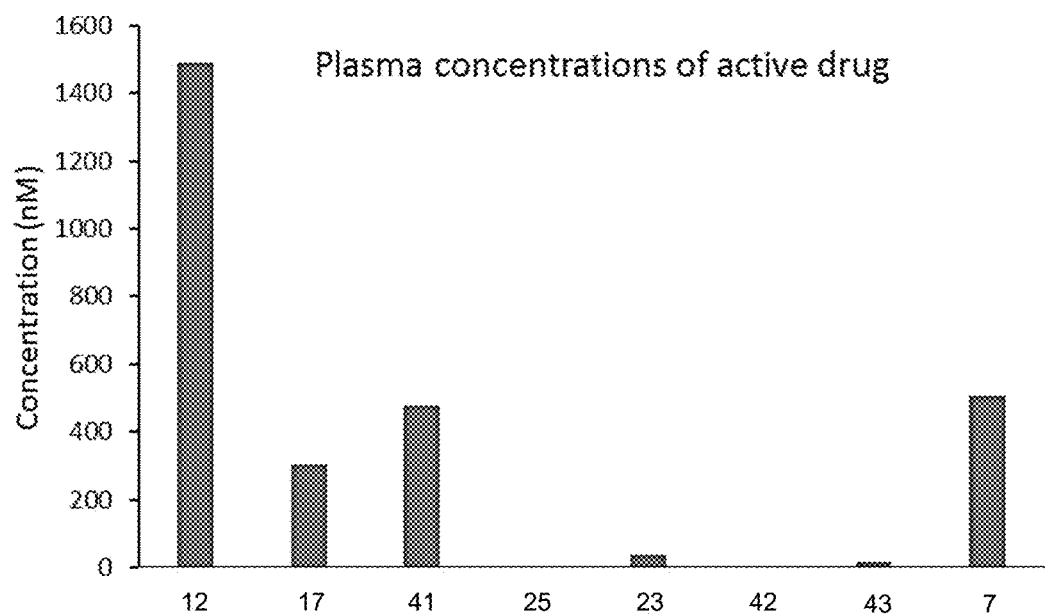
Figure 2A:
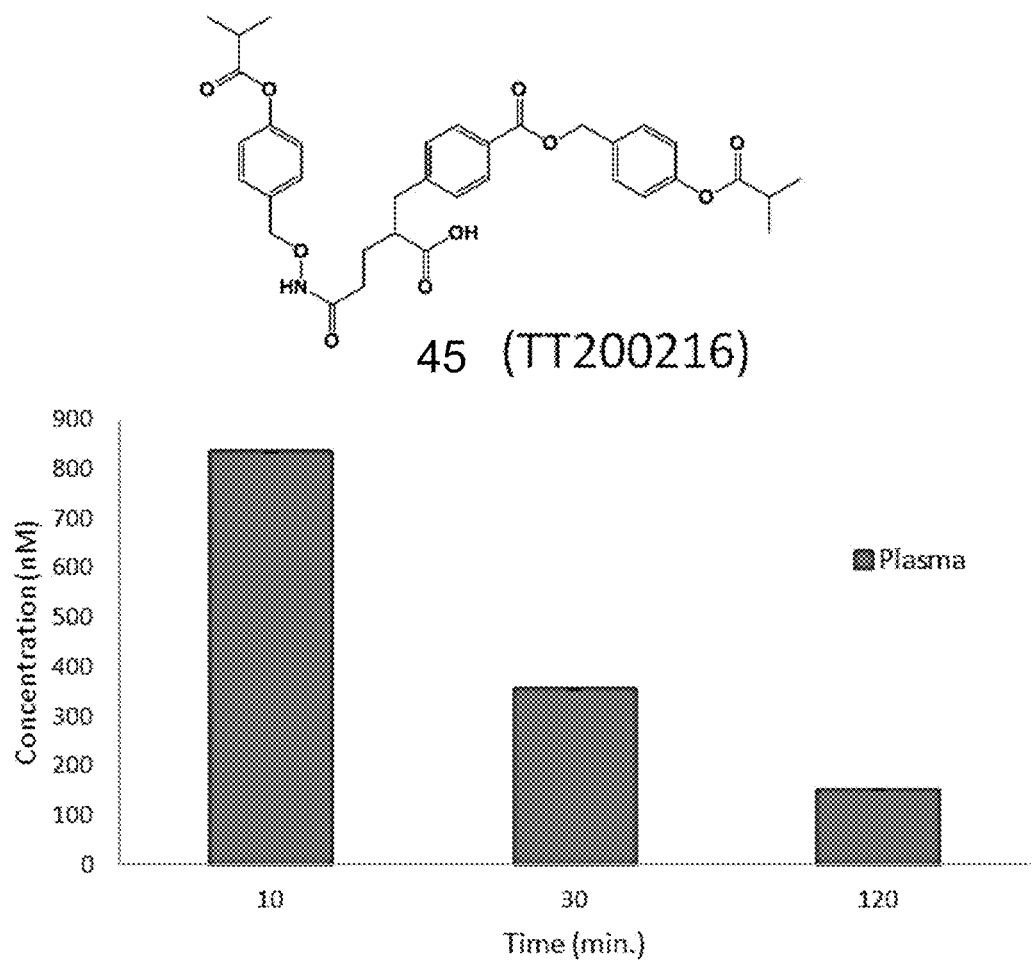
Figure 2B:
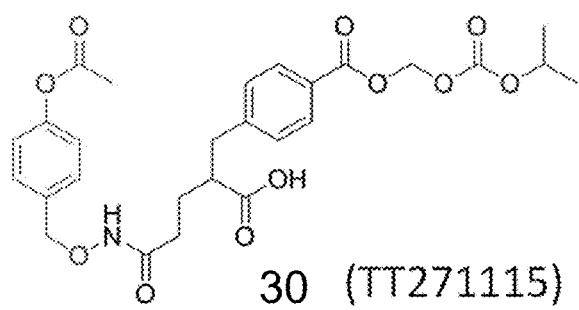
Figure 2B:
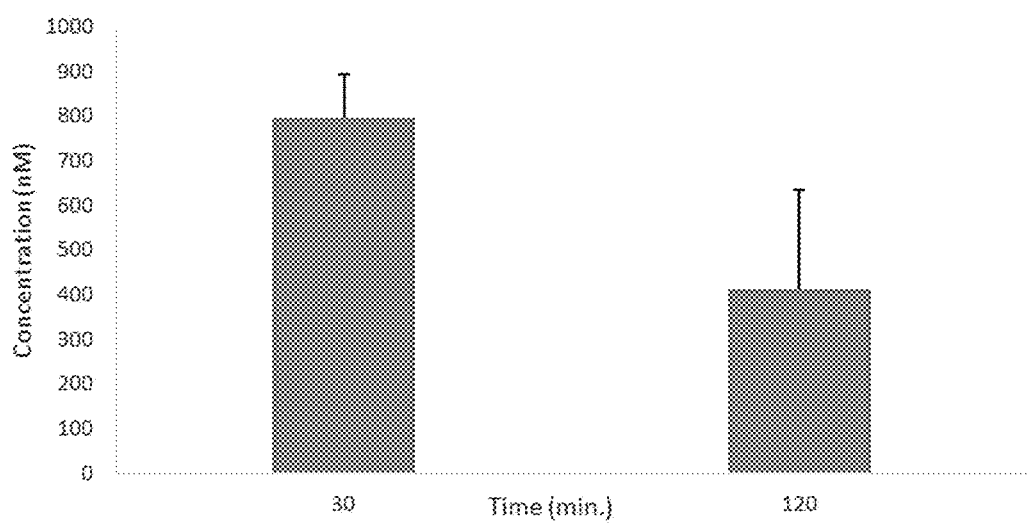
Figure 3A:
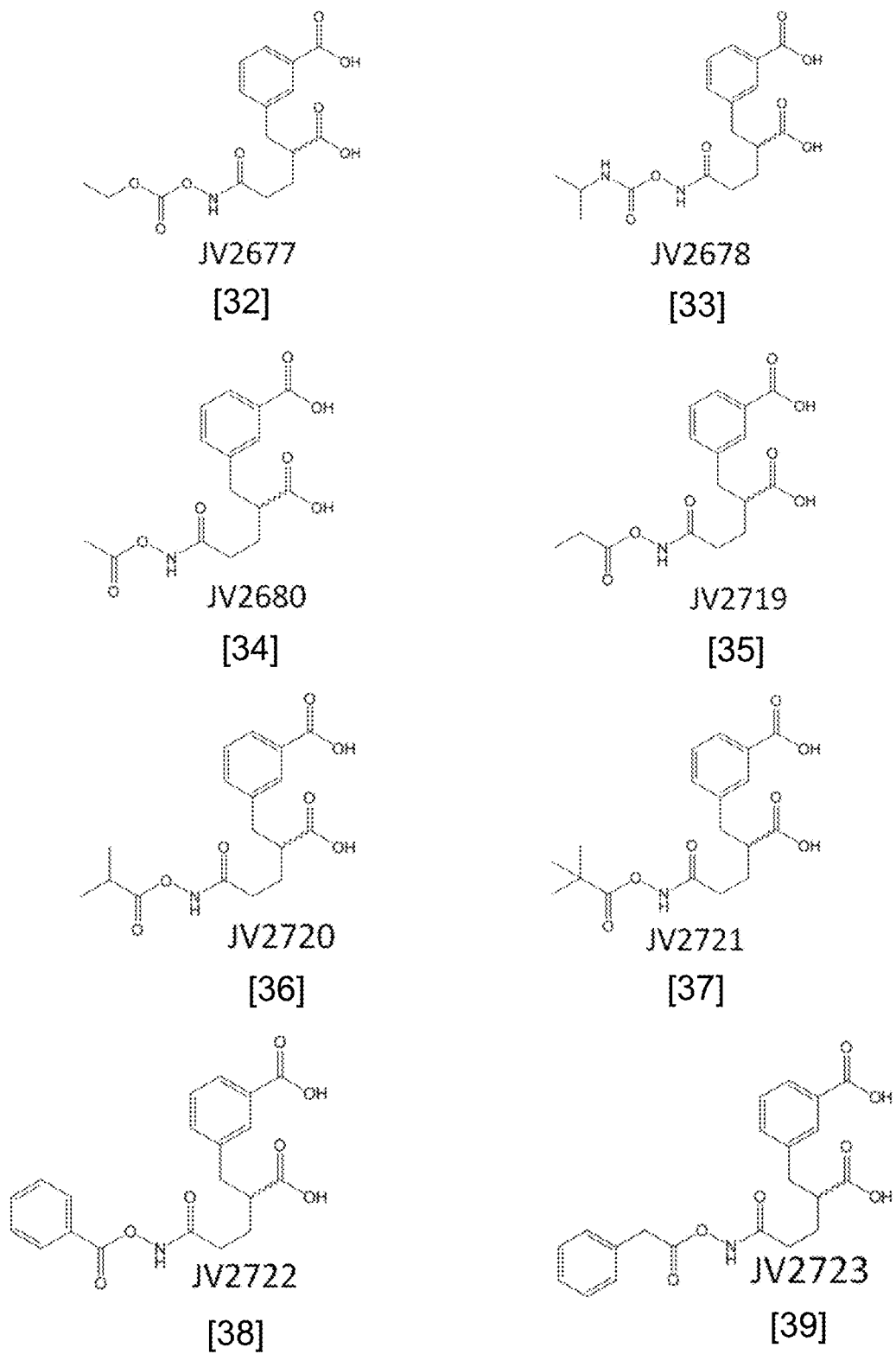
Figure 3B:
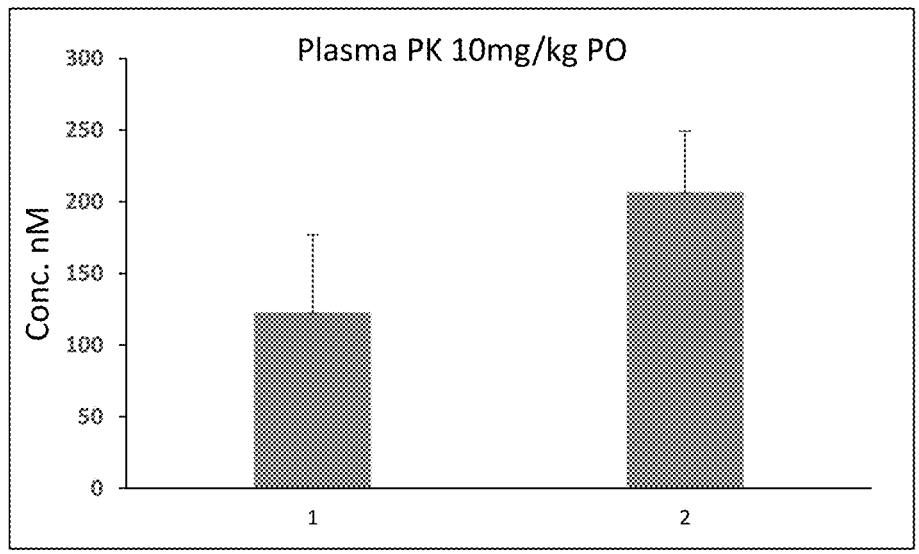
Figure 3C:
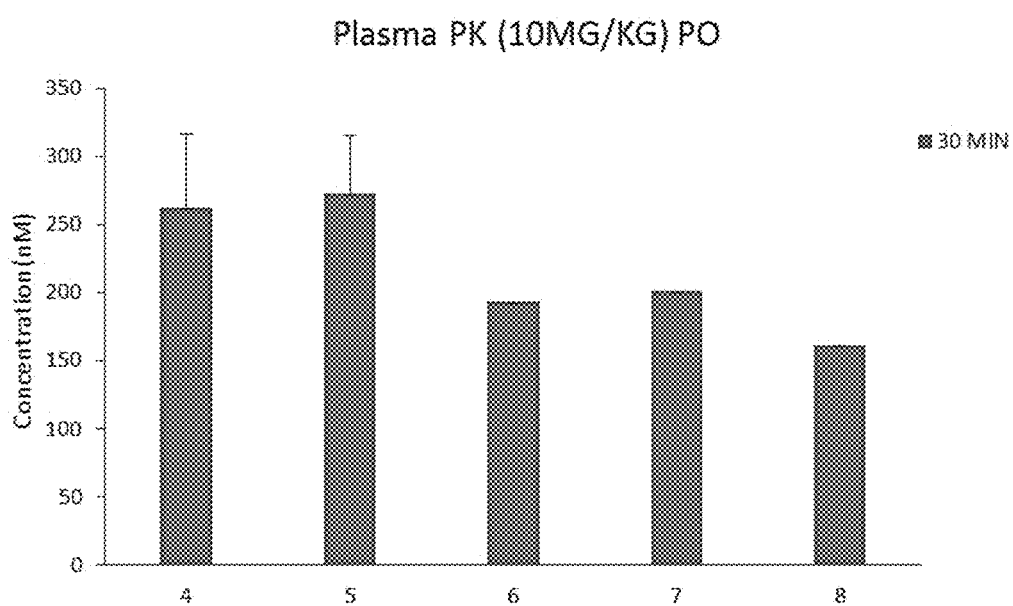
Figure 4A:
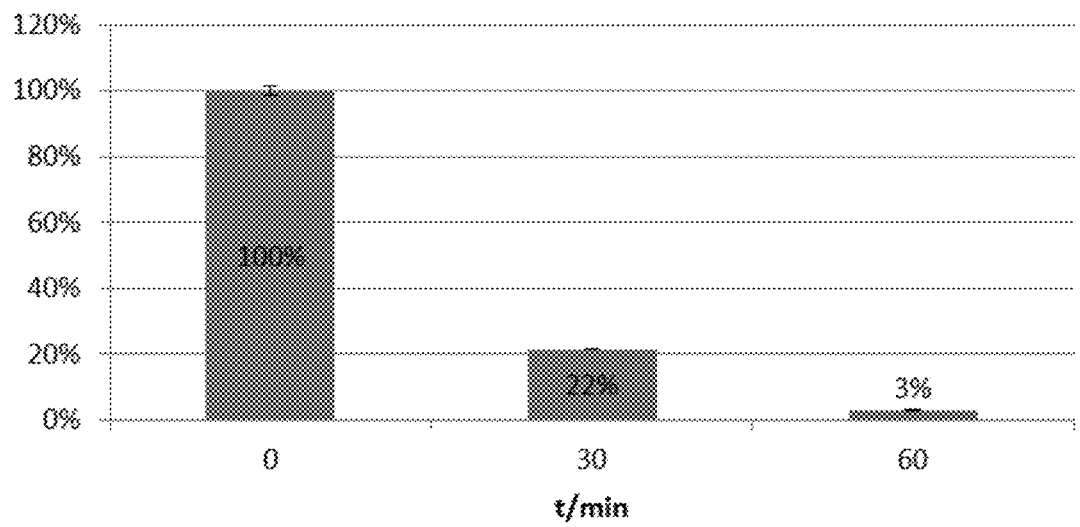
Figure 4B:
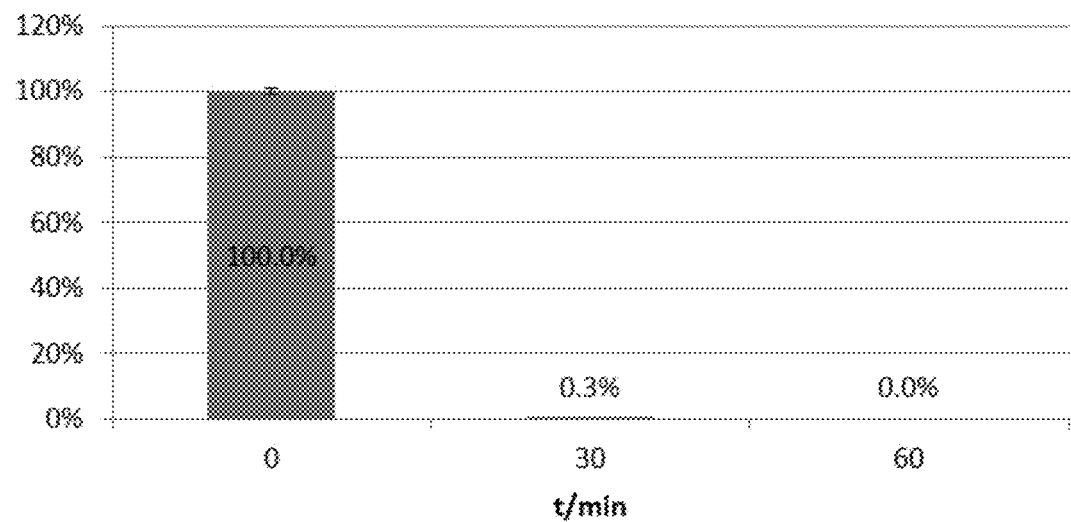
Figure 4C:
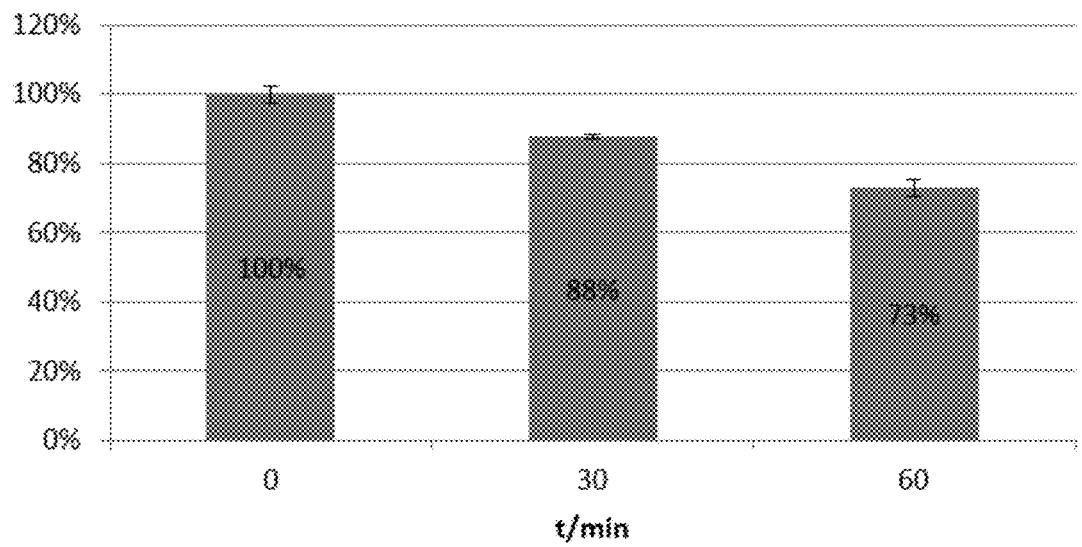
Figure 4D:
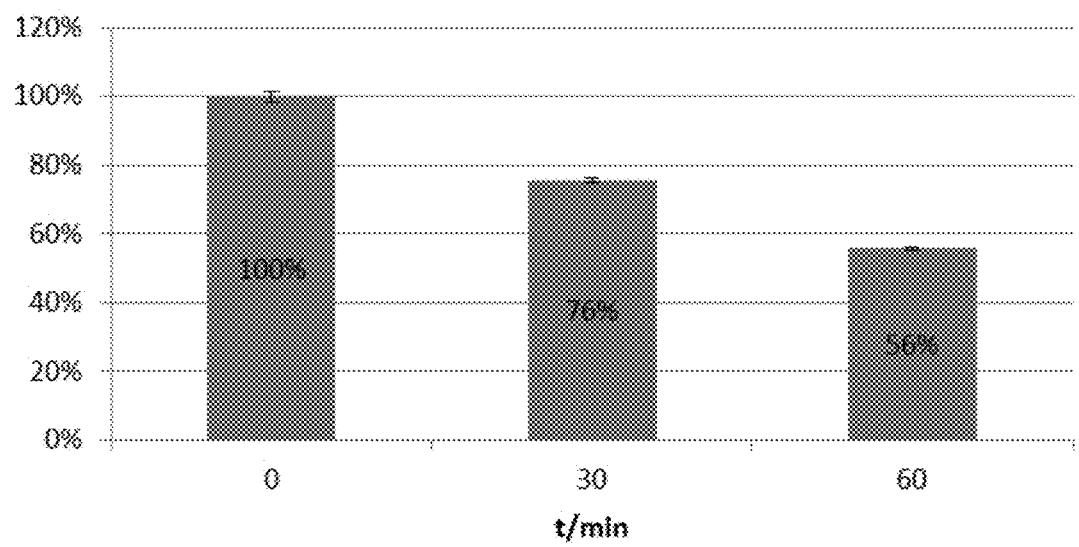
Figure 5A:
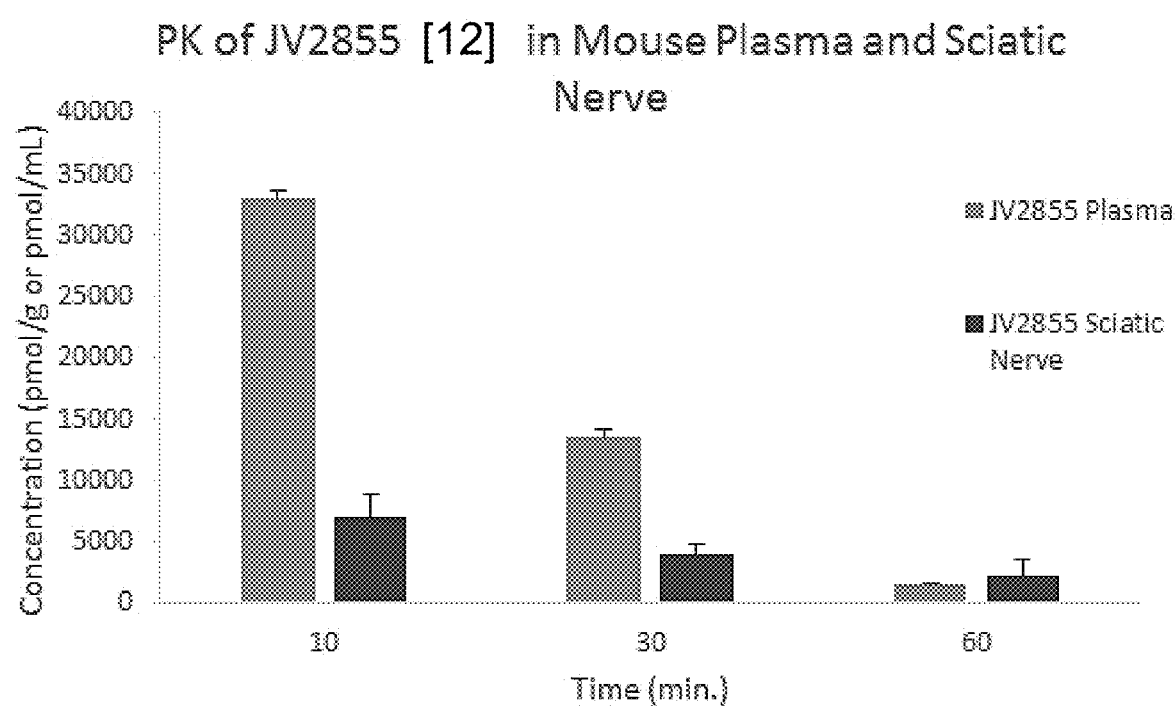
Figure 5B:
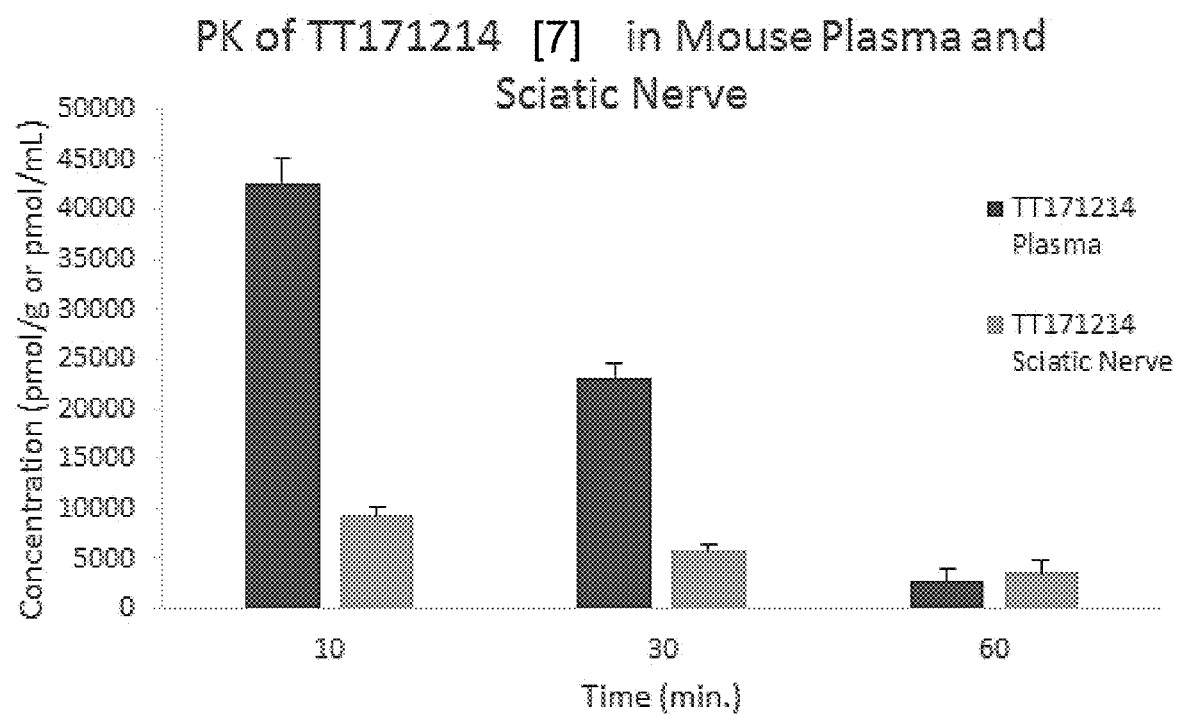
Figure 5C:
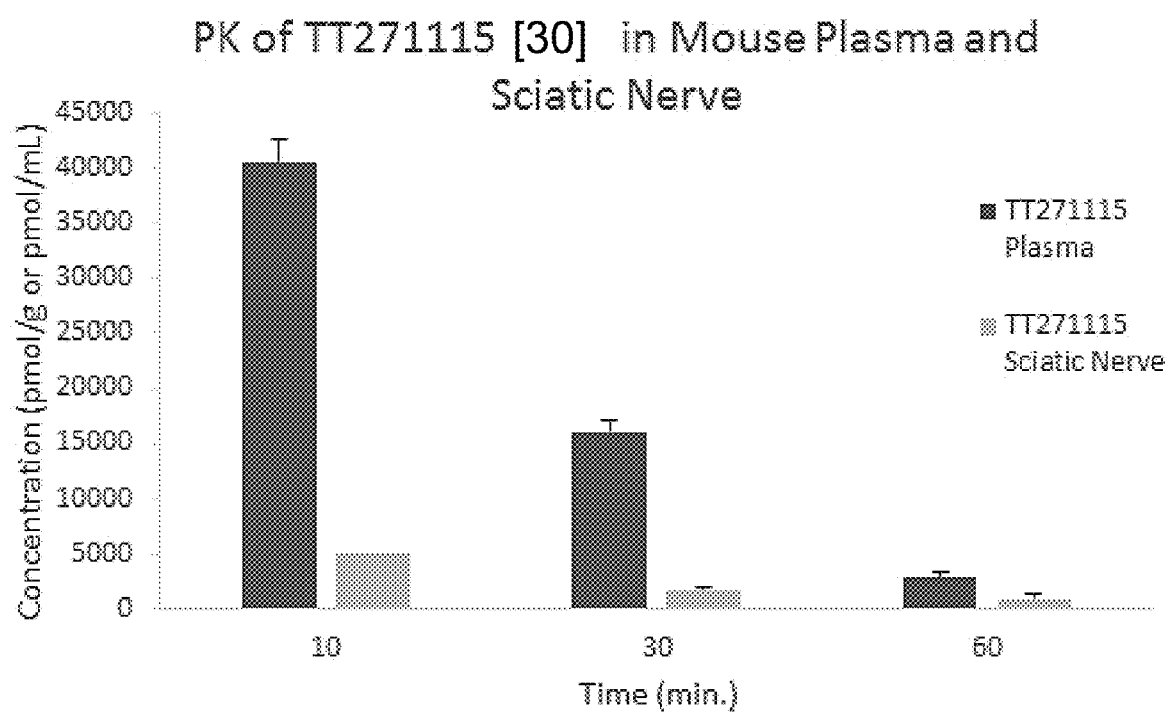
Figure 6A:
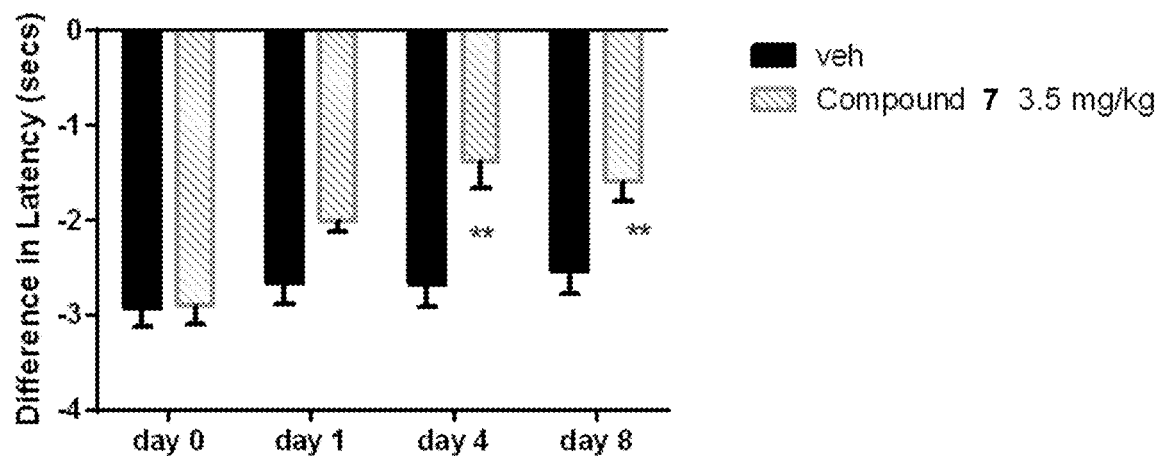
Figure 6B:
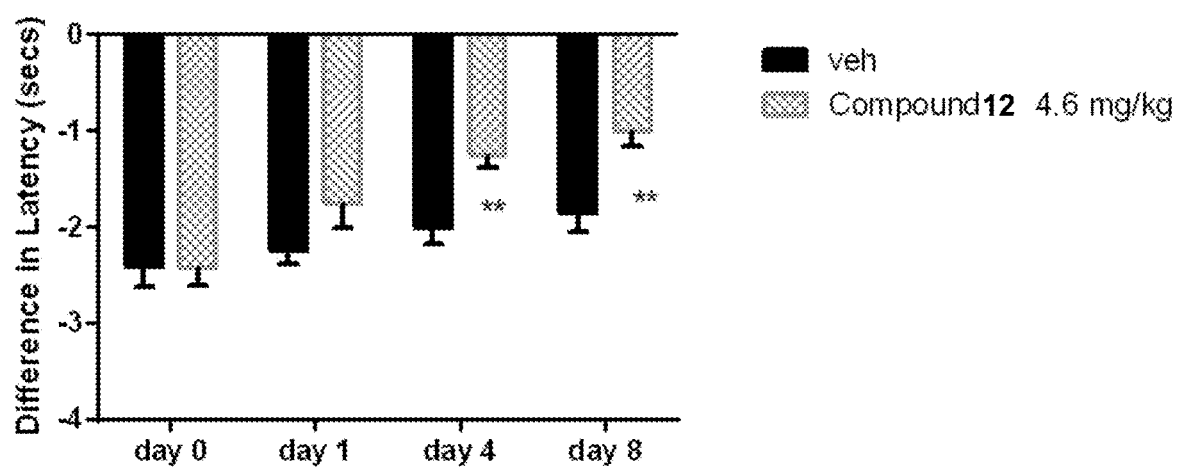
Figure 7:
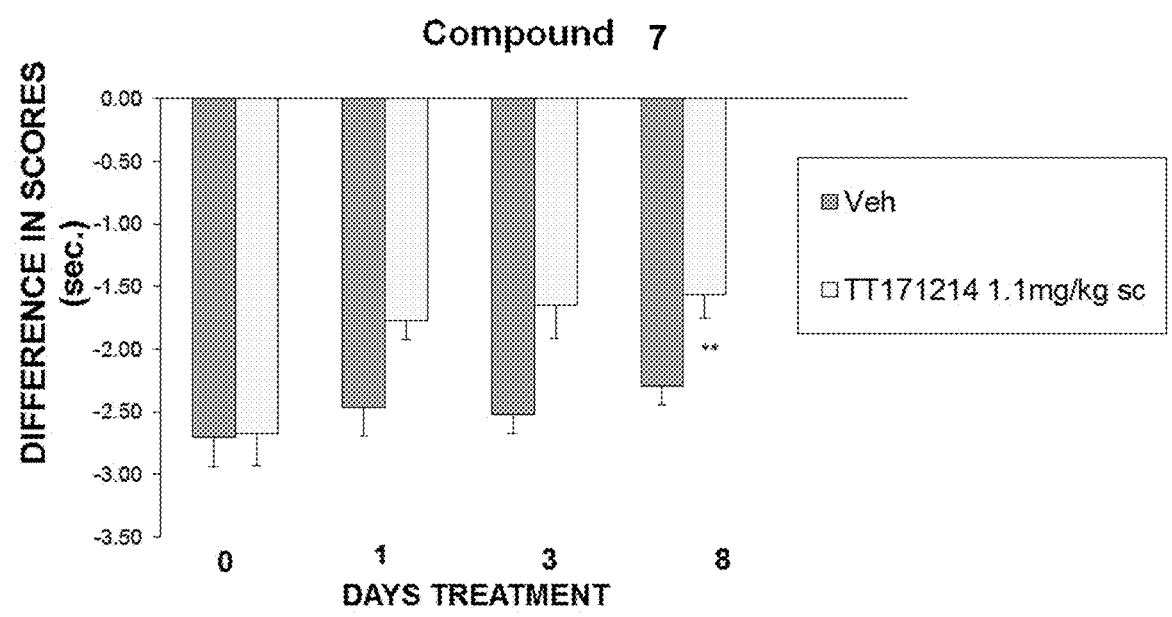

Having thus described the presently disclosed subject matter in general terms, reference will now be made to the accompanying Figures, which are not necessarily drawn to scale, and wherein:

FIG. 1A and FIG. 1B show representative para substituted hydroxamate prodrugs (FIG. 1A); and results (FIG. 1B) from oral plasma pharmacokinetic studies in mice, which demonstrate that the presently disclosed para substituted hydroxamate prodrugs dosed orally result in plasma exposure of active compound 50 (JHU241); mice (n=3) were dosed at 10 mg/kg equivalent dose and drug concentrations were measured in plasma 30 min post dose; compounds 12, 17, 41, and 7 showed best release of active compound 50;

FIG. 2A and FIG. 2B show analogs of compound 12, e.g., compound 30 (FIG. 2B) and compound 45 (FIG. 2A), which when dosed orally also result in plasma exposure of active compound 50; mice (n=3) were dosed orally at 10 mg/kg equivalent dose and drug concentrations were measured in plasma 10-120 min post dose;

FIG. 3A, FIG. 3B, and FIG. 3C show representative meta substituted hydroxamate prodrugs (FIG. 3A); and results (FIG. 3B and FIG. 3C) from oral plasma pharmacokinetic studies in mice, which demonstrate that the presently disclosed meta substituted hydroxamate prodrugs dosed orally also result in plasma exposure of active compound 50; mice (n=3) were dosed at 10 mg/kg equivalent dose and drug concentrations were measured in plasma 30 min post dose; compound 34 showed the best release;

FIG. 4A, FIG. 4B, FIG. 4C, and FIG. 4D show in vitro metabolic stability studies of compound 12 (FIG. 4A and FIG. 4B) and compound 7 (FIG. 4C and FIG. 4D); compound 12 is rapidly metabolized in human and mouse plasma, while compound 7 is moderately stable in human and mouse plasma;

FIG. 5A, FIG. 5B, and FIG. 5C show results from subcutaneous (sq) plasma pharmacokinetic studies in mice, which demonstrate that compound 12 (FIG. 5A), compound 30 (FIG. 5B), and compound 7 (FIG. 5C) dosed subcutaneously result in excellent plasma and sciatic nerve exposure of active compound 50; mice (n=3) were dosed at 10 mg/kg equivalent s.q. and 50 concentrations were measured in plasma and sciatic nerve at 10-120 min post dose; compounds 12, 30, and 7 showed high systemic levels and excellent nerve exposure of active JHU 241;

FIG. 6A and FIG. 6B show that oral hydroxamate prodrugs reverse thermal hyperalgesia in Chronic Constrictive Injury (CCI) Model of Neuropathic Pain in rats; compound 7 (FIG. 6A) and compound 12 (FIG. 6B) are efficacious at 3 mg/kg per os (po) (dose equivalent of 50);

FIG. 7 shows that subcutaneous hydroxamate prodrugs reverse thermal hyperalgesia in Chronic Constrictive Injury (CCI) Model of Neuropathic Pain in rats; compound 7 is efficacious at 1 mg/kg subcutaneous dose (dose equivalent of 50).

Figure 8:
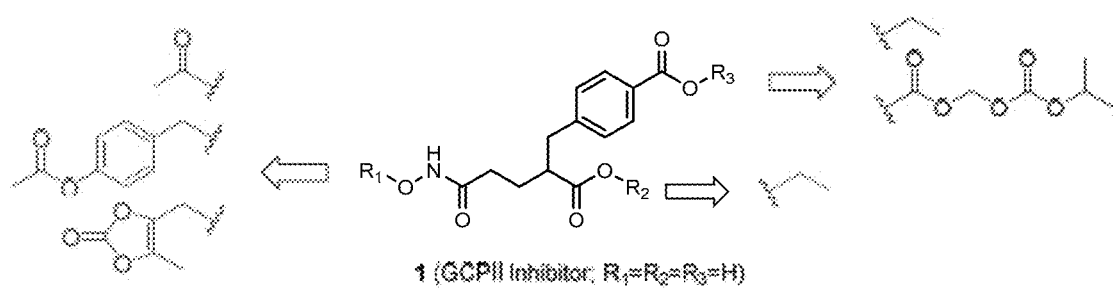
Figure 9:
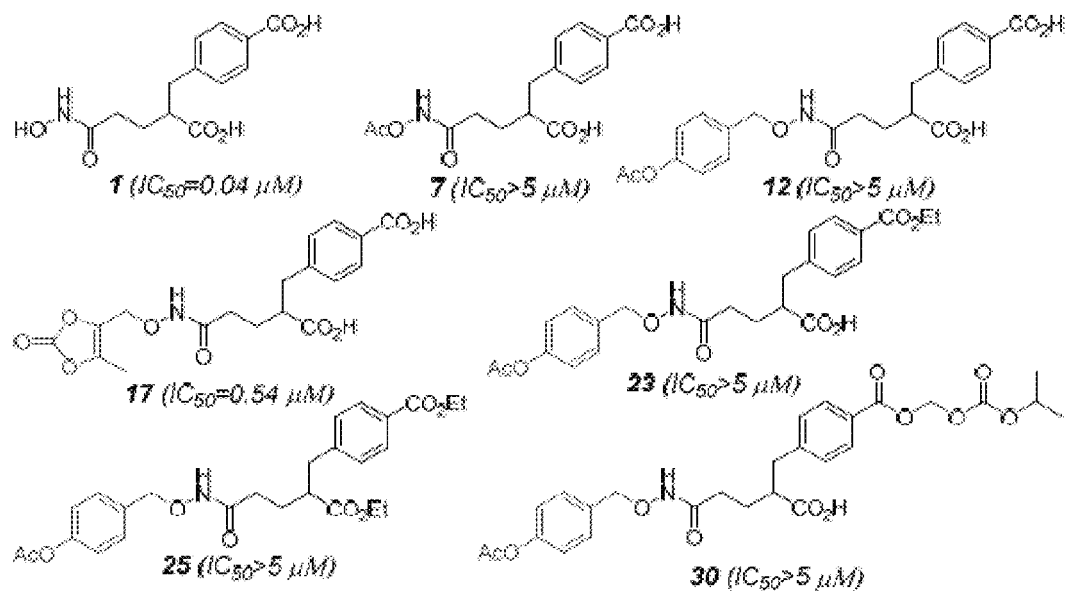
Figure 9:
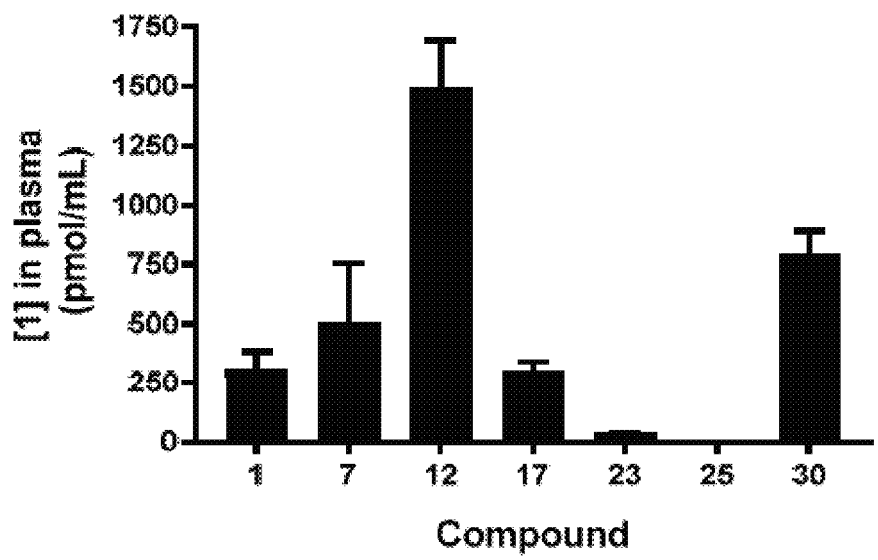
Figure 11A:
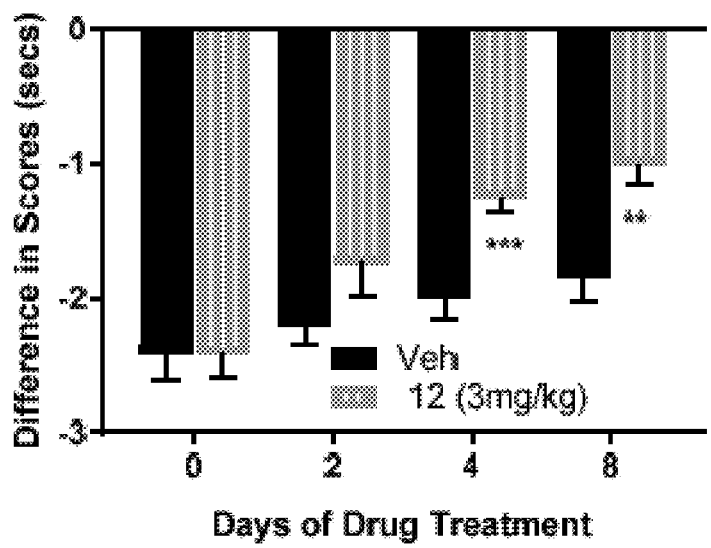
Figure 11B:
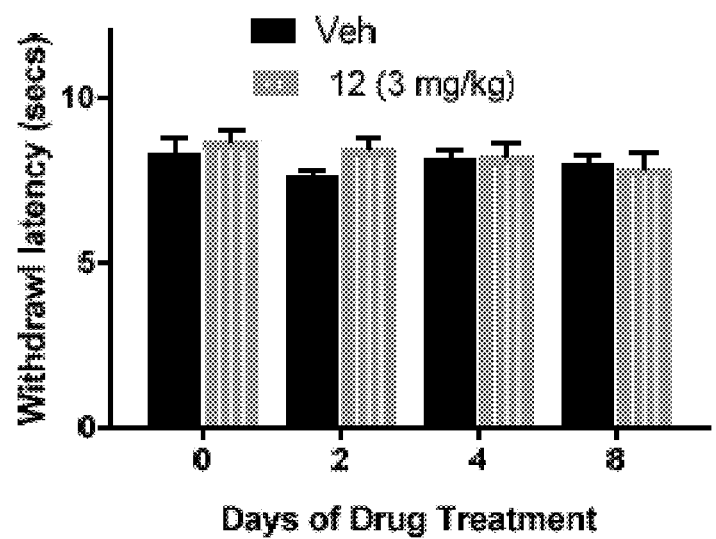
Figure 12:
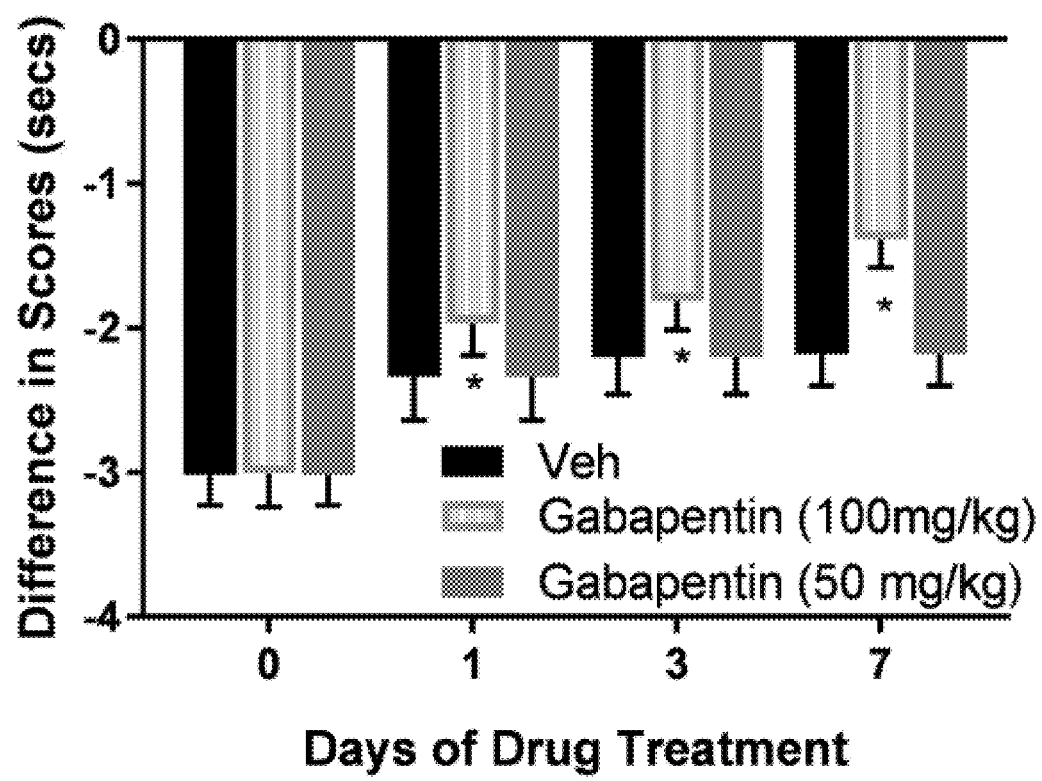

FIG. 8 illustrates the presently disclosed prodrug approach for hydroxamate-based GCPII inhibitor 1;

FIG. 9 shows structures, $IC_{50}$ and plasma concentrations of Compound 1 following oral administration of prodrugs in mice. All prodrugs except 17 were >10 fold less potent versus 1 in inhibiting GCP II activity. Six prodrugs 7, 12, 17, 23, 25, and 30 given p.o. to mice at a dose equivalent of 10 mg/kg of compound 1 and plasma levels of 1 were measured 30 min after administration. Compound 12 showed the highest improvement, delivering concentrations of 1 at greater than 5-fold in plasma vs 1. Data expressed as mean±SEM, (n=3);

FIGS. 10A, 10B, 10C, 10D, 10E, 10F, 10G, 10H, and 10I show metabolism of prodrugs 12, 23, and 30 in mouse plasma. (FIG. 10A) Putative metabolic pathways for 12, 23, and 30 in plasma. Mass extracted chromatograms of 1 and its prodrugs 12, 23, and 30 in mouse plasma at 0 min (FIG. 10B, FIG. 10D, FIG. 10F, FIG. 10H, and FIG. 10I) and after 60 min incubation (FIG. 10C, FIG. 10E, FIG. 10G, FIG. 10H, and FIG. 10I);

FIGS. 11A and 111B show antinociceptive effects of prodrug 12 in the rat chronic constriction injury (CCI) model of neuropathic pain. (FIG. 11A) Oral administration of 12 at 4.6 mg/kg/day (equivalent of 3 mg/kg/day of compound 1) significantly attenuated CCI-induced hyperalgesic state on the ligated side relative to the vehicle-treated control ( denotes p<0.01, * denotes p<0.001). (FIG. 11B) Compound 12 did not affect the response latency to the thermal stimulus applied to the sham-operated side; and FIG. 12 shows antinociceptive effects of gabapentin in the rat chronic constriction injury (CCI) model of neuropathic pain. Oral administration of gabapentin at 100 mg/kg/day significantly attenuated CCI-induced hyperalgesic state on the ligated side relative to the vehicle-treated control (* denotes p<0.05). 50 mg/kg/day did not significantly attenuate the hyperalgesic state.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Prodrugs of Hydroxamate-Based GCPII Inhibitors

The presently disclosed subject matter, in some embodiments, provides prodrugs of hydroxamate-based GCPII inhibitors that are useful as therapeutic agents for the treatment of diseases associated with a pathological increase of glutamate concentration or an excessive activation of glutamatergic systems.

In some embodiments, the presently disclosed subject matter provides a compound of formula (I):

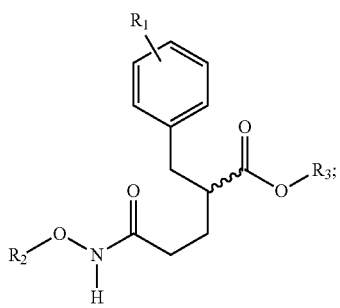

wherein: $R_1$ is selected from the group consisting of —C(=O)—O—$R_4$ and —Ar—C(=O)—O—$R_4$; $R_2$ is selected from the group consisting of substituted and unsubstituted $C_1$-$C_6$ alkyl, substituted and unsubstituted $C_3$-$C_8$ cycloalkyl, substituted and unsubstituted $C_6$-$C_{12}$ aryl, substituted and unsubstituted $C_6$-$C_{12}$ heteroaryl, —($CR_5R_6$), —$R_7$, —C(=O)—O—$R_7$, —C(=O)—$R_7$, —C(=O)—$NR_7R_8$, —($CR_5R_6$)$_n$—O—C(=O)—O—$R_7$, —($CR_5R_6$)$_n$—Ar—O—C(=O)—$R_7$; $R_3$ is selected from the group consisting of H, substituted and unsubstituted $C_1$-$C_6$ alkyl, substituted and unsubstituted $C_3$-$C_{12}$ cycloalkyl, substituted and unsubstituted $C_6$-$C_{12}$ aryl, substituted and unsubstituted $C_5$-$C_{12}$ heteroaryl; $R_4$ is selected from the group consisting of H, substituted and unsubstituted $C_1$-$C_6$ alkyl, substituted and unsubstituted $C_3$-$C_{12}$ cycloalkyl, substituted and unsubstituted $C_6$-$C_{12}$ aryl, substituted and unsubstituted $C_5$-$C_{12}$ heteroaryl, —($CR_5R_6$)$_n$—O—C(=O)—O—$R_9$, and —($CR_5R_6$)$_n$—Ar—O—C(=O)—$R_9$; each $R_5$ and $R_6$ is independently selected from the group consisting of H, $C_1$-$C_{10}$ alkyl, and $C_6$-$C_{12}$ aralkyl; $R_7$ is selected from the group consisting of H, and substituted and unsubstituted $C_1$-$C_{10}$ alkyl, substituted and unsubstituted $C_1$-$C_{10}$ heteroalkyl, substituted and unsubstituted $C_3$-$C_{16}$ cycloalkyl, substituted and unsubstituted $C_3$-$C_{12}$ cycloheteroalkyl, substituted and unsubstituted $C_3$-$C_{12}$ cycloheteroalkenyl, substituted and unsubstituted $C_6$-$C_{12}$ aryl, substituted and unsubstituted $C_6$-$C_{12}$ heteroaryl, and substituted and unsubstituted $C_6$-$C_{12}$ aralkyl; $R_8$ is selected from the group consisting of H, and substituted and unsubstituted $C_1$-$C_6$ alkyl; $R_9$ is selected from the group consisting of H, and substituted and unsubstituted $C_1$-$C_6$ alkyl; n is an integer selected from the group consisting of 0, 1, 2, 3, 4, 5, and 6; Ar is selected from the group consisting of substituted and unsubstituted $C_6$-$C_{12}$ aryl, and substituted and unsubstituted $C_6$-$C_{12}$ heteroaryl; and stereoisomers and pharmaceutically acceptable salts thereof.

In some embodiments, the compound of formula (I) is selected from the group consisting of:

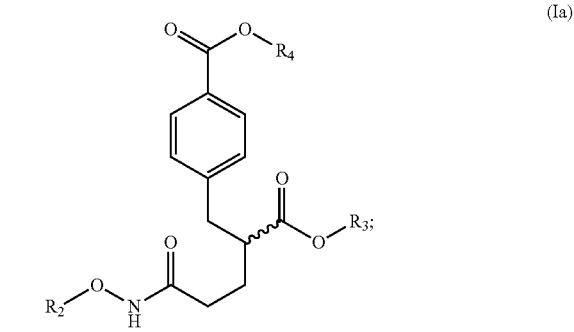

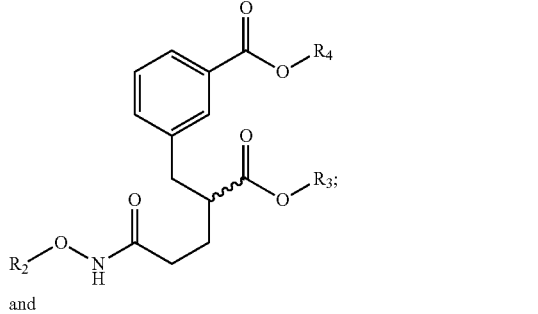

and

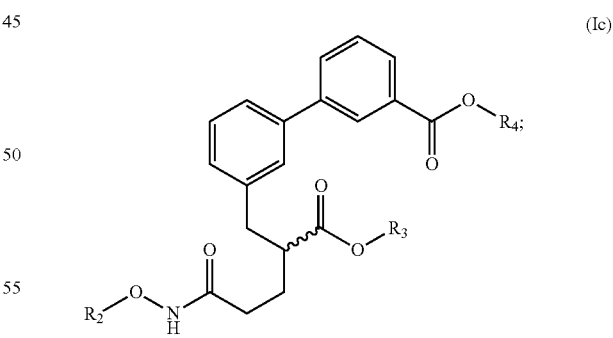

wherein $R_2$, $R_3$, and $R_4$, are as defined hereinabove; and stereoisomers and pharmaceutically acceptable salts thereof.

In some embodiments, $R_2$ is as defined hereinabove; $R_3$ is selected from the group consisting of H and substituted and unsubstituted $C_1$-$C_6$ alkyl; $R_4$ is selected from the group consisting of H, substituted and unsubstituted $C_1$-$C_6$ alkyl, —($CR_5R_6$)$_n$—Ar—O—C(=O)—$R_9$, and —($CR_5R_6$)$_n$—O—C(=O)—O—$R_9$; n is 1; $R_5$ and $R_6$ are H; Ar is phenyl; $R_9$ is selected from the group consisting of substituted $C_1$-$C_3$ alkyl, and unsubstituted $C_1$-$C_3$ alkyl; and stereoisomers and pharmaceutically acceptable salts thereof.

In some embodiments $R_2$ is —$(CR_5R_6)_n$—Ar—O—C(=O)—$R_7$, n is 1, Ar is phenyl, and $R_7$ is substituted or unsubstituted $C_1$-$C_6$ alkyl.

In particular embodiments, the compound of formula (I) is selected from the group consisting of:

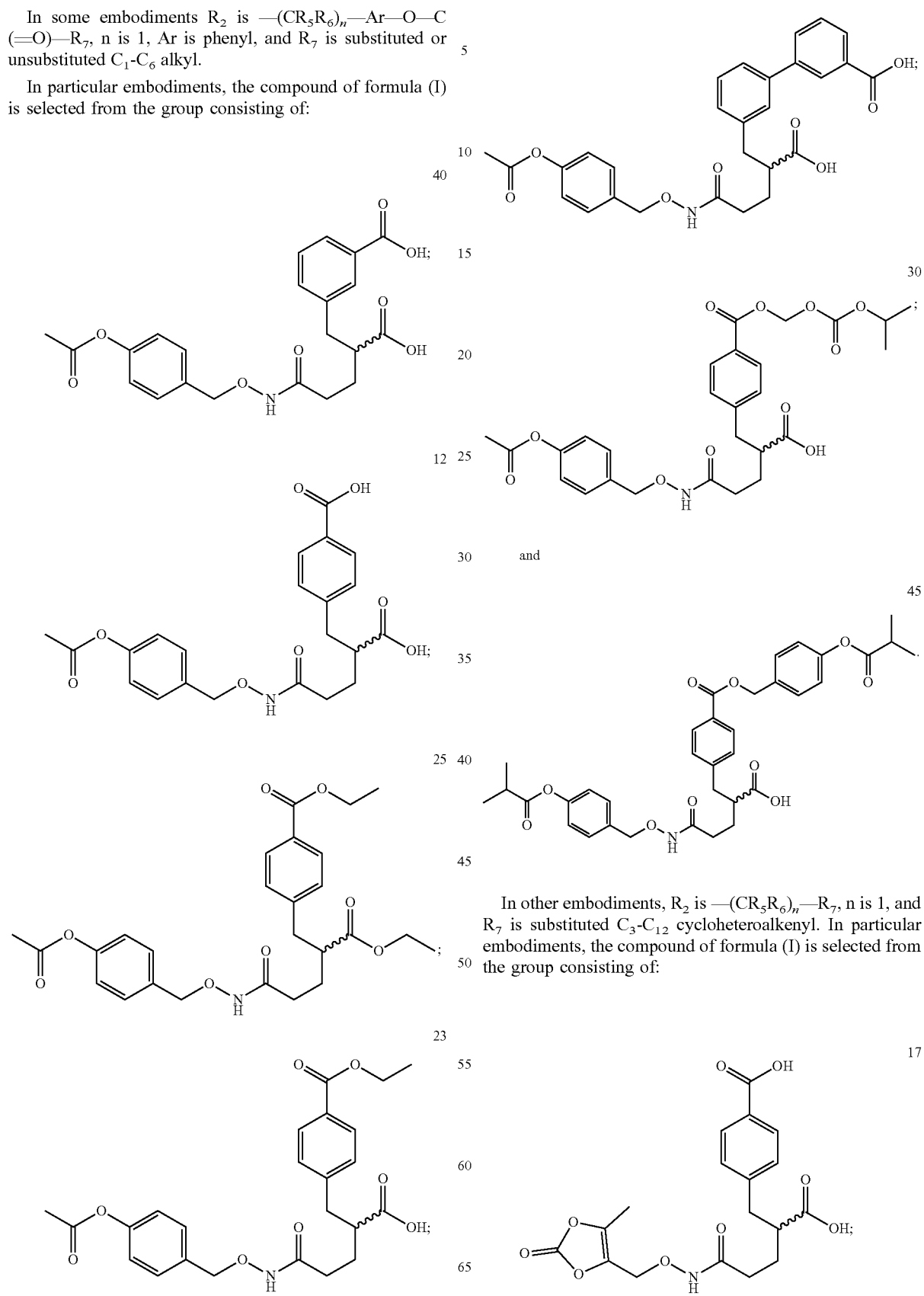

In other embodiments, $R_2$ is —$(CR_5R_6)_n$—$R_7$, n is 1, and $R_7$ is substituted $C_3$-$C_{12}$ cycloheteroalkenyl. In particular embodiments, the compound of formula (I) is selected from the group consisting of:

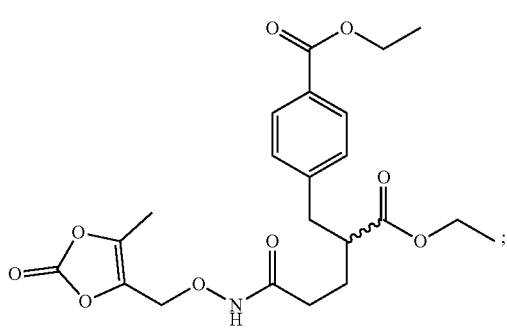
42
and
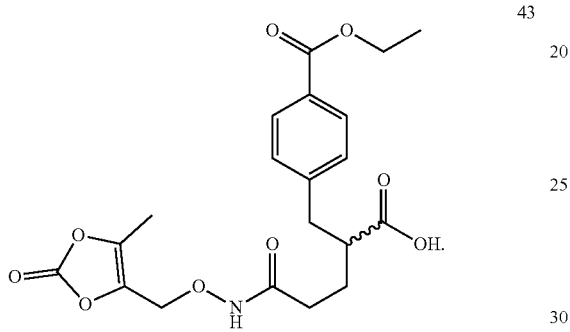
43
In some embodiments R₂ is —C(=O)—R₇, and R₇ is unsubstituted $C_1$-$C_6$ alkyl, substituted $C_1$-$C_6$ alkyl, unsubstituted $C_6$-$C_{12}$ aryl, or unsubstituted $C_6$-$C_{12}$ aralkyl. In particular embodiments, the compound of formula (I) is selected from the group consisting of:
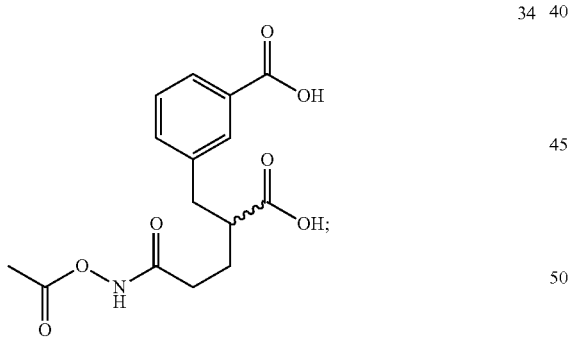
34
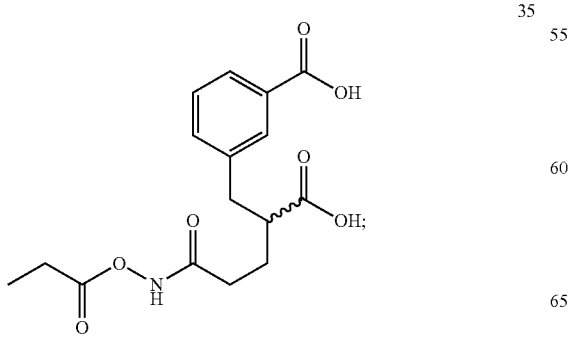
35
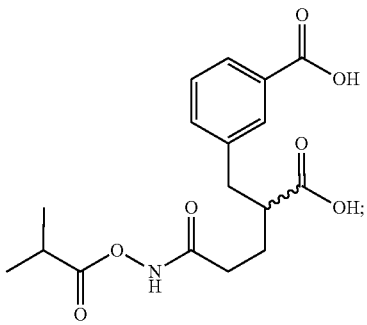
36
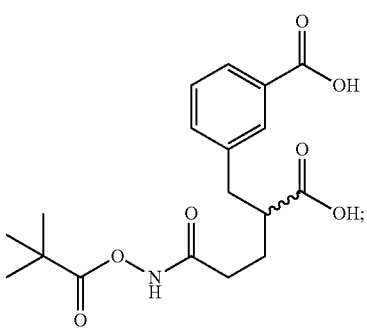
37
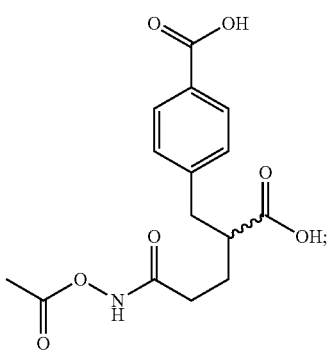
7
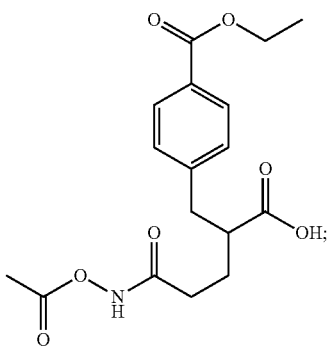
46

-continued

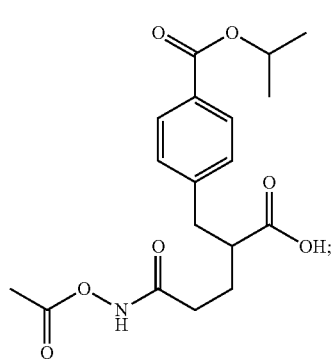
47

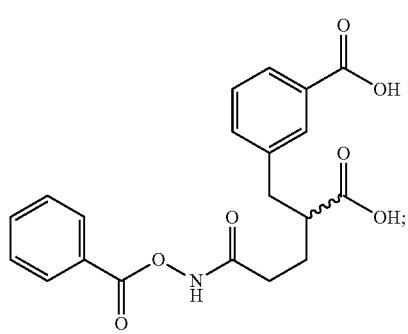
38

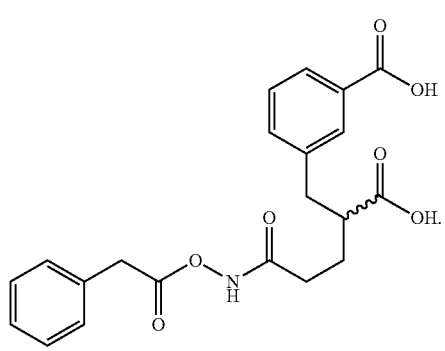
39

In some embodiments, R$_2$ is —C(=O)—O—R$_7$, and R$_7$ is unsubstituted C$_1$-C$_6$ alkyl. In particular embodiments, the compound of formula (I) is:

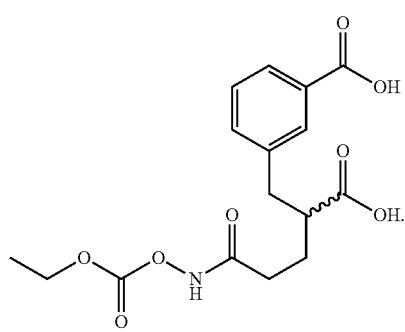
32

In some embodiments, R$_2$ is —C(=O)—NR$_7$R$_8$, R$_7$ is substituted C$_1$-C$_6$ alkyl, or substituted C$_3$-C$_{16}$ cycloalkyl, and R$_8$ is H. In particular embodiments, the compound of formula (I) is selected from the group consisting of:

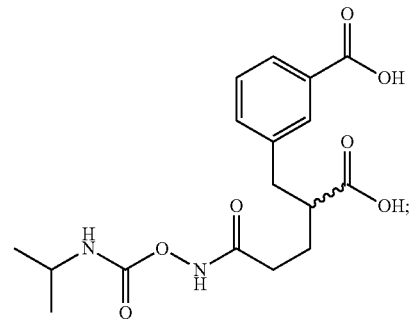
33

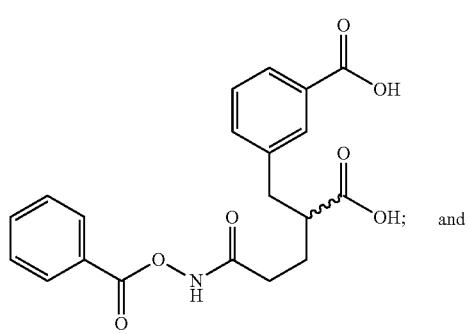
48

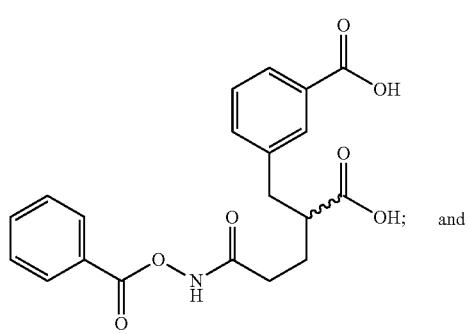
49

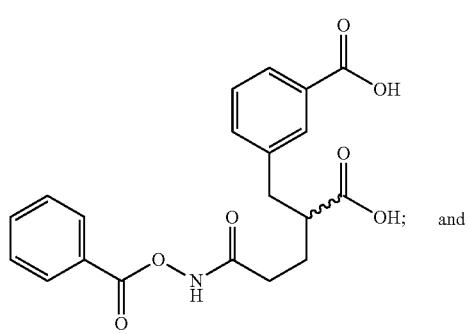
41

Representative structures of prodrugs of hydroxamate-based GCPII inhibitors are provided in Table 1.

TABLE 1

STRUCTURES OF REPRESENTATIVE PRODRUGS OF
HYDROXAMATE-BASED GCPII INHIBITORS

| IOCB No./Compound No. | Structure | MW |
|---|---|---|
| JV2677 / 32 | | 353.33 |
| JV2678 / 33 | | 366.37 |
| JV2680 / 34 | | 323.30 |
| JV2719 / 35 | | 337.33 |

TABLE 1-continued

STRUCTURES OF REPRESENTATIVE PRODRUGS OF
HYDROXAMATE-BASED GCPII INHIBITORS

| IOCB No./Compound No. | Structure | MW |
|---|---|---|
| JV2720 / 36 | | 351.36 |
| JV2721 / 37 | | 365.38 |
| JV2722 / 38 | | 385.37 |
| JV2723 / 39 | | 399.40 |

TABLE 1-continued

STRUCTURES OF REPRESENTATIVE PRODRUGS OF HYDROXAMATE-BASED GCPII INHIBITORS

| IOCB No./Compound No. | Structure | MW |
|---|---|---|
| JV2837<br>40 | | 429.43 |
| JV2855<br>12 | | 429.43 |
| JV2925<br>17 | | 393.35 |
| JV2928<br>41 | | 486.57 |

TABLE 1-continued
STRUCTURES OF REPRESENTATIVE PRODRUGS OF
HYDROXAMATE-BASED GCPII INHIBITORS
| IOCB No./ Compound No. | Structure | MW |
|---|---|---|
| JV2946 25 | 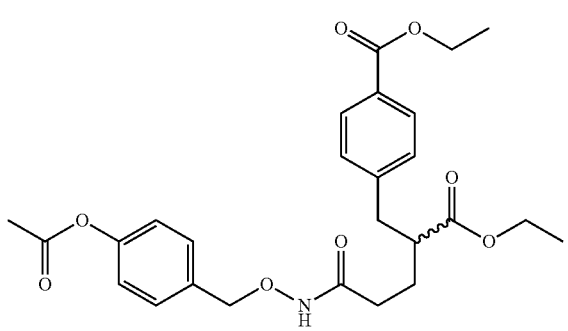 [SMILES: CCOC(=O)c1ccc(CC(CCC(=O)NOCc2ccc(OC(C)=O)cc2)C(=O)OCC)cc1] | 485.53 |
| JV2956 23 | 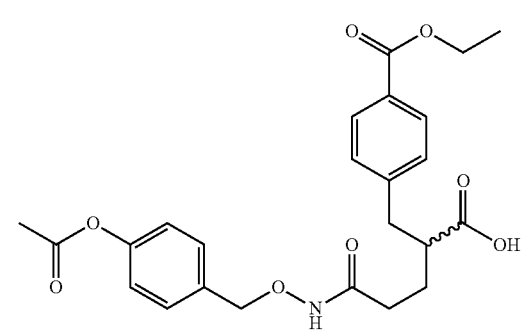 [SMILES: CCOC(=O)c1ccc(CC(CCC(=O)NOCc2ccc(OC(C)=O)cc2)C(=O)O)cc1] | 457.48 |
| JV2947 42 | 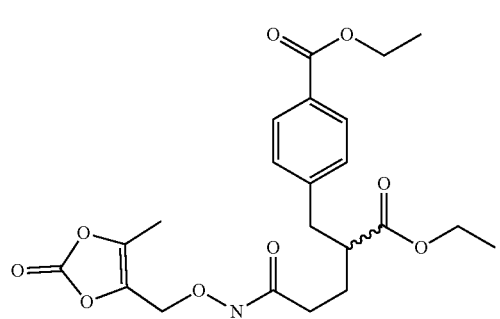 | 449.46 |
| JV2957 43 | 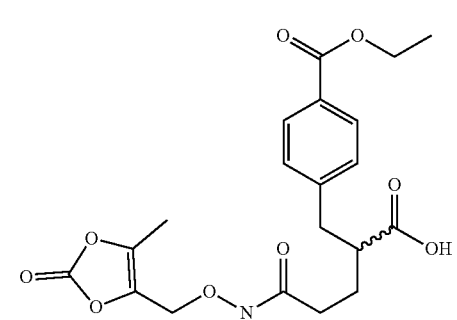 | 421.40 |

TABLE 1-continued

STRUCTURES OF REPRESENTATIVE PRODRUGS OF
HYDROXAMATE-BASED GCPII INHIBITORS

| IOCB No./ Compound No. | Structure | MW |
|---|---|---|
| JV3055 44 | 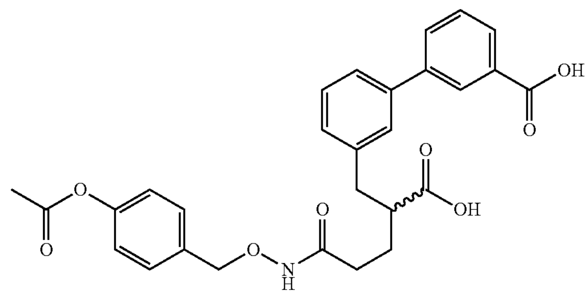 [SMILES: CC(=O)Oc1ccc(CONC(=O)CCC(Cc2cccc(-c3cccc(C(=O)O)c3)c2)C(=O)O)cc1] | 505.52 |
| TT271115 30 | 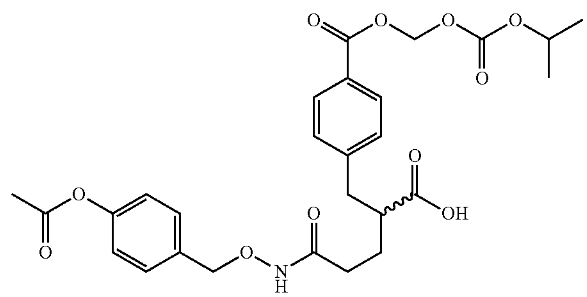 [SMILES: CC(=O)Oc1ccc(CONC(=O)CCC(Cc2ccc(C(=O)OCOC(=O)OC(C)C)cc2)C(=O)O)cc1] | 545.54 |
| TT200216 45 | 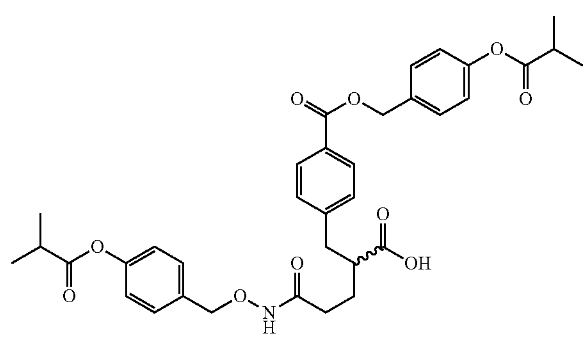 [SMILES: CC(C)C(=O)Oc1ccc(CONC(=O)CCC(Cc2ccc(C(=O)OCc3ccc(OC(=O)C(C)C)cc3)cc2)C(=O)O)cc1] | 633.69 |
| TT171214 7 | 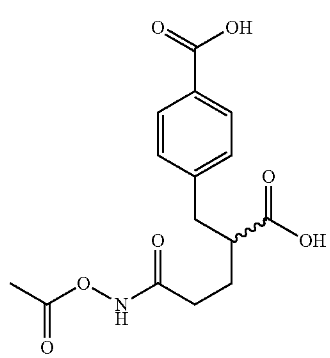 [SMILES: CC(=O)ONC(=O)CCC(Cc1ccc(C(=O)O)cc1)C(=O)O] | 323.30 |

TABLE 1-continued

STRUCTURES OF REPRESENTATIVE PRODRUGS OF
HYDROXAMATE-BASED GCPII INHIBITORS

| IOCB No./ Compound No. | Structure | MW |
|---|---|---|
| JV3113 46 | 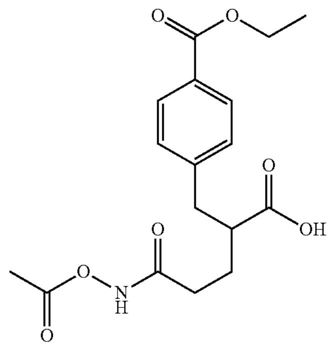 [SMILES: CCOC(=O)c1ccc(CC(CCC(=O)NOC(C)=O)C(=O)O)cc1] | 351.36 |
| JV3138 47 | 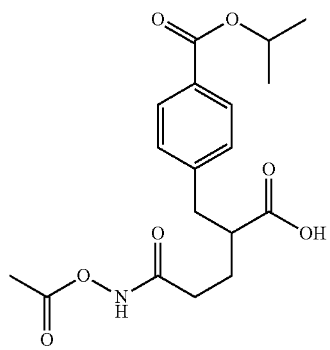 [SMILES: CC(=O)ONC(=O)CCC(Cc1ccc(C(=O)OC(C)C)cc1)C(=O)O] | 365.38 |
| JV3126 48 | 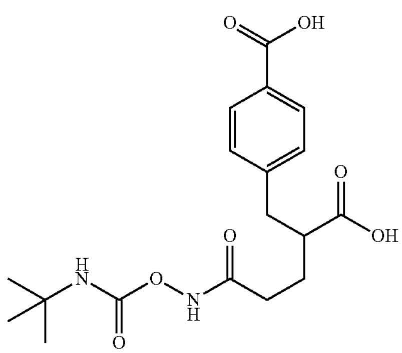 [SMILES: CC(C)(C)NC(=O)ONC(=O)CCC(Cc1ccc(C(=O)O)cc1)C(=O)O] | 380.40 |
| JV3127 49 | 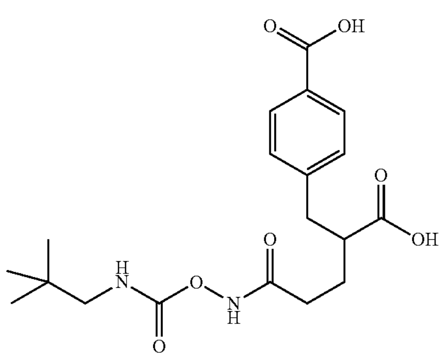 [SMILES: CC(C)(C)CNC(=O)ONC(=O)CCC(Cc1ccc(C(=O)O)cc1)C(=O)O] | 394.42 |

II. Pharmaceutical Compositions and Administration

In another aspect, the present disclosure provides a pharmaceutical composition including a compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including oral and subcutaneous administration. Techniques and formulations generally may be found in Remington: The Science and Practice of Pharmacy (20$^{th}$ ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a controlled release, timed- or sustained-slow release, or extended release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, e.g., subcutaneous injection, the agents of the disclosure may be formulated and diluted in aqueous solutions, such as in physiologically compatible buffers such as Hank's solution, Ringer's solution, or physiological saline buffer.

The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

III. Methods for Treating a Disease or Disorder

The presently disclosed compounds, which are orally bioavailable prodrugs of hydroxamate-based GCPII inhibitors, allow a clinically acceptable dosing paradigm for diseases or conditions wherein excess PSMA/GCPII activity is implicated. These diseases or conditions include, but are not limited to, a neurodegenerative disease, cancer, angiogenesis, and inflammatory bowel disease.

As used herein, a "neurodegenerative disease" is a disease or condition that results in the progressive loss of the structure and/or function of neurons in a subject. Representative neurodegenerative diseases include, but are not limited to, amyotrophic lateral sclerosis (ALS), Parkinson's disease (PD), Alzheimer's disease (AD), Huntington's disease, dementia with Lewy Bodies (DLB), schizophrenia, inflammatory and neuropathic pain, peripheral neuropathy, epilepsy, brain ischemia, stroke, spinal cord and traumatic brain injury (TBI), cognition, motoneuron disease, drug addiction/tolerance, and multiple sclerosis (MS).

In certain embodiments, the disease or condition results in excess PSMA activity. In such embodiments, the presently disclosed methods comprise inhibiting the excess PSMA activity when the compound of formula (I), or a pharmaceutical composition thereof, is administered.

As used herein, the terms "PSMA" or "PSMA polypeptide" refer to a naturally occurring or endogenous PSMA and to proteins having an amino acid sequence which is the same as that of a naturally occurring or endogenous PSMA (e.g., recombinant proteins). Accordingly, as defined herein, the term includes mature PSMA, glycosylated or unglycosylated PSMA proteins, polymorphic or allelic variants, and other isoforms of PSMA (e.g., produced by alternative splicing or other cellular processes).

As used herein, an "inhibitor" of PSMA is a molecule that decreases or inhibits the activity of PSMA when administered. The inhibitor may interact with PSMA directly or may interact with another molecule that results in a decrease in the activity of PSMA.

The presently disclosed subject matter shows that there is a marked elevation or excess of PSMA activity in subjects with certain diseases or conditions. As used herein, the term "excess PSMA activity" means an increase of PSMA activity in a subject with a disease or condition as compared to the PSMA activity in a subject without a similar disease or condition, such as an increase of approximately 100%, 200%, 300%, 400%, 500%, 600%, 700%, 800%, 900%, 1000%, or more.

In some embodiments, the presently disclosed subject matter provides methods for inhibiting the excess PSMA activity found in a subject with a disease or condition. As used herein, the term "inhibit" means to decrease or diminish the excess PSMA activity found in a subject. The term "inhibit" also may mean to decrease, suppress, attenuate, diminish, arrest, or stabilize the development or progression of a disease or condition. Inhibition may occur, for e.g., by at least 10%, 20%, 30%, 40%, 50%, 60%, 70%, 80%, 90%, 95%, 98%, 99%, or even 100% compared to an untreated control subject or a subject without the disease or disorder.

In general, the presently disclosed methods result in a decrease in the severity of a disease or condition in a subject. The term "decrease" is meant to inhibit, suppress, attenuate, diminish, arrest, or stabilize a symptom of a disease or condition.

As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

Accordingly, in some embodiments, the presently disclosed subject matter provides a method for treating a disease or a condition, the method comprising administering to a subject in need of treatment thereof, a compound of formula (I), or a pharmaceutical composition thereof, in an amount effective for treating the disease or condition.

IV. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) 0, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —$SO_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloheteroalkenyl" as used herein refers to a saturated monocyclic or bicyclic alkenyl radical in which one carbon atom is replaced with N, O or S. The cycloheteroalkenyl may contain up to four heteroatoms independently selected from N, O or S. Examples of cycloheteroalkenyl groups include, but are not limited to, radicals derived from imidazolyl, pyrazolyl, pyrrolyl, indolyl, pyranyl, and the like. A specific example of cycloheteroalkenyl group is 5-methyl-2-oxo-1,3-dioxol-4-yl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($—CH_2—$); ethylene ($—CH_2—CH_2—$); propylene ($—(CH_2)_3—$); cyclohexylene ($—C_6H_{10}—$); $—CH=CH—CH=CH—$; $—CH=CH—CH_2—$; $—CH_2CH_2CH_2CH_2—$, $—CH_2CH=CHCH_2—$, $—CH_2C\equiv CCH_2—$, $—CH_2CH_2CH(CH_2CH_2CH_3)CH_2—$, $—(CH_2)_q—N(R)—(CH_2)_r—$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($—O—CH_2—O—$); and ethylenedioxyl ($—O—(CH_2)_2—O—$). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula $—C(O)OR'—$ represents both $—C(O)OR'—$ and $—R'OC(O)—$.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

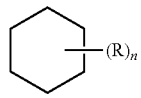

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

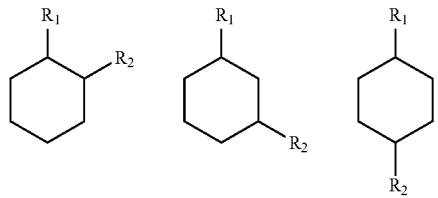

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol (( ～～～ )) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R', —OC(O)R', —C(O)R', —CO$_2$R', —C(O)NR'R", —OC(O)NR'R", —NR"C(O)R', —NR'—C(O)NR"R', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR"R''', —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R''', wherein R', R", and R' are each independently selected from the group consisting of alkyl groups. Additionally, R', R", and/or R''' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO₄ group.

The term thiohydroxyl or thiol, as used herein, refers to —SH.

The term ureido refers to a urea group of the formula —NH—CO—NH₂.

Unless otherwise explicitly defined, a "substituent group," as used herein, includes a functional group selected from one or more of the following moieties, which are defined herein:

(A) —OH, —NH₂, —SH, —CN, —CF₃, —NO₂, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxo, —OH, —NH₂, —SH, —CN, —CF₃, —NO₂, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

allyl

Bn

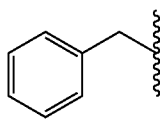

Cbz

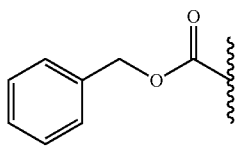

Alloc

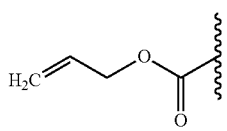

Me

t-butyl

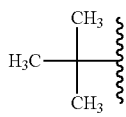

TBDMS

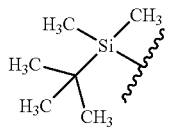

Teoc

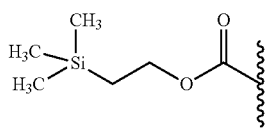

Boc

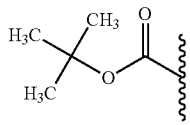

pMB

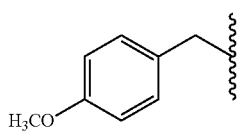

tosyl

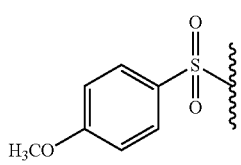

trityl

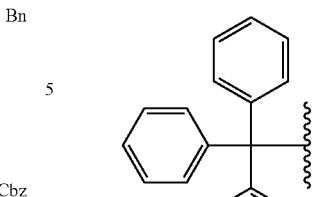

acetyl

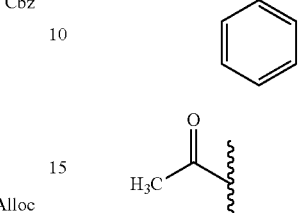

Fmoc

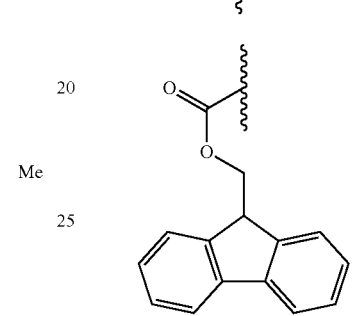

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Prodrugs of a Hydroxamate-Based Glutamate Carboxypeptidase II Inhibitors Overview 4-Carboxy-α-[3-(hydroxyamino)-3-oxopropyl]-benzenepropanoic acid 1 is a potent hydroxamate-based inhibitor of glutamate carboxypeptidase II. In an attempt to improve its poor oral pharmacokinetics, a series of prodrugs were synthesized by masking its hydrophilic hydroxamate group. Prodrugs were evaluated for oral availability in mice and showed varying degree of plasma exposure to 1. Of these prodrugs, para-acetoxybenzyl-based, 4-(5-(((4-acetoxybenzyl)oxy)amino)-2-carboxy-5-oxopentyl)benzoic acid, 12, provided 5-fold higher plasma levels of 1 compared to oral administration of 1 itself.

Subsequently, para-acetoxybenzylbased prodrugs with additional ester promoiety(ies) on carboxylate(s) were examined for their ability to deliver 1 to plasma. Isopropyloxycarbonyloxymethyl (POC) ester 30 was the only prodrug that achieved substantial plasma levels of 1. In vitro metabolite identification studies confirmed stability of the ethyl ester of benzoate, while the POC group was rapidly hydrolyzed. At oral daily dose-equivalent of 3 mg/kg, 12 exhibited analgesic efficacy comparable to dose of 10 mg/kg of 1 in the rat chronic constrictive injury model of neuropathic pain.

Example 2

Prodrugs of a Hydroxamate-Based Glutamate Carboxypeptidase II Inhibitors Background In the nervous system, a membrane-bound metalloprotease, termed glutamate carboxypeptidase II (GCPII), catalyzes the hydrolysis of the abundant neuropeptide N-acetylaspartylglutamate (NAAG), generating glutamate, a major excitatory neurotransmitter, in the extracellular compartment. (Slusher, et al., 2013) Inhibition of GCPII has been extensively explored as a therapeutic approach to treatment of neurological disorders associated with glutamate excitotoxicity. To date, a wide variety of small molecule GCPII inhibitors have been identified (Vornov, et al., 2016) and many have shown in vivo efficacy in preclinical models of neurological disorders, including neuropathic pain. (Barinka, et al., 2012; Yamamoto, et al., 2001; Yamamoto, et al., *Brain Res,* 2001)

Nearly all potent GCPII inhibitors possess a zinc-binding group, such as phosphonate, (Jackson, et al., 1996) phosphinate, (Jackson, et al., 2001) urea, (Kozikowski, et al., 2001) thiol, (Majer, et al., 2003) and hydroxamate, (Novakova, et al., 2016) that interact with the catalytic zinc atom(s) in the enzyme's active site. Among them, the hydroxamate-based inhibitors represented by 1 (FIG. 8) exhibit an unprecedented mode of binding, in which its two carboxylate groups occupy the non-prime side of the carboxypeptidase while the glutamate-binding S 1 pocket remains unoccupied. (Novakova, et al., 2016) In addition, despite its high polarity, compound 1 exhibited good distribution to sciatic nerves (Novakova, et al., 2016), which is believed to be the site of action for GCPII inhibitors for attenuating neuropathic pain. Yamamoto, et al., 2001; Vornov, et al., 2013)

Compound 1, however, suffers from poor oral bioavailability, limiting its therapeutic utility as a treatment for chronic pain. A similar challenge was encountered with 2-phosphonomethyl pentanedioic acid (2-PMPA), (Jackson, et al., 1996) a potent GCPII inhibitor with negligible oral availability due to its highly polar molecular characteristics. A series of prodrugs of 1 was investigated, in which the hydroxamate and/or carboxylate group(s) was (were) masked to form more lipophilic species in an attempt to improve oral absorption. The presently disclosed subject matter provides the design, synthesis, and pharmacological evaluation of prodrugs derived from 1 (FIG. 8). In addition to acetyl derivatives, O-4-acetoxy benzyl (PAB) and 2-oxo-1,3-dioxol-4-yl methyl (ODOL) groups were introduced for the first time as promoieties for hydroxamate-based drugs. A representative prodrug with the most desirable pharmacokinetics properties was evaluated in an animal model of neuropathic pain following oral administration to assess its in vivo efficacy.

Example 3

Prodrugs of a Hydroxamate-Based Glutamate Carboxypeptidase II Inhibitors Chemistry In representative prodrugs disclosed herein, a promoiety was incorporated into the hydroxamate group of 1. Prodrugs also were investigated in which carboxylate group(s) of 1 were modified in addition to the hydroxamate group to assess the effects of the added promoiety(ies) on the oral pharmacokinetic profile. Synthesis of three prodrugs of 1 bearing a single promoiety at its hydroxamate group is illustrated in Scheme 1. Dicarboxylate 2 was converted to the corresponding di-t-butyl ester 3. The terminal olefin of 3 was oxidized to a carboxylate group, providing compound 4. Coupling with hydroxylamine followed by acetylation and subsequent ester hydrolysis afforded acetylated prodrug 7. A similar approach, but involving coupling of 4 with 4-((aminooxy)methyl)phenyl acetate 10 or 4-((aminooxy)methyl)-5-methyl-1,3-dioxol-2-one 15, provided PAB and ODOL-based prodrugs 12 and 17, respectively.

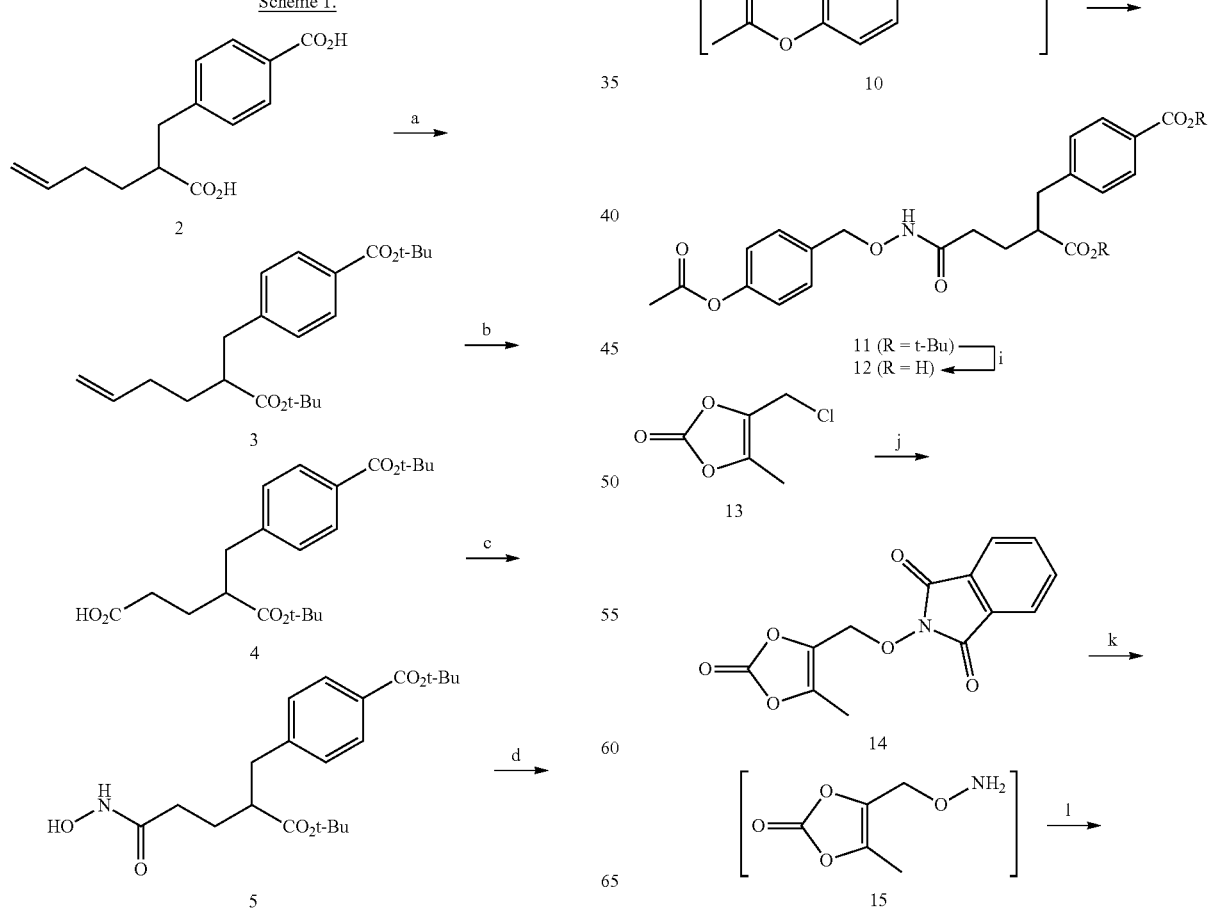

-continued

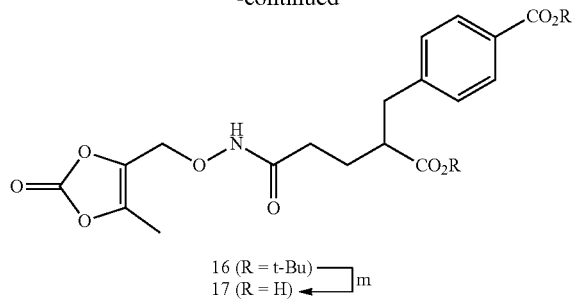

16 (R = t-Bu) ⎤
17 (R = H) ⎦ m

Synthesis of 7, 12, and 17. Reagents and conditions: (a) isobutylene, CH₂Cl₂, rt; (b) RuO₂·H₂O, NaIO₄, CH₃CN—H₂O, rt; (c) triethylamine, ethyl chloroformate NH₂OH, THF-methanol, rt; (d) Ac₂O, pyridine, 0° C.; (e) TFA, i-Pr₃SiH, CH₂Cl₂, rt; (f) Nhydroxyphthalimide, NaH, DMF, rt; (g) N₂H₄, THF, rt; (h) 4, EDC·HCl, DMAP, DIEA, DMF, rt; (i) TFA, i-Pr₃SiH, CH₂Cl₂, rt; (j) N-hydroxyphthalimide, NaH, DMF, 60° C.; (k) N₂H₄, THF, rt (l) 4, Et₃N, EtOCOCl, THF, rt; (m) TFA, i-Pr₃SiH, CH₂Cl₂, rt.

Scheme 2 illustrates the synthesis of prodrugs 23, 25, and 30 containing multiple promoieties. Prodrug 23 was synthesized by first converting dicarboxylate 2 into the diethyl ester 18. Two-step conversion of the aliphatic carboxylate ethyl ester into t-butyl ester 20 followed by oxidation of the terminal olefin afforded 21. Coupling of 21 to 10 and subsequent hydrolysis of the t-butyl ester afforded the desired prodrug 23. Triple-promoiety prodrug 25 also was synthesized by oxidizing diethyl ester 18 followed by coupling with 10. Preparation of prodrug 30 bearing a benzoate isopropyloxycarbonylmethyl (POC) was initiated by conversion of dicarboxylate 2 into mono-POC ester 26. The selective incorporation of the POC group into the benzoate moiety of 26 was confirmed by $^1H$-$^{13}C$ HMBC spectrum (not shown). The methylene protons (5.99 ppm) of the POC group showed three-bond coupling with the carbonate carbonyl (153.4 ppm) of the POC group and another carbonyl peak at 164.9 ppm. This peak (164.9 ppm) was assigned to the benzoate carbonyl because of its three-bond coupling with the aromatic protons at 8.01 ppm. Compound 26 was subsequently condensed with 2-(trimethylsilyl)ethan-1-ol to give diester 27. Oxidation of 27 into 28 followed by coupling with 10 and selective hydrolysis of trimethylsilylethyl ester by TFA afforded the desired product 30.

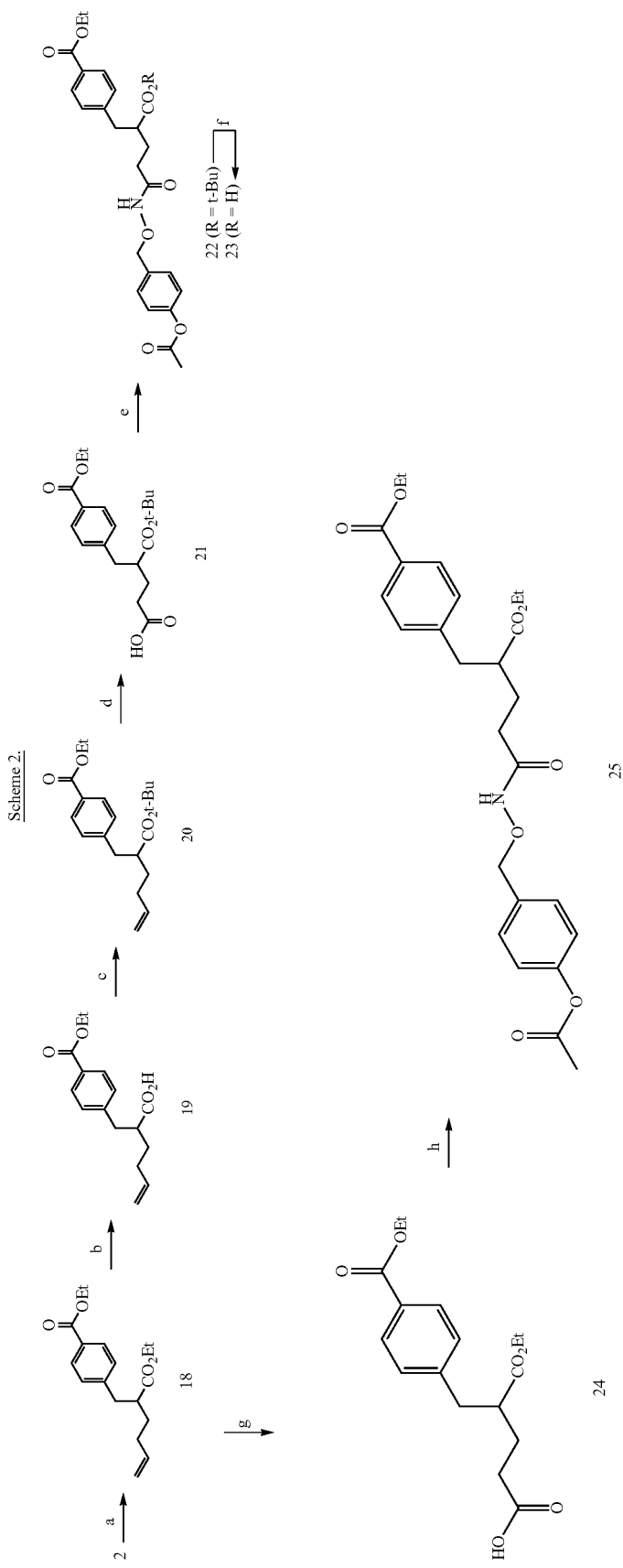

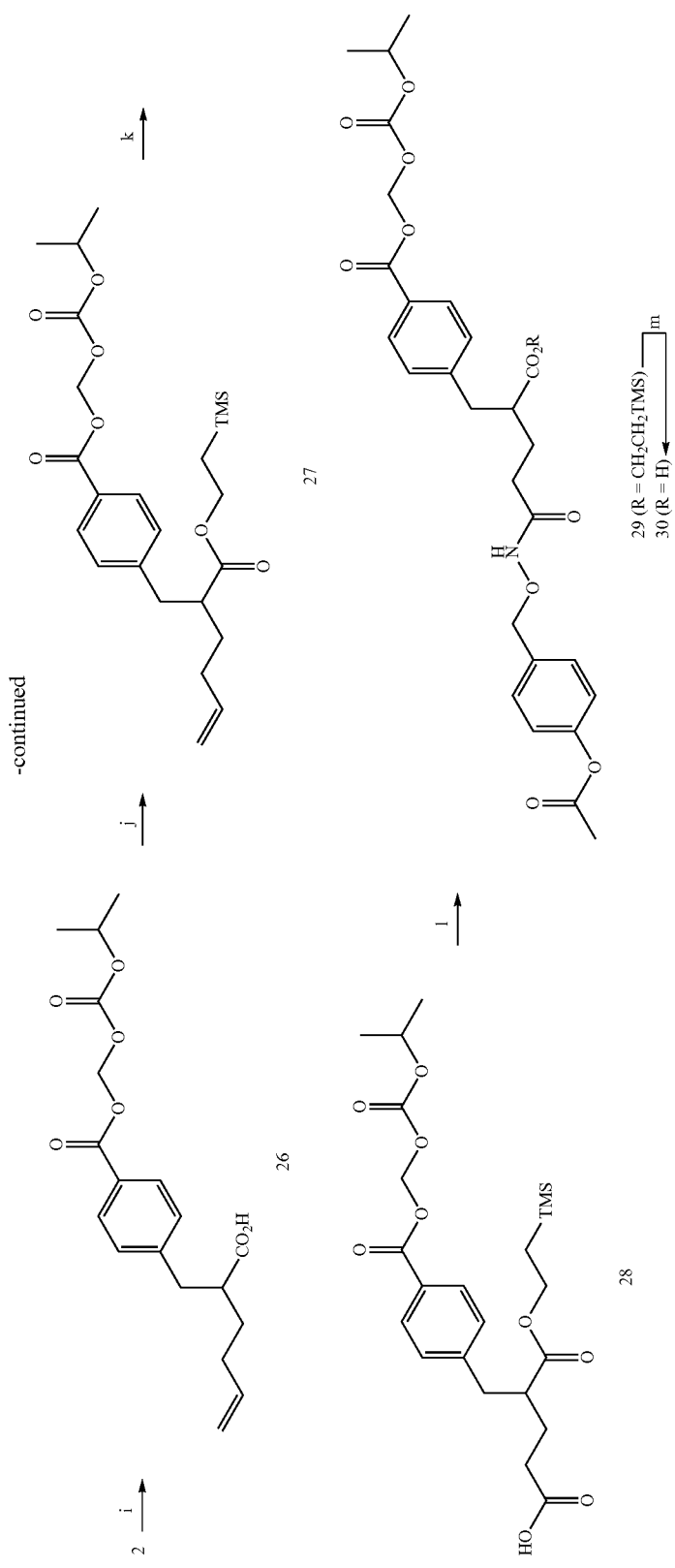

Synthesis of 23, 25, and 30. Reagents and conditions: (a) SOCl$_2$, EtOH, rt; (b) NaOH, EtOH—H$_2$O; rt; (c) isobutylene, H$_2$SO$_4$, CH$_2$Cl$_2$, rt; (d) RuO$_2$·H$_2$O, NaIO$_4$, CH$_3$CN—H$_2$O, rt; (e) triethylamine, ethyl chloroformate, 10, THF, rt; (f) TFA, i-Pr$_3$SiH, CH$_2$Cl$_2$, rt; (g) RuO$_2$·H$_2$O, NaIO$_4$, CH$_3$CN—H$_2$O, rt; (h) triethylamine, ethyl chloroformate, 10, THF, rt; (i) triethylamine, chloromethyl isopropyl carbonate, DMF, rt; (j) 2-(trimethylsilyl)ethan-1-ol, DCC, DMAP, CH$_2$Cl$_2$, rt; (k) RuO$_2$·H$_2$O, NaIO$_4$, CH$_3$CN—H$_2$O, rt; (l) triethylamine, ethyl chloroformate, 10, THF, rt; (m) TFA, CH$_2$Cl$_2$, rt.

Example 4

Prodrugs of a Hydroxamate-Based Glutamate Carboxypeptidase II Inhibitors GCPII Activity of Representative Prodrugs Compound 1 and its six prodrugs 7, 12, 17, 23, 25, and 30 were tested for their inhibition potency against GCPII. While 1 exhibited nM potency as previously described (IC50=44 nM) (Novakova, et al., *J. Med. Chem,* 2016), prodrugs 7, 12, 23, 25, and 30 had $IC_{50}$ values >5 µM (FIG. 9). Considering structural data on the compound 1/GCPII complex reported previously (Novakova, et al., *J. Med. Chem,* 2016) the lack of inhibitory potency of the prodrugs is likely due to the inability of the modified hydroxamate function to chelate active-site zinc ions. The only exception was 17 which exhibited GCPII inhibition, albeit with 12-fold less potency compared to 1 ($IC_{50}$=540 nM; FIG. 9). Subsequent stability testing of 17 under identical GCPII enzyme assay conditions (30 m in aqueous buffer; pH 8.0) however, revealed partial hydrolysis to 1, likely accounting for its GCPII inhibitory activity.

Example 5

Prodrugs of a Hydroxamate-Based Glutamate Carboxypeptidase II Inhibitors Drug Metabolism and Pharmacokinetics The six prodrugs 7, 12, 17, 23, 25, and 30 were given to mice orally at a dose equivalent of 10 mg/kg of compound 1 and plasma levels of 1 were measured 30 min after the administration (FIG. 9). For comparison, compound 1 also was administered orally at 10 mg/kg to assess the ability of the prodrugs to achieve enhanced plasma levels of 1. Plasma levels of 1 following oral administration of the prodrugs containing a single promoiety at the hydroxamate group, such as 7, 12, and 17, were found to be equal or higher than those following oral administration of compound 1 itself. Compound 12 masked with a paraacetoxybenzyl moiety at the hydroxamate group was a particularly effective prodrug displaying 5-fold increase in plasma exposure to compound 1. Oral administration of para-acetoxybenzyl based prodrugs with additional ester promoiety(ies) 23 and 25, however, resulted in negligible plasma levels of 1. In contrast, para-acetoxybenzyl-based prodrug 30 with a benzoate isopropyloxycarbonyloxymethyl (POC) ester achieved 4-fold increase in plasma levels of 1 as compared to those of oral administration of compound 1 itself.

Figure 10A:
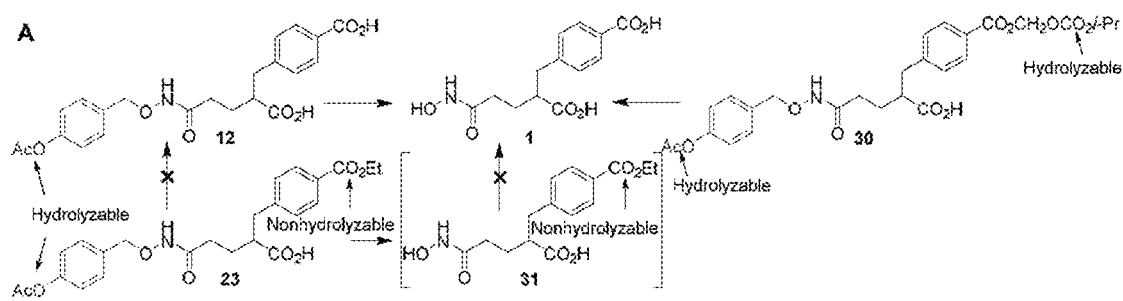
Figure 10B:
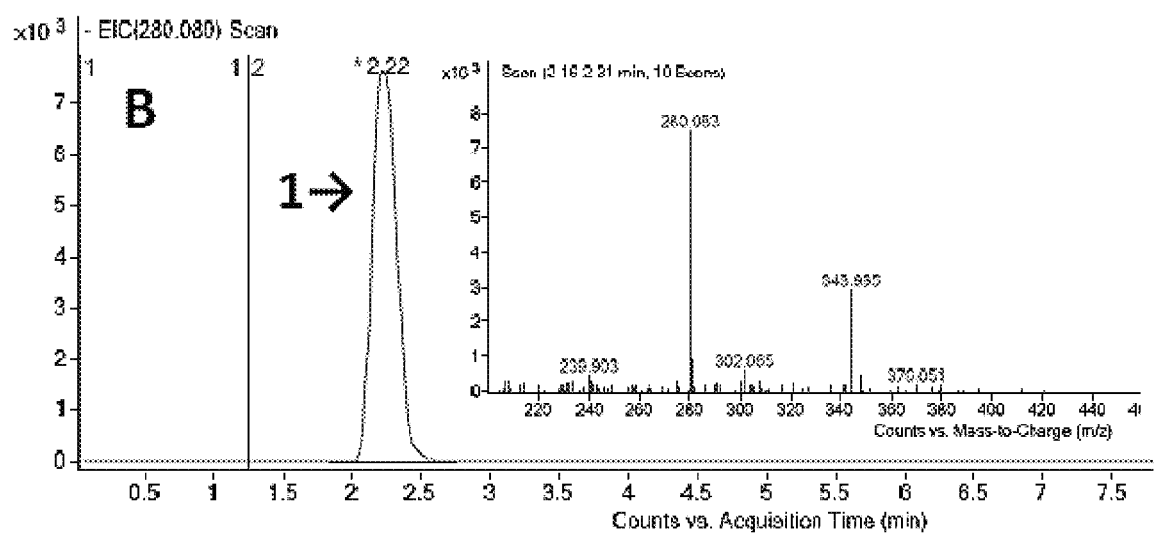
Figure 10C:
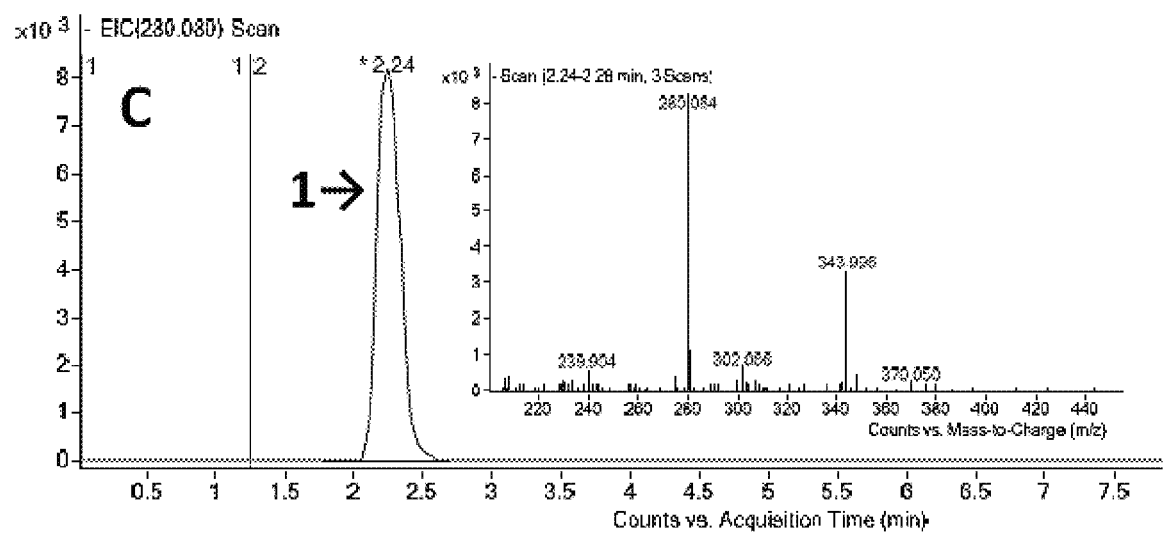
Figure 10D:
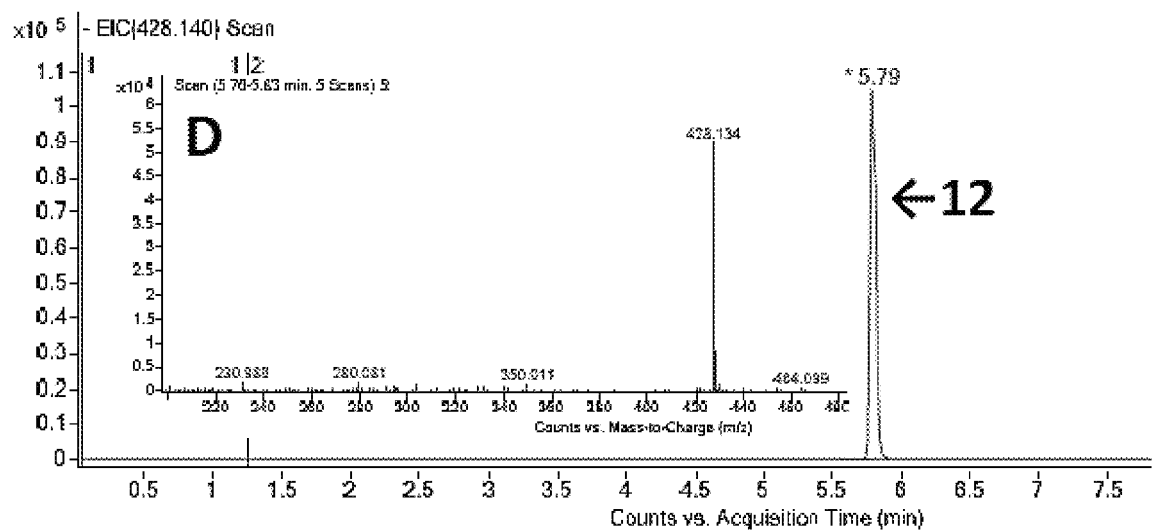
Figure 10E:
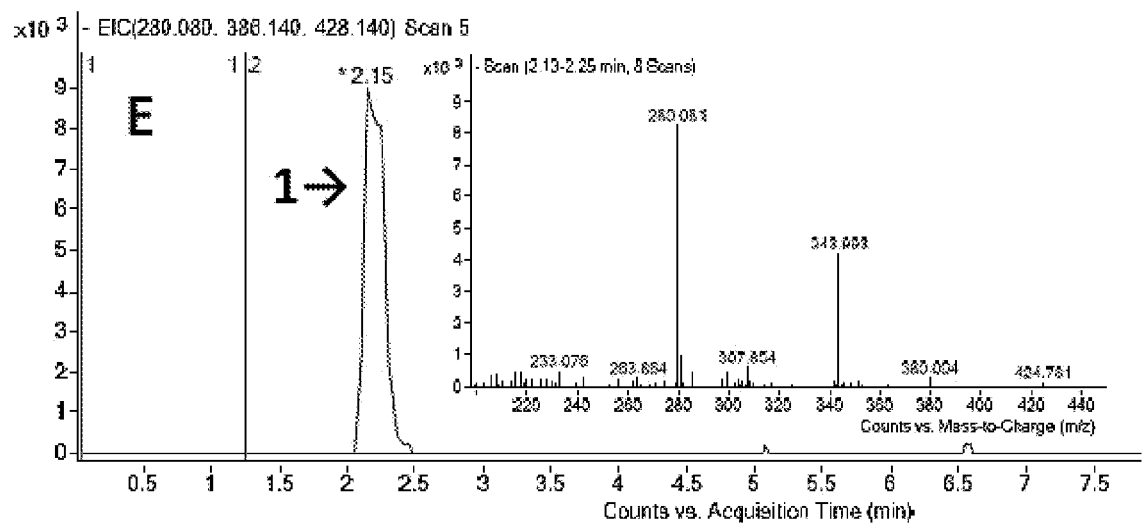
Figure 10F:
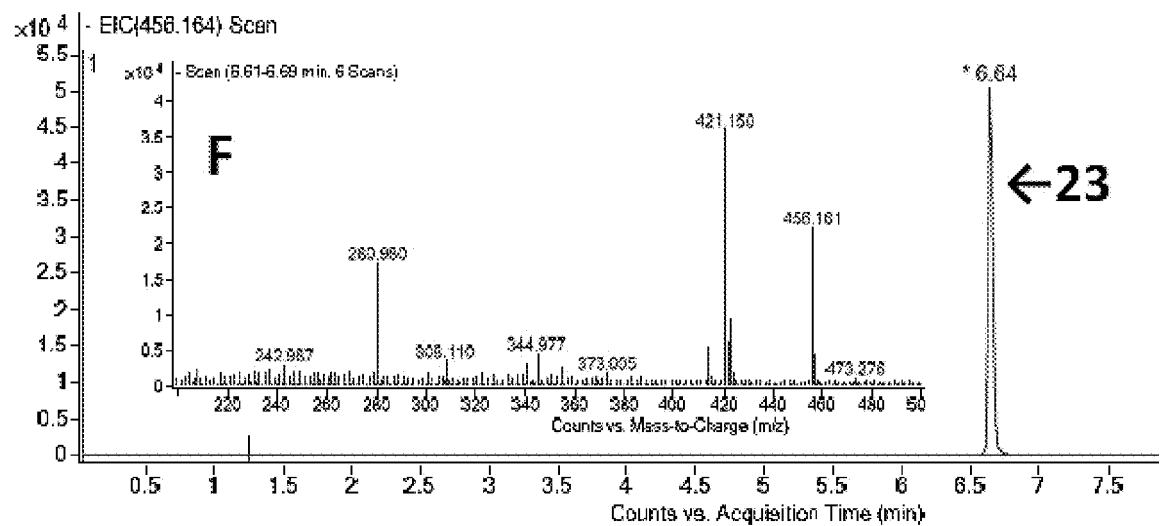
Figure 10G:
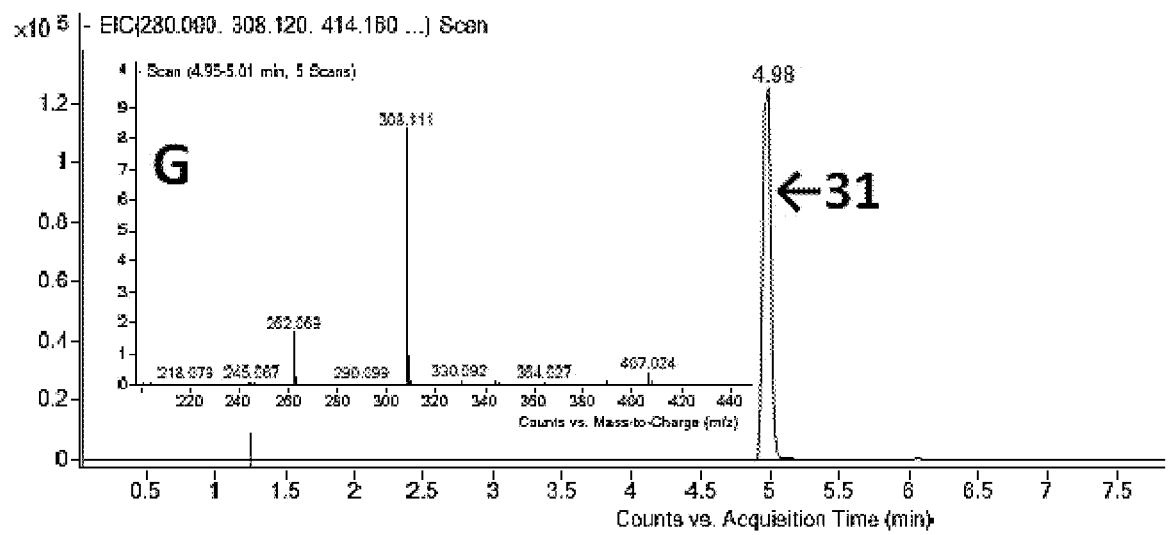
Figure 10H:
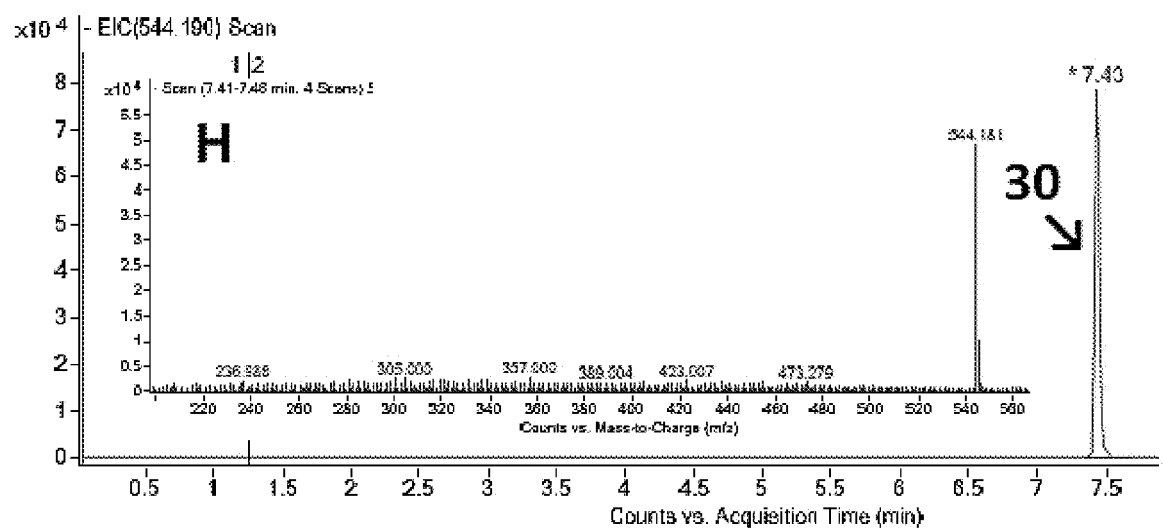
Figure 10I:
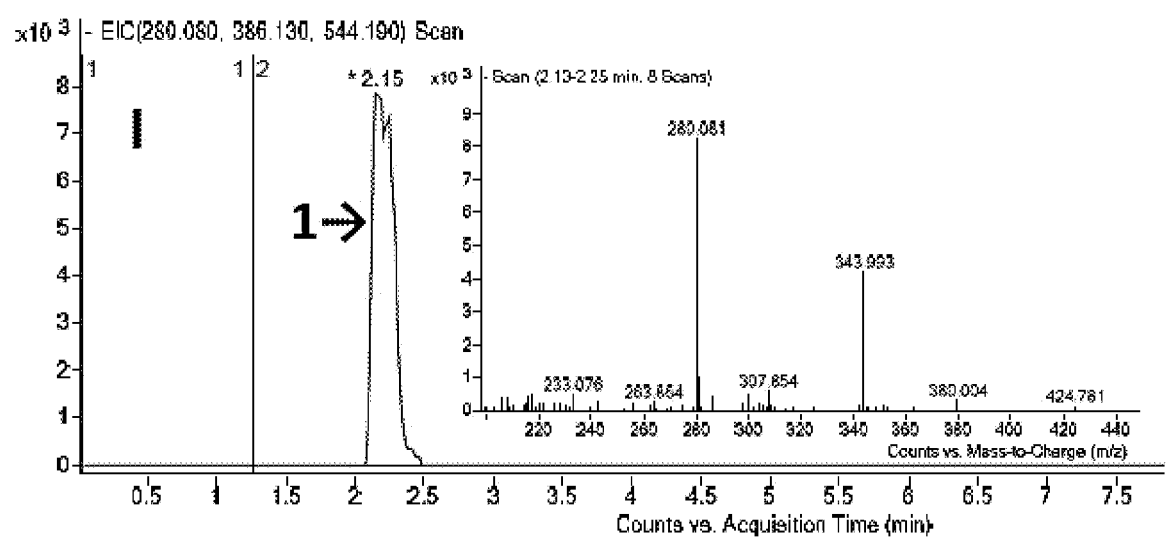

To understand the structure-activity relationship in terms of bioconversion of prodrugs into compound 1, metabolism of prodrugs 12, 23, and 30 in plasma was assessed (FIG. 10A). Since compound 1 (FIG. 10B) was found to be completely stable in mouse plasma (FIG. 10C), it was assumed that the plasma samples treated with a prodrug contain the remaining prodrug, partially hydrolyzed intermediate(s), and/or compound 1. FIG. 10D shows an extracted-ion (428.142 for 12) chromatogram of 12 as reference. An extracted mass (280.080 for 1 and 428.080 for 12) chromatogram of plasma sample treated with 12 for 60 min (FIG. 10E) lost the peak corresponding to 12 and displayed a new peak corresponding to 1, suggesting complete conversion of prodrug 12 to 1 in plasma. In contrast, prodrug 23 (FIG. 10F) was not converted into 1 in plasma despite the complete loss of 23 after 60 min incubation. An extracted mass (280.080 for 1, 308.120 for 31, and 428.080 for 12) chromatogram shows a new peak matching the mass of 31, ethyl ester of 1 (FIG. 10G). The results suggest that only para-acetoxybenzyl moiety was removed from 23 in plasma. This explains the negligible plasma levels of 1 following oral administration of 23 (FIG. 9). Without wishing to be bound to any one particular theory, this could be partially attributable to the inability of plasma-rich hydrolases to recognize benzoate esters as a substrate. The inability to hydrolyze the benzoate ester likely prevented formation of 17 from 23, as well. This is apparent as formation of 17 would be immediately followed by the generation of 1 as is evident from the plasma stability data of 17 (FIG. 10D). Interestingly, prodrug 30 (FIG. 10H) containing a POC ester was completely hydrolyzed in plasma along with its para-acetoxybenzyl moiety to produce 1 as a sole metabolite as shown in an extracted mass (280.090 for 1 and 428.142 for 30) chromatogram (FIG. 10I) of plasma treated with prodrug 30. This can be attributed to the ability of hydrolases to act on the carbonate portion of the POC ester away from the benzoate carbonyl moiety. (Wiemer, et al., 2015) This is in a good agreement with the enhanced plasma levels of 1 following oral administration of 30 as compared to 23 (FIG. 9).

Example 6

Prodrugs of a Hydroxamate-Based Glutamate Carboxypeptidase II Inhibitors Chronic Constrictive Injury Model of Neuropathic Pain Based on the highest exposure to compound 1 achieved by oral administration, prodrug 12 was subsequently tested for its antinociceptive effects following oral administration using the rat chronic constriction injury model of neuropathic pain. (Bennett, et al., 1988) The analgesic effects of compound 1 in the same model following 10 mg/kg/day oral dosing have previously been shown. Given the improved plasma exposure achieved by oral administration of 12, compound 12 was tested at 4.6 mg/kg, an equivalent of 3 mg/kg of compound 1. Gabapentin (50 mg/kg and 100 mg/kg p.o. daily) was used as a positive control. Hyperalgesia testing was initiated 10 days post-surgery by determining withdrawal latencies in response to a constant thermal stimulus. As shown in FIG. 11A, prodrug 12 significantly reduced thermal hyperalgesia relative to the vehicle-treated control on days 4 and 8. In contrast, as shown in FIG. 11B, prodrug 12 had no significant effect on absolute latency of the sham operated side, suggesting a selective antihyperalgesic effect on the injured nerve. Similarly, gabapentin (100 mg/kg p.o.) significantly reversed allodynia that was maintained throughout the dosing period (FIG. 12).

When compared directly to 1, despite the higher doses (10 mg/kg/day), oral administration of 1 itself first displayed significantly reduced thermal hyperalgesia on day 8 (Novakova, et al., 2016) as opposed to day 4 for the lower dose of 12. These findings clearly demonstrate the pharmacological advantages of prodrug 12 over the parent compound 1, presumably due to the improved oral pharmacokinetics of 1 achieved by prodrug 12.

Example 7

Prodrugs of a Hydroxamate-Based Glutamate Carboxypeptidase II Inhibitors Summary The concept of hydroxamate prodrugs has been only recently reported in the literature, including carbamates, (Schlimme, et al., 2011; Silhar, et al., 2013) O-acyl derivatives, (Raji, et al., 2017) and 1,4,2-dioxazol-5-one. (Flipo, et al., 2009) Little has been investigated, however, on the oral pharmacokinetics of these prodrugs to assess their pharmacological advantages over the parent compounds. In the presently disclosed subject matter, systematic assessment of prodrugs derived from hydroxamate-based GCPII inhibitor 1 provided key insights into the design strategy for creating an improved oral pharmacokinetic profile. As far as the hydroxamate group is concerned, incorporation of a para-acetoxybenzyl group as represented by prodrug 12 resulted in substantial improvement in pharmacokinetics of 1 as compared to acetyl and (5-methyl-2-oxo-1,3-dioxol-4-yl) methyl groups. Prodrugs 23 and 25 containing additional pro-moiety(ies), however, failed to deliver 1 in plasma following oral administration. The inability of 23 and 25 to generate 1 in plasma can be attributed to the resistance of the benzoate ethyl ester to enzymatic hydrolysis reaction. Indeed, para-acetoxybenzyl-based prodrug 30 containing a POC ester was able to release 1 in plasma, presumably because of its carbonate site prone to enzymatic hydrolysis reaction. Consistent with the improved oral pharmacokinetics demonstrated by prodrug 12, at oral daily doses equivalent of 3 mg/kg of 1, prodrug 12 exhibited analgesic efficacy superior to that of oral daily doses of 10 mg/kg of 1 (Vornov, et al., 2013), and similar to standard of care gabapentin in the rat chronic constrictive injury model (CCI) of neuropathic pain. These findings collectively suggest that the presently disclosed prodrug approach is an effective strategy for improving oral activity of hydroxamate-based GCPII inhibitors. Compound 12 represents the first example of hydroxamate-derived prodrugs with improved in vivo oral pharmacokinetics.

Example 8

Prodrugs of a Hydroxamate-Based Glutamate Carboxypeptidase II Inhibitors General Experimental The commercially available HPLC grade methanol, catalysts, and reagent grade materials were used without further purification. TLC was performed on silica gel 60 F254-coated aluminum sheets (Merck), and spots were detected by the solution of $Ce(SO_4)_2 \cdot 4H_2O$ (1%) and $H_3P(Mo_3O_{10})_4$ (2%) in sulfuric acid (10%). Flash chromatography was performed on silica gel 60 (0.040-0.063 mm, Fluka) or on Biotage KP-C18-HS or KP-Sil SNAP cartridges using the Isolera One HPFC system (Biotage, Inc.). All chemicals were purchased from Sigma-Aldrich and were used without further purification. Preparative HPLC was performed on a JASCO system equipped with Jasco PU-986 pump and UV-975 detector using an YMC C18 Column (5 μm, 20 mm×250 mm) with a linear gradient of 2-60% acetonitrile/water (0.1% TFA) over 50 min at a flow rate 10 mL/min. NMR spectra were measured on a Bruker AVANCE III 400 or 500 spectrometer operating at 400.1 MHz ($^1$H) and 100.8 MHz ($^{13}$C), or at 500.0 MHz ($^1$H) and 125.7 MHz ($^{13}$C). Chemical shift assignment and confirmation of the structure of compound 26 was achieved by a combination of $^1$H, $^{13}$C, and $^1$H-$^{13}$C HMBC NMR experiments. The ESI mass spectra were recorded using Waters Micromass ZQ Mass Spectrometer equipped with an ESCi multimode ion source and operated by MassLynx software. The low resolution ESI mass spectra were recorded using a quadrupole orthogonal acceleration time-of-flight tandem mass spectrometer (Q-Tof micro, Waters) and high-resolution ESI mass spectra using a hybrid FT mass spectrometer combining a linear ion trap MS and the Orbitrap mass analyzer (LTQ Orbitrap XL, Thermo Fisher Scientific). The conditions were optimized for suitable ionization in the ESI Orbitrap source (sheath gas flow rate 35 au, aux gas flow rate 10 au of nitrogen, source voltage 4.3 kV, capillary voltage 40 V, capillary temperature 275° C., tube lens voltage 155 V). Purity for each compound was established using HPLC (Jasco Inc.)

Example 9

Prodrugs of a Hydroxamate-Based Glutamate Carboxypeptidase II Inhibitors Compound Preparation and Analytical Data General Procedures: The $^1$H NMR spectra were measured at 400.13. $^1$H NMR spectra are standardized to the internal signal of TMS (δ 0.0, $CDCl_3$). The chemical shifts are given in δ-scale, the coupling constants J are given in Hz. The IR spectra were measured in $CHCl_3$ on FT-IR spectrometer Bruker Equinox 55. Low and high resolution CI mass spectra were measured using an orthogonal acceleration time-of-flight (OA-TOF) mass spectrometer (GCT premier, Waters) at an ionising voltage of 70 eV, the m/z values are given with their relative intensities (%). The spectra were recorded in positive mode and the source temperature was 150° C. Methane was present as a reagent gas in the CI source. For exact measurement the spectra were internally calibrated using Heptacosa or 2,4,6-tris(trifluoromethyl)-1,3,5-triazine (Metri). The ESI mass spectra were recorded with a ZQ micromass mass spectrometer (Waters) equipped with an ESCi multi-mode ion source and controlled by MassLynx software. THF was freshly distilled from sodium/benzophenone under nitrogen. The flash chromatography was performed on Silica gel 60 (0.040-0.063 mm, Fluka).

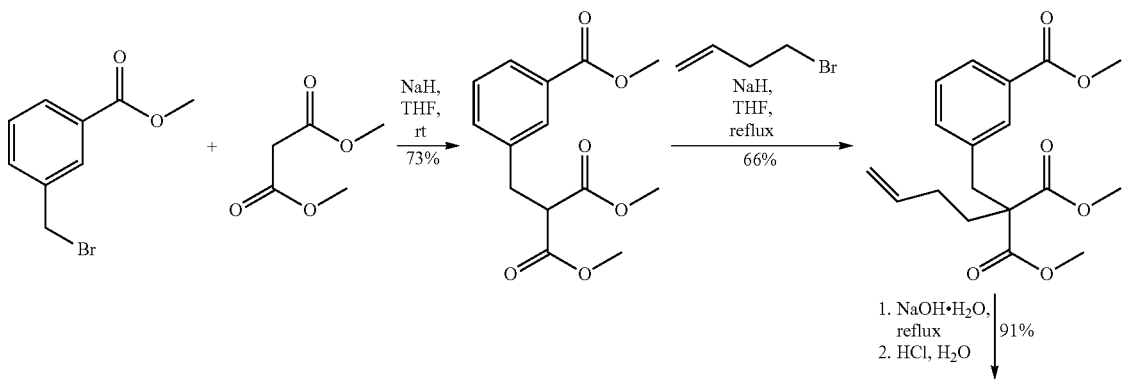

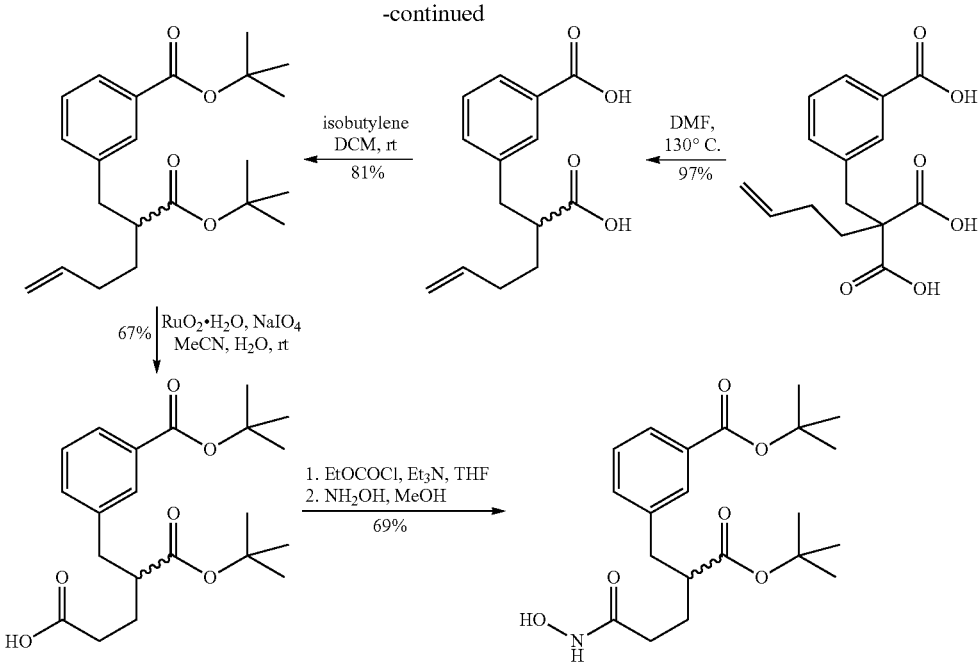

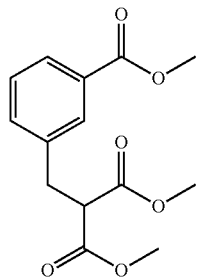 [SMILES: COC(=O)c1cccc(CC(C(=O)OC)C(=O)OC)c1]

Dimethyl 2-(3-(methoxycarbonyl)benzyl)malonate

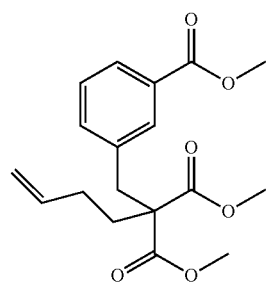 [SMILES: C=CCCC(Cc1cccc(C(=O)OC)c1)(C(=O)OC)C(=O)OC]

2-(But-3-en-1-yl)-2-(3-(methoxycarbonyl)benzyl)

NaH (8.13 g, 0.203 mol, 2.4 eq) was placed in a Schlenk flask and put under an argon atmosphere. 800 mL of THF was added, the mixture was homogenised by stirring, cooled to 0° C. and dimethyl malonate (27.40 g, 0.203 mol, 2.4 eq) was then added dropwise by way of a cannula in 200 mL of THF in the course of 1 h. The resulting heterogeneous mixture was warmed to rt and the bromide (20.00 g, 0.085 mol) was added in 200 mL of THF in the course of 5 h using a syringe pump. The mixture was stirred overnight. It was quenched with 100 mL of saturated NH$_4$Cl, 100 mL of water was then added, the organic layer was separated and the aqueous layer was extracted 2× with 400 mL of AcOEt. Combined organic layers were dried with MgSO$_4$, filtered, volatiles were removed on rotavap and the residue was distilled in Kugelrohr at 250° C. in vacuum (after dimethyl malonate was removed at 175° C.) to afford 17.37 g (73%, 0.062 mol) of colorless oil. $^1$H NMR (400 MHz, CDCl$_3$): δ 3.27 (d, J=7.8 Hz, 2H), 3.66-3.76 (m, 1H), 3.71 (s, 6H), 3.91 (s, 3H), 7.33-7.42 (m, 2H), 7.87-7.93 (m, 2H). $^{13}$C NMR (151 MHz, CDCl$_3$): δ 34.6, 52.3, 52.8, 53.5, 128.3, 128.8, 130.0, 133.6, 138.3, 167.1, 169.1. MS (ESI) m/z (%): 303 (100, [M+Na]$^+$). HRMS (ESI): [M+H] (C$_{14}$H$_{16}$O$_6$) calc. 303.08391, found 303.08389.

NaH (0.78 g, 19.37 mmol, 1.1 eq) was placed in a rbf equipped with a reflux condenser and put under an argon atmosphere. Dimethyl 2-(3-(methoxycarbonyl)benzyl)malonate (4.94 g, 17.61 mmol) in THF (75 mL) was added followed by 4-bromobut-1-ene (2.95 mL, 28.18 mmol, 1.6 eq). The mixture was refluxed (105° C.) for 24 h. After cooling down volatiles were removed on rotavap, 150 mL of AcOEt and 50 mL of water was added, the layers were separated and aqueous layer was washed twice more with 150 mL of AcOEt. The combined organic layers were dried with MgSO$_4$, filtered, volatiles were removed on rotavap and the residue was chromatographed on silica (5×15 cm, eluent hex/AcOEt 4:1) to afford 3.87 g (66%, 11.56 mmol) of colorless oil. $^1$H NMR (400 MHz, CDCl$_3$) δ 1.80-1.88 (m, 2H), 2.00-2.09 (m, 2H), 3.28 (s, 2H), 3.71 (s, 6H), 3.88 (s, 3H), 4.93-5.08 (m, 2H), 5.68-5.80 (m, 1H), 7.22-7.26 (m, 1H), 7.29-7.36 (t, J=7.7 Hz, 1H), 7.72-7.76 (m, 1H), 7.85-7.91 (m, 1H). $^{13}$C NMR (151 MHz, CDCl$_3$): δ 28.7, 31.4, 38.4, 52.2, 52.5, 58.7, 115.4, 128.4, 128.5, 130.3, 131.0, 134.5, 136.4, 137.2, 167.0, 171.4. MS (ESI) m/z (%): 357 (100, [M+Na]$^+$), 335 (10, [M+H]$^+$). HRMS (ESI): [M+H] (C$_{18}$H$_{23}$O$_6$) calc. 335.14891, found 335.14899.

2-(But-3-en-1-yl)-2-(3-carboxybenzyl)malonic acid

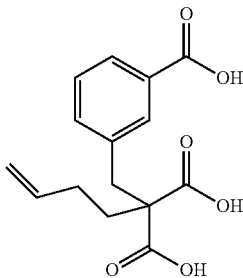 [SMILES: C=CCCC(Cc1cccc(C(=O)O)c1)(C(=O)O)C(=O)O]

Dimethyl 2-(but-3-en-1-yl)-2-(3-(methoxycarbonyl)benzyl) malonate (3.87 g, 11.56 mmol) was placed in a rbf and dissolved in 50 mL of MeOH. NaOH (4.72 g, 115.62 mmol, 10 eq) in 30 mL of water was added and the mixture was refluxed (110° C.) for 24 h. Then most of MeOH was removed on rotavap and the residue was acidified with conc. HCl to pH~1. The mixture was cooled to 0° C. and filtered to afford, after drying in lyophilisator overnight, 3.08 g (91%, 10.53 mmol) of white solid. $^1$H NMR (400 MHz, DMSO-d$_6$): δ 1.53-1.68 (m, 2H), 1.96-2.11 (m, 2H), 3.17 (s, 2H), 4.89-5.09 (m, 2H), 5.72-5.84 (m, 1H), 7.34-7.46 (m, 2H), 7.71-7.86 (m, 2H). $^{13}$C NMR (151 MHz, DMSO-d$_6$): δ 28.2, 30.8, 37.3, 57.6, 115.2, 127.8, 128.4, 130.6, 130.7, 134.5, 137.2, 137.9, 167.4, 172.5. MS (ESI) m/z (%): 291 (30, [M−H]$^−$), 247 (100, [M−CO$_2$H]$^−$). HRMS (ESI): [M−H] (C$_{15}$H$_{15}$O$_6$) calc. 291.08741, found 291.08715.

3-(2-Carboxyhex-5-en-1-yl)benzoic acid

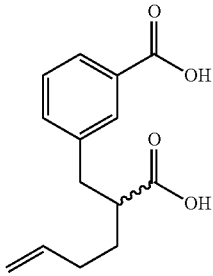 [SMILES: C=CCCC(Cc1cccc(C(=O)O)c1)C(=O)O]

2-(But-3-en-1-yl)-2-(3-carboxybenzyl)malonic acid (3.88 g, 13.27 mmol) was placed in a rbf and put under an argon atmosphere. 80 mL of degassed DMF was added and the mixture as stirred at 130° C. for 4 h. It bubbled first, later no gas evolved. After cooling down most of DMF was removed on rotavap. 100 mL of water was added and the mixture was extracted 3× with 150 mL of AcOEt. The combined organic layers were 5× washed with 300 mL of water, dried with MgSO$_4$, filtered, volatiles were removed on rotavap and the residue was dried in a lyophilizer overnight to afford 3.20 g (97%, 12.89 mmol) of white solid. $^1$H NMR (400 MHz, CDCl$_3$): δ 1.56-1.67 (m, 1H), 1.76-1.88 (m, 1H), 2.05-2.22 (m, 2H), 2.64-2.73 (m, 1H), 4.95-5.07 (m, 2H), 5.70-5.82 (m, 1H), 7.32-7.43 (m, 2H), 7.86-7.92 (m, 2H). $^{13}$C NMR (151 MHz, CDCl$_3$): δ 30.8, 31.0, 37.4, 46.3, 115.3, 127.3, 128.5, 129.7, 130.9, 133.4, 138.0, 140.1, 167.5, 176.0. MS (ESI) m/z (%): 247 (100, [M−H]$^−$). HRMS (ESI): [M−H] (C$_{14}$H$_{15}$O$_4$) calc. 247.09758, found 247.09728.

tert-Butyl 3-(2-(tert-butoxycarbonyl)hex-5-en-1-yl)benzoate 3-(2-Carboxyhex-5-en-1-yl)benzoic acid (2.17 g, 8.76 mmol) was placed in a pressure tube and put under an argon atmosphere. 40 mL of DCM was added dissolving it. The solution was cooled to −78° C. and approx. 10 mL of isobutylene was added followed by H$_2$SO$_4$ (487 μL, 8.76 mmol). Once added the flask was closed, let warm up to rt and stirred over the weekend (43 h, overnight should be enough). The mixture was then cooled again to −78° C. and the content was poured quickly into a 100 mL of saturated aqueous NaHCO$_3$. The mixture was extracted 3× with 100 mL of DCM, the combined organic layers were dried with MgSO$_4$, filtered and volatiles were removed. The residue was chromatographed on silica (4×15 cm, eluent hex/AcOEt 6:1) to afford 2.54 g (81%, 7.05 mmol) of yellowish oil. $^1$H NMR (400 MHz, CDCl$_3$): δ 1.32 (s, 9H), 1.47-1.55 (m, 1H), 1.57 (s, 9H), 1.67-1.78 (m, 1H), 1.97-2.15 (m, 2H), 2.51-2.60 (m, 1H), 2.70-2.78 (m, 1H), 2.85-2.93 (m, 1H), 4.92-5.03 (m, 2H), 5.69-5.81 (m, 1H), 7.26-7.34 (m, 2H), 7.77 (s, 1H), 7.78-7.83 (m, 1H). $^{13}$C NMR (151 MHz, CDCl$_3$): δ 28.1, 28.3, 31.6, 31.8, 38.6, 47.8, 80.5, 81.1, 115.3, 127.5, 128.2, 130.1, 132.1, 133.3, 138.0, 139.8, 166.0, 174.6. MS (ESI) m/z (%): 383 (100, [M+Na]$^+$). HRMS (ESI): [M+Na] (C$_{22}$H$_{32}$O$_4$Na) calc. 383.21928, found 383.21937.

5-(tert-Butoxy)-4-(3-(tert-butoxycarbonyl)benzyl)-5-oxopentanoic acid

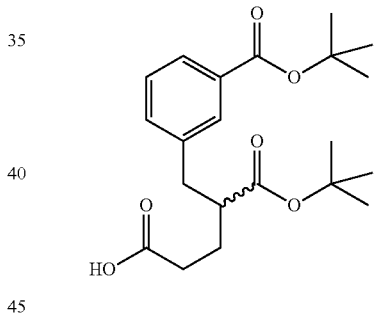

tert-Butyl 3-(2-(tert-butoxycarbonyl)hex-5-en-1-yl)benzoate (2.29 g, 6.36 mmol) was dissolved in MeCN (120 mL) and 120 mL of water was added followed by RuO$_2$·H$_2$O (96 mg, 0.64 mmol, 0.1 eq). Then NaIO$_4$ (13.62 g, 63.55 mmol, 10 eq) was added portionwise over the course of 10 min. The mixture was cooled to 0° C. and let warm up to rt while stirring overnight. The mixture was then filtered through a Celite pad and washed with additional MeCN. Most of MeCN was then removed on rotavap. The residue was extracted 3× with 150 mL of AcOEt, the combined organic layers were dried with MgSO$_4$, filtered and volatiles were removed on rotavap. The residue was chromatographed on silica (3×16 cm), eluent hex/AcOEt 1:1+1% AcOH) to afford 1.62 g (67%, 4.27 mmol) of light orange oil. $^1$H NMR (400 MHz, CDCl$_3$): δ 1.32 (s, 9H), 1.57 (s, 9H), 1.77-1.95 (m, 2H), 2.30-2.48 (m, 2H), 2.56-2.65 (m, 1H), 2.71-2.80 (m, 1H), 2.88-2.96 (m, 1H), 7.26-7.35 (m, 2H), 7.77 (s, 1H), 7.79-7.86 (m, 1H). $^{13}$C NMR (151 MHz, CDCl$_3$): δ 27.1, 28.1, 28.3, 31.7, 38.5, 47.4, 81.1, 81.2, 127.7, 128.3, 130.0, 132.1, 133.3, 139.2, 165.9, 173.9, 178.8. MS (ESI) m/z (%): 401 (100, [M+Na]$^+$), 345 (27, [M+Na−tBu]$^+$). HRMS (ESI): [M+Na] (C$_{21}$H$_{30}$O$_6$Na) calc. 401.19346, found 401.19363.

61 tert-Butyl 3-(2-(tert-butoxycarbonyl)-5-(hydroxyamino)-5-oxopentyl)benzoate 0

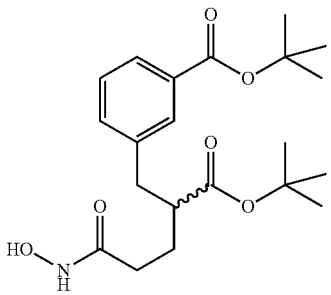 [SMILES: CC(C)(C)OC(=O)c1cccc(CC(CCC(=O)NO)C(=O)OC(C)(C)C)c1]

NH$_2$OH·HCl (3.60 g, 50.73 mmol, 8 eq) and NaOH (2.07 g, 50.73 mmol, 8 eq) were placed in a Schlenk flask and put under an argon atmosphere. MeOH (30 mL) was added and the mixture was cooled to 0° C. while stirring. After 15 min the cooling bath was removed and stirring went on for 45 min. Then the mixture was filtered through a Celite pad and the filtrate containing NH$_2$OH was used further. Meanwhile 5-(tert-butoxy)-4-(3-(tert-butoxycarbonyl)benzyl)-5-oxopentanoic acid (1.56 g, 4.12 mmol) in a Schlenk flask was put under an argon atmosphere and 50 mL of THF was added dissolving it. Et$_3$N (869 μL, 6.14 mmol, 1.5 eq) followed by EtOCOCl (609 μL, 6.17 mmol, 1.5 eq) were added and the mixture was stirred at rt for 1 h. A white precipitate formed almost immediately. Then NH$_2$OH solution prepared earlier was added and the mixture was stirred at rt overnight. Volatiles were then removed on rotavap, 50 mL of water was added and the mixture was 3× extracted with 180 mL of AcOEt. The combined organic layers were dried with MgSO$_4$, filtered, volatiles were removed on rotavap and the residue was chromatographed on silica (3×18 cm, eluent hex/AcOEt 2:3+1% AcOH) to afford 1.12 g (69%, 2.84 mmol) of light beige oil. $^1$H NMR (400 MHz, CDCl$_3$): δ 1.31 (s, 9H), 1.56 (s, 9H), 1.81-1.95 (m, 2H), 2.08-2.17 (m, 1H), 2.18-2.29 (m, 1H), 2.52-2.65 (m, 1H), 2.71-2.80 (m, 1H), 2.84-2.96 (m, 1H), 7.26-7.34 (m, 2H), 7.76 (s, 1H), 7.78-7.84 (m, 1H). $^{13}$C NMR (151 MHz, CDCl$_3$): δ 27.9, 28.0, 28.3, 30.7, 38.4, 47.7, 81.3, 81.4, 127.7, 128.4, 130.0, 132.0, 133.3, 139.1, 166.1, 170.7, 174.3. MS (ESI) m/z (%): 416 (100, [M+Na]$^+$), 360 (33, [M+Na-tBu]$^+$). HRMS (ESI): [M+Na] (C$_{21}$H$_{31}$O$_6$NNa) calc. 416.20436, found 416.20440.

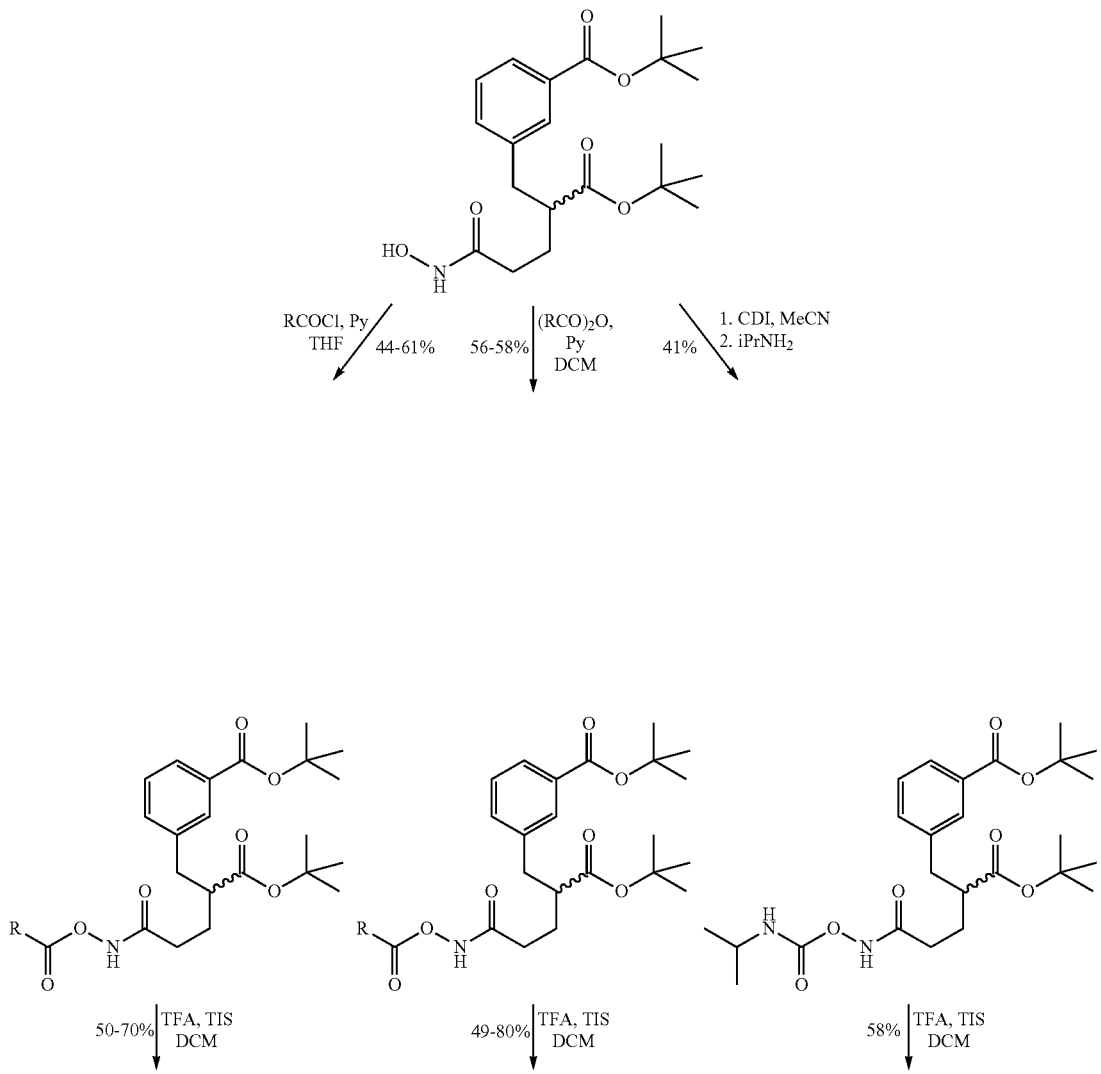

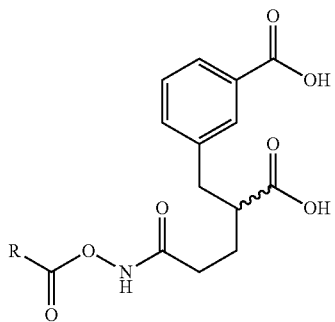
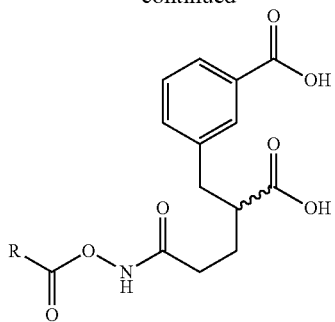

tert-Butyl 3-(2-(tert-butoxycarbonyl)-5-(((ethoxycarbonyl)oxy)amino)-5-oxopentyl)benzoate

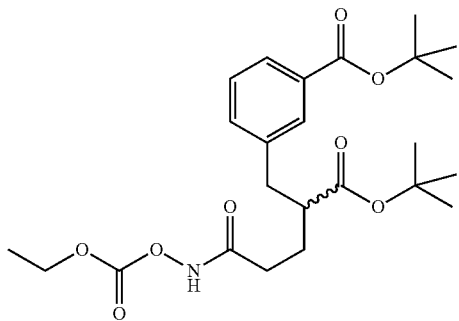 [SMILES: CCOC(=O)ONC(=O)CCC(Cc1cccc(C(=O)OC(C)(C)C)c1)C(=O)OC(C)(C)C]

tert-Butyl 3-(2-(tert-butoxycarbonyl)-5-(hydroxyamino)-5-oxopentyl)benzoate (203 mg, 0.52 mmol) was placed in a Schlenk flask and put under an argon atmosphere. THF (10 mL) was added dissolving it and the mixture was cooled to 0° C. Pyridine (55 µL, 0.67 mmol, 1.3 eq) was added, the mixture was stirred for 5 min and EtOCOCl (66 µL, 0.67 mmol, 1.3 eq) followed. A white precipitate formed almost immediately. The mixture was stirred at 0° C. for 6 h, then silica was added, the volatiles were removed on rotavap and the residue was chromatographed on silica (2×16 cm, eluent hex/AcOEt 1:1) to afford 135 mg (56%, 0.29 mmol) of colorless oil. $^1$H NMR (400 MHz, CDCl$_3$): δ 1.35 (s, 9H), 1.36 (t, J=7.1 Hz, 3H), 1.59 (s, 9H), 1.84-2.05 (m, 2H), 2.14-2.41 (m, 2H), 2.71-2.86 (m, 2H), 2.88-2.99 (m, 1H), 4.33 (q, J=7.1 Hz, 2H), 7.29-7.38 (m, 2H), 7.79 (s, 1H), 7.81-7.86 (m, 1H). $^{13}$C NMR (151 MHz, CDCl$_3$): δ 14.3, 27.6, 28.1, 28.3, 30.8, 38.4, 47.3, 66.5, 81.1, 81.6, 127.8, 128.4, 130.1, 132.1, 133.2, 139.1, 154.7, 165.9, 171.7, 174.3. MS (ESI) m/z (%): 488 (100, [M+Na]$^+$), 432 (48, [M-tBu+Na]$^+$). HRMS (ESI): [M+H] (C$_{24}$H$_{35}$O$_8$NNa) calc. 488.22549, found 488.22551.

tert-Butyl 3-(2-(tert-butoxycarbonyl)-5-(((isopropylcarbamoyl)oxy)amino)-5-oxopentyl)benzoate

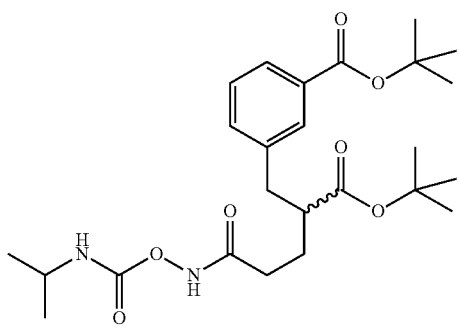 [SMILES: CC(C)NC(=O)ONC(=O)CCC(Cc1cccc(C(=O)OC(C)(C)C)c1)C(=O)OC(C)(C)C]

tert-Butyl 3-(2-(tert-butoxycarbonyl)-5-(hydroxyamino)-5-oxopentyl)benzoate (199 mg, 0.51 mmol) and CDI (127 mg, 0.76 mmol, 1.5 eq) were placed in a Schlenk flask and put under an argon atmosphere. The mixture was cooled to 0° C. and MeCN (10 mL) was added dissolving it. The mixture was stirred at 0° C. for 1 h and then iPrNH$_2$ (54 µL, 0.61 mmol, 1.2 eq) was added. The mixture was let warm up to rt and stirred overnight. Then volatiles were removed on rotavap and the residue was chromatographed on silica (2×16 cm, eluent hex/AcOEt 1:1) to afford 100 mg (41%, 0.21 mmol) of colorless oil. $^1$H NMR (400 MHz, CDCl$_3$): δ 1.18 (d, J=6.5 Hz, 6H), 1.32 (s, 9H), 1.56 (s, 9H), 1.82-1.97 (m, 2H), 2.14-2.35 (m, 2H), 2.65-2.80 (m, 2H), 2.85-2.96 (m, 1H), 3.74-3.88 (m, 1H), 5.09 (bs, 1H), 7.26-7.37 (m, 2H), 7.77-7.80 (m, 1H), 7.80-7.84 (m, 1H). $^{13}$C NMR (151 MHz, CDCl$_3$): δ 22.9, 27.9, 28.1, 28.3, 30.7, 38.4, 44.3, 47.5, 81.1, 81.3, 127.7, 128.4, 130.1, 132.1, 133.2, 139.2, 154.0, 165.9, 171.5, 174.1. MS (ESI) m/z (%): 501 (100, [M+Na]$^+$), 479 (1, [M+H]$^+$). HRMS (ESI): [M+Na] (C$_{25}$H$_{38}$O$_7$N$_2$Na) calc. 501.25712, found 501.25707.

tert-Butyl 3-(5-(acetoxyamino)-2-(tert-butoxycarbonyl)-5-oxopentyl)

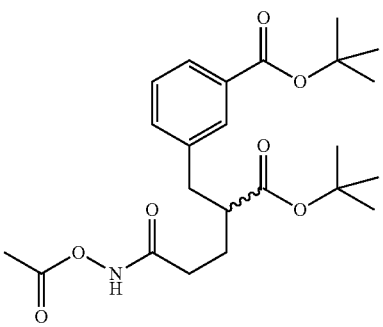 [SMILES: CC(=O)ONC(=O)CCC(Cc1cccc(C(=O)OC(C)(C)C)c1)C(=O)OC(C)(C)C]

tert-Butyl 3-(2-(tert-butoxycarbonyl)-5-(hydroxyamino)-5-oxopentyl)benzoate (178 mg, 0.45 mmol) was placed in a Schlenk flask and put under an argon atmosphere. DCM (8 mL) was added dissolving it and pyridine (55 µL, 0.68 mmol, 1.5 eq) and Ac$_2$O (65 µL, 0.68 mmol, 1.5 eq) followed. The mixture was stirred at rt overnight. Then volatiles were removed on rotavap and the residue was chromatographed on silica (2×16 cm, eluent hex/AcOEt 1:1) to afford 116 mg (58%, 0.27 mmol) of colorless oil. $^1$H NMR (400 MHz, CDCl$_3$): δ 1.34 (s, 9H), 1.58 (s, 9H), 1.85-2.00 (m, 2H), 2.22 (s, 3H), 2.24-2.38 (m, 2H), 2.72-2.81 (m, 2H), 2.88-2.97 (m, 1H), 7.29-7.37 (m, 2H), 7.7-

7.80 (m, 1H), 7.80-7.85 (m, 1H). $^{13}$C NMR (151 MHz, CDCl$_3$): δ 18.4, 27.9, 28.1, 28.3, 30.9, 38.4, 47.4, 81.1, 81.4, 127.8, 128.4, 130.1, 132.1, 133.2, 139.1, 165.9, 168.9, 170.4, 174.2. MS (ESI) m/z (%): 458 (100, [M+Na]$^+$). HRMS (ESI): [M+Na] (C$_{23}$H$_{33}$O$_7$NNa) calc. 458.21492, found 458.21493.

tert-Butyl 3-(2-(tert-butoxycarbonyl)-5-oxo-5-((propionyloxy)amino)pentyl)benzoate

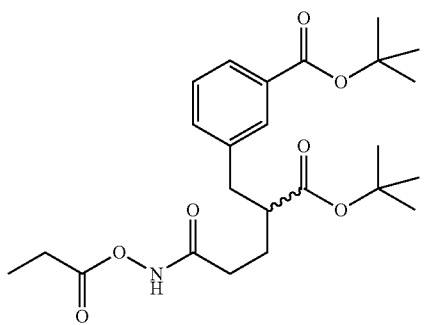 [SMILES: CCC(=O)ONC(=O)CCC(Cc1cccc(C(=O)OC(C)(C)C)c1)C(=O)OC(C)(C)C]

tert-Butyl 3-(2-(tert-butoxycarbonyl)-5-(hydroxyamino)-5-oxopentyl)benzoate (179 mg, 0.45 mmol) was placed in a Schlenk flask and put under an argon atmosphere. DCM (10 mL) was added dissolving it followed by pyridine (55 μL, 0.68 mmol, 1.5 eq) and propionic anhydride (92 μL, 0.68 mmol, 1.5 eq). The mixture was stirred at rt overnight (22 h). Then silica was added, volatiles were removed on rotavap and the residue was placed on a silica column (2.5×18 cm) and chromatographed (eluent hex/AcOEt 1:1) to afford 114 mg (56%, 0.25 mmol) of colourless oil. $^1$H NMR (400 MHz, CDCl$_3$): δ 1.15 (t, J=7.6 Hz, 1H), 1.33 (s, 9H), 1.58 (s, 9H), 1.81-1.97 (m, 2H), 2.11-2.32 (m, 2H), 2.38 (q, J=7.5 Hz, 1H), 2.55-2.68 (m, 1H), 2.73-2.82 (m, 1H), 2.87-2.97 (m, 1H), 7.29-7.35 (m, 2H), 7.76-7.85 (m, 2H). $^{13}$C NMR (151 MHz, CDCl$_3$): δ 9.0, 27.9, 28.1, 28.3, 30.9, 31.7, 38.5, 47.5, 81.1, 81.4, 127.7, 128.3, 130.0, 132.1, 133.3, 139.2, 166.0, 174.2, 178.0, 179.7. MS (ESI) m/z (%): 472 (100, [M+Na]$^+$). HRMS (ESI): [M+Na] (C$_{24}$H$_{35}$O$_7$NNa) calc. 472.23057, found 472.23056.

tert-Butyl 3-(2-(tert-butoxycarbonyl)-5-((isobutyryloxy)amino)-5-oxopentyl)benzoate

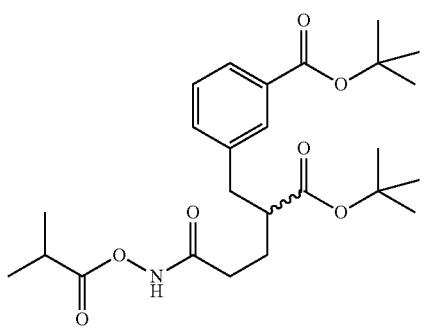 [SMILES: CC(C)C(=O)ONC(=O)CCC(Cc1cccc(C(=O)OC(C)(C)C)c1)C(=O)OC(C)(C)C]

tert-Butyl 3-(2-(tert-butoxycarbonyl)-5-(hydroxyamino)-5-oxopentyl)benzoate (215 mg, 0.55 mmol) was placed in a Schlenk flask and put under an argon atmosphere. DCM (10 mL) was added dissolving it followed by pyridine (58 μL, 0.71 mmol, 1.3 eq) and isobutyric anhydride (120 μL, 0.71 mmol, 1.3 eq). The mixture was stirred at rt overnight (22 h). Then silica was added, volatiles were removed on rotavap and the residue was placed on a silica column (2×18 cm) and chromatographed (eluent hex/AcOEt 3:1) to afford 141 mg (56%, 0.30 mmol) of colourless oil. $^1$H NMR (400 MHz, CDCl$_3$): δ 1.19 (d, J=7.0 Hz, 6H), 1.33 (s, 9H), 1.58 (s, 9H), 1.81-1.97 (m, 2H), 2.12-2.48 (m, 2H), 2.52-2.69 (m, 2H), 2.73-2.82 (m, 1H), 2.87-2.97 (m, 1H), 7.30-7.37 (m, 2H), 7.76-7.80 (m, 1H), 7.80-7.85 (m, 1H). $^{13}$C NMR (151 MHz, CDCl$_3$): δ 18.9, 27.9, 28.1, 28.3, 30.7, 31.7, 33.9, 38.4, 47.5, 81.1, 81.3, 127.8, 128.4, 130.0, 132.1, 133.3, 139.1, 166.1, 174.2, 178.2, 182.7. MS (ESI) m/z (%): 486 (43, [M+Na]$^+$), 416 (100, [M-C$_4$H$_7$O+Na]$^+$). HRMS (ESI): [M−H] (C$_{25}$H$_{37}$O$_7$NNa) calc. 486.24622, found 486.24651.

tert-Butyl 3-(2-(tert-butoxycarbonyl)-5-oxo-5-((pivaloyloxy)amino)pentyl)

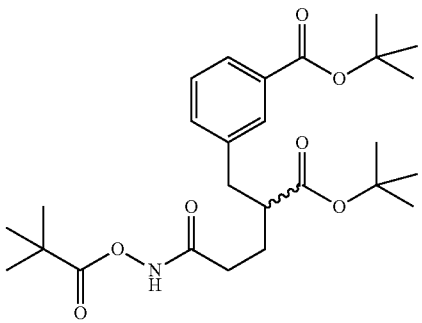 [SMILES: CC(C)(C)OC(=O)c1cccc(CC(CCC(=O)NOC(=O)C(C)(C)C)C(=O)OC(C)(C)C)c1]

tert-Butyl 3-(2-(tert-butoxycarbonyl)-5-(hydroxyamino)-5-oxopentyl)benzoate (205 mg, 0.52 mmol) was placed in a Schlenk flask and put under an argon atmosphere. THF (10 mL) was added dissolving it followed by pyridine (55 μL, 0.68 mmol, 1.3 eq) and pivaloyl chloride (84 μL, 0.68 mmol, 1.3 eq). The mixture was stirred at rt overnight (22 h). Then silica was added, volatiles were removed on rotavap and the residue was placed on a silica column (2.5×18 cm) and chromatographed (eluent hex/AcOEt 3:1) to afford 109 mg (44%, 0.23 mmol) of colourless oil. $^1$H NMR (400 MHz, CDCl$_3$): δ 1.23 (s, 9H), 1.33 (s, 9H), 1.58 (s, 9H), 1.81-1.97 (m, 2H), 2.10-2.48 (m, 2H), 2.54-2.67 (m, 1H), 2.72-2.82 (m, 1H), 2.86-2.98 (m, 1H), 7.28-7.36 (m, 2H), 7.76-7.85 (m, 2H). $^{13}$C NMR (151 MHz, CDCl$_3$): δ 27.1, 27.9, 28.1, 28.3, 30.7, 31.7, 38.4, 47.5, 81.1, 81.3, 127.8, 128.4, 130.0, 132.1, 133.3, 139.1, 166.0, 174.2, 178.3, 184.6. MS (ESI) m/z (%): 500 (100, [M+Na]$^+$). HRMS (ESI): [M+Na] (C$_{26}$H$_{39}$O$_7$NNa) calc. 500.26187, found 500.26201.

tert-Butyl 3-(5-((benzoyloxy)amino)-2-(tert-butoxy-carbonyl)-5-oxopentyl)

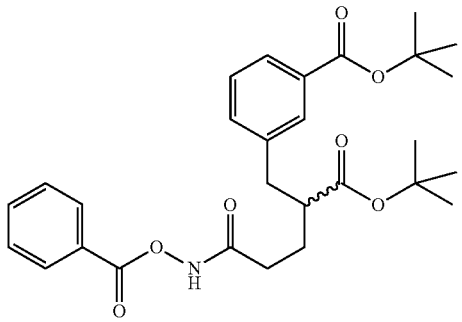 [SMILES: CC(C)(C)OC(=O)c1cccc(CC(CCC(=O)NOC(=O)c2ccccc2)C(=O)OC(C)(C)C)c1]

tert-Butyl 3-(2-(tert-butoxycarbonyl)-5-(hydroxyamino)-5-oxopentyl)benzoate (168 mg, 0.43 mmol) was placed in a Schlenk flask and put under an argon atmosphere. THF (10 mL) was added dissolving it followed by pyridine (45 µL, 0.55 mmol, 1.3 eq) and benzoyl chloride (65 µL, 0.55 mmol, 1.3 eq). The mixture was stirred at rt overnight (22 h). Then silica was added, volatiles were removed on rotavap and the residue was placed on a silica column (2.5×18 cm) and chromatographed (eluent hex/AcOEt 3:1) to afford 116 mg (55%, 0.23 mmol) of colourless oil. $^1$H NMR (400 MHz, CDCl$_3$): δ 1.35 (s, 9H), 1.58 (s, 9H), 1.90-2.06 (m, 2H), 2.26-2.48 (m, 2H), 2.73-2.89 (m, 2H), 2.91-3.00 (m, 1H), 7.30-7.40 (m, 2H), 7.45-7.51 (m, 2H), 7.64 (t, J=7.5 Hz, 1H), 7.79-7.86 (m, 2H), 8.11 (d, J=7.4 Hz, 2H). $^{13}$C NMR (151 MHz, CDCl$_3$): δ 27.9, 28.1, 28.3, 31.0, 38.5, 47.4, 81.1, 81.4, 126.7, 127.8, 128.4, 128.8, 130.1, 130.2, 132.1, 133.2, 134.4, 139.1, 165.0, 165.9, 170.8, 174.2. MS (ESI) m/z (%): 520 (100, [M+Na]$^+$). HRMS (ESI): [M+Na] (C$_{28}$H$_{35}$O$_7$NNa) calc. 520.23057, found 520.23065.

tert-Butyl 3-(2-(tert-butoxycarbonyl)-5-oxo-5-((2-phenylacetoxy)amino)pentyl)benzoate

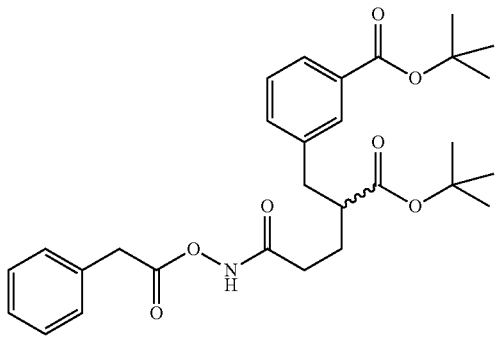 [SMILES: CC(C)(C)OC(=O)c1cccc(CC(CCC(=O)NOC(=O)Cc2ccccc2)C(=O)OC(C)(C)C)c1]

tert-Butyl 3-(2-(tert-butoxycarbonyl)-5-(hydroxyamino)-5-oxopentyl)benzoate (215 mg, 0.55 mmol) was placed in a Schlenk flask and put under an argon atmosphere. DCM (10 mL) was added dissolving it followed by pyridine (58 µL, 0.71 mmol, 1.3 eq) and 2-phenylacetyl chloride (158 µL, 0.71 mmol, 1.3 eq). The mixture was stirred at rt overnight (22 h). Then silica was added, volatiles were removed on rotavap and the residue was placed on a silica column (2×18 cm) and chromatographed (eluent hex/AcOEt 3:1) to afford 170 mg (61%, 0.33 mmol) of colourless oil. $^1$H NMR (400 MHz, CDCl$_3$): δ 1.33 (s, 9H), 1.59 (s, 9H), 1.80-1.96 (m, 2H), 2.11-2.47 (m, 2H), 2.57-2.67 (m, 1H), 2.72-2.81 (m, 1H), 2.87-2.98 (m, 1H), 3.66 (s, 2H), 7.26-7.37 (m, 7H), 7.77-7.80 (m, 1H), 7.81-7.85 (m, 1H). $^{13}$C NMR (151 MHz, CDCl$_3$): δ 27.1, 28.1, 28.3, 31.7, 38.5, 41.1, 47.4, 81.1, 81.2, 127.5, 127.7, 128.3, 128.8, 129.5, 130.0, 132.1, 133.3, 133.5, 139.2, 165.9, 174.0, 177.1, 178.3. MS (ESI) m/z (%): 534 (31, [M+Na]$^+$), 416 (87, [M-C$_8$H$_8$O+Na]$^+$). HRMS (ESI): [M-H] (C$_{29}$H$_{37}$O$_7$NNa) calc. 534.24622, found 534.24637.

3-(2-Carboxy-5-(((ethoxycarbonyl)oxy)amino)-5-oxopentyl)benzoic acid JV2677 [32]

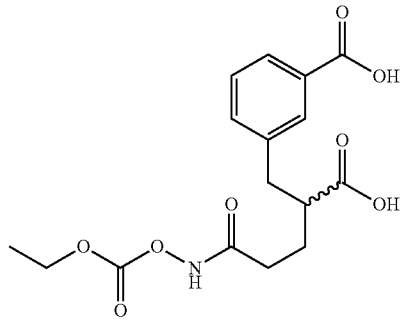 [SMILES: CCOC(=O)ONC(=O)CCC(Cc1cccc(C(=O)O)c1)C(=O)O]

tert-Butyl 3-(2-(tert-butoxycarbonyl)-5-(((ethoxycarbonyl)oxy)amino)-5-oxopentyl)benzoate (121 mg, 0.26 mmol) was placed in a Schlenk flask and put under an argon atmosphere. DCM (1 mL) was added followed by TFA (1 mL) and iPr$_3$SiH (106 µL, 0.52 mmol, 2 eq). The mixture was stirred at rt for 1 h, when disappearance of the stm on TLC was observed. Volatiles were removed on rotavap and the residue was chromatographed on silica (1.5×12 cm, eluent hex/AcOEt 1:1+1% AcOH) to afford 90 mg of colourless oil. 1 mL of Et$_2$O was added to the oil, the mixture was sonicated, centrifuged and the supernatant was separated. Then 1 mL of DCM was added, the mixture was sonicated, centrifuged and the supernatant was separated affording 46 mg (50%, 0.13 mmol) of white solid. $^1$H NMR (400 MHz, DMSO-d$_6$): δ 1.25 (t, J=7.1 Hz, 3H), 1.66-1.79 (m, 2H), 2.09-2.24 (m, 2H), 2.57-2.67 (m, 1H), 2.76-2.93 (m, 2H), 4.23 (q, J=7.1 Hz, 2H), 7.34-7.48 (m, 2H), 7.73-7.84 (m, 2H). $^{13}$C NMR (151 MHz, CDCl$_3$): δ 14.0, 26.8, 29.5, 37.1, 45.9, 65.6, 127.3, 128.5, 129.7, 130.7, 133.4, 139.8, 153.9, 167.3, 169.5, 175.6. MS (ESI) m/z (%): 352 (100, [M-H]$^-$). HRMS (ESI): [M-H] (C$_{16}$H$_{18}$O$_8$N) calc. 352.10379, found 352.10345.

3-(2-Carboxy-5-(((isopropylcarbamoyl)oxy)amino)-5-oxopentyl)benzoic acid JV2678

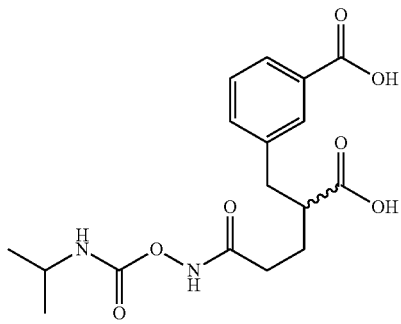 [SMILES: CC(C)NC(=O)ONC(=O)CCC(Cc1cccc(C(=O)O)c1)C(=O)O]

tert-Butyl 3-(2-(tert-butoxycarbonyl)-5-(((isopropylcarbamoyl)oxy)amino)-5-oxopentyl)benzoate (100 mg, 0.21 mmol) was placed in a Schlenk flask and put under an argon atmosphere. DCM (1 mL) was added followed by TFA (1 mL) and iPr$_3$SiH (86 µL, 0.42 mmol, 2 eq). The mixture was stirred at rt for 1 h, when disappearance of the stm on TLC was observed. Volatiles were removed on rotavap and the residue was chromatographed on silica (1.5×12 cm, eluent hex/AcOEt 1:1+1% AcOH) to afford 103 mg of colourless oil. 1 mL of Et$_2$O was added to the oil, the mixture was sonicated, centrifuged and the supernatant was separated. Then 1 mL of DCM was added, the mixture was sonicated, centrifuged and the supernatant was separated affording 45 mg (58%, 0.12 mmol) of off-white solid. $^1$H NMR (400 MHz, DMSO-d$_6$): δ 1.07 (d, J=6.6 Hz, 6H), 1.64-1.79 (m, 2H), 2.05-2.20 (m, 2H), 2.56-2.66 (m, 1H), 2.78-2.91 (m, 2H), 3.53-3.63 (m, 1H), 7.37-7.47 (m, 2H), 7.73-7.84 (m, 2H). $^{13}$C NMR (151 MHz, DMSO-d$_6$): δ 22.4, 27.1, 29.7, 37.2, 43.1, 46.1, 127.3, 128.5, 129.7, 130.9, 133.4, 139.8, 167.5, 169.4, 174.5, 175.8. MS (ESI) m/z (%): 365 (48, [M–H]$^-$), 280 (100, [M-iPrNHCO]$^+$). HRMS (ESI): [M–H] (C$_{17}$H$_{21}$O$_7$N$_2$) calc. 365.13542, found 365.13507.

3-(5-(Acetoxyamino)-2-carboxy-5-oxopentyl)benzoic acid JV2680 [34]

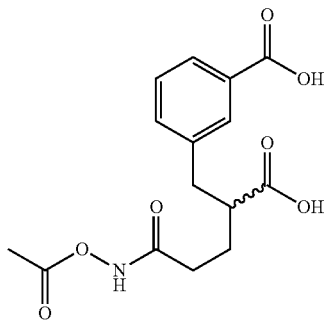 [SMILES: CC(=O)ONC(=O)CCC(Cc1cccc(C(=O)O)c1)C(=O)O]

tert-Butyl 3-(5-(acetoxyamino)-2-(tert-butoxycarbonyl)-5-oxopentyl)benzoate (116 mg, 0.27 mmol) was placed in a Schlenk flask and put under an argon atmosphere. DCM (1 mL) was added followed by TFA (1 mL) and iPr$_3$SiH (110 µL, 0.54 mmol, 2 eq). The mixture was stirred at rt for 1 h, when disappearance of the stm on TLC was observed. Volatiles were removed on rotavap and the residue was chromatographed on silica (1.5×12 cm, eluent hex/AcOEt 1:1+1% AcOH) to afford 126 mg of colourless oil. 1 mL of Et$_2$O was added to the oil, the mixture was sonicated, centrifuged and the supernatant was removed. Then 1 mL of DCM was added, the mixture was sonicated, centrifuged and the supernatant was removed affording 69 mg (80%, 0.21 mmol) of white solid. $^1$H NMR (400 MHz, DMSO-d$_6$): δ 1.63-1.80 (m, 2H), 2.13 (s, 3H), 2.14-2.26 (m, 2H), 2.56-2.68 (m, 1H), 2.76-2.92 (m, 2H), 7.33-7.49 (m, 2H), 7.71-7.85 (m, 2H). $^{13}$C NMR (151 MHz, DMSO-d$_6$): δ 18.1, 27.0, 29.8, 37.2, 46.0, 127.3, 128.5, 129.7, 130.9, 133.4, 139.8, 167.5, 168.6, 169.2, 175.1. MS (ESI) m/z (%): 346 (100, [M+Na]$^+$). HRMS (ESI): [M–H] (C$_{15}$H$_{16}$O$_7$N) calc. 322.09323, found 322.09296.

3-(2-Carboxy-5-oxo-5-((propionyloxy)amino)pentyl)benzoic acid JV2719 [35]

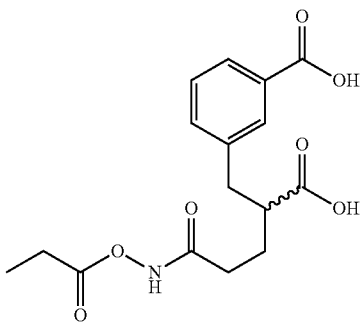 [SMILES: CCC(=O)ONC(=O)CCC(Cc1cccc(C(=O)O)c1)C(=O)O]

tert-Butyl 3-(2-(tert-butoxycarbonyl)-5-oxo-5-((propionyloxy)amino)pentyl)benzoate (150 mg, 0.33 mmol) was placed in a Schlenk flask and put under an argon atmosphere. DCM (4 mL) was added followed by 0 OH TFA (1 mL) and iPr$_3$SiH (136 µL, 0.66 mmol, 2 eq). The mixture was stirred at rt for 2 h, when disappearance ° of the stm on TLC was observed. Volatiles were removed on rotavap and the residue was chromatographed on silica (2×12 cm, eluent hex/AcOEt 1:1+1% AcOH) to give a colourless oil. 1 mL of DCM was added, the mixture was sonicated, centrifuged and the supernatant was removed to afford 55 mg (49%, 0.16 mmol) of white solid. $^1$H NMR (400 MHz, DMSO-d$_6$): δ 1.07 (t, J=7.5 Hz, 1H), 1.66-1.82 (m, 2H), 2.08-2.28 (m, 2H), 2.39-2.49 (m, 2H), 2.52-2.65 (m, 1H), 2.73-2.92 (m, 2H), 7.34-7.54 (m, 2H), 7.69-7.85 (m, 2H). $^{13}$C NMR (151 MHz, DMSO-d$_6$): δ 8.8, 24.4, 27.0, 29.8, 37.1, 46.0, 127.3, 128.5, 129.7, 130.7, 133.4, 139.8, 167.3, 169.2, 172.0, 175.6. MS (ESI) m/z (%): 336 (36, [M–H]$^-$). HRMS (ESI): [M–H] (C$_{16}$H$_{18}$O$_7$N) calc. 336.10888, found 336.10852.

3-(2-Carboxy-5-((isobutyryloxy)amino)-5-oxopentyl)benzoic acid JV2720 [36]

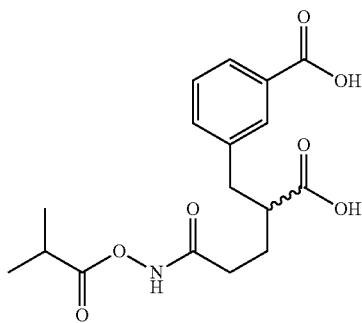

tert-Butyl 3-(2-(tert-butoxycarbonyl)-5-((isobutyryloxy)amino)-5-oxopentyl)benzoate (120 mg, 0.26 mmol) was placed in a Schlenk flask and put under an argon atmosphere. DCM (4 mL) was added followed by TFA (1 mL) and iPr$_3$SiH (106 µL, 0.52 mmol, 2 eq). The mixture was stirred at rt for 2 h, when disappearance of the stm on TLC was observed. Volatiles were removed on rotavap and the residue was chromatographed on silica (2×12 cm, eluent hex/AcOEt 1:1+1% AcOH) to give a colourless oil. 1 mL of DCM was added, the mixture was sonicated, centrifuged and the supernatant was removed to afford 68 mg (75%, 0.19 mmol) of white solid. $^1$H NMR (400 MHz, DMSO-d$_6$): δ 1.14 (d, J=7.0 Hz, 6H), 1.65-1.80 (m, 2H), 2.06-2.25 (m, 2H), 2.57-2.65 (m, 1H), 2.66-2.74 (m, 1H), 2.77-2.92 (m, 2H), 7.37-7.47 (m, 2H), 7.75-7.81 (m, 2H). $^{13}$C NMR (151 MHz, DMSO-d$_6$): δ 18.7, 26.9, 29.6, 31.3, 37.2, 46.0, 127.3, 128.5, 129.7, 130.8, 133.4, 139.8, 167.4, 169.2, 174.5, 175.6. MS (ESI) m/z (%): 350 (100, [M−H]$^-$). HRMS (ESI): [M−H] (C$_{17}$H$_{20}$O$_7$N) calc. 350.12453, found 350.12433.

3-(2-Carboxy-5-oxo-5-((pivaloyloxy)amino)pentyl)benzoic acid JV2721 [37]

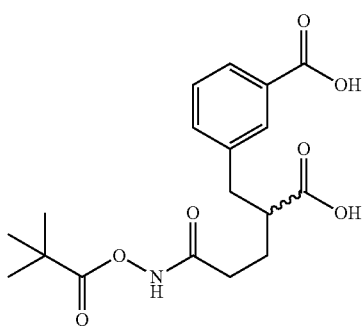

tert-Butyl 3-(2-(tert-butoxycarbonyl)-5-oxo-5-((pivaloyloxy)amino)pentyl)benzoate (150 mg, 0.31 mmol) was placed in a Schlenk flask and put under an argon atmosphere. DCM (4 mL) was added followed by TFA (1 mL) and iPr$_3$SiH (128 µL, 0.62 mmol, 2 eq). The mixture was stirred at rt for 2 h, when disappearance of the stm on TLC was observed. Volatiles were removed on rotavap and the residue was chromatographed on silica (2×12 cm, eluent hex/AcOEt 1:1+1% AcOH) to give a colourless oil. 1 mL of DCM was added, the mixture was sonicated, centrifuged and the supernatant was separated to afford 67 mg (58%, 0.18 mmol) of white solid. $^1$H NMR (400 MHz, DMSO-d$_6$): δ 1.21 (s, 9H), 1.65-1.83 (m, 2H), 2.05-2.28 (m, 2H), 2.53-2.68 (m, 1H), 2.73-2.92 (m, 2H), 7.35-7.48 (m, 2H), 7.70-7.85 (m, 2H). $^{13}$C NMR (151 MHz, DMSO-d$_6$): δ 26.8, 26.9, 29.6, 37.1, 45.9, 79.9, 127.3, 128.5, 129.7, 130.7, 133.4, 139.8, 167.3, 169.3, 173.3, 175.8. MS (ESI) m/z (%): 364 (100, [M−H]$^-$). HRMS (ESI): [M−H] (C$_{18}$H$_{22}$O$_7$N) calc. 364.14018, found 364.13997.

3-(5-((Benzoyloxy)amino)-2-carboxy-5-oxopentyl)benzoic acid JV2722 [38]

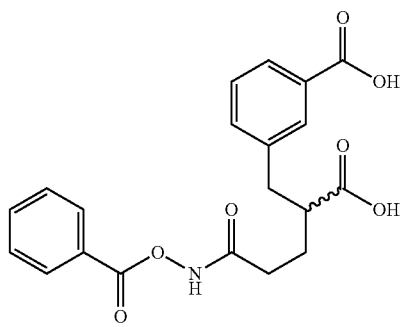 [SMILES: O=C(CCC(Cc1cccc(C(=O)O)c1)C(=O)O)NOC(=O)c1ccccc1]

tert-Butyl 3-(5-((benzoyloxy)amino)-2-(tert-butoxycarbonyl)-5-oxopentyl)benzoate (152 mg, 0.30 mmol) was placed in a Schlenk flask and put under an argon atmosphere. DCM (4 mL) was added followed by TFA (1 mL) and iPr$_3$SiH (124 µL, 0.60 mmol, 2 eq). The mixture was stirred at rt for 2 h, when disappearance of the stm on TLC was observed. Volatiles were removed on rotavap and the residue was chromatographed on silica (2×12 cm, eluent hex/AcOEt 1:1+1% AcOH) to give a colourless oil. 1 mL of DCM was added, the mixture was sonicated, centrifuged and the supernatant was removed to afford 83 mg (70%, 0.21 mmol) of white solid. $^1$H NMR (400 MHz, DMSO-d$_6$): δ 1.68-1.87 (m, 2H), 2.19-2.35 (m, 2H), 2.60-2.72 (m, 1H), 2.80-2.96 (m, 2H), 7.38-7.49 (m, 2H), 7.58 (t, J=7.8 Hz, 2H), 7.70-7.84 (m, 3H), 7.98-8.05 (m, 2H). $^{13}$C NMR (151 MHz, DMSO-d$_6$): δ 27.0, 29.7, 37.2, 46.0, 126.9, 127.3, 128.5, 129.1, 129.5, 129.8, 130.8, 133.5, 134.3, 139.8, 164.2, 167.4, 169.5, 175.8. MS (ESI) m/z (%): 384 (100, [M−H]$^-$). HRMS (ESI): [M−H] (C$_{20}$H$_{18}$O$_7$N) calc. 384.10888, found 384.10837.

3-(2-Carboxy-5-oxo-5-((2-phenylacetoxy)amino)pentyl)benzoic acid JV2723 [39]

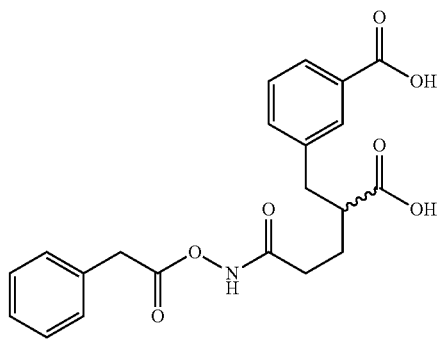 [SMILES: O=C(CCC(Cc1cccc(C(=O)O)c1)C(=O)O)NOC(=O)Cc1ccccc1]

tert-Butyl 3-(2-(tert-butoxycarbonyl)-5-oxo-5-((2-phenylacetoxy)amino)pentyl)benzoate (110 mg, 0.22 mmol) was placed in a Schlenk flask and put under an argon atmosphere. DCM (4 mL) was added followed by TFA (1 mL) and iPr$_3$SiH (88 μL, 0.44 mmol, 2 eq). The mixture was stirred at rt for 2 h, when disappearance of the stm on TLC was observed. Volatiles were removed on rotavap and the residue was chromatographed on silica (2×12 cm, eluent hex/AcOEt 1:1+1% AcOH) to give a colourless oil. 1 mL of DCM was added, the mixture was sonicated, centrifuged and the supernatant was separated to afford 55 mg (64%, 0.14 mmol) of white solid. $^1$H NMR (400 MHz, DMSO-d$_6$): δ 1.66-1.84 (m, 2H), 2.10-2.28 (m, 2H), 2.56-2.65 (m, 1H), 2.77-2.91 (m, 2H), 3.84 (s, 2H), 7.25-7.47 (m, 7H), 7.74-7.80 (m, 2H). $^{13}$C NMR (151 MHz, DMSO-d$_6$): δ 26.9, 29.6, 37.1, 37.6, 45.9, 127.1, 127.3, 128.5, 128.5, 129.4, 129.7, 130.8, 133.4, 133.4, 139.8, 167.4, 169.2, 169.5, 175.6. MS (ESI) m/z (%): 398 (37, [M−H]$^−$). HRMS (ESI): [M−H] (C$_{21}$H$_{20}$O$_7$N) calc. 398.12453, found 398.12416.

4-((1,3-Dioxoisoindolin-2-yloxy)methyl)phenyl acetate [9]

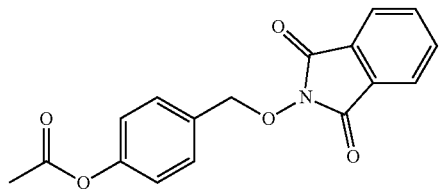 [SMILES: CC(=O)Oc1ccc(CON2C(=O)c3ccccc3C2=O)cc1]

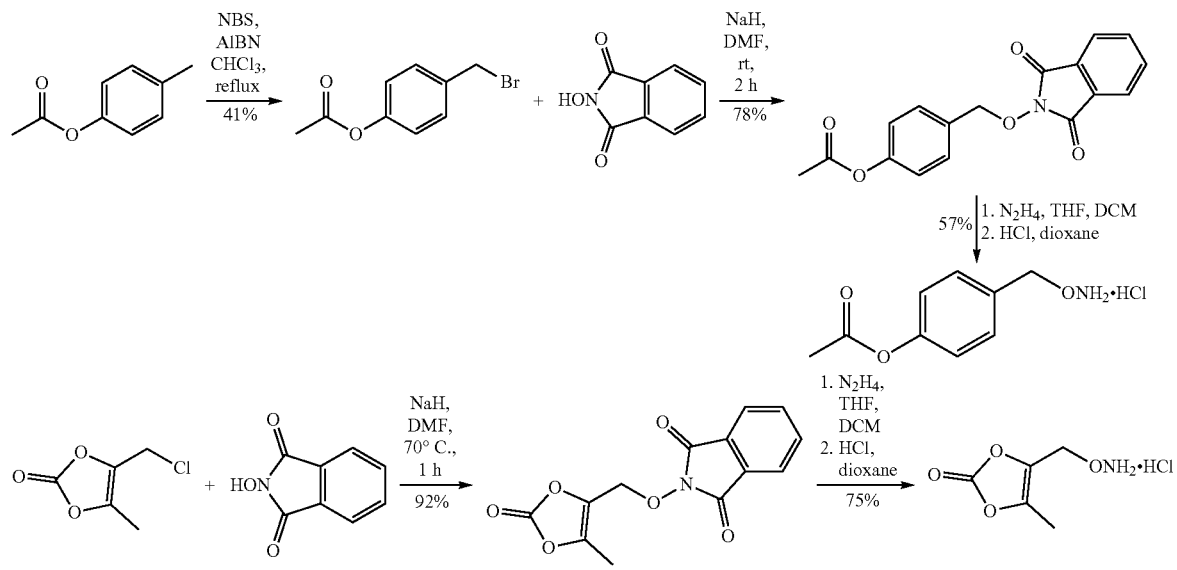

4-(Bromomethyl)phenyl acetate

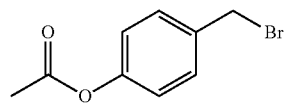

NBS (13.91 g, 0.12 mol, 0.9 eq) and AIBN (2.17 g, 0.01 mol, 0.1 eq) were placed in a Schlenk flask and put under an argon atmosphere. CHCl$_3$ was added followed by p-tolyl acetate (19.67 g, 0.13 mol). The mixture was refluxed for 4 h. After cooling down the volume of the mixture was reduced on rotavap to approximately a third and the 0 Br suspension was filtered. 200 mL of CHCl$_3$ was added to the filtrate and it was 3× washed with 80 mL of water, the combined organic layers were dried with MgSO$_4$, filtered and volatiles were removed on rotavap. 5 mL of AcOEt was added, the mixture was shortly sonicated and while stirring, 40 mL of hexane was added causing precipitation. The mixture was put to a freezer overnight and then filtered washing the white solid with 25 mL of hexane giving 12.05 g (41%, 0.05 mol) of the product. It was stored in the freezer. The NMR spectrum was in accordance with the literature (J. Org. Chem. 1981, 46 (15), 3029-3035).

To a suspension of NaH (768 mg, 19.2 mmol, 1.1 eq) in DMF (40 mL) was slowly (over 10 min) added a solution of N-hydroxyphthalimide (3.23 g, 19.2 mmol, 1.1 eq) in DMF (40 mL) at 0° C. under an argon atmosphere. After 10 minutes of stirring, a solution of 4-(bromomethyl)phenyl acetate 8 (4.00 g, 17.5 mmol) in DMF (40 mL) was added. The mixture was stirred at rt for 2 h, then water (100 mL) was added and the mixture was extracted with EtOAc (200 mL×3). The combined organic extracts were washed with water (200 mL×3), dried over MgSO$_4$, and concentrated to give a yellowish solid, which was sonicated in EtOAc (10 mL). After adding hexanes (40 mL), the mixture was sonicated for additional 5 min. The resulting mixture was filtered to afford 4.23 g of 9 as an off-white solid (78% yield, 13.6 mmol): $^1$H NMR (CDCl$_3$) δ 2.29 (s, 3H), 5.20 (s, 2H), 7.12 (d, J=8.5 Hz, 2H), 7.57 (d, J=8.5 Hz, 2H), 7.71-7.78 (m, 2H), 7.79-7.86 (m, 2H). $^{13}$C NMR (CDCl$_3$) δ 21.3, 79.3, 121.9, 123.7, 129.0, 131.2, 131.5, 134.6, 151.5, 163.6, 189.4. HRMS (ESI): [M+Na]$^+$ m/z 334.06863 (calcd 334.06859 for C$_{17}$H$_{13}$O$_5$NNa).

4-((Aminooxy)methyl)phenyl acetate hydrochloride

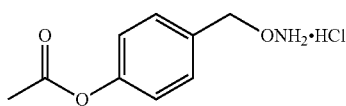

4-(((1,3-Dioxoisoindolin-2-yl)oxy)methyl)phenyl acetate (1.00 g, 3.21 mmol) was placed in a Schlenk flask and put under an argon atmosphere. 10 mL of DCM was added dissolving it and the mixture was cooled to 0° C. While stirring 1.0M $N_2H_4$ (3.2 mL, 3.21 mmol) in THF was added. A precipitate formed almost immediately. The mixture was let warm up to rt and stirred for 1 h. Then it was filtered under an argon atmosphere and HCl in dioxane (0.8 mL, 3.21 mmol) was added dropwise (5 min) to the filtrate. A white precipitate formed during the addition. After 15 minutes, volatiles were removed on rotavap. The resulting solid was sonicated in 10 mL of MeOH for 10 min and then precipitated with 50 mL of $Et_2O$. Yield: 0.40 g (57%, 1.84 mmol) of white solid. $^1$H NMR (400 MHz, DMSO-$d_6$): δ 2.27 (s, 3H), 5.06 (s, 2H), 7.17 (d, J=8.5 Hz, 2H), 7.46 (d, J=8.5 Hz, 2H). $^{13}$C NMR (151 MHz, DMSO-$d_6$): δ 20.9, 75.0, 122.1, 130.6, 131.3, 151.0, 169.1. MS (ESI) m/z (%): 204 (100, [M−HCl+Na]$^+$), 182 (20, [M−Cl]$^+$). HRMS (ESI): [M−Cl] ($C_9H_{12}O_3N$) calc. 182.08117, found 182.08119.

2-((5-Methyl-2-oxo-1,3-dioxol-4-yl)methoxy)isoindoline-1,3-dione [14]

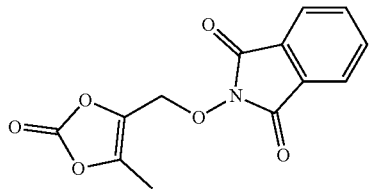 [SMILES: Cc1oc(=O)oc1CON1C(=O)c2ccccc2C1=O]

To a suspension of NaH (287 mg, 7.18 mmol, 1.1 eq) in DMF (10 mL) was slowly added (over 5 min) a solution of N-hydroxyphthalimide (1.21 g, 7.18 mmol, 1.1 eq) in DMF (10 mL) at 0° C. under an argon atmosphere. After 5 minutes of stirring, a solution of 13 (1.00 g, 6.53 mmol) in DMF (5 mL) was added. The mixture was warmed up to rt and then heated at 70° C. for 1 h, during which time the dark red mixture turned middle beige and the starting material disappeared on TLC. Water (50 mL) was then added to the mixture and the resulting mixture was extracted with EtOAc (120 mL×3). The combined organic extracts were washed with water (100 mL×3) to remove DMF, dried over $MgSO_4$, and concentrated. EtOAc (4 mL) was then added to the residual material and it was sonicated for 10 min. Hexanes (40 mL) was added and after a short sonication and filtration 1.64 g of 14 was obtained as an off-white solid (92% yield, 5.98 mmol): $^1$H NMR (CDCl$_3$) δ 2.14 (s, 3H), 4.95 (s, 2H), 7.76-7.81 (m, 2H), 7.83-7.88 (m, 2H). $^{13}$C NMR (CDCl$_3$) δ 9.5, 66.7, 124.0, 128.7, 132.8, 135.0, 142.2, 151.9, 163.3. HRMS (ESI): [M+Na]$^+$ m/z 298.03227 (calcd 298.03221 for $C_{13}H_9O_6NNa$).

4-((Aminooxy)methyl)-5-methyl-1,3-dioxol-2-one hydrochloride

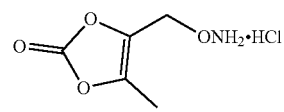

2-((5-Methyl-2-oxo-1,3-dioxol-4-yl)methoxy)isoindoline-1,3-dione (1.00 g, 3.63 mmol) was placed in a Schlenk flask and put under an argon atmosphere. DCM (10 mL) was added dissolving it and the solution was cooled to 0° C. While stirring 1.0M $N_2H_4$ in THF (3.6 mL, 3.63 mmol) was added and the mixture was let warm up to rt and stirred for 2 h. Then it was filtered under an argon atmosphere and the filtrate was acidified with HCl in dioxane (1.82 mL, 7.28 mmol). The white precipitate was stirred at rt for 20 min, then volatiles were removed on rotavap and the solid was recrystallized: dissolved in 5 mL of MeOH and precipitated with 50 mL of $Et_2O$ affording after filtration and drying 0.49 g (75%, 2.72 mmol) of white solid. $^1$H NMR (400 MHz, DMSO-$d_6$) δ: 2.20 (s, 3H), 5.00 (s, 2H). $^{13}$C NMR (151 MHz, DMSO-$d_6$) δ: 9.1, 63.1, 131.2, 142.6, 152.0. MS (ESI) m/z (%): 146 (55, [M−Cl]$^+$). HRMS (ESI): [M−Cl] ($C_5H_8O_4N$) calc. 146.0453, found 146.0451.

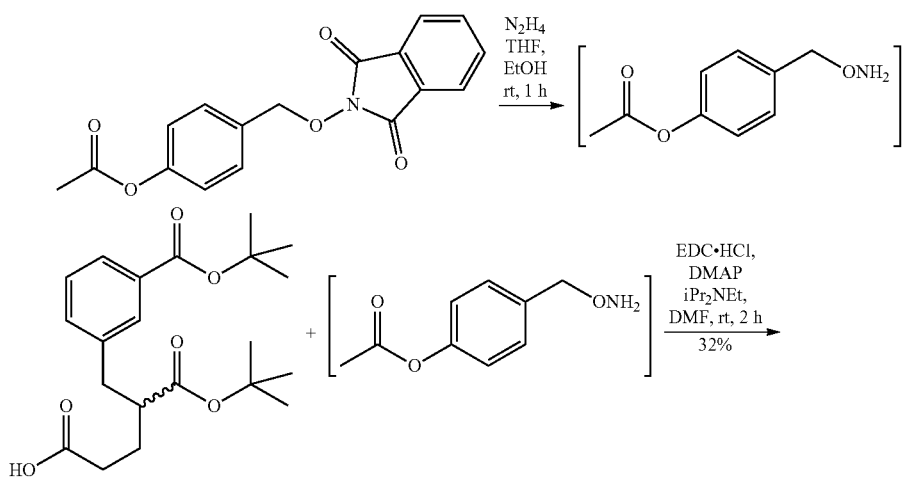

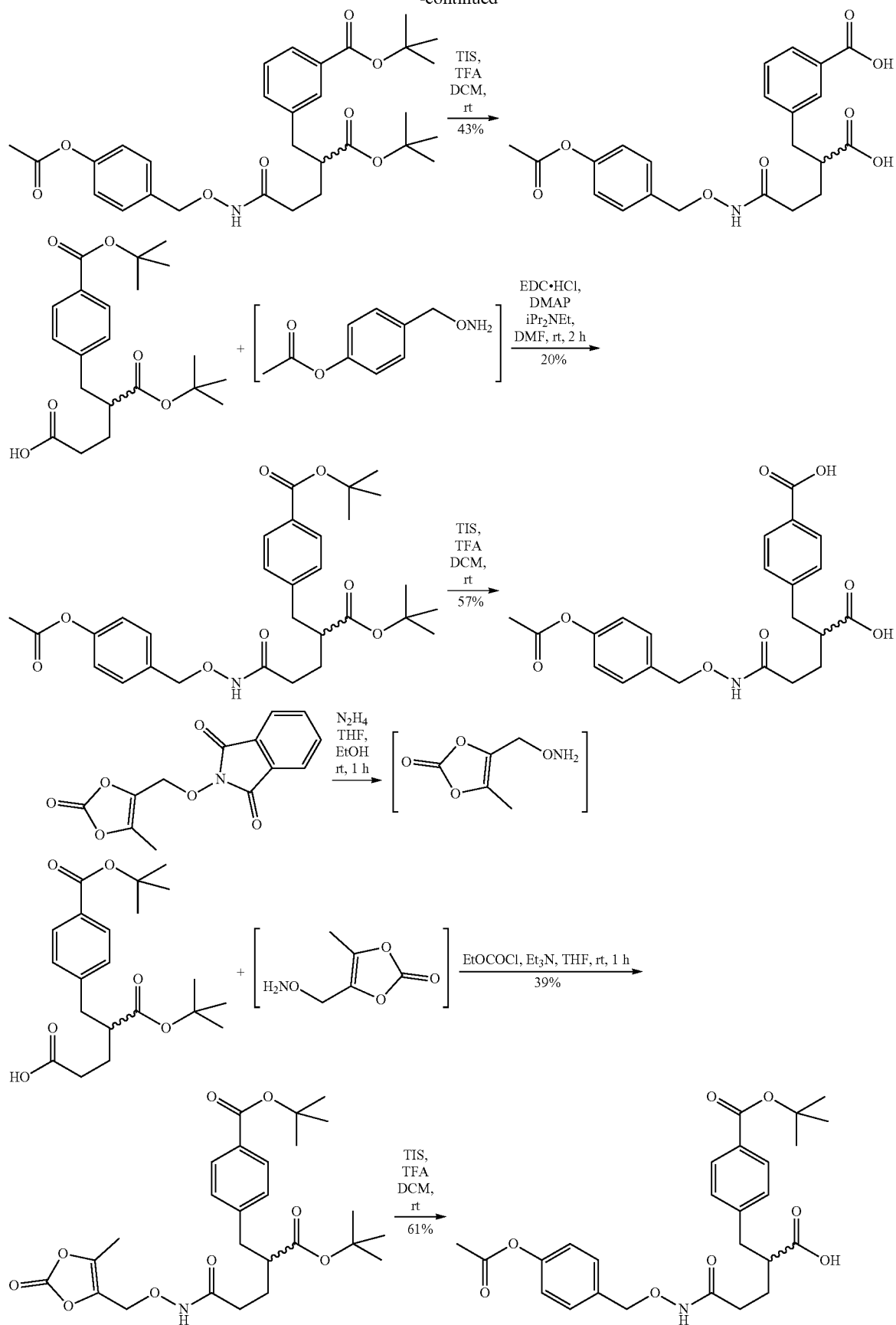

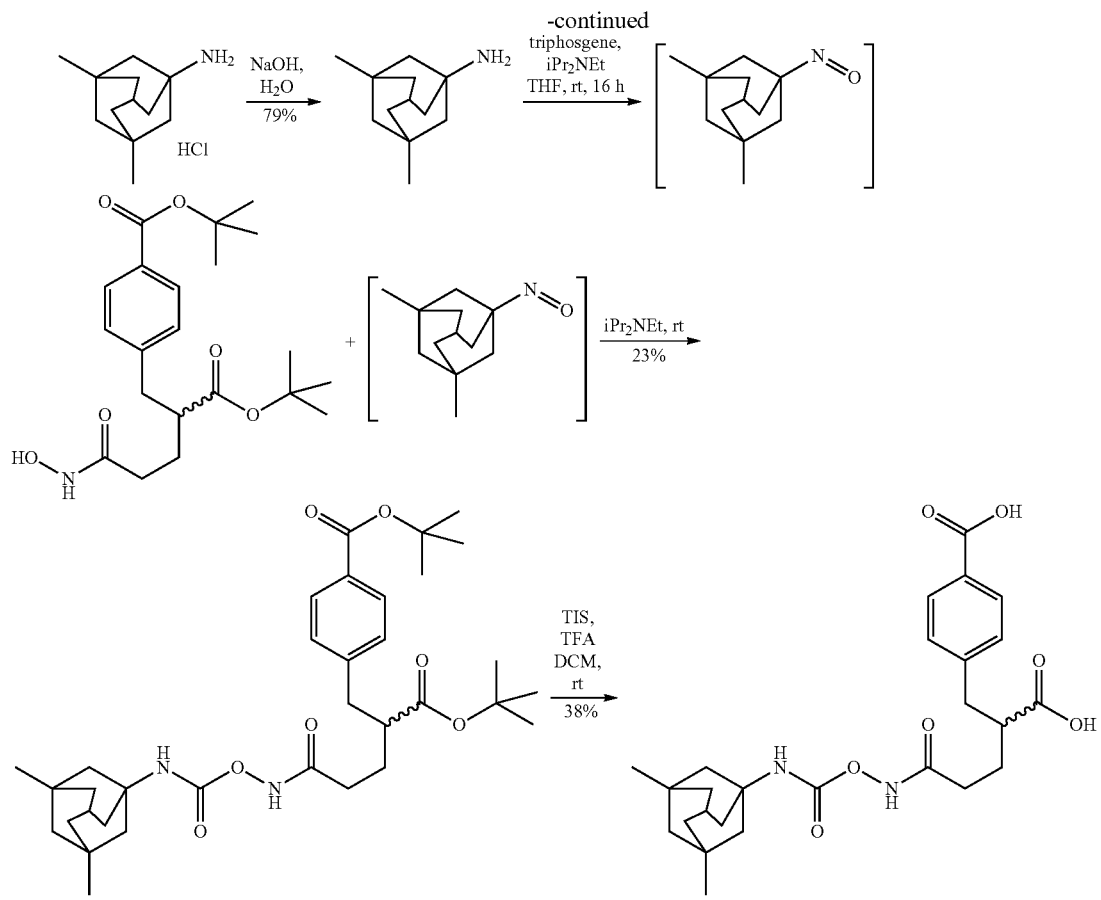

4-(Aminooxymethyl)phenyl acetate [10]

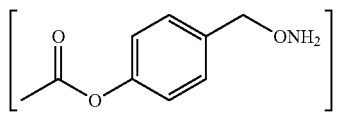

To a suspension of 9 (3.80 g, 12.2 mmol) in THF (30 mL) and ethanol (3 mL) was added 1 M $N_2H_4$ in THF (12.22 mL, 12.22 mmol, 1 eq) at rt under an argon atmosphere. The mixture turned slightly yellowish and the solid dissolved. In a minute a precipitate appeared again. The mixture was stirred at rt for 1 h and then it was filtered under an argon atmosphere. The filtrate was used immediately in the subsequent reaction.

tert-Butyl 3-(5-(((4-acetoxybenzyl)oxy)amino)-2-(tert-butoxycarbonyl)-5-oxopentyl)benzoate

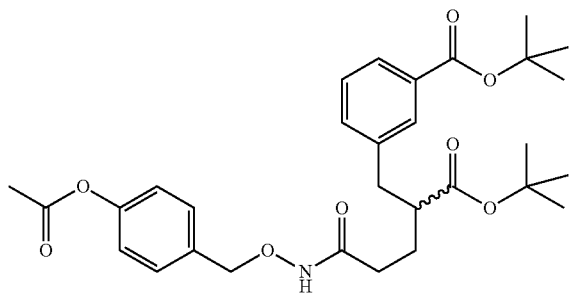 [SMILES: CC(=O)Oc1ccc(CONC(=O)CCC(Cc2cccc(C(=O)OC(C)(C)C)c2)C(=O)OC(C)(C)C)cc1]

5-(tert-Butoxy)-4-(3-(tert-butoxycarbonyl)benzyl)-5-oxopentanoic acid (400 mg, 1.06 mmol) as oil, EDC·HCl (304 mg, 1.56 mmol, 1.5 eq) and DMAP (7 mg, 0.05 mmol, 0.05 eq) were placed in a Schlenk flask and put under an argon atmosphere. 10 mL of DMF was added and the mixture was homogenised by stirring. Then $iPr_2NEt$ (567 µL, 3.17 mmol, 3 eq) and 4-((aminooxy)methyl)phenyl acetate (theoretically 287 mg, 1.59 mmol, 1.5 eq) in THF/EtOH were added at once. The mixture was stirred at rt for 3 h. Then 50 mL of water was added and the mixture was 3× extracted with 100 mL of AcOEt. The combined organic layers were washed 3× with 100 mL of water, dried with $MgSO_4$, filtered and volatiles were removed on rotavap. The residue was chromatographed on silica (3×18 cm, eluent hex/AcOEt 6:4 to 1:1) to afford a yellowish oil containing a solid. The mixture was 4× sonicated in ½ mL of AcOEt, then 2.5 mL of hexane was added, the mixture was sonicated shortly again, kept for 10 min for the suspension to settle, and the supernatant was separated. The combined supernatants after volatiles removal afforded 174 mg (32%, 0.32 mmol) of yellowish oil. $^1H$ NMR (400 MHz, $CDCl_3$): δ 1.32 (s, 9H), 1.58 (s, 9H), 1.81-1.94 (m, 2H), 1.95-2.26 (m, 2H), 2.30 (s, 3H), 2.54-2.66 (m, 1H), 2.71-2.82 (m, 1H), 2.87-2.98 (m, 1H), 4.72-4.99 (m, 2H), 7.09 (d, J=8.0 Hz, 2H), 7.28-7.35 (m, 2H), 7.39 (d, J=8.0 Hz, 2H), 7.78 (s, 1H), 7.81-7.85 (m, 1H). $^{13}C$ NMR (151 MHz, $CDCl_3$): δ 21.3, 28.0, 28.1, 28.3, 31.0, 38.5, 47.7, 77.7, 81.2, 81.2, 122.0, 127.8, 128.4, 130.1, 130.5, 132.2, 133.0, 133.2, 139.2, 151.1, 165.9, 169.5, 171.4, 174.0. MS (ESI) m/z (%): 564

3-(5-(((4-Acetoxybenzyl)oxy)amino)-2-carboxy-5-oxopentyl)benzoic acid JV2837 [40]

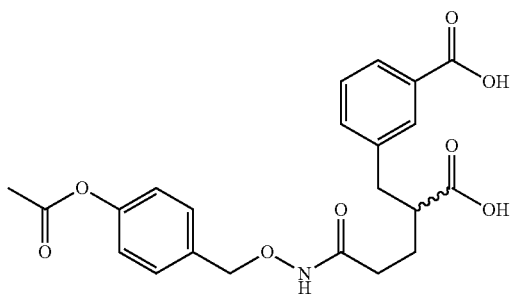 [SMILES: CC(=O)Oc1ccc(CONC(=O)CCC(Cc2cccc(C(=O)O)c2)C(=O)O)cc1]

tert-Butyl 3-(5-(((4-acetoxybenzyl)oxy)amino)-2-(tert-butoxycarbonyl)-5-oxopentyl)benzoate (50 mg, 0.09 mmol) was placed in a Schlenk flask and put under an argon atmosphere. DCM (3 mL) was added followed by TFA (1 mL) and TIS (38 μL, 0.18 mmol, 2 eq). The mixture was stirred at rt for 1 h, after which time no stm was detected by TLC. Volatiles were removed on rotavap and the residue was filtered through a short plug of silica using hex/AcOEt 2:3+1% AcOH eluent to afford colourless oil. 1 mL of DCM was added, the mixture was sonicated, centrifuged and the supernatant was separated. Then 1 mL of DCM and 1 mL of Et$_2$O was added, the mixture was sonicated causing a formation of white precipitate. The mixture was centrifuged and the supernatant was removed. The white solid left gave after drying 17 mg (43%, 0.04 mmol) of the product. $^1$H NMR (400 MHz, DMSO-d$_6$): δ 1.61-1.79 (m, 2H), 1.93-2.11 (m, 2H), 2.27 (s, 3H), 2.49-2.64 (m, 1H), 2.71-2.81 (m, 1H), 2.82-2.91 (m, 1H), 4.75 (s, 2H), 7.12 (d, J=8.4 Hz, 2H), 7.30-7.46 (m, 4H), 7.72-7.82 (m, 2H). $^{13}$C NMR (151 MHz, DMSO-d$_6$): δ 20.9, 27.2, 30.0, 37.3, 46.3, 76.1, 121.7, 127.2, 128.3, 129.7, 130.0, 130.2, 132.9, 133.6, 139.7, 150.4, 168.1, 168.8, 169.2, 175.9. MS (ESI) m/z (%): 452 (100, [M+Na]$^+$). HRMS (ESI): [M–H] (C$_{22}$H$_{22}$O$_8$N) calc. 452.13159, found 452.13162.

tert-Butyl 4-(5-(((4-acetoxybenzyl)oxy)amino)-2-(tert-butoxycarbonyl)-5-oxopentyl)benzoate [11]

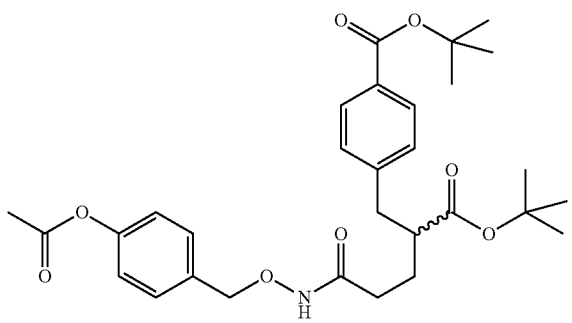 [SMILES: CC(=O)Oc1ccc(CONC(=O)CCC(Cc2ccc(C(=O)OC(C)(C)C)cc2)C(=O)OC(C)(C)C)cc1]

To a mixture of 5-(tert-butoxy)-4-(4-(tert-butoxycarbonyl)benzyl)-5-oxopentanoic acid 4 (3.08 g, 8.15 mmol), EDC·HCl (2.34 g, 12.2 mmol, 1.5 eq), and DMAP (50 mg, 0.41 mmol, 0.05 eq) in DMF (60 mL) were added i-Pr$_2$NEt (4.28 mL, 24.4 mmol, 3 eq) and the filtrate containing 4-(aminooxymethyl)phenyl acetate 10 prepared as above (theoretically 2.21 g, 12.2 mmol, 1.5 eq) at once at rt under an argon atmosphere. The mixture was stirred at rt for 3 h. Then water (100 mL) was added and the mixture was extracted with EtOAc (120 mL×3). The combined organic extracts were washed water (100 mL×3), dried over MgSO$_4$, and concentrated. The residue was chromatographed on a silica gel column (hexanes/EtOAc, 1:1) to afford a yellowish oil containing a solid. The mixture was sonicated in EtOAc (5 mL×5), and then with hexanes (25 mL). The suspension was kept still for 10 min for the recipitate to settle, and the supernatant was separated. The combined supernatants were concentrated to give 881 mg of 11 as a yellowish oil (20% yield, 1.63 mmol): $^1$H NMR (CDCl$_3$) δ 1.32 (s, 9H), 1.58 (s, 9H), 1.81-1.93 (m, 2H), 1.96-2.21 (m, 2H), 2.30 (s, 3H), 2.54-2.66 (m, 1H), 2.70-2.80 (m, 1H), 2.88-2-.98 (m, 1H), 4.73-4.94 (m, 2H), 7.08 (d, J=8.1 Hz, 2H), 7.20 (d, J=7.9 Hz, 2H), 7.39 (d, J=7.7 Hz, 2H), 7.88 (d, J=8.3 Hz, 2H). $^{13}$C NMR (CDCl$_3$) δ 21.2, 27.8, 28.0, 28.2, 30.8, 38.4, 47.2, 77.5, 80.9, 81.2, 121.8, 128.8, 129.5, 130.2, 130.4, 133.0, 143.8, 150.9, 165.8, 169.5, 170.2, 173.9. HRMS (ESI): [M+Na]$^+$ m/z 564.25690 (calcd 564.25679 for C$_{30}$H$_{39}$O$_8$NNa).

4-(5-(((4-Acetoxybenzyl)oxy)amino)-2-carboxy-5-oxopentyl)benzoic acid JV2855 [12]

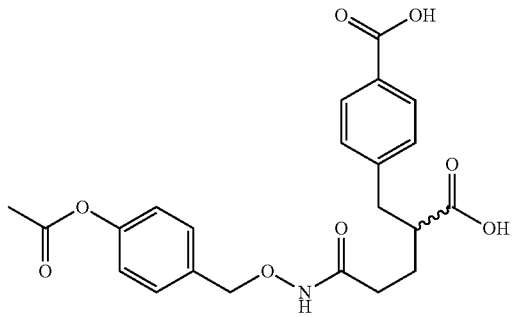 [SMILES: CC(=O)Oc1ccc(CONC(=O)CCC(Cc2ccc(C(=O)O)cc2)C(=O)O)cc1]

To a solution of 11 (365 mg, 0.67 mmol) in dichloromethane (10 mL) were added TFA (5 mL) and i-Pr$_3$SiH (276 μL, 1.35 mmol, 2 eq) under an argon atmosphere. The mixture was stirred at rt for 1 h, after which time no starting material was detected by TLC. Volatiles were removed on rotavap and residual TFA was co-evaporated with toluene (5 mL×3). EtOAc (1 mL) was then added to the residual material and the mixture was sonicated for 5 min resulting in white precipitate formation. The mixture was centrifuged and the supernatant was removed. The precipitate was sonicated in chloroform (2 mL), filtered, and washed with chloroform (5 mL) to give 165 mg of 12 as a white solid (57% yield, 0.38 mmol): 1H NMR (DMSO-d$_6$) δ 1.61-1.79 (m, 2H), 1.92-2.11 (m, 2H), 2.27 (s, 3H), 2.53-2.64 (m, 1H), 2.73-2.92 (m, 2H), 4.75 (s, 2H), 7.12 (d, J=8.5 Hz, 2H), 7.30 (d, J=8.3 Hz, 2H), 7.41 (d, J=8.5 Hz, 2H), 7.85 (d, J=8.3 Hz, 2H). $^{13}$C NMR (DMSO-d$_6$) δ 20.9, 27.1, 29.9, 37.3, 45.8, 76.1, 121.7, 128.8, 129.0, 129.3, 130.0, 133.6, 144.7, 150.4, 167.2, 168.7, 169.1, 175.6. HRMS (ESI): [M–H]– m/z 428.13480 (calcd 428.13509 for C$_{22}$H$_{22}$O$_8$N).

4-((Aminooxy)methyl)-5-methyl-1,3-dioxol-2-one [15]

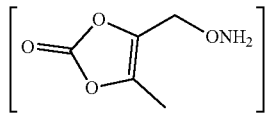

To a solution of 14 (218 mg, 0.79 mmol) in THF (5 mL) was added N₂H₄ (1.0M solution in THF, 793 µL, 0.79 mmol) under an argon atmosphere. A precipitate formed almost immediately, which slowly (5 min) disappeared leaving a homogeneous mixture and then rapidly a precipitate formed again. The mixture was stirred at rt for 1 h, then it was filtered through a microfilter syringe and the resulting filtrate containing 15 was used immediately in the subsequent reaction.

tert-Butyl 4-(2-(tert-butoxycarbonyl)-5-(((5-methyl-2-oxo-1,3-dioxol-4-yl)methoxy)amino)-5-oxopentyl)benzoate [16]

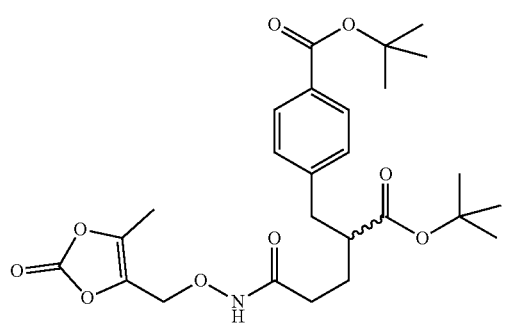 [SMILES: Cc1oc(=O)oc1CONC(=O)CCC(Cc1ccc(C(=O)OC(C)(C)C)cc1)C(=O)OC(C)(C)C]

To a solution of 4 (200 mg, 0.53 mmol) in THF (10 mL) were added triethylamine (89 µL, 0.63 mmol, 1.2 eq) and ethyl chloroformate (63 µL, 0.63 mmol, 1.2 eq). The mixture was stirred at rt for 1.5 h, then the filtrate containing prepared above was added at once. The mixture was stirred at rt for 16 h. Water (30 mL) was then added and the mixture was extracted with EtOAc (100 mL×3), dried over MgSO₄, and concentrated. The residual material was chromatographed on a silica gel column (hexanes/EtOAc, 1:1) to afford 104 mg of 16 as a yellowish oil (39% yield, 0.21 mmol): $^1$H NMR (CDCl₃) δ 1.35 (s, 9H), 1.58 (s, 9H), 1.81-1.94 (m, 2H), 2.05-2.26 (m, 2H), 2.13 (s, 3H), 2.56-2.66 (m, 1H), 2.76 (dd, J=6.3, 13.8, Hz, 1H), 2.95 (dd, J=8.8, 13.8, Hz, 1H), 4.67 (s, 2H), 7.20 (d, J=8.2 Hz, 2H), 7.88 (d, J=8.1 Hz, 2H). $^{13}$C NMR (CDCl₃) δ 9.5, 27.7, 28.1, 28.3, 30.7, 38.5, 47.3, 65.4, 81.1, 81.4, 128.9, 129.7, 130.4, 133.7, 141.1, 143.8, 152.3, 165.8, 168.8, 174.0. HRMS (ESI): [M+Na]⁺ m/z 528.22055 (calcd 528.22040 for C₂₆H₃₅O₉NNa).

4-(2-Carboxy-5-(((5-methyl-2-oxo-1,3-dioxol-4-yl)methoxy)amino)-5-oxopentyl)benzoic acid JV2925 [17]

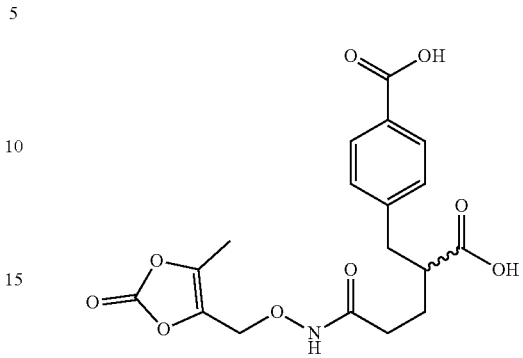

To a solution of 16 (74 mg, 0.15 mmol) in dichloromethane (5 mL) were added TFA (1 mL) and i-Pr₃SiH (60 µL, 0.29 mmol, 2 eq) under an argon atmosphere. The mixture was stirred at rt for 30 min Volatiles were removed on rotavap, and residual TFA was co-evaporated with toluene (2 mL×2). The residual material was sonicated in chloroform (1 mL), filtered, and washed with chloroform (3 mL) to give 35 mg of 17 as a white solid (61% yield, 0.09 mmol): $^1$H NMR (CDCl₃) δ 1.62-1.74 (m, 2H), 1.91-2.10 (m, 2H), 2.05 (s, 3H), 2.54-2.63 (m, 1H), 2.74-2.93 (m, 2H), 4.59 (s, 2H), 7.31 (d, J=7.8 Hz, 2H), 7.85 (d, J=7.9 Hz, 2H). $^{13}$C NMR (CDCl₃) δ 8.7, 27.0, 27.6, 29.9, 37.3, 45.8, 63.9, 128.8, 129.0, 129.3, 133.5, 140.9, 144.6, 152.1, 167.2, 168.8, 175.5. HRMS (ESI): [M−H]− m/z 392.09845 (calcd 392.09870 for C₁₈H₁₈O₉N).

3,5-Dimethyladamantan-1-amine

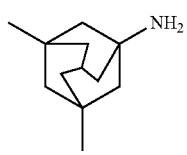

Memantine hydrochloride (200 mg, 0.92 mmol) was placed in a rbf and 4 mL of water was added. NaOH (375 mg, 9.18 mmol, 10 eq) in 4 mL of water was added dropwise (2 min). An oil formed immediately. The mixture was then extracted 3× with 30 mL of DCM, dried with MgSO₄, filtered and volatiles were removed affording 130 mg (79%, 0.73 mol) of colourless oil. The NMR spectrum was in accordance with literature. *Org. Lett.* 2015, 17 (19), 4702-4705.

1-Isocyanato-3,5-dimethyladamantane

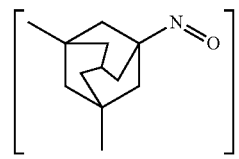

Triphosgene (49 mg, 0.16 mmol, 0.35 eq) was placed in a Schlenk flask and put under an argon atmosphere. 5 mL of THF was added dissolving it followed by iPr$_2$NEt (89 µL, 0.51 mmol, 1.1 eq) and memantine (83 mg, 0.46 mmol). The mixture was stirred overnight (16 h).

tert-Butyl 4-(2-(tert-butoxycarbonyl)-5-((((3,5-dimethyladamantan-1-yl)carbamoyl)oxy)amino)-5-oxopentyl)benzoate

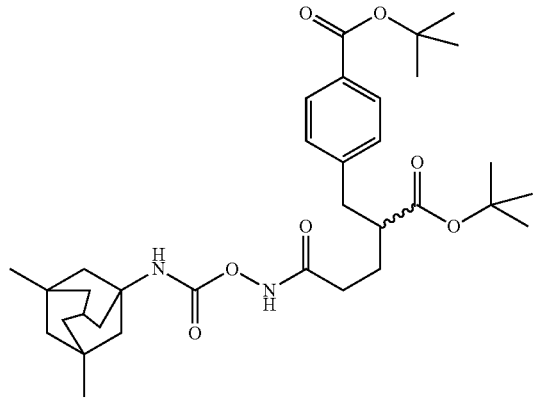 [SMILES: CC12CC3CC(C)(C1)CC(NC(=O)ONC(=O)CCC(Cc1ccc(C(=O)OC(C)(C)C)cc1)C(=O)OC(C)(C)C)(C3)C2]

tert-Butyl 4-(2-(tert-butoxycarbonyl)-5-(hydroxyamino)-5-oxopentyl)benzoate (200 mg, 0.51 mmol, 1.1 eq) and iPr$_2$NEt (89 µL, 0.51 mmol, 1.1 eq) were added to the solution of previously prepared 1-isocyanato-3,5-dimethyladamantane. The mixture was stirred over the weekend (48 h), then 30 mL of water was added and it was extracted 3× with 100 mL of AcOEt, dried with MgSO$_4$, filtered and volatiles were removed. The resulting oil was chromatographed on silica (2.5×17 cm, eluent hex/AcOEt 5:1) to afford 64 mg (23%, 0.11 mmol) of yellowish oil slowly solidifying to a yellowish solid. $^1$H NMR (400 MHz, CDCl$_3$): δ 0.86 (s, 6H), 1.15 (s, 2H), 1.23-1.34 (m, 8H), 1.34 (s, 9H), 1.58 (s, 9H), 1.78 (d, J=3.2 Hz, 2H), 1.86-1.97 (m, 2H), 2.13-2.17 (m, 1H), 2.18-2.37 (m, 2H), 2.71-2.86 (m, 2H), 2.87-2.99 (m, 1H), 7.23 (d, J=8.3 Hz, 2H), 7.88 (d, J=8.3 Hz, 1H). $^{13}$C NMR (151 MHz, CDCl$_3$): δ 27.9, 28.1, 28.4, 29.8, 30.1, 30.2, 30.8, 32.6, 38.5, 40.2, 42.6, 47.0, 47.6, 50.6, 53.7, 80.9, 81.3, 129.0, 129.6, 130.3, 144.0, 165.9, 174.1. MS (ESI) m/z (%):1219 (100, [2M+Na]$^+$), 621 (62, [M+Na]$^+$). HRMS (ESI): [M+Na] (C$_{34}$H$_{50}$O$_7$N$_2$Na) calc. 621.35102, found 621.35083.

4-(2-Carboxy-5-((((3,5-dimethyladamantan-1-yl)carbamoyl)oxy)amino)-5-oxopentyl)benzoic acid JV2928 [41]

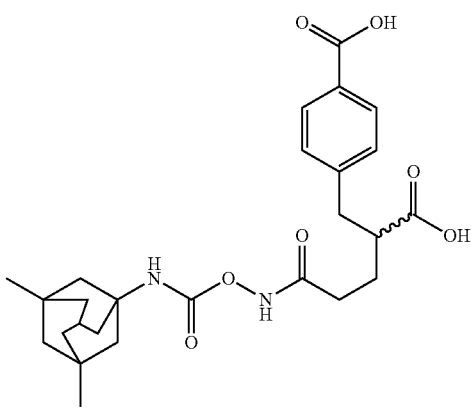 [SMILES: CC12CC3CC(C)(C1)CC(NC(=O)ONC(=O)CCC(Cc1ccc(C(=O)O)cc1)C(=O)O)(C3)C2]

tert-Butyl 4-(2-(tert-butoxycarbonyl)-5-((((3,5-dimethyladamantan-1-yl)carbamoyl)oxy)amino)-5-oxopentyl)benzoate (64 mg, 0.11 mmol) was placed in a Schlenk flask and put under an argon atmosphere. 5 mL of DCM was added dissolving it followed by 1 mL of TFA and TIS (44 µL, 0.21 mmol, 2 eq). The mixture was stirred at rt for 30 min, volatiles were then removed on rotavap, and the remaining TFA was removed by repeating twice: addition of 2 mL of toluene and volatiles removal on rotavap. The obtained solid was sonicated in 1 mL of CHCl$_3$, filtered and washed with additional 3 mL of CHCl$_3$. The product was obtained as white solid (20 mg, 38%, 0.04 mmol). $^1$H NMR (400 MHz, CDCl$_3$): δ 0.81 (s, 6H), 1.09 (s, 2H), 1.18-1.35 (m, 5H), 1.43-4.57 (m, 4H), 1.65-1.78 (m, 4H), 1.99-2.22 (m, 3H), 2.59-2.68 (m, 1H), 2.77-2.93 (m, 2H), 7.32 (d, J=8.1 Hz, 2H), 7.85 (d, J=8.2 Hz, 2H). $^{13}$C NMR (151 MHz, CDCl$_3$): δ 27.0, 27.6, 29.5, 29.7, 30.0, 31.9, 37.2, 42.1, 45.6, 47.0, 50.1, 52.0, 128.8, 129.1, 129.3, 144.7, 152.6, 167.2, 169.3, 175.6. MS (ESI) m/z (%): 485 (100, [M−H]$^+$). HRMS (ESI): [M−H] (C$_{26}$H$_{33}$O$_7$N$_2$) calc. 485.22932, found 485.22909.

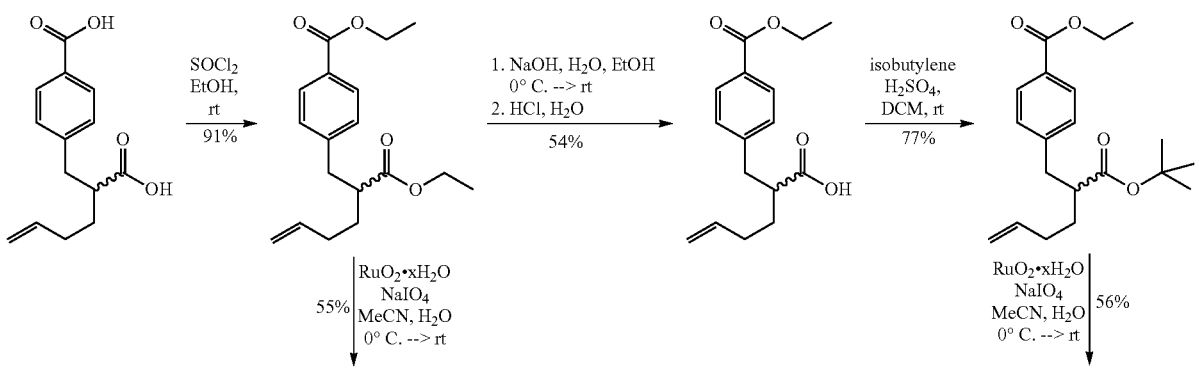

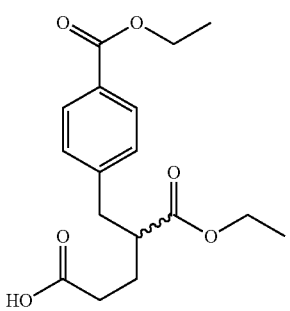
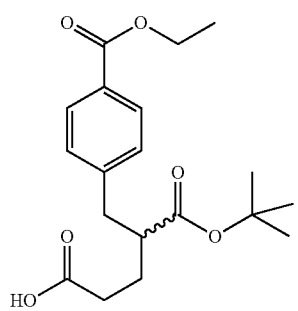

Ethyl 4-(2-(ethoxycarbonyl)hex-5-en-1-yl)benzoate [18]

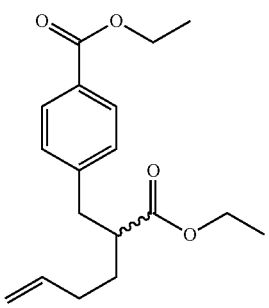 [SMILES: C=CCCC(Cc1ccc(C(=O)OCC)cc1)C(=O)OCC]

To a solution of 2 (1.00 g, 4.03 mmol) in ethanol (20 mL) was dropwise added SOCl$_2$ (1.77 mL, 24.4 mmol) at 0° C. over 10 min. The mixture was stirred at rt for 24 h. Volatiles were then removed on rotavap and the residual material was chromatographed on a silica gel column (hexanes/EtOAc, 6:1) to afford 1.12 g of 18 as a yellow oil (91% yield, 3.68 mmol): $^1$H NMR (CDCl$_3$) δ 1.14 (t, J=7.1 Hz, 3H), 1.38 (t, J=7.1 Hz, 3H), 1.52-1.62 (m, 1H), 1.72-1.83 (m, 1H), 1.98-2.15 (m, 2H), 2.64-2.73 (m, 2H), 2.80 (dd, J=13.6, 6.4 Hz, 1H), 2.97 (dd, J=13.5, 8.8 Hz, 1H), 3.98-4.11 (m, 2H), 4.36 (q, J=7.1 Hz, 2H), 4.94-5.04 (m, 2H), 5.68-5.80 (m, 1H), 7.22 (d, J=8.3 Hz, 2H), 7.94 (d, J=8.3 Hz, 2H). $^{13}$C NMR (CDCl$_3$) δ 14.3, 14.5, 31.4, 31.5, 38.5, 46.8, 60.5, 61.0, 115.5, 128.8, 129.0, 129.8, 137.6, 144.8, 166.7, 175.2. HRMS (ESI): [M+Na]$^+$ m/z 327.15670 (calcd 327.15668 for C$_{18}$H$_{24}$O$_4$Na).

5-Ethoxy-4-(4-(ethoxycarbonyl)benzyl)-5-oxopentanoic acid [24]

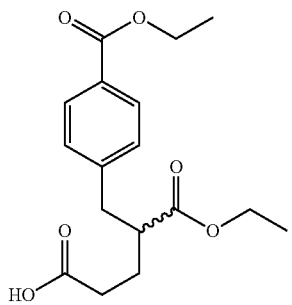

To a solution of 18 (1.00 g, 3.29 mmol) in acetonitrile (50 mL) and water (50 mL) was added RuO$_2$ hydrate (66 mg, 0.49 mmol) followed by addition of NaIO$_4$ (7.04 g, 32.85 mmol) at 0° C. The mixture was stirred at 0° C. for 10 min and at rt for 18 h. The reaction mixture was then filtered through a pad of Celite and washed with additional acetonitrile. The volatile solvents were then removed on rotavap and the mixture was extracted with EtOAc (150 mL×3). The combined organic extracts were dried over MgSO$_4$ and concentrated. The residual material was chromatographed on a silica gel column (hexanes/EtOAc, 1:1 containing 1% AcOH) to give 579 mg of 24 as a colorless oil (55%, 1.80 mmol): $^1$H NMR (CDCl$_3$) δ 1.15 (t, J=7.1 Hz, 3H), 1.38 (t, J=7.1 Hz, 3H), 1.81-2.02 (m, 2H), 2.30-2.51 (m, 2H), 2.69-2.78 (m, 1H), 2.79-3.05 (m, 2H), 4.06 (qd, J=7.1, 1.4 Hz, 2H), 4.36 (q, J=7.1 Hz, 2H), 7.23 (d, J=8.3 Hz, 2H), 7.95 (d, J=8.4 Hz, 2H). $^{13}$C NMR (CDCl$_3$) δ 14.3, 14.5, 26.8, 31.7, 38.5, 46.4, 60.8, 61.0, 129.0, 129.0, 129.9, 144.2, 166.7, 174.5, 178.6. HRMS (ESI): [M+Na]$^+$ m/z 345.13093 (calcd 345.13086 for C$_{17}$H$_{22}$O$_6$Na).

2-(4-(Ethoxycarbonyl)benzyl)hex-5-enoic acid [19]

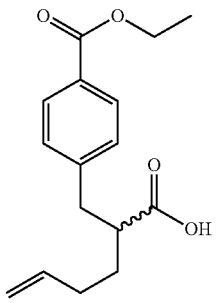 [SMILES: C=CCCC(Cc1ccc(C(=O)OCC)cc1)C(=O)O]

To a solution of 18 (500 mg, 1.64 mmol) in EtOH (20 mL) was dropwise added a solution of NaOH (74 mg, 1.81 mmol, 1.1 eq) in water (10 mL) over 10 min at 0° C. The mixture was stirred at 0° C. for 3 h and at rt for 68 h. Volatiles were removed on rotavap, and the residue was acidified with concentrated HCl to pH~1 at at 0° C. The mixture was extracted with EtOAc (100 mL×3), dried over MgSO$_4$, and concentrated. The residual material was chromatographed on a silica gel column (hexanes/EtOAc, 1:1) to afford 243 mg of 19 as a yellowish solid (54% yield, 0.75 mmol): $^1$H NMR (CDCl$_3$) δ 1.14 (t, J=7.2 Hz, 1H), 1.53-1.64 (m, 1H), 1.74-1.85 (m, 1H), 1.99-2.17 (m, 2H), 2.65-2.75 (m, 2H), 2.83 (dd, J=13.6, 6.2 Hz, 1H), 3.00 (dd, J=13.6, 8.9 Hz, 1H), 3.99-4.10 (m, 2H), 4.95-5.06 (m, 2H), 5.69-5.82 (m, 1H), 7.27 (d, J=8.3 Hz, 2H), 8.02 (d, J=8.2 Hz, 2H). $^{13}$C NMR (CDCl$_3$) δ 14.3, 31.5, 31.5, 38.6, 46.8, 60.5, 115.8, 127.6, 129.2, 130.5, 137.6, 146.0, 172.0, 175.2. HRMS (ESI): [M−H]− m/z 275.12885 (calcd 275.12888 for C$_{16}$H$_{19}$O$_4$).

Ethyl 4-(2-(tert-butoxycarbonyl)hex-5-en-1-yl)benzoate [20]

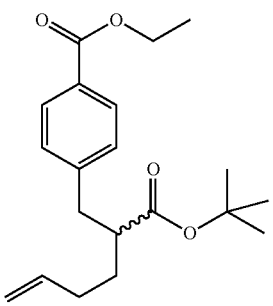 [SMILES: C=CCCC(Cc1ccc(C(=O)OCC)cc1)C(=O)OC(C)(C)C]

To a solution of 19 (243 mg, 0.88 mmol) in dichloromethane 0 (30 mL) were added isobutylene (10 mL) and H$_2$SO$_4$ (49 μL, 0.88 mmol) at −78° C. The flask was sealed and the mixture was stirred at rt for 40 h. The mixture was cooled to −78° C. again and poured into a saturated solution of NaHCO$_3$. After warming up to rt, dichloromethane was removed on rotavap and the mixture was extracted with EtOAc (80 mL×3). The combined organic extracts were dried over MgSO$_4$ and concentrated. The residual material was chromatographed on a silica gel column (hexanes/EtOAc, 6:1) to afford 225 mg of 20 as a colorless oil (77% yield, 0.68 mmol): $^1$H NMR (CDCl$_3$) δ 1.16 (t, J=7.1 Hz, 3H), 1.51-1.57 (m, 1H), 1.58 (s, 9H), 1.71-1.82 (m, 1H), 1.98-2.15 (m, 2H), 2.62-2.72 (m, 1H), 2.79 (dd, J=13.5, 6.5 Hz, 1H), 2.97 (dd, J=13.6, 8.6 Hz, 1H), 3.99-4.13 (m, 2H), 4.93-5.04 (m, 2H), 5.68-5.80 (m, 1H), 7.20 (d, J=8.3 Hz, 2H), 7.89 (d, J=8.2 Hz, 1H). $^{13}$C NMR (CDCl$_3$): δ 14.3, 28.3, 31.4, 31.5, 38.5, 46.8, 60.5, 81.0, 115.5, 128.9, 129.7, 130.3, 137.7, 144.3, 165.9, 175.2. HRMS (ESI): [M+Na]$^+$ m/z 355.18804 (calcd 355.18798 for C$_{20}$H$_{28}$O$_4$Na).

5-(tert-Butoxy)-4-(4-(ethoxycarbonyl)benzyl)-5-oxopentanoic acid [21]

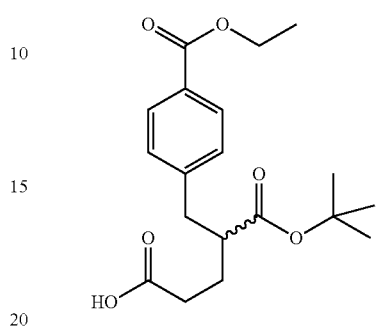

To a solution of 20 (225 mg, 0.68 mmol) in acetonitrile (15 mL) and water (15 mL) was added RuO$_2$ hydrate (14 mg, 0.10 mmol) followed by addition of NaIO$_4$ (1.45 g, 6.77 mmol) at 0° C. The mixture was stirred at 0° C. for 15 min and at rt for 6 h, after which no starting material was seen on TLC. The HO reaction mixture was then filtered through a pad of Celite and washed with additional acetonitrile. The solvents were then removed on rotavap and the residual material was extracted with EtOAc (100 mL×3). The combined organic extracts were dried over MgSO$_4$ and concentrated. The residual material was chromatographed on a silica gel column (hexanes/EtOAc, 1:1 containing 1% AcOH) to give 132 mg of 21 as a colorless oil (56% yield, 0.38 mmol): $^1$H NMR (CDCl$_3$) δ 1.16 (t, J=7.1 Hz, 1H), 1.58 (s, 9H), 1.80-2.00 (m, 2H), 2.30-2.49 (m, 2H), 2.69-2.77 (m, 1H), 2.81 (dd, J=13.5, 6.6 Hz, 1H), 3.01 (dd, J=13.5, 8.2 Hz, 1H), 4.01-4.13 (m, 2H), 7.21 (d, J=8.3 Hz, 2H), 7.90 (d, J=8.3 Hz, 2H). $^{13}$C NMR (CDCl$_3$) δ 14.3, 26.7, 28.3, 31.6, 38.4, 46.4, 60.8, 81.1, 128.9, 129.7, 130.5, 143.7, 165.8, 174.5, 178.3. HRMS (ESI): [M+Na]$^+$ m/z 373.16211 (calcd 373.16216 for C$_{19}$H$_{26}$O$_6$Na.

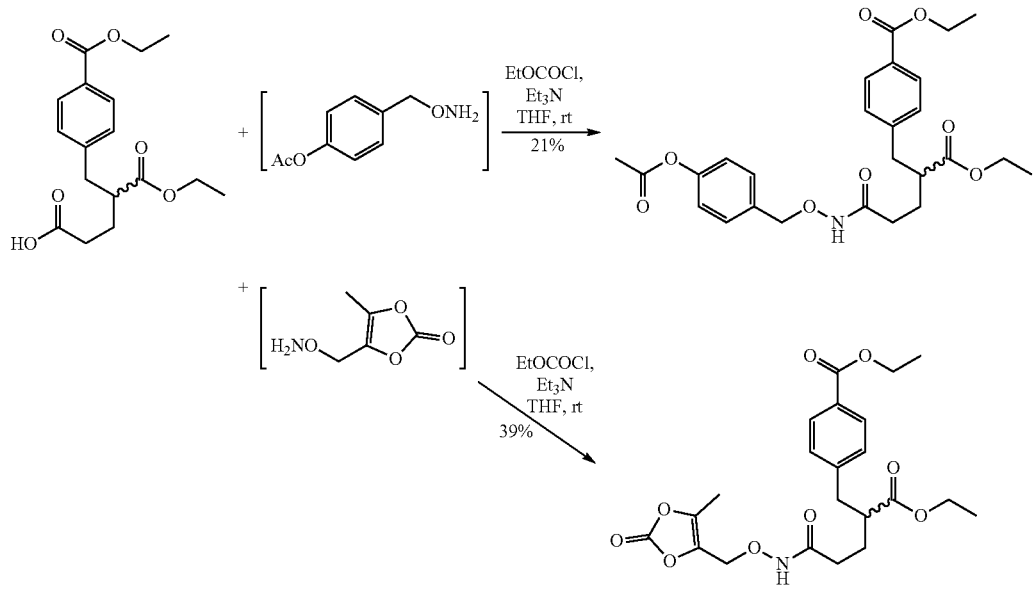

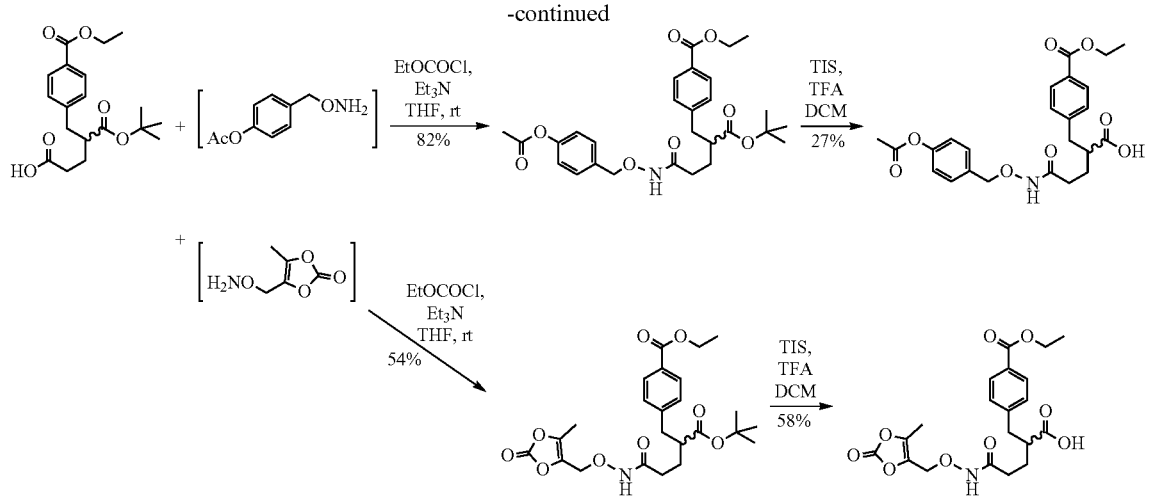

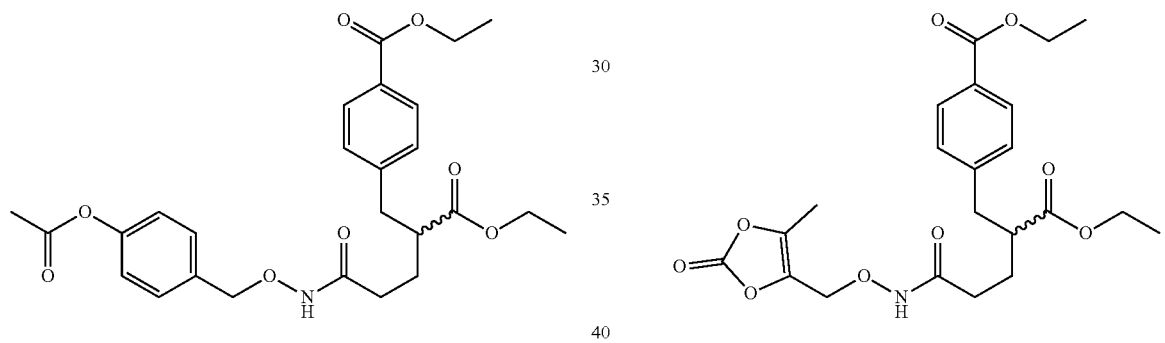

Ethyl 4-(5-(((4-acetoxybenzyl)oxy)amino)-2-(ethoxycarbonyl)-5-oxopentyl)benzoate JV2946 [25]

Ethyl 4-(2-(ethoxycarbonyl)-5-(((5-methyl-2-oxo-1,3-dioxol-4-yl)methoxy)amino)-5-oxopentyl)benzoate JV2947 [42]

A solution of 24 (100 mg, 0.31 mmol) in THF (5 mL) were added triethylamine (57 μL, 0.40 mmol, 1.3 eq) and ethyl chloroformate (40 μL, 0.40 mmol, 1.3 eq). After stirring at rt for 1.5 h, a freshly prepared THF solution of 10 (theoretically 84 mg, 0.46 mmol) was added to the mixture. The mixture was stirred at rt for 14 h, quenched with water (50 mL), and extracted EtOAc (100 mL×3). The combined organic extracts were dried over MgSO$_4$ and concentrated. The residual material was chromatographed on a silica gel column (hexanes/EtOAc, 1:1) to afford 55 mg, which was further purified by preparative HPLC to give 31 mg of 25 as a colorless oil (21%, 0.06 mmol): $^1$H NMR (CDCl$_3$) δ 1.12 (t, J=7.1 Hz, 3H), 1.38 (t, J=7.1 Hz, 3H), 1.84-1.97 (m, 2H), 2.05-2.19 (m, 2H), 2.30 (s, 3H), 2.64-2.76 (m, 1H), 2.81 (dd, J=13.6, 6.1 Hz, 1H), 2.99 (dd, J=13.6, 8.7 Hz, 1H), 4.04 (q, J=7.2 Hz, 2H), 4.36 (q, J=7.1 Hz, 2H), 4.71-4.94 (m, 2H), 7.09 (d, J=8.1 Hz, 2H), 7.21 (d, J=8.0 Hz, 2H), 7.38 (d, J=8.1 Hz, 2H), 7.94 (d, J=8.4 Hz, 2H). $^{13}$C NMR (CDCl$_3$) δ 14.3, 14.5, 21.3, 30.9, 38.5, 60.8, 61.0, 77.4, 122.0, 128.9, 129.0, 129.9, 130.5, 134.4, 144.2, 151.2, 166.7, 169.6, 174.6. HRMS (ESI): [M+H]$^+$ m/z 486.21229 (calcd 486.21224 for C$_{26}$H$_{32}$O$_8$N).

5-Ethoxy-4-(4-(ethoxycarbonyl)benzyl)-5-oxopentanoic acid (100 mg, 0.31 mmol) was placed in a Schlenk flask and put under an argon atmosphere. THF (5 mL) was added followed by Et$_3$N (57 μL, 0.40 mmol, 1.3 eq) and EtOCOCl (40 μL, 0.40 mmol, 1.3 eq). A white precipitate formed immediately. The mixture was stirred at rt for 1.5 h, then a solution of freshly prepared 4-((aminooxy)methyl)-5-methyl-1,3-dioxol-2-one (theoretically 68 mg, 0.46 mmol, 1.5 eq) was added. The mixture was stirred at rt overnight (14 h). The reaction was quenched with water (50 mL) and extracted 3× with 100 mL of AcOEt. The combined organic layers were dried with MgSO$_4$, filtered and volatiles were removed on rotavap. The residue was chromatographed on silica (2×18 cm, eluent hex/AcOEt 1:1) to afford 54 mg (39%, 0.12 mmol) of colourless oil. $^1$H NMR (400 MHz, CDCl$_3$): δ 1.15 (t, J=7.1 Hz, 3H), 1.38 (t, J=7.1 Hz, 3H), 1.88-1.96 (m, 2H), 2.05-2.29 (m, 2H), 2.13 (s, 3H), 2.66-2.76 (m, 1H), 2.82 (dd, J=13.6, 6.4 Hz, 1H), 3.00 (dd, J=13.6, 8.5 Hz, 1H), 4.06 (q, J=7.2 Hz, 2H), 4.35 (q, J=7.1 Hz, 2H), 4.58-4.72 (m, 2H), 7.22 (d, J=8.3 Hz, 2H), 7.94 (d, J=8.3 Hz, 2H). $^{13}$C NMR (151 MHz, CDCl$_3$): δ 9.4, 14.3, 14.5, 27.4, 30.8, 38.5, 46.6, 60.9, 61.1, 65.4, 128.3, 129.0, 129.9, 133.3, 141.2, 144.1, 152.3, 166.6, 170.8, 174.6. MS (ESI) m/z (%): 472 (100, [M+Na]$^+$), 450 (56, [M+H]$^+$). HRMS (ESI): [M+Na] (C$_{22}$H$_{27}$O$_9$NNa) calc. 472.15780, found 472.15744.

Ethyl 4-(5-(((4-acetoxybenzyl)oxy)amino)-2-(tert-butoxycarbonyl)-5-oxopentyl)benzoate [22]

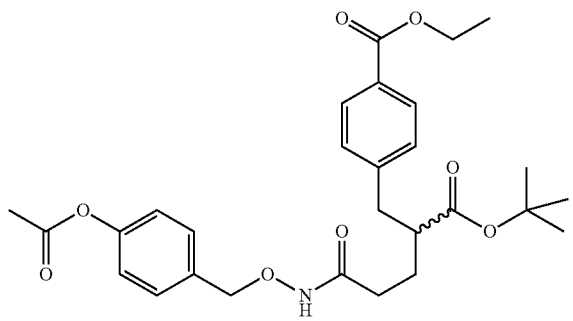 [SMILES: CCOC(=O)c1ccc(CC(CCC(=O)NOCc2ccc(OC(C)=O)cc2)C(=O)OC(C)(C)C)cc1]

A solution of 21 (65 mg, 0.19 mmol) in THF (10 mL) were added triethylamine (31 µL, 0.22 mmol, 1.2 eq) and ethyl chloroformate (22 µL, 0.22 mmol, 1.2 eq). After stirring at rt for 1.5 h, a freshly prepared THF solution of 10 (theoretically 50 mg, 0.28 mmol) was added to the mixture. The mixture was stirred at rt for 14 h, quenched with water (20 mL), and extracted EtOAc (70 mL×3). The combined organic extracts were dried over MgSO$_4$ and concentrated. The residual material was chromatographed on a silica gel column (hexanes/EtOAc, 1:1) to afford 78 mg of 22 as a colorless oil (82% yield, 0.15 mmol): $^1$H NMR (CDCl$_3$) δ 1.13 (t, J=7.1 Hz, 1H), 1.57 (s, 9H), 1.82-1.95 (m, 2H), 2.03-2.19 (m, 2H), 2.30 (s, 3H), 2.64-2.75 (m, 1H), 2.79 (dd, J=13.6, 6.3 Hz, 1H), 2.97 (dd, J=13.6, 8.6 Hz, 1H), 4.03 (q, J=7.1 Hz, 2H), 4.62-4.94 (m, 2H), 7.0d, J=8.1 Hz, 2H), 7.18 (d, J=8.1 Hz, 2H), 7.37 (d, J=8.1 Hz, 2H), 7.88 (d, J=8.4 Hz, 2H). $^{13}$C NMR (CDCl$_3$) δ 14.3, 21.2, 27.6, 28.3, 30.9, 38.4, 46.6, 60.7, 77.4, 81.0, 121.9, 128.9, 129.1, 129.7, 130.5, 133.1, 143.7, 151.1, 165.8, 169.5, 170.2, 174.6. HRMS (ESI): [M+Na]$^+$ m/z 536.22475 (calcd 536.22549 for C$_{28}$H$_{35}$O$_8$NNa).

Ethyl 4-(2-(tert-butoxycarbonyl)-5-(((5-methyl-2-oxo-1,3-dioxol-4-yl)methoxy)amino)-5-oxopentyl)benzoate

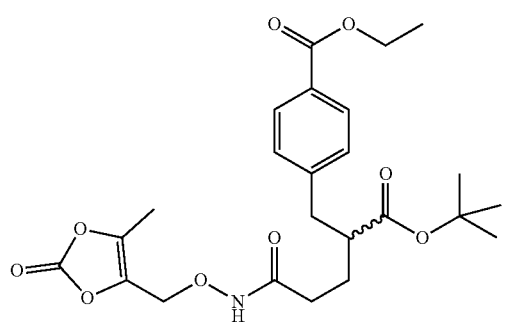 [SMILES: CCOC(=O)c1ccc(CC(CCC(=O)NOCc2oc(=O)oc2C)C(=O)OC(C)(C)C)cc1]

5-(tert-Butoxy)-4-(4-(ethoxycarbonyl)benzyl)-5-oxopentanoic acid (65 mg, 0.19 mmol) was placed in a Schlenk flask and put under an argon atmosphere. THF (10 mL) was added followed by Et$_3$N (31 µL, 0.22 mmol, 1.2 eq) and EtOCOCl (22 µL, 0.22 mmol, 1.2 eq). A white precipitate formed immediately. The mixture was stirred at rt for 1.5 h, then a solution of freshly prepared 4-((aminooxy)methyl)-5-methyl-1,3-dioxol-2-one (theoretically 40 mg, 0.28 mmol, 1.5 eq) was added. The mixture was stirred at rt overnight (14 h). The reaction was quenched with water (20 mL) and extracted 3× with 70 mL of AcOEt. The combined organic layers were dried with MgSO$_4$, filtered and volatiles were removed on rotavap. The residue was chromatographed on silica (2×18 cm, eluent hex/AcOEt 1:1) to afford 48 mg (54%, 0.10 mmol) of colourless oil. $^1$H NMR (400 MHz, CDCl$_3$): δ 1.17 (t, J=7.1 Hz, 3H), 1.58 (s, 9H), 1.87-1.95 (m, 2H), 2.06-2.26 (m, 2H), 2.13 (s, 3H), 2.64-2.76 (m, 1H), 2.81 (dd, J=13.6, 6.5 Hz, 1H), 3.00 (dd, J=13.6, 8.4 Hz, 1H), 4.07 (q, J=7.1 Hz, 2H), 4.66 (bs, 2H), 7.19 (d, J=8.4 Hz, 2H), 7.88 (d, J=8.3 Hz, 2H). $^{13}$C NMR (151 MHz, CDCl$_3$): δ 9.4, 13.4, 27.3, 28.3, 30.8, 38.4, 46.6, 60.9, 65.4, 81.1, 128.9, 129.8, 130.5, 133.6, 141.2, 143.6, 152.3, 165.8, 171.0, 174.6. MS (ESI) m/z (%): 500 (100, [M+Na]$^+$). HRMS (ESI): [M+Na] (C$_{24}$H$_{31}$O$_9$NNa) calc. 500.18910, found 500.18906.

5-(((4-Acetoxybenzyl)oxy)amino)-2-(4-(ethoxycarbonyl)benzyl)-5-oxopentanoic acid JV2956 [23]

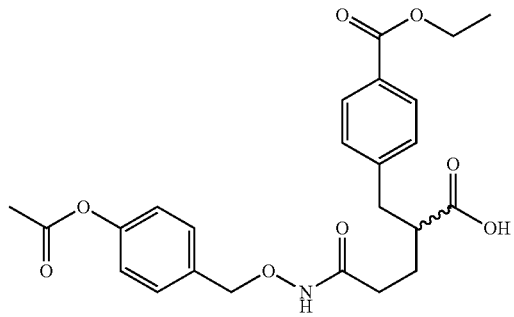 [SMILES: CCOC(=O)c1ccc(CC(CCC(=O)NOCc2ccc(OC(C)=O)cc2)C(=O)O)cc1]

To a solution of 22 (88 mg, 0.15 mmol) in dichloromethane (1 mL) were added i-Pr$_3$SiH (31 µL, 0.15 mmol) and TFA (0.5 mL) under an argon atmosphere. The mixture was stirred at rt for 1 h. Then volatiles were removed on rotavap H and TFA was removed by co-evaporating with toluene (1 mL×3). The residual material was purified by preparative HPLC to give 19 mg of 23 as a white hygroscopic solid (27%, 0.04 mmol): $^1$H NMR (DMSO-d$_6$) δ 1.05 (t, J=7.1 Hz, 3H), 1.66-1.79 (m, 2H), 1.92-2.05 (m, 2H), 2.27 (s, 3H), 2.62-2.71 (m, 1H), 2.84 (d, J=7.6 Hz, 2H), 3.97 (q, J=7.1 Hz, 2H), 4.76 (bs, 2H), 7.12 (d, J=8.5 Hz, 2H), 7.27 (d, J=8.3 Hz, 2H), 7.41 (d, J=8.5 Hz, 2H), 7.84 (d, J=8.2 Hz, 2H). $^{13}$C NMR (151 MHz, DMSO-d$_6$): δ 14.0, 20.9, 27.2, 29.8, 37.4, 45.8, 59.9, 76.1, 121.7, 129.0, 129.1, 129.3, 130.0, 133.6, 144.1, 150.4, 167.3, 168.6, 169.2, 174.0. HRMS (ESI): [M+Na]$^+$ m/z 458.18099 (calcd 458.18094 for C$_{24}$H$_{28}$O$_8$N).

2-(4-(Ethoxycarbonyl)benzyl)-5-(((5-methyl-2-oxo-1,3-dioxol-4-yl)methoxy)amino)-5-oxopentanoic acid JV2957 [43]

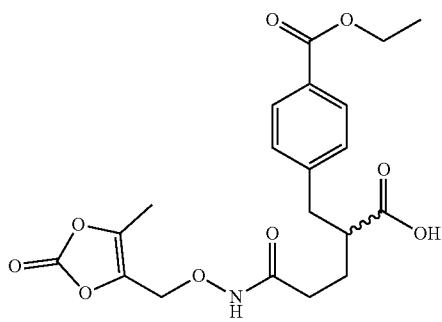 [SMILES: CCOC(=O)c1ccc(CC(CCC(=O)NOCc2oc(=O)oc2C)C(=O)O)cc1]

Ethyl 4-(2-(tert-butoxycarbonyl)-5-(((5-methyl-2-oxo-1,3-dioxol-4-yl)methoxy)amino)-5-oxopentyl)benzoate (48 mg, 0.10 mmol) was placed in a Schlenk flask and put under an argon atmosphere. DCM (1 mL) was added followed by TFA (m/z mL) and TIS (20 μL, 0.10 mmol). The mixture was stirred at rt for 1 h. Then volatiles were removed on rotavap and the residual TFA was removed by 3× adding 1 mL of toluene and its removal on rotavap. 1 mL of hex/AcOEt 1:1 mixture was added to the resulting oil, it was shortly sonicated, centrifuged and the supernatant was separated. This procedure with sonication was repeated twice more to afford 25 mg (58%, 0.06 mmol) of white solid. $^1$H NMR (400 MHz, DMSO-$d_6$): δ 1.05 (t, J=7.1 Hz, 3H), 1.72 (q, J=7.5 Hz, 2H), 1.90-2.03 (m, 2H), 2.05 (s, 3H), 2.62-2.74 (m, 1H), 2.85 (d, J=6.6 Hz, 2H), 3.98 (q, J=7.1 Hz, 2H), 4.60 (bs, 2H), 7.28 (d, J=8.3 Hz, 2H), 7.85 (d, J=8.2 Hz, 2H). $^{13}$C NMR (151 MHz, DMSO-$d_6$): δ 8.7, 14.0, 27.1, 29.7, 37.4, 45.8, 59.9, 63.9, 128.9, 129.0, 129.3, 133.5, 140.9, 144.2, 152.1, 167.2, 168.6, 174.0. MS (ESI) m/z (%): 444 (81, [M+Na]$^+$), 422 (100, [M+H]$^+$). HRMS (ESI): [M+Na] ($C_{20}H_{24}O_9N$) calc. 422.14456, found 422.14464.

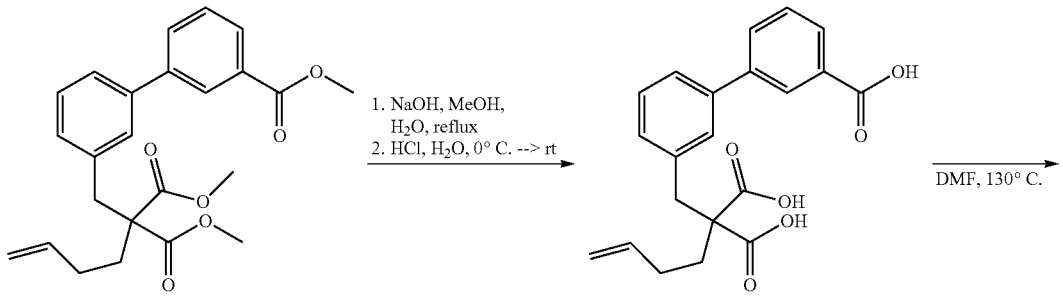

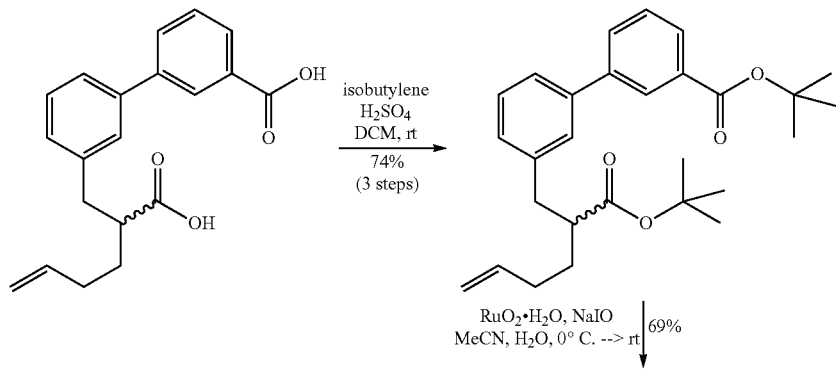

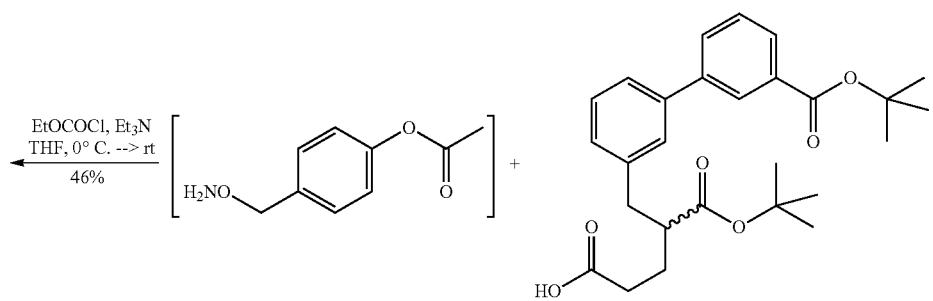

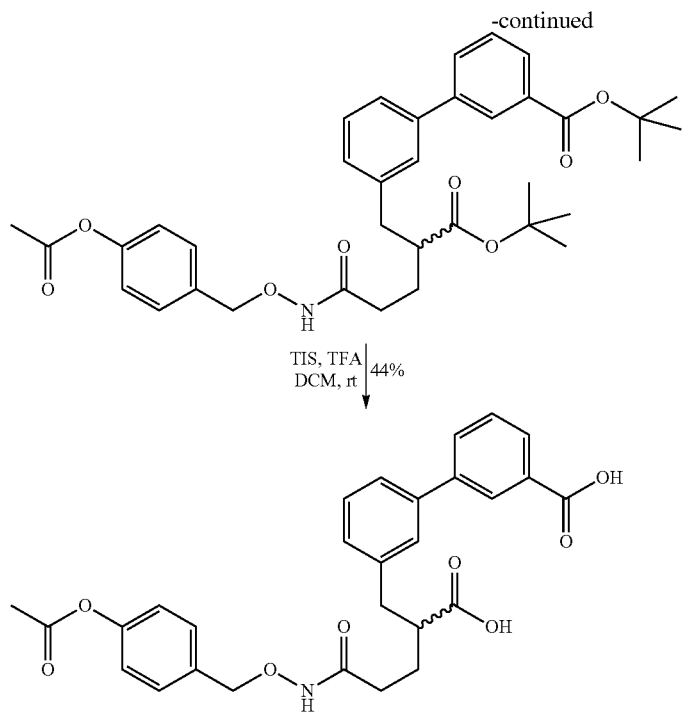

2-(But-3-en-1-yl)-2-((3'-carboxy-[1,1'-biphenyl]-3-yl)methyl)malonic acid

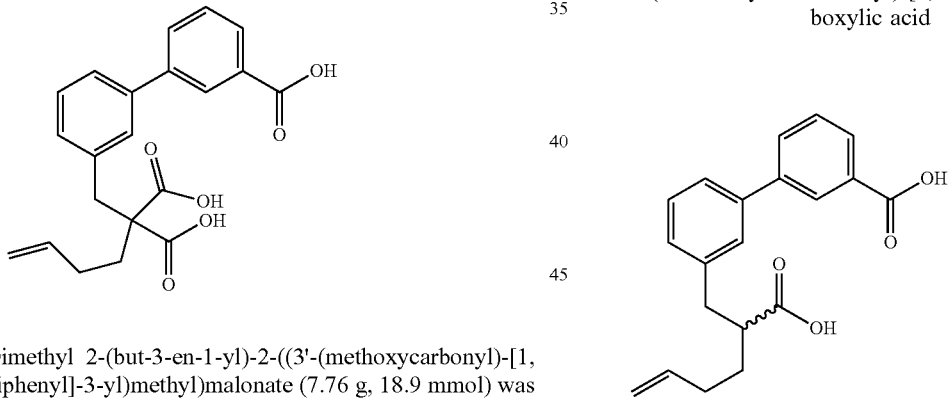

Dimethyl 2-(but-3-en-1-yl)-2-((3'-(methoxycarbonyl)-[1,1'-biphenyl]-3-yl)methyl)malonate (7.76 g, 18.9 mmol) was placed in a rbf equipped with a reflux condenser. 100 mL of MeOH was added, the mixture was homogenised and NaOH (7.71 g, 188.9 mmol, 10 eq) in 70 mL of water was added. The mixture was refluxed 24 h. After cooling down most MeOH was removed on rotavap, 70 mL of water was added and the mixture was cooled to 0° C. and acidified to pH~1 with conc. HCl (dropwise, 15 min). After warming up to rt it was extracted 3× with 150 mL of AcOEt, combined organic layers were dried with MgSO₄, filtered and volatiles were removed on rotavap giving 7.67 g of the crude product as white solid. It was used without further purification. ¹H NMR (400 MHz, CDCl₃): δ 1.61-1.75 (m, 2H), 2.03-2.15 (m, 2H), 3.21 (s, 2H), 4.92-4.98 (m, 1H), 5.01-5.10 (m, 1H), 5.74-5.87 (m, 1H), 7.18 (d, J=7.7 Hz, 1H), 7.40 (t, J=7.7 Hz, 1H), 7.44 (t, J=1.7 Hz, 1H), 7.53-7.57 (m, 1H), 7.60 (t, J=7.7 Hz, 1H), 7.82-7.89 (m, 1H), 7.94 (dt, J=7.7, 1.3 Hz, 1H), 8.15 (t, J=1.6 Hz, 1H). ¹³C NMR (151 MHz, CDCl₃): δ 28.1, 30.3, 37.1, 57.6, 115.1, 115.1, 125.3, 127.3, 128.3, 128.9, 129.3, 129.4, 131.2, 131.5, 137.5, 137.9, 139.1, 140.6, 167.2, 172.4.

3'-(2-Carboxyhex-5-en-1-yl)-[1,1'-biphenyl]-3-carboxylic acid

Crude 2-(but-3-en-1-yl)-2-((3'-carboxy-[1,1'-biphenyl]-3-yl)methyl)malonic acid (7.67 g) in a rbf was put under an argon atmosphere. DMF (150 mL) was added and the mixture was stirred at 130° C. for 4 h. After cooling down most DMF was removed on rotavap, 50 mL of water was added and the mixture was 3× extracted with 150 mL of AcOEt, dried, filtered OH and volatiles were removed on rotavap giving 8.09 g of colourless oil. It was used without further purification. H NMR (400 MHz, CDCl₃): δ 1.64-1.75 (m, 1H), 1.81.-1.93 (m, 1H), 2.12.-2.27 (m, 2H), 2.76-2.85 (m, 1H), 2.91 (dd, J=13.6, 6.0 Hz, 1H), 3.05 (dd, J=13.6, 8.8 Hz, 1H), 4.98-5.10 (m, 2H), 5.74-5.86 (m, 1H), 7.22 (d, J=7.5 Hz, 1H), 7.38 (t, J=7.6 Hz, 1H), 7.44-7.51 (m, 3H), 7.77-7.84 (m, 1H), 7.94-8.01 (m, 1H), 8.29 (t, J=1.8 Hz, 1H). ¹³C NMR (151 MHz, CDCl₃): δ 31.2, 31.5, 38.3, 47.2, 115.7, 125.4, 127.9, 128.5, 128.8, 129.1, 129.1, 129.2, 129.9, 132.4, 137.5, 139.7, 140.1, 141.5, 172.3, 182.1. MS (ESI) m/z (%): 323 (100, [M−H]−). HRMS (ESI): [M−H] ($C_{20}H_{19}O_4$) calc. 323.12888, found 323.12921.

tert-Butyl 3'-(2-(tert-butoxycarbonyl)hex-5-en-1-yl)-[1,1'-biphenyl]-3-carboxylate

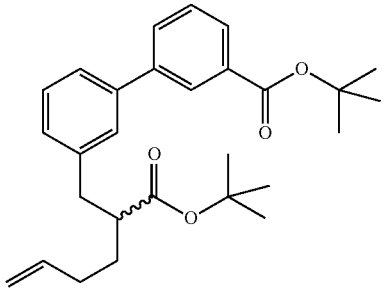 [SMILES: C=CCCC(Cc1cccc(-c2cccc(C(=O)OC(C)(C)C)c2)c1)C(=O)OC(C)(C)C]

Crude 3'-(2-carboxyhex-5-en-1-yl)-[1,1'-biphenyl]-3-carboxylic acid (8.09 g) was dissolved under an argon atmosphere in DCM (200 mL) and the solution was transferred to a pressure flask. The mixture was cooled to −78° C. and isobutylene (~18 mL) was condensed into the flask. $H_2SO_4$ (2.10 mL, 2 eq) was added, the flask was closed and the mixture was let warm and stirred at rt for 38 h. Then it was cooled to −78° C. and poured into saturated aqueous $NaHCO_3$ solution (100 mL). After warming up, DCM was removed on rotavap and the residue was extracted 3× with 250 ml of AcOEt. The combined organic layers were dried with $MgSO_4$ and filtered. After volatiles removal the residue was chromatographed on silica (6×18 cm, eluent hex/AcOEt 6:1) to afford 6.08 g (74%/3 steps, 13.9 mmol) of colourless oil. $^1H$ NMR (400 MHz, $CDCl_3$): δ 1.33 (s, 9H), 1.53-1.61 (m, 1H), 1.62 (s, 9H), 1.72-1.82 (m, 1H), 2.01-2.19 (m, 2H), 2.59-2.68 (m, 1H), 2.80 (dd, J=13.7, 6.4 Hz, 1H), 2.95 (dd, J=13.6, 8.9 Hz, 1H), 4.95-5.06 (m, 2H), 5.73-5.84 (m, 1H), 7.19 (d, J=7.6 Hz, 1H), 7.35 (t, J=7.6 Hz, 1H), 7.41-7.50 (m, 3H), 7.71-7.75 (m, 1H), 7.96 (dt, J=7.8, 1.5 Hz, 2H), 8.20 (t, J=1.8 Hz, 1H). $^{13}C$ NMR (151 MHz, $CDCl_3$): δ 28.1, 28.4, 31.7, 31.7, 38.9, 47.8, 80.4, 81.3, 115.3, 125.2, 128.0, 128.2, 128.3, 128.5, 128.7, 128.9, 131.2, 132.6, 138.0, 140.3, 140.4, 141.4, 165.9, 174.8. MS (ESI) m/z (%): 459 (100, [M+Na]+). HRMS (ESI): [M+Na] ($C_{28}H_{36}O_4Na$) calc. 459.25058, found 459.25059.

5-(tert-Butoxy)-4-((3'-(tert-butoxycarbonyl)-[1,1'-biphenyl]-3-yl)methyl)-5-oxopentanoic acid

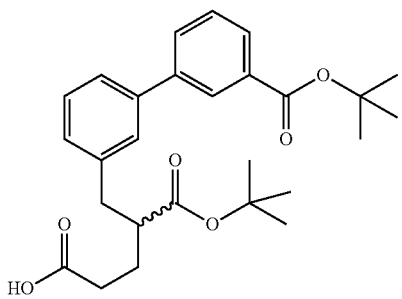 [SMILES: CC(C)(C)OC(=O)c1cccc(-c2cccc(CC(CCC(=O)O)C(=O)OC(C)(C)C)c2)c1]

tert-Butyl 3'-(2-(tert-butoxycarbonyl)hex-5-en-1-yl)-[1,1'-biphenyl]-3-carboxylate (6.08 g) was dissolved in acetonitrile (300 mL) and 300 mL of water was added. The mixture was cooled to 0° C. and $RuO_2·xH_2O$ (278 mg, 0.15 eq (anhydr.)) was added at once followed by portionwise (15 min) addition of $NaIO_4$ (29.85 g, 10 eq). The mixture was stirred overnight (14 h) while warming up to rt. Then it was filtered through a Celite pad washing the pad with additional MeCN. Most MeCN was removed on rotavap and the aqueous residue was extracted 3× with 300 mL AcOEt, dried, filtered. After volatiles removal the residue was chromatographed on silica (6×16 cm, eluent hex/AcOEt 1:1+1% AcOH) to afford 4.37 g (69%, 9.61 mmol) of dark brown transparent oil. $^1H$ NMR (400 MHz, $CDCl_3$): δ 1.33 (s, 9H), 1.62 (s, 9H), 1.83-2.01 (m, 2H), 2.33-2.52 (m, 2H), 2.65-2.74 (m, 1H), 2.82 (dd, J=13.7, 6.7 Hz, 1H), 3.00 (dd, J=13.7, 8.5 Hz, 1H), 7.19 (d, J=7.6 Hz, 1H), 7.36 (t, J=7.6 Hz, 1H), 7.41-7.50 (m, 3H), 7.70-7.75 (m, 1H), 7.93-7.98 (m, 1H), 8.20 (t, J=1.8 Hz, 1H). $^{13}C$ NMR (151 MHz, $CDCl_3$): δ 27.0, 28.1, 28.4, 31.8, 38.7, 47.4, 81.0, 81.4, 125.4, 128.0, 128.2, 128.3, 128.5, 128.8, 129.0, 131.2, 132.8, 139.7, 140.5, 141.4, 165.9, 174.2, 178.7. MS (ESI) m/z (%): 477 (100, [M+Na]+). HRMS (ESI): [M+Na] ($C_{27}H_{34}O_6Na$) calc. 477.22476, found 477.22479.

tert-Butyl 3'-(5-(((4-acetoxybenzyl)oxy)amino)-2-(tert-butoxycarbonyl)-5-oxopentyl)-[1,1'-biphenyl]-3-carboxylate

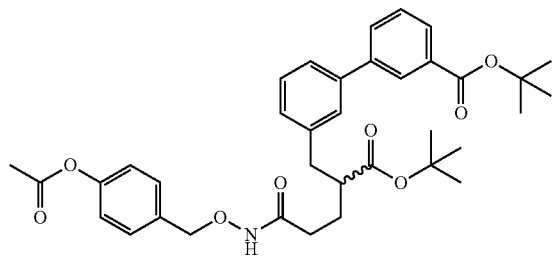 [SMILES: CC(=O)Oc1ccc(CONC(=O)CCC(Cc2cccc(-c3cccc(C(=O)OC(C)(C)C)c3)c2)C(=O)OC(C)(C)C)cc1]

5-(tert-Butoxy)-4-((3'-(tert-butoxycarbonyl)-[1,1'-biphenyl]-3-yl)methyl)-5-oxopentanoic acid (250 mg, 0.55 mmol) was placed in a Schlenk flask and put under an argon NH atmosphere. THF (10 mL) was added followed by $Et_3N$ (90 μL, 0.64 mmol, 1.1 eq). The mixture was cooled to 0° C. and EtOCOCl (65 μL, 0.66 mmol, 1.2 eq) was added. A white precipitate formed within a minute. The mixture was stirred at 0° C. for 1 h and at rt for 0.5 h. Then 4-((aminooxy)methyl)phenyl acetate prepared in situ in THF was added. The mixture was stirred at rt overnight (14 h). It was quenched with 30 mL of water and extracted with 3×100 mL of AcOEt, the combined organic layers were dried with $MgSO_4$, filtered and volatiles were removed on rotavap. The residue was chromatographed on silica (3×20 cm, eluent hex/AcoEt 1:1) to afford 143 mg (42%, 0.23 mmol) of yellowish oil. $^1H$ NMR (400 MHz, $CDCl_3$): δ 1.31 (s, 9H), 1.62 (s, 9H), 1.84-1.97 (m, 2H), 1.99-2.25 (m, 2H), 2.29 (s, 3H), 2.59-2.72 (m, 1H), 2.80 (dd, J=13.8, 6.1 Hz, 1H), 2.96 (dd, J=13.6, 8.9 Hz, 1H), 4.72-4.93 (m, 2H), 7.07 (d, J=8.1 Hz, 2H), 7.17 (d, J=7.5 Hz, 1H), 7.32-7.51 (m, 6H), 7.70-7.75 (m, 1H), 7.95 (dt, J=7.7, 1.4 Hz, 1H), 8.19 (t, J=1.8 Hz, 1H). $^{13}C$ NMR (151 MHz, $CDCl_3$): δ 21.3, 27.3, 28.1, 28.4, 31.1, 38.8, 47.7, 77.5, 81.1, 81.3, 121.9, 125.4, 128.0, 128.2, 128.3, 128.5, 128.8, 129.0, 130.4, 130.5, 131.2, 134.4, 139.7, 140.5, 141.3, 151.1, 165.9, 169.5, 170.4, 174.3. MS (ESI) m/z (%): 640 (100, [M+Na]$^+$), 618 (29, [M+H]$^+$). HRMS (ESI): [M−H] (C$_{36}$H$_{43}$O$_8$NNa) calc. 640.28809, found 640.28815.

3'-(5-(((4-Acetoxybenzyl)oxy)amino)-2-carboxy-5-oxopentyl)-[1,1'-biphenyl]-3-carboxylic acid JV3055 [44]

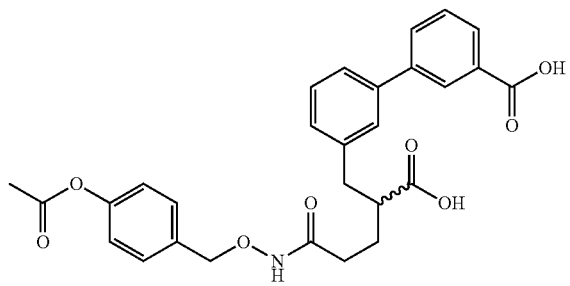 [SMILES: CC(=O)Oc1ccc(CONC(=O)CCC(Cc2cccc(-c3cccc(C(=O)O)c3)c2)C(=O)O)cc1]

tert-Butyl 3'-(5-(((4-acetoxybenzyl)oxy)amino)-2-(tert-butoxycarbonyl)-5-oxopentyl)-[1,1'-biphenyl]-3-carboxylate (1.19 g, 1.93 mmol) in a rbf was put under an argon atmosphere. DCM (40 mL) was added dissolving it followed by TIS (790 μL, 3.86 mmol, 2 eq) and TFA (8 mL). The mixture was stirred at rt for 1 h. Then volatiles were removed on rotavap and the residue of TFA was removed by 3× adding 5 mL of toluene and its rotavap removal. The resulting oil was then solidified by dissolving in chloroform and its rotavap removal. The residue was purified by HPLC giving the product after lyophilisation as a white fluffy solid (429 mg, 44%, 0.85 mmol). $^1$H NMR (400 MHz, DMSO-d$_6$): δ 1.60-1.82 (m, 2H), 1.93-2.12 (M, 2H), 2.26 (s, 3H), 2.58-2.72 (m, 1H), 2.86 (ddd, J=36.9, 13.6, 7.3 Hz, 2H), 4.75 (s, 2H), 7.11 (d, J=8.5 Hz, 2H), 7.23 (d, J=7.6 Hz, 1H), 7.37-7.43 (m, 3H), 7.50-7.55 (m, 2H), 7.59 (t, J=7.7 Hz, 1H), 7.88-7.96 (m, 2H), 8.17 (t, J=1.6 Hz, 1H). $^{13}$C NMR (151 MHz, DMSO-d$_6$): δ 20.8, 27.2, 30.0, 37.4, 46.2, 76.1, 121.7, 124.7, 127.3, 127.3, 128.2, 128.5, 129.0, 129.3, 129.9, 131.1, 131.4, 133.6, 139.2, 140.2, 140.5, 150.4, 167.2, 168.8, 169.1, 175.8. MS (ESI) m/z (%): 504 (100, [M−H]−). HRMS (ESI): [M−H] (C$_{28}$H$_{26}$O$_8$N) calc. 504.16639, found 504.16550.

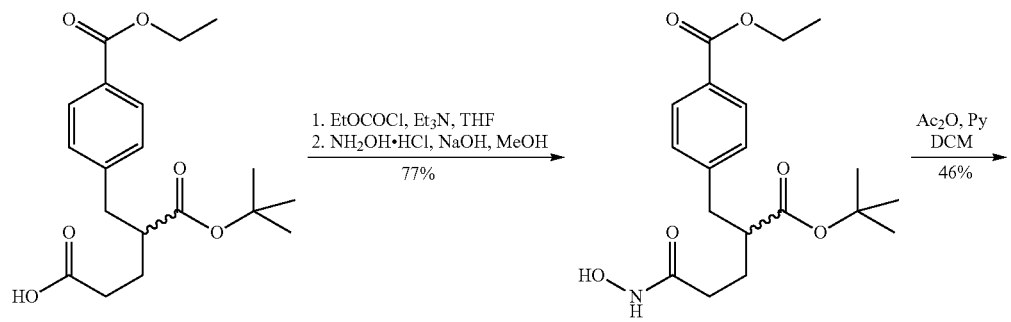

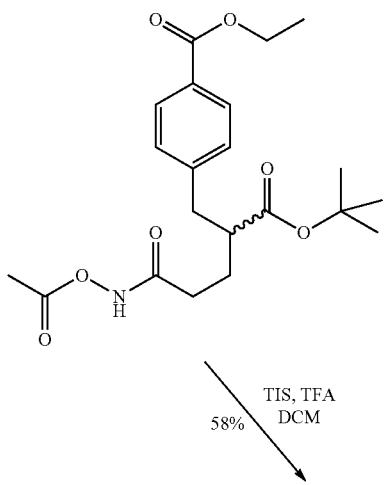

Ethyl 4-(2-(tert-butoxycarbonyl)-5-(hydroxyamino)-5-oxopentyl)benzoate

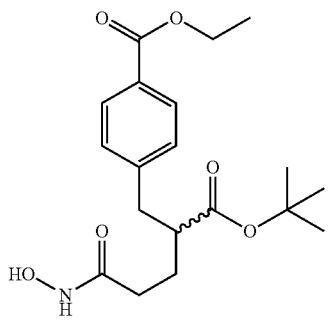 [SMILES: CCOC(=O)c1ccc(CC(CCC(=O)NO)C(=O)OC(C)(C)C)cc1]

NH$_2$OH·HCl (629 mg, 9.05 mmol, 10 eq) and NaOH (370 mg, 9.05 mmol, 10 eq) were placed in a Schlenk flask and put under an argon atmosphere. MeOH (5 mL) was added and the mixture was cooled to 0° C. while stirring. After 15 min the cooling bath was removed and stirring went on for 45 min. Then the mixture was filtered through a Celite pad and the filtrate containing NH$_2$OH was used further. Meanwhile 5-(tert-butoxy)-4-(4-(ethoxycarbonyl)benzyl)-5-oxopentanoic acid (317 mg, 0.91 mmol) in a Schlenk flask was put under an argon atmosphere and 10 mL of THF was added dissolving it. Et$_3$N (191 μL, 1.36 mmol, 1.5 eq) followed by EtOCOCl (134 μL, 1.36 mmol, 1.5 eq) were added and the mixture was stirred at rt for 1 h. A white precipitate formed almost immediately. Then NH$_2$OH solution prepared earlier was added and the mixture was stirred at rt overnight. Volatiles were then removed on rotavap, 50 mL of water was added and the mixture was 3× extracted with 80 mL of AcOEt. The combined organic layers were dried with MgSO$_4$, filtered, volatiles were removed on rotavap and the residue was chromatographed on silica (2.5×15 cm, eluent hex/AcOEt 2:3+1% AcOH) to afford 256 mg (77%, 0.70 mmol) of light yellowish oil. $^1$H NMR (400 MHz, CDCl$_3$): δ 1.14 (t, J=7.1 Hz, 3H), 1.57 (s, 9H), 1.83-1.98 (m, 2H), 2.07-2.26 (m, 2H), 2.64-2.74 (m, 1 h), 2.79 (dd, J=13.6, 6.3 Hz, 1H), 2.97 (dd, J=13.6, 8.5 Hz, 1H), 4.05 (q, J=7.1 Hz, 2H), 7.18 (d, J=8.0 Hz, 2H), 7.88 (d, J=8.0 Hz, 2H). $^{13}$C NMR (151 MHz, CDCl$_3$): δ 14.3, 27.6, 28.3, 30.6, 38.4, 46.9, 60.9, 81.1, 128.9, 129.7, 130.5, 143.6, 165.9, 170.5, 174.8. MS (ESI) m/z (%): 388 (100, [M+Na]$^+$). HRMS (ESI): [M–H] (C$_{19}$H$_{27}$O$_6$NNa) calc. 388.17306, found 388.17311.

Ethyl 4-(5-(acetoxyamino)-2-(tert-butoxycarbonyl)-5-oxopentyl)benzoate

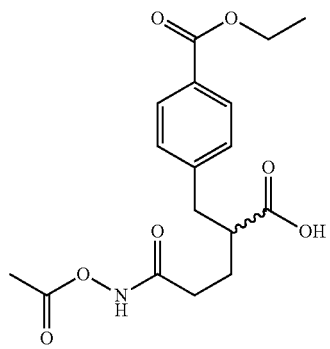

Ethyl 4-(2-(tert-butoxycarbonyl)-5-(hydroxyamino)-5-oxopentyl)benzoate (240 mg, 0.66 mmol) was placed in a Schlenk flask and put under an argon atmosphere. DCM (10 mL) was added dissolving it followed by pyridine (80 μL, 0.98 mmol, 1.5 eq.) and Ac$_2$O (94 μL, 0.99 mmol, 1.5 eq.). The mixture was stirred at rt overnight. Then volatiles were removed on rotavap and the residue was chromatographed on silica (2×20 cm, eluent hex/AcOEt 1:1) to afford 122 mg (46%, 0.30 mmol) of yellowish oil. $^1$H NMR (400 MHz, CDCl$_3$): δ 1.16 (t, J=7.2 Hz, 3H), 1.58 (s, 9H), 1.82-2.03 (m, 2H), 2.28 (s, 3H), 2.49-2.78 (m, 3H), 2.81 (dd, J=13.3, 6.7 Hz, 1H), 3.01 (dd, J=13.4, 8.1 Hz, 1H), 3.99-4.12 (m, 1H), 7.20 (d, J=8.2 Hz, 2H), 7.89 (d, J=8.3 Hz, 2H). $^{13}$C NMR (151 MHz, CDCl$_3$): δ 14.3, 18.1, 26.1, 28.3, 33.9, 38.5, 46.2, 60.7, 81.0, 128.9, 129.7, 130.5, 143.7, 165.8, 167.5, 170.0, 174.5. MS (ESI) m/z (%): 430 (100, [M+Na]$^+$). HRMS (ESI): [M–H] (C$_{21}$H$_{29}$O$_7$NNa) calc. 430.18417, found 430.18412.

105

5-(Acetoxyamino)-2-(4-(ethoxycarbonyl)benzyl)-5-oxopentanoic acid JV3113 [46]

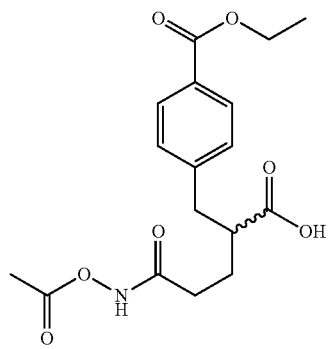 [SMILES: CCOC(=O)c1ccc(CC(CCC(=O)NOC(C)=O)C(=O)O)cc1]

106

Ethyl 4-(5-(acetoxyamino)-2-(tert-butoxycarbonyl)-5-oxopentyl)benzoate (120 mg, 0.29 mmol) in a rbf was put under an argon atmosphere. DCM (5 mL) was added dissolving it followed by TIS (61 µL, 0.29 mmol, 1 eq) and TFA (1 mL). The mixture was stirred at rt for 1 h. Then volatiles were removed on rotavap and TFA residue was removed by 3× addition of 1 mL of toluene and its rotavap removal. The crude product was purified by HPLC giving the product after lyophilisation as colourless oil (60 mg, 58%, 0.17 mmol). $^1$H NMR (400 MHz, CDCl$_3$): δ 1.15 (t, J=7.2 Hz, 3H), 1.86-2.03 (m, 2H), 2.30 (s, 3H), 2.53-2.92 (m, 4H), 3.04 (dd, J=13.5, 8.4 Hz, 1H), 4.01-4.12 (m, 2H), 7.28 (d, J=8.3 Hz, 2H), 8.02 (d, J=8.3 Hz, 2H). $^{13}$C NMR (151 MHz, CDCl$_3$): δ 14.3., 18.1, 26.3, 34.0, 38.7, 46.1, 60.8, 127.6, 129.3, 130.6, 145.4, 167.5, 170.0, 141.4, 174.5. MS (ESI) m/z (%): 350 (100, [M-H]-). HRMS (ESI): [M-H] (C$_{17}$H$_{20}$NO$_7$) calc. 350.12343, found 350.12369.

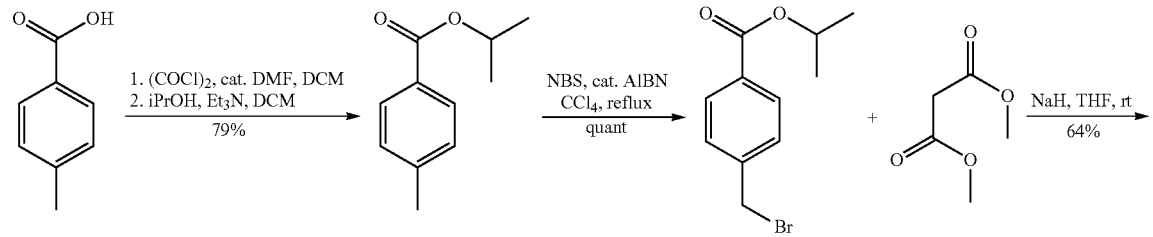

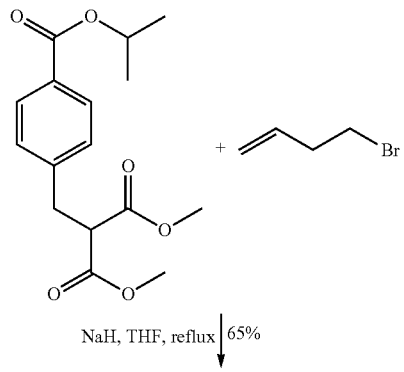

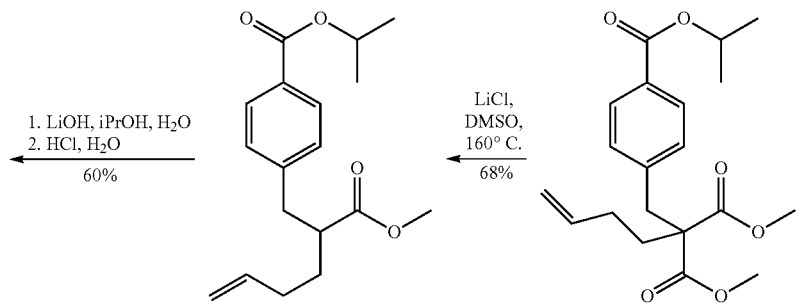

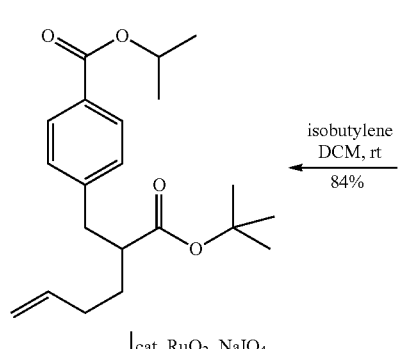
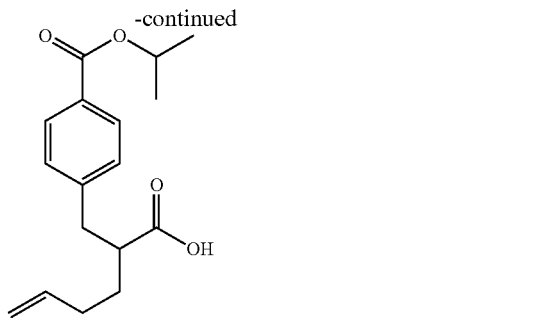

Isopropyl 4-methylbenzoate

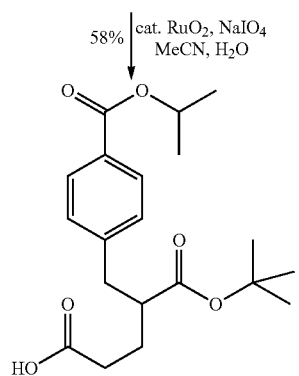

4-Methylbenzoic acid (10.00 g, 73.44 mmol) was placed in a Schlenk flask and put under an argon atmosphere. DCM (60 mL) was added followed by oxalyl chloride (9.4 mL, 110.14 mmol, 1.5 eq.) and a few drops of DMF. The mixture started to bubble. It was stirred at rt for 2 h and then volatiles were removed on rotavap. DCM (50 mL) was added to the residue dissolving it. This solution was added to a cooled mixture of iPrOH (8.4 mL, 110.15 mmol, 1.5 eq.) and Et$_3$N (15.5 mL, 110.16 mmol, 1.5 eq.) in DCM (50 mL). The mixture was let warm to rt and stirred over the weekend. It was quenched with 100 mL of saturated aqueous NH$_4$Cl and extracted 2× with 100 mL of DCM. The combined organic layers were dried with MgSO$_4$, filtered and volatiles were removed on rotavap. Kugelrohr distillation of the residue afforded 10.32 g (79%, 57.90 mmol) of colourless oil. The NMR was in accordance with the published data (Chem. Eur. J. 2006, 12 (36), 9314-9322).

Isopropyl 4-(bromomethyl)benzoate

NBS (1.45 g, 63.69 mmol) and AIBN (485 mg, 2.90 mmol, 0.05 eq.) were placed in a rbf equipped with a reflux condenser and put under an argon atmosphere. CCl$_4$ (80 mL) was added followed by isopropyl 4-methylbenzoate (10.32 g, 57.90 mmol). Stirring and heating were turned on and at -80° C. the colourless mixture turned yellow and started to reflux by itself. After ~15 min the reflux ceased, the temperature of the heating bath was raised to 100° C. and after 15 min heating was switched off. After cooling down, the mixture was filtered to remove the by-product and the filtrate was put on rotavap to remove volatiles. After attempts at recrystallisation or Kugelrohr distillation failed, the crude product was purified on silica (5×20 cm, eluent hex/AcOEt 6:1) to afford 15.33 g of yellowish oil containing some impurities in the NMR. It was used directly in the following reaction.

Dimethyl 2-(4-(isopropoxycarbonyl)benzyl)malonate

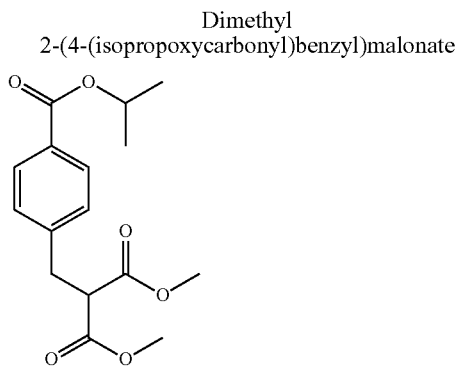

NaH (5.56 g, 139.00 mmol, 2.4 eq.) was placed in a rbf and put under an argon atmosphere. 250 mL of THF was added, the mixture was cooled to 0° C. and dimethyl malonate (16.2 mL, 139.00 mmol, 2.4 eq) in 100 mL of THF was added dropwise (30 min). The mixture was let warm up to rt and isopropyl 4-(bromomethyl)benzoate (14.89 g, 57.91 mmol) in 100 mL of THF was added dropwise (2 h) by way of syringe pump. The mixture was stirred at rt overnight (14 h) and quenched with 100 mL of aqueous NH$_4$Cl. 50 mL of water was added, the organic layer was separated and the aqueous one was extracted 2× with 150 mL of AcOEt. The combined organic layers were dried with MgSO$_4$, filtered and volatiles were removed on rotavap. Dimethyl malonate was removed in vacuo in Kugelrohr and the residue was chromatographed on silica (5×2 cm, eluent hex/AcOEt 6:1) to afford 11.36 g (64%, 36.84 mmol) of colourless oil. $^1$H NMR (400 MHz, CDCl$_3$): δ 1.35 (d, J=6.3 Hz, 6H), 3.26 (d, J=7.7 Hz, 2H), 3.63-3.71 (m, 1H), 3.69 (s, 6H), 5.17-5.28 (m, 1H), 7.25 (d, J=8.4 Hz, 2H), 7.94 (d, J=8.4 Hz, 2H). $^{13}$C NMR (151 MHz, CDCl$_3$): δ 22.1, 34.8, 52.8, 53.3, 68.4, 128.8, 129.7, 129.9, 142.9, 166.0, 169.0. MS (ESI) m/z (%): 331 (100, [M+Na]$^+$). HRMS (ESI): [M+Na] (C$_{16}$H$_{20}$O$_6$Na) calc. 331.11521, found 331.11530.

Dimethyl 2-(but-3-en-1-yl)-2-(4-(isopropoxycarbonyl)benzyl)malonate

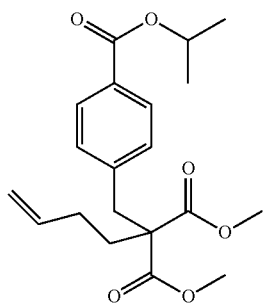 [SMILES: C=CCCC(Cc1ccc(C(=O)OC(C)C)cc1)(C(=O)OC)C(=O)OC]

NaH (1.77 g, 44.25 mmol, 1.2 eq.) was placed in a rbf equipped with a reflux condenser and put under an argon atmosphere. Dimethyl 2-(4-(isopropoxycarbonyl)benzyl) malonate (11.36 g, 36.84 mmol) in THF (150 mL) was added followed by 4-bromobut-1-ene (6.2 mL, 58.92 mmol, 1.6 eq). The mixture was refluxed for 24 h. After cooling down water (100 mL) was added and the mixture was extracted 3× with 150 mL of AcOEt, the combined organic layers were dried with MgSO$_4$, filtered and volatiles were removed on rotavap. The residue was chromatographed on silica (7×22 cm, eluent hex/AcOEt 5:1) affording 8.80 g (66%, 24.28 mmol) of yellowish oil. $^1$H NMR (400 MHz, CDCl$_3$): δ 1.35 (d, J=6.2 Hz, 6H), 1.83-1.91 (m, 2H), 2.01-2.09 (m, 2H), 3.30 (s, 2H), 3.71 (s, 6H), 4.95-5.07 (m, 2H), 5.17-5.28 (m, 1H), 5.69-5.81 (m, 1H), 7.13 (d, J=8.5 Hz, 2H), 7.93 (d, J=8.2 Hz, 2H). $^{13}$C NMR (151 MHz, CDCl$_3$): δ 22.1, 28.7, 31.5, 38.6, 52.6, 58.7, 68.4, 115.4, 129.7, 129.9, 129.9, 137.1, 141.3, 166.0, 171.4. MS (ESI) m/z (%): 385 (100, [M+Na]$^+$). HRMS (ESI): [M+Na] (C$_{20}$H$_{26}$O$_6$Na) calc. 385.16216, found 385.16223.

2-(4-(Isopropoxycarbonyl)benzyl)-2-(methoxycarbonyl)hex-5-enoic acid

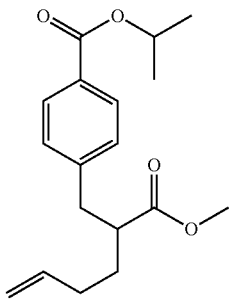 [SMILES: C=CCCC(Cc1ccc(C(=O)OC(C)C)cc1)C(=O)OC]

Dimethyl 2-(but-3-en-1-yl)-2-(4-(isopropoxycarbonyl)benzyl)malonate (5.00 g, 13.80 mmol) and LiCl (768 mg, 17.93 mmol, 1.3 eq.) were placed in a Schlenk flask and put under an argon atmosphere. DMSO (60 mL) and 20 drops of water were added and the mixture was stirred at 160° C. for 2 h. After cooling down 100 mL of water was added and the mixture was washed 3× with 200 mL of AcOEt. The combined organic layers were then washed 5× with 200 mL of water to remove DMSO. The organic layer was dried with MgSO$_4$, filtered and after volatiles removal the residue was chromatographed on silica (6×18 cm, eluent hex/AcOEt 5:1) to afford 2.84 g (68%, 9.33 mmol) of colourless oil. $^1$H NMR (400 MHz, CDCl$_3$): δ 1.35 (d, J=6.3 Hz, 6H), 1.50-1.64 (m, 1H), 1.72-1.83 (m, 1H), 1.97-2.15 (m, 2H), 2.66-2.74 (m, 1H), 2.80 (dd, J=13.5, 6.4 Hz, 1H), 2.98 (dd, J=13.5, 8.6 Hz, 1H), 3.59 (s, 3H), 4.94-5.04 (m, 2H), 5.18-5.29 (m, 1H), 5.68-5.79 (m, 1H), 7.21 (d, J=8.4 Hz, 2H), 7.94 (d, J=8.3 Hz, 2H). $^{13}$C NMR (151 MHz, CDCl$_3$): δ 22.1, 31.4, 31.6, 38.5, 46.8, 51.6, 68.4, 115.5, 128.9, 129.3, 129.8, 137.6, 144.6, 166.1, 175.7. MS (ESI) m/z (%): 327 (100, [M+Na]$^+$). HRMS (ESI): [M+Na] (C$_{18}$H$_{24}$O$_4$Na) calc. 327.15668, found 327.15670.

2-(4-(Isopropoxycarbonyl)benzyl)hex-5-enoic acid

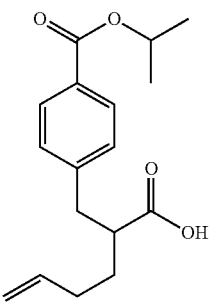 [SMILES: C=CCCC(Cc1ccc(C(=O)OC(C)C)cc1)C(=O)O]

Isopropyl 4-(2-(methoxycarbonyl)hex-5-en-1-yl)benzoate (2.84 g, 9.33 mmol) was dissolved in iPrOH (30 mL) and cooled to 0° C. While stirring LiOH (251 mg, 10.27 mmol, 1.1 eq.) in water (30 mL) was added dropwise (45 min). The cooling bath was then removed and the mixture was stirred at rt for 24 h. Volatiles were removed on rotavap and the mixture was acidified with conc. HCl and extracted 3× with 150 mL of AcOEt. The combined organic layers were dried with MgSO$_4$, filtered and after volatiles removal the residue was chromatographed on silica (5×20 cm, eluent hex/AcOEt 8:2, then 1:1+1% AcOH) to afford 1.63 g (60%, 5.61 mmol) of colourless oil. $^1$H NMR (400 MHz, CDCl$_3$): δ 1.35 (d, J=6.3 Hz, 6H), 1.55-1.65 (m, 1H), 1.72-1.84 (m, 1H), 2.02-2.21 (m, 2H), 2.69-2.77 (m, 1H), 2.83 (dd, J=13.6, 6.7 Hz, 1H), 3.03 (dd, J=13.6, 8.1 Hz, 1H), 4.96-5.05 (m, 2H), 5.19-5.29 (m, 1H), 5.69-5.80 (m, 1H), 7.24 (d, J=8.3 Hz, 2H), 7.96 (d, J=8.3 Hz, 2H). $^{13}$C NMR (151 MHz, CDCl$_3$): δ 22.1, 30.9, 31.4, 38.0, 46.4, 68.4, 115.7, 129.0, 129.4, 129.9, 137.4, 144.2, 166.2, 181.0. MS (ESI) m/z (%): 289 (100, [M–H]−). HRMS (ESI): [M–H] (C$_{17}$H$_{21}$O$_4$) calc. 289.14453, found 289.14410.

Isopropyl 4-(2-(tert-butoxycarbonyl)hex-5-en-1-yl)benzoate

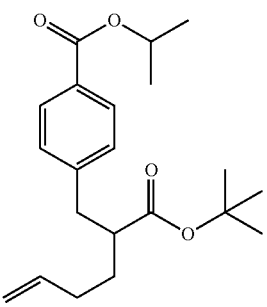 [SMILES: C=CCCC(Cc1ccc(C(=O)OC(C)C)cc1)C(=O)OC(C)(C)C]

2-(4-(Isopropoxycarbonyl)benzyl)hex-5-enoic acid (1.63 g, 5.61 mmol) was placed in a pressure flask and put under an argon atmosphere. DCM (50 mL) was added dissolving it and the solution was cooled to −78° C. Isobutylene (~8 mL) was condensed into the flask, H$_2$SO$_4$ (310 μL, 5.73 mmol) was added. The flask was closed, let warm up to rt and the mixture was stirred for 36 h. It was cooled to −78° C. and the cold content was poured into a saturated solution of NaHCO$_3$. After warming up to rt DCM was removed on rotavap and the residue was 3× extracted with 100 mL of AcOEt, the combined organic layers were dried with MgSO$_4$, filtered and after volatiles removal the residue was chromatographed on silica (4×15 cm, eluent hex/AcOEt 5:1) to afford 1.63 g (84%, 4.69 mmol) of yellowish oil. $^1$H NMR (400 MHz, CDCl$_3$): δ 1.34 (s, 9H), 1.36 (d, J=6.3 Hz, 6H), 1.47-1.58 (m, 1H), 1.68-1.79 (m, 1H), 1.99-2.16 (m, 2H), 2.54-2.63 (m, 1H), 2.75 (dd, J=13.7, 6.3 Hz, 1H), 2.93 (dd, J=13.6, 8.9 Hz, 1H), 4.94-5.04 (m, 2H), 5.18-5.28 (m, 1H), 5.70-5.82 (m, 1H), 7.23 (d, J=8.3 Hz, 2H), 7.93 (d, J=8.3 Hz, 2H). $^{13}$C NMR (151 MHz, CDCl$_3$): δ 22.1, 28.2, 31.5, 31.7, 38.7, 47.5, 68.3, 80.6, 115.4, 129.1, 129.5, 129.6, 137.9, 144.9, 166.2, 174.5. MS (ESI) m/z (%): 369 (100, [M+Na]$^+$). HRMS (ESI): [M+Na] (C$_{21}$H$_{30}$O$_4$Na) calc. 369.20363, found 369.20374.

5-(tert-Butoxy)-4-(4-(isopropoxycarbonyl)benzyl)-5-oxopentanoic acid

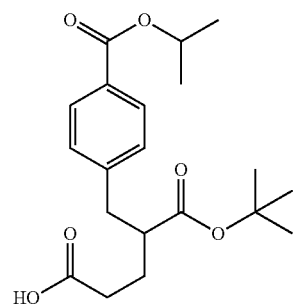 [SMILES: CC(C)OC(=O)c1ccc(CC(CCC(=O)O)C(=O)OC(C)(C)C)cc1]

Isopropyl 4-(2-(tert-butoxycarbonyl)hex-5-en-1-yl)benzoate (1.60 g, 4.62 mmol) was dissolved in acetonitrile (100 mL) and 100 mL of water was added. The mixture was cooled to 0° C. and RuO$_2$·xH$_2$O (92 mg, 0.69 mmol, 0.15 eq (anhydr.)) was added at once followed by portionwise (15 min) addition of NaIO$_4$ (9.90 g, 46.18 mmol, 10 eq). The mixture was stirred overnight (14 h) after it warmed up to rt. Then it was filtered through a Celite pad washing the pad with additional MeCN. Most MeCN was removed on rotavap and the aqueous residue was extracted 3× with 150 mL AcOEt, the combined organic layers were dried with MgSO$_4$ and filtered. After volatiles removal the residue was chromatographed on silica (4×15 cm, eluent hex/AcOEt 1:1+1% AcOH) to afford 971 mg (58%, 2.66 mmol) of colourless oil. $^1$H NMR (400 MHz, CDCl$_3$): δ 1.34 (s, 9H), 1.36 (d, J=6.3 Hz, 6H), 1.78-1.96 (m, 2H), 2.30-2.49 (m, 2H), 2.59-2.68 (m, 1H), 2.77 (dd, J=13.7, 6.4 Hz, 1H), 2.97 (dd, J=13.7, 8.7 Hz, 1H), 5.18-5.29 (m, 1H), 7.24 (d, J=8.3 Hz, 2H), 7.94 (d, J=8.3 Hz, 2H). $^{13}$C NMR (151 MHz, CDCl$_3$): δ 22.1, 27.1, 28.1, 31.7, 38.6, 47.1, 68.4, 81.2, 129.1, 129.2, 129.7, 144.3, 168.2, 173.8, 178.8. MS (ESI) m/z (%): 387 (100, [M+Na]$^+$). HRMS (ESI): [M–H] (C$_{20}$H$_{27}$O$_6$) calc. 363.18131, found 363.18118.

Isopropyl 4-(2-(tert-butoxycarbonyl)-5-(hydroxyamino)-5-oxopentyl)benzoate

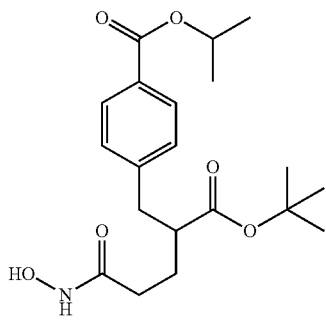 [SMILES: CC(C)OC(=O)c1ccc(CC(CCC(=O)NO)C(=O)OC(C)(C)C)cc1]

NH$_2$OH·HCl (1.81 g, 25.54 mmol, 10 eq) and NaOH (1.04 g, 25.55 mmol, 10 eq) were placed in a Schlenk flask and put under an argon atmosphere. MeOH (10 mL) was added and the mixture was cooled to 0° C. while stirring. After 15 min the cooling bath was removed and stirring went on for 45 min. Then the mixture was filtered through a Celite pad and the filtrate containing NH$_2$OH was used further. Meanwhile 5-(tert-butoxy)-4-(4-(isopropoxycarbonyl)benzyl)-5-oxopentanoic (950 mg, 2.61 mmol) in a Schlenk flask was put under an argon atmosphere and 20 mL of THF was added dissolving it. Et$_3$N (550 µL, 3.91 mmol, 1.5 eq) followed by EtOCOCl (385 µL, 3.91 mmol, 1.5 eq) were added and the mixture was stirred at rt for 1 h. A white precipitate formed almost immediately. Then NH$_2$OH solution prepared earlier was added and the mixture was stirred at rt overnight. Volatiles were then removed on rotavap, 50 mL of water was added and the mixture was 3× extracted with 150 mL of AcOEt. The combined organic layers were dried with MgSO$_4$, filtered, volatiles were removed on rotavap and the residue was chromatographed on silica (4×17 cm, eluent hex/AcOEt 2:3+1% AcOH) to afford 744 mg (75%, 1.96 mmol) of light orange oil. $^1$H NMR (400 MHz, CDCl$_3$): δ 1.35 (s, 9H), 1.38 (d, J=6.3 Hz, 6H), 1.85-1.99 (m, 2H), 2.11-2.31 (m, 2H), 2.57-2.69 (m, 1H), 2.79 (dd, J=13.7, 6.1 Hz, 1H), 2.95 (dd, J=13.7, 9.1 Hz, 1H), 5.20-5.31 (m, 1H), 7.24 (d, J=8.1 Hz, 2H), 7.95 (d, J=8.2 Hz, 2H). $^{13}$C NMR (151 MHz, CDCl$_3$): δ 22.1, 28.0, 28.1, 30.7, 38.5, 47.4, 68.5, 81.5, 129.0, 129.3, 129.7, 144.2, 166.2, 170.6, 174.1. MS (ESI) m/z (%): 402 (100, [M+Na]$^+$). HRMS (ESI): [M+Na] (C$_{20}$H$_{29}$O$_6$NNa) calc. 402.18871, found 402.18881.

Isopropyl 4-(5-(acetoxyamino)-2-(tert-butoxycarbonyl)-5-oxopentyl)benzoate

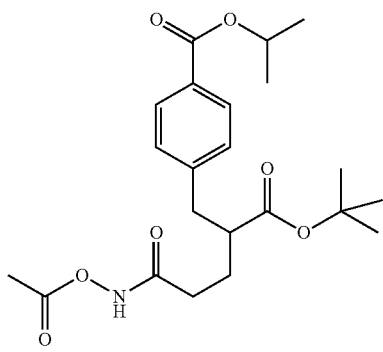 [SMILES: CC(=O)ONC(=O)CCC(Cc1ccc(C(=O)OC(C)C)cc1)C(=O)OC(C)(C)C]

Isopropyl 4-(2-(tert-butoxycarbonyl)-5-(hydroxyamino)-5-oxopentyl)benzoate (362 mg, 0.95 mmol) was placed in a Schlenk flask and put under an argon atmosphere. DCM (10 mL) was added dissolving it followed by pyridine (101 µL, 1.24 mmol, 1.3 eq.) and Ac$_2$O (118 µL, 1.24 mmol, 1.3 eq.). The mixture was stirred at rt overnight. Then volatiles were removed on rotavap and the residue was chromatographed on silica (3×20 cm, eluent hex/AcOEt 1:1) to afford 198 mg (49%, 0.47 mmol) of colourless oil. $^1$H NMR (400 MHz, CDCl$_3$): δ 1.34 (s, 9H), 1.35 (d, J=6.3 Hz, 6H), 1.82-2.01 (m, 2H), 2.22 (s, 3H), 2.24-2.39 (m, 2H), 2.69-2.86 (m, 2H), 2.88-3.01 (m, 1H), 5.17-5.28 (m, 1H), 7.24 (d, J=8.3 Hz, 2H), 7.93 (d, J=8.3 Hz, 2H). $^{13}$C NMR (151 MHz, CDCl$_3$): δ 18.3, 22.0, 27.8, 28.0, 30.7, 38.4, 46.8, 68.2, 81.4, 128.9, 129.1, 129.6, 144.1, 166.0, 168.8, 174.0. MS (ESI) m/z (%): 349 (100, [M−H]$^-$). HRMS (ESI): [M+Na] (C$_{22}$H$_{31}$O$_7$NNa) calc. 444.19927, found 444.19941.

5-(Acetoxyamino)-2-(4-(isopropoxycarbonyl)benzyl)-5-oxopentanoic acid JV3138

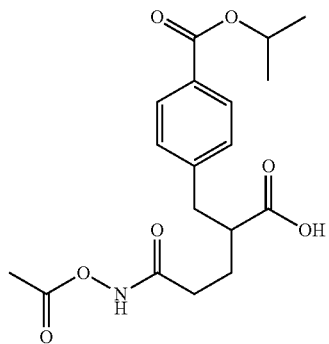 [SMILES: CC(=O)ONC(=O)CCC(Cc1ccc(C(=O)OC(C)C)cc1)C(=O)O]

Isopropyl 4-(5-(acetoxyamino)-2-(tert-butoxycarbonyl)-5-oxopentyl)benzoate (178 mg, 0.42 mmol) in a rbf was put under an argon atmosphere. DCM (5 mL) was added a dissolving it followed by TIS (88 µL, 0.42 mmol, 1 eq) and TFA (1 mL). The mixture was stirred at rt for 1 h. Then volatiles were removed on rotavap and TFA residue was removed by 3× addition of 1 mL of toluene and its rotavap removal. The residue was purified by HPLC giving the product after lyophilisation as a colourless oil (101 mg, 65%, 0.28 mmol). $^1$H NMR (400 MHz, CDCl$_3$): δ 1.34 (d, J=6.2 Hz, 6H), 1.88-2.02 (m, 2H), 2.18 (s, 3H), 2.23-2.42 (m, 2H), 2.72-2.91 (m, 2H), 2.96-3.10 (m, 1H), 5.16-5.27 (m, 2H), 7.24 (d, J=8.3 Hz, 2H), 7.94 (d, J=8.3 Hz, 2H). $^{13}$C NMR (151 MHz, CDCl$_3$): δ 18.4, 22.1, 27.1, 30.3, 38.2, 46.0, 68.6, 129.0, 129.4, 129.9, 143.7, 166.3, 169.0, 170.2, 179.2. MS (ESI) m/z (%): 364 (100, [M−H]−). HRMS (ESI): [M−H] (C$_{18}$H$_{22}$O$_7$N) calc. 364.14018, found 364.13987.

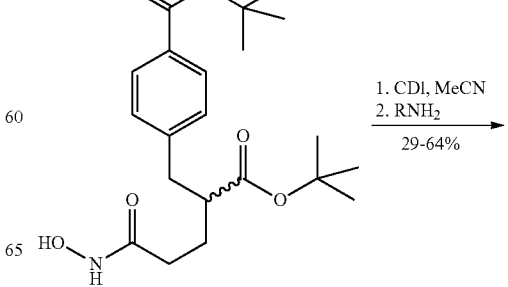

-continued

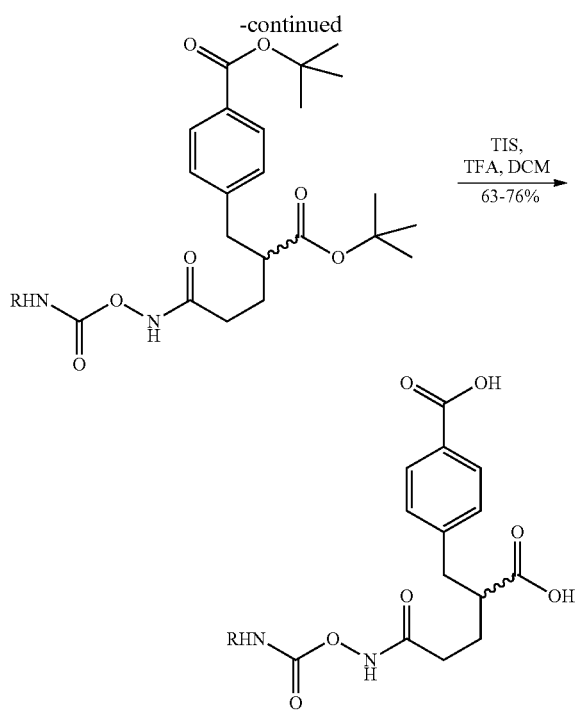

TIS,
TFA, DCM
───────→
63-76% tert-Butyl 4-(2-(tert-butoxycarbonyl)-5-(((tert-butyl-carbamoyl)oxy)amino)-5-oxopentyl)benzoate

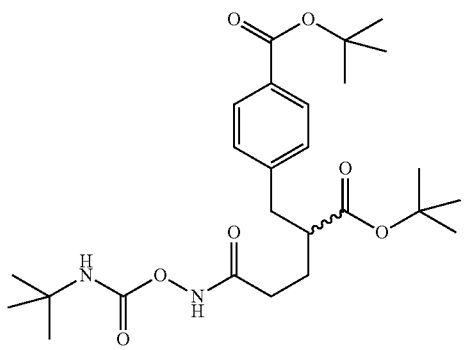 [SMILES: CC(C)(C)NC(=O)ONC(=O)CCC(Cc1ccc(C(=O)OC(C)(C)C)cc1)C(=O)OC(C)(C)C]

tert-Butyl 4-(2-(tert-butoxycarbonyl)-5-(hydroxyamino)-5-oxopentyl)benzoate (200 mg, 0.51 mmol) and CDI (128 mg, 0.76 mmol, 1.5 eq) were placed in a Schlenk flask and put under an argon atmosphere. The mixture was cooled to 0° C. and MeCN (10 mL) was added dissolving it. The mixture was stirred at 0° C. for 1 h and then tBuNH$_2$ (65 µL, 0.61 mmol, 1.2 eq) was added. The mixture was let warm up to rt and stirred overnight. Then volatiles were removed on rotavap and the residue was chromatographed on silica (2.5×18 cm, eluent hex/AcOEt 1:1) to afford 72 mg (29%, 0.15 mmol) of colourless oil. $^1$H NMR (400 MHz, CDCl$_3$): δ 1.33 (s, 9H), 1.34 (s, 9H), 1.57 (s, 9H), 1.83-1.98 (m, 2H), 2.15-2.36 (m, 2H), 2.63-2.84 (m, 2H), 2.87-2.99 (m, 1H), 7.22 (d, J=8.2 Hz, 2H), 7.87 (d, J=8.3 Hz, 2H). $^{13}$C NMR (151 MHz, CDCl$_3$): δ 27.8, 28.1, 28.3, 28.8, 30.7, 38.5, 47.1, 51.7, 80.9, 81.2, 128.9, 129.6, 130.3, 144.0, 153.0, 165.9, 171.1, 174.1. MS (ESI) m/z (%): 515 (100, [M+Na]$^+$). HRMS (ESI): [M+Na] (C$_{26}$H$_{40}$O$_7$N$_2$Na) calc. 515.27277, found 515.27289.

tert-Butyl 4-(2-(tert-butoxycarbonyl)-5-(((neopentyl-carbamoyl)oxy)amino)-5-oxopentyl)benzoate

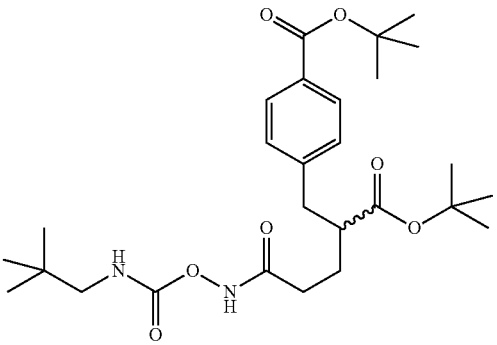 [SMILES: CC(C)(C)CNC(=O)ONC(=O)CCC(Cc1ccc(C(=O)OC(C)(C)C)cc1)C(=O)OC(C)(C)C]

tert-Butyl 4-(2-(tert-butoxycarbonyl)-5-(hydroxyamino)-5-oxopentyl)benzoate (200 mg, 0.51 mmol) and CDI (128 mg, 0.76 mmol, 1.5 eq) were placed in a Schlenk flask and put under an argon atmosphere. The mixture was cooled to 0° C. and MeCN (10 mL) was added dissolving it. The mixture was stirred at 0° C. for 1 h and then neopentylamine (76 µL, 0.61 mmol, 1.2 eq) was added. The mixture was let warm up to rt and stirred overnight. Then volatiles were removed on rotavap and the residue was chromatographed on silica (2.5×18 cm, eluent hex/AcOEt 1:1) to afford 166 mg (64%, 0.33 mmol) of colourless oil. $^1$H NMR (400 MHz, CDCl$_3$): δ 0.91 (s, 9H), 1.34 (s, 9H), 1.58 (s, 9H), 1.83-1.98 (m, 2H), 2.15-2.37 (m, 2H), 2.67-2.83 (m, 2H), 2.88-2.97 (m, 1H), 3.01 (d, J=6.5 Hz, 2H), 7.21 (d, J=8.3 Hz, 2H), 7.87 (d, J=8.3 Hz, 1H). $^{13}$C NMR (151 MHz, CDCl$_3$): δ 27.1, 27.8, 28.1, 28.3, 30.7, 32.2, 38.5, 47.0, 53.2, 80.9, 81.3, 128.9, 129.6, 130.3, 144.0, 155.5, 165.9, 171.2, 174.1. MS (ESI) m/z (%): 529 (100, [M+Na]$^+$). HRMS (ESI): [M+Na] (C$_{27}$H$_{42}$O$_7$N$_2$Na) calc. 529.28842, found 529.28839.

4-(5-(((tert-Butylcarbamoyl)oxy)amino)-2-carboxy-5-oxopentyl)benzoic acid JV3126

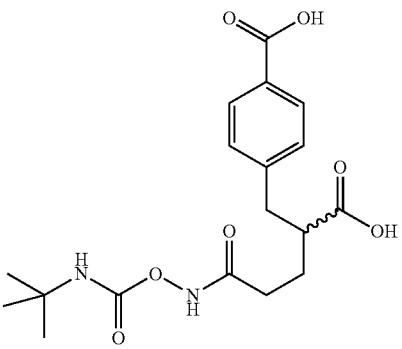 [SMILES: CC(C)(C)NC(=O)ONC(=O)CCC(Cc1ccc(C(=O)O)cc1)C(=O)O]

tert-Butyl 4-(2-(tert-butoxycarbonyl)-5-(((tert-butylcarbamoyl)oxy)amino)-5-oxopentyl)benzoate (65 mg, 0.13 mmol) in a rbf was put under an argon atmosphere. DCM (2 mL) was added dissolving it followed by TIS (55 µL, 0.26 mmol, 2 eq) and TFA (1 N mL). The mixture was stirred at rt for 1 h. Then volatiles were removed on rotavap and TFA residue was removed by 3× addition of 1 mL of toluene and its rotavap removal. The residue was sonicated in 1 mL of AcOEt shortly and after volatiles removal an off-white solid was obtained. This was sonicated in 3 mL of CHCl$_3$ and filtered washing the solid with additional 3 ml of CHCl$_3$. The product was obtained as white solid (32 mg, 63%, 0.08 mmol). $^1$H NMR (400 MHz, DMSO-d$_6$): δ 1.23 (s, 9H), 1.62-1.81 (m, 2H), 2.02-2.26 (m, 2H), 2.59-2.69 (m, 1H), 2.76-2.94 (m, 2H), 7.32 (d, J=7.6 Hz, 2H), 7.84 (d, J=7.8 Hz, 2H). $^{13}$C NMR (151 MHz, DMSO-d$_6$): δ 27.0, 28.4, 29.7, 37.2, 45.7, 50.1, 128.8, 129.1, 129.3, 144.7, 153.1, 167.2, 169.3, 175.6. MS (ESI) m/z (%): 349 (100, [M−H]−). HRMS (ESI): [M−H] (C$_{19}$H$_{25}$O$_6$) calc. 349.16566, found 349.16498.

4-(2-Carboxy-5-(((neopentylcarbamoyl)oxy)amino)-5-oxopentyl)benzoic acid JV3127

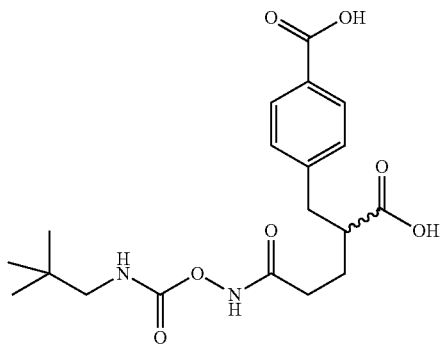 [SMILES: CC(C)(C)CNC(=O)ONC(=O)CCC(Cc1ccc(C(=O)O)cc1)C(=O)O]

tert-Butyl 4-(2-(tert-butoxycarbonyl)-5-(((neopentylcarbamoyl)oxy)amino)-5-oxopentyl)benzoate (146 mg, 0.29 mmol) in a rbf was put under an argon atmosphere. DCM (2 mL) was added dissolving it followed by TIS (119 μL, 0.57 mmol, 2 eq) and TFA (1 mL). The mixture was stirred at rt for 1 h. Then volatiles were removed on rotavap and TFA residue was removed by 3× addition of 1 mL of toluene and its rotavap removal. The residue was sonicated in 1 mL of AcOEt shortly and after volatiles removal an off-white solid was obtained. This was sonicated in 3 mL of CHCl$_3$ and filtered washing the solid with additional 3 ml of CHCl$_3$. The product was obtained as white solid (86 mg, 76%, 0.22 mmol). $^1$H NMR (400 MHz, DMSO-d$_6$): δ 0.83 (s, 9H), 1.61-1.81 (m, 2H), 2.03-2.22 (m, 2H), 2.58-2.69 (m, 1H), 2.75-2.94 (m, 4H), 7.32 (d, J=8.0 Hz, 2H), 7.84 (d, J=8.3 Hz, 2H). $^{13}$C NMR (151 MHz, DMSO-d$_6$): δ 26.9, 27.0, 29.6, 32.2, 37.2, 45.7, 52.1, 128.8, 129.1, 129.3, 144.7, 155.6, 167.2, 169.4, 175.8. MS (ESI) m/z (%): 349 (100, [M−H]−). HRMS (ESI): [M−H] (C$_{19}$H$_{25}$O$_6$) calc. 349.16566, found 349.16498.

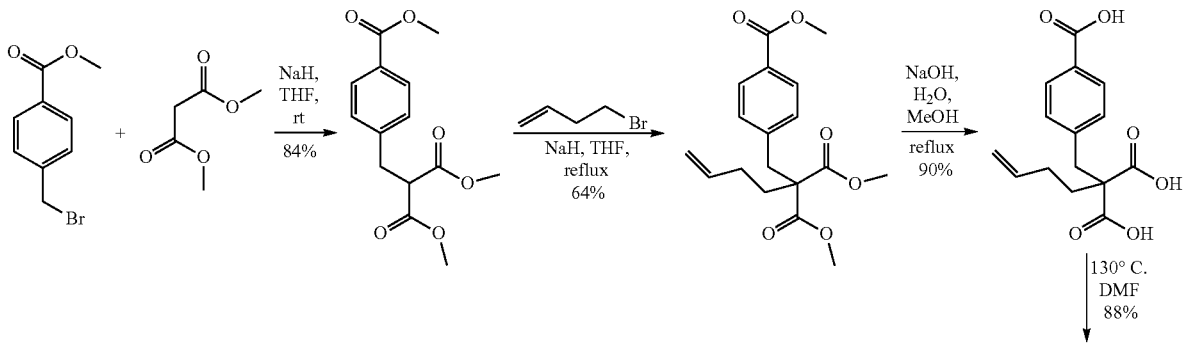

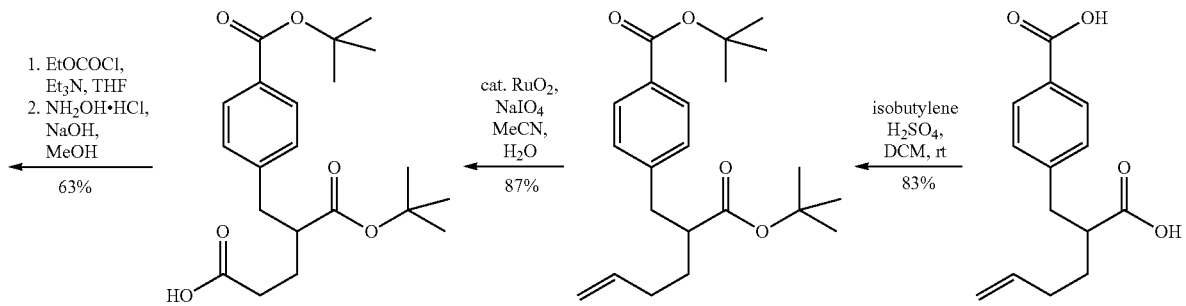

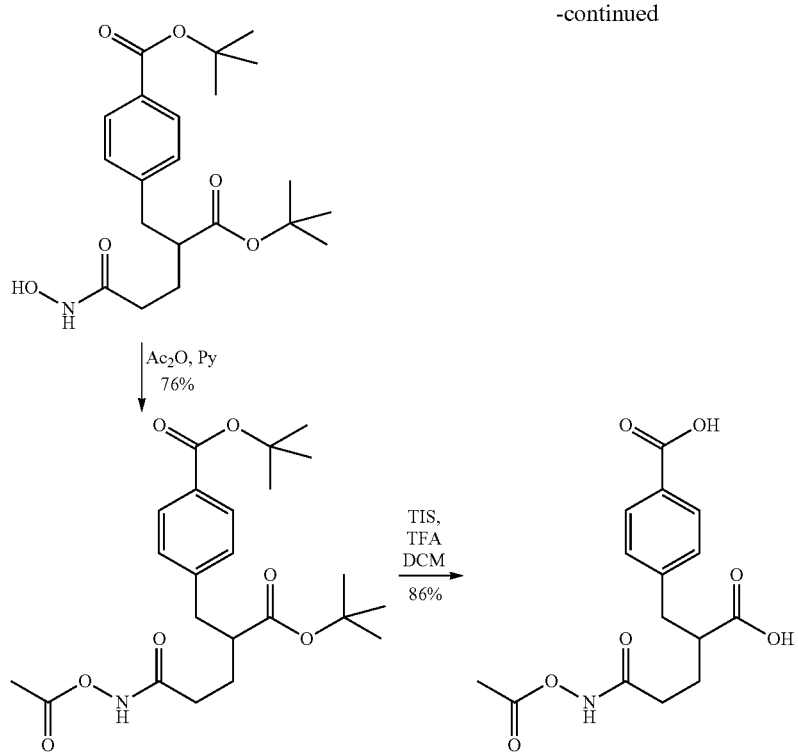

Dimethyl 2-(4-(methoxycarbonyl)benzyl)malonate

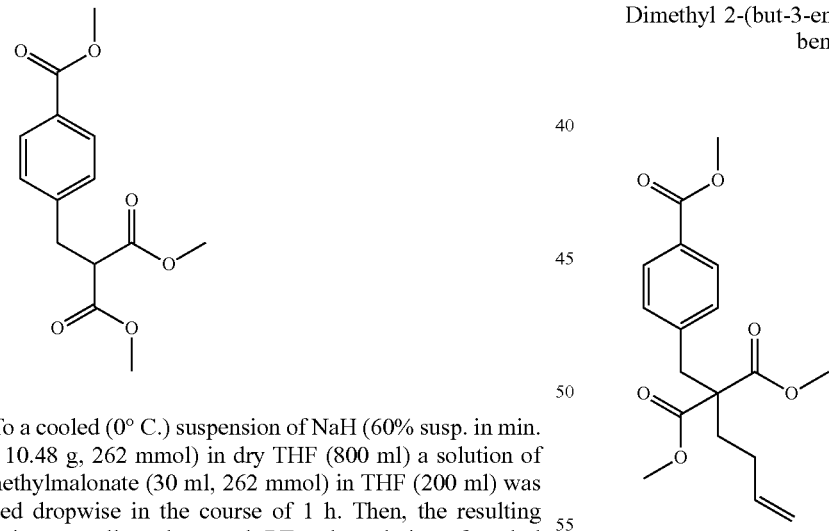

To a cooled (0° C.) suspension of NaH (60% susp. in min. oil, 10.48 g, 262 mmol) in dry THF (800 ml) a solution of dimethylmalonate (30 ml, 262 mmol) in THF (200 ml) was added dropwise in the course of 1 h. Then, the resulting solution was allowed to reach RT and a solution of methyl 4-(bromomethyl)benzoate (25.0 g, 109 mmol) in THF (200 ml) was added dropwise. The mixture was stirred overnight, then treated with saturated aqueous solution of ammonium sulphate (1 l). Aqueous phase was extracted with EtOAc (2×250 ml). Combined organic portions were dried with $MgSO_4$ and evaporated. The syrupy residue was crystallized from toluene-hexane, yield 25.8 g (84%); m.p. 49° C. $^1$H NMR (400 MHz, DMSO-$d_6$): δ 3.16 (d, 2H, J=8.0), 3.60 (s, 6H), 3.83 (s, 3H), 3.95 (t, 1H, J=8.0), 7.37 (m, 2H), 7.87 (m, 2H). $^{13}$C NMR (151 MHz, DMSO-$d_6$): δ 34.2, 52.3, 52.4, 52.6, 128.3, 129.4, 129.4, 143.6, 166.3, 168.9. MS (ESI) m/z (%): 303.1 (100) [M+Na]$^+$, 583.2 (58) [2M+Na]$^+$. HRMS (ESI): [M+Na]$^+$ ($C_{14}H_{16}O_6Na$) calc. 303.08391, found 303.08398.

Dimethyl 2-(but-3-en-1-yl)-2-(4-(methoxycarbonyl)benzyl)malonate

To a solution of dimethyl 2-(4-(methoxycarbonyl)benzyl)malonate (25.5 g, 91.0 mmol) in dry THF (500 ml) NaH (60% susp. in min. oil, 4.37 g, 109 mmol) was added and the mixture was stirred till hydrogen release finished completely. Then 4-bromo but-1-ene (14.8 ml, 146 mmol) was added and the mixture was refluxed 72 h under inert atmosphere. Then, the mixture was cooled to RT and quenched with saturated solution of $(NH_4)_2SO_4$ (500 ml). The aqueous phase was reextracted with $CHCl_3$ (2×250 ml). Combined organic extracts were dried with $MgSO_4$, evaporated and the residue was chromatographed on a silica gel column in acetone-hexane (1:3) giving 19.4 g (64%) of syrupy product which slowly crystallized; m.p. 51° C. $^1$H NMR (400 MHz, DMSO-d$_6$): δ 1.69 (m, 2H), 2.02 (m, 2H), 3.25 (s, 2H), 3.67 (s, 6H), 3.83 (s, 3H), 4.96 (dm, 1H, J=10.2), 5.04 (dm, 1H, J=17.1), 5.76 (ddt, 1H, J=17.1, 10.2, J=6.5), 7.22 (m, 2H), 7.88 (m, 2H). $^{13}$C NMR (151 MHz, DMSO-d$_6$): δ 28.0, 30.9, 37.6, 52.3, 52.7, 58.0, 115.6, 128.6, 129.3, 130.4, 137.5, 141.6, 166.2, 170.8. MS (ESI) m/z (%): 357.1 (100) [M+Na]$^+$; 691.3 (34) [2M+Na]$^+$. HRMS (ESI): [M+Na]$^+$ (C$_{18}$H$_{22}$O$_6$Na) calc. 357.13086, found 357.13088.

2-(But-3-en-1-yl)-2-(4-carboxybenzyl)malonic acid

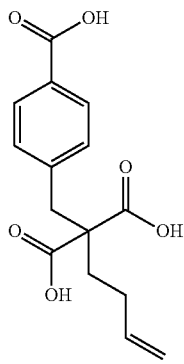

To a solution of dimethyl 2-(but-3-en-1-yl)-2-(4-(methoxycarbonyl)benzyl)malonate (19.3 g, 57.8 mmol) in MeOH (200 ml) an aqueous solution of NaOH (4 M, 150 ml) was added and the mixture was refluxed for 24 h. Methanol was evaporated and the aqueous residue was diluted with water to approx. 400 ml. The solution was acidified with conc. H$_2$SO$_4$ (18 ml) while cooling. Precipitated product was filtered off, washed with water and dried, yield 15.2 g (90%); m.p. 103° C. $^1$H NMR (400 MHz, DMSO-d$_6$): δ 1.60 (m, 2H), 2.03 (m, 2H), 3.16 (s, 2H), 4.95 (dm, 1H, J=10.2), 5.03 (dm, 1H, J=17.1); 5.78 (ddt, 1H, J=17.1, 10.2, 6.5), 7.25 (m, 2H), 7.83 (m, 2H), 12.96 (bs, 3H). $^{13}$C NMR (151 MHz, DMSO-d$_6$): δ 28.2, 30.6, 37.5, 57.7, 115.2, 129.3, 129.4, 130.2, 138.0, 142.2, 167.4, 172.5. MS (ESI) m/z (%): 247.1 (100) [M–CO$_2$–H]$^-$, 291.1 (33) [M–H]$^-$. HRMS (ESI): [M–H] (C$_{15}$H$_{15}$O$_6$) calc. 291.08741, found 291.08731.

4-(2-Carboxyhex-5-en-1-yl)benzoic acid

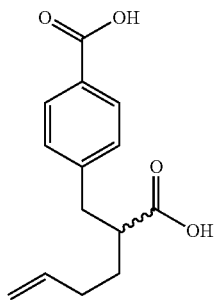 [SMILES: C=CCCC(Cc1ccc(C(=O)O)cc1)C(=O)O]

A solution of 2-(but-3-en-1-yl)-2-(4-carboxybenzyl)malonic acid (13.8 g, 47.2 mmol) in DMF (200 ml) was heated to 130° C. for 4 h. Solvent was evaporated, the residue was codistilled with xylene and dried in vacuo. Product was crystallized from toluene-hexan, yield 10.3 g (88%); m.p. 153° C. $^1$H NMR (400 MHz, DMSO-d$_6$): δ 1.50 (m, 1H), 1.61 (m, 1H), 1.96-2.10 (m, 2H), 2.59 (m, 1H). 2.79 (dd, 1H, J=13.6, 6.2), 2.87 (dd, 1H, J=13.6, 8.7); 4.95 (dm, 1H, J=10.2); 4.99 (dm, 1H, J=17.2); 5.76 (ddt, 1H, J=17.2, 10.2, 6.6), 7.30 (m, 2H), 7.84 (m, 2H), 12.49 (bs, 2H). $^{13}$C NMR (151 MHz, DMSO-d$_6$): δ 30.9, 31.1, 37.7, 46.2, 115.5, 129.2, 129.2, 129.5, 138.1, 145.0, 167.5, 176.1. MS (ESI) m/z (%): 247.1 (100) [M–H]$^-$; 495.2 (36) [2M–H]$^-$. HRMS (ESI): [M–H] (C$_{14}$H$_{15}$O$_4$) calc. 247.09758, found 247.09761.

tert-butyl 4-(2-(tert-butoxycarbonyl)hex-5-en-1-yl)benzoate [3]

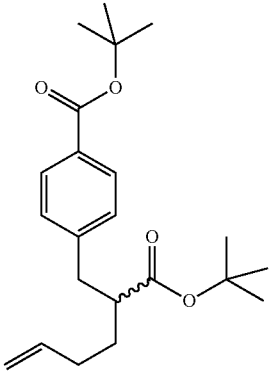 [SMILES: C=CCCC(Cc1ccc(C(=O)OC(C)(C)C)cc1)C(=O)OC(C)(C)C]

A solution of 4-(2-carboxyhex-5-en-1-yl)benzoic acid 2 (7.07 g, 28.5 mmol) in anhydrous dichloromethane (120 mL) was cooled to –65° C. and excess of isobutylene (23.7 g, 422 mmol) was condensed into the mixture followed by addition of conc. H$_2$SO$_4$ (1.6 mL, 28.5 mmol). The reaction vessel was sealed and allowed to reach room temperature. The mixture was stirred overnight, then cooled to –65° C. and poured into saturated aqueous solution of NaHCO$_3$. The reaction mixture was extracted with ether (100 mL×2) and combined organic extracts were dried over MgSO$_4$ and concentrated in vacuo. The residual oil was chromatographed on silica gel (acetone/hexane, 1:6) to yield 8.49 g of 3 as a syrupy oil (83% yield): $^1$H NMR (DMSO-d$_6$) δ 1.28 (s, 9H), 1.53 (s, 9H), 1.52 (m, 1H), 1.61 (m, 1H), 1.96-2.08 (m, 2H), 2.55 (m, 1H), 2.80 (m, 2H), 4.96 (dm, 1H, J=10.2), 5.00 (dm, J=17.1 Hz, 1H), 5.77 (ddt, J=10.3, 17.1, 6.6 Hz, 1H), 7.29 (m, 2H), 7.80 (m, 2H); $^{13}$C NMR (DMSO-d$_6$) δ 27.8, 28.0, 31.0, 31.3, 37.9, 46.9, 80.0, 80.7, 115.6, 129.1, 129.3, 129.5, 138.0, 144.8, 165.1, 173.8. HRMS (ESI): [M+Na]$^+$ m/z 383.21938 (calcd 383.21928 for C$_{22}$H$_{32}$O$_4$Na$^+$).

5-(tert-butoxy)-4-(4-(tert-butoxycarbonyl)benzyl)-5-oxopentanoic acid [4]

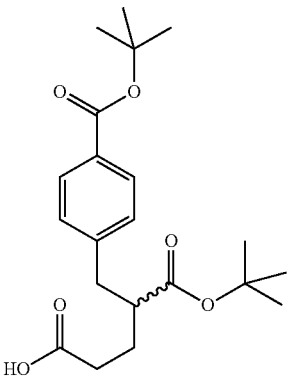 [SMILES: CC(C)(C)OC(=O)c1ccc(CC(CCC(=O)O)C(=O)OC(C)(C)C)cc1]

To a solution of 3 (8.48 g, 23.5 mmol) in acetonitrile (450 mL) and water (450 mL), was added RuO₂ hydrate (356 mg, 2.35 mmol) followed by addition of NaIO₄ (50.4 g, 235 mmol) portion wise over the course of 80 min at −65° C. The mixture was slowly warmed up to 20° C. and stirred until the starting material disappeared on TLC (~2 h). The reaction mixture was then filtered through a pad of Celite and washed with additional acetonitrile. The solvents were then removed on rotavap an the residual material was extracted with EtOAc (250 mL×3). The combined organic extracts were dried over MgSO₄ and concentrated. The residual material was chromatographed on silica gel (acetone/hexane, 3:7) to give 7.78 g of 4 as an oil (87% yield): $^1$H NMR (DMSO-d₆) δ 1.29 (s, 9H), 1.53 (s, 9H), 1.66-1.71 (m, 2H), 2.16-2.28 (m, 2H), 2.58 (m, 1H), 2.77-2.84 (m, 2H), 7.30 (m, 2H), 7.80 (m, 2H). $^{13}$C NMR (DMSO-d₆) δ 27.2, 27.8, 28.0, 31.4, 37.7, 46.7, 80.2, 80.7, 129.1, 129.3, 129.6, 144.7, 165.1, 173.5, 174.0. HRMS (ESI): [M−H]− m/z 377.19682 (calcd 377.19696 for C₂₁H₂₉O₆).

tert-Butyl 4-(2-(tert-butoxycarbonyl)-5-(hydroxyamino)-5-oxopentyl)benzoate [5]

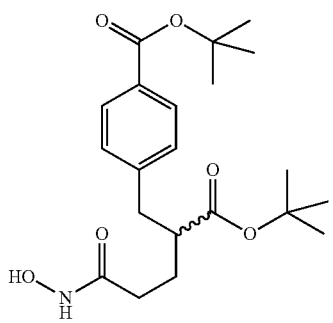 [SMILES: CC(C)(C)OC(=O)c1ccc(CC(CCC(=O)NO)C(=O)OC(C)(C)C)cc1]

Hydroxylamine hydrochloride (5.94 g, 84.6 mmol, 8 eq) and NaOH (3.45 g, 84.55 mmol, 8 eq) were placed in a Schlenk flask and put under an argon atmosphere. After adding methanol (60 mL), the mixture was cooled to 0° C. while stirring. After 15 min, the cooling bath was removed and the mixture was stirred for additional 1 h. The mixture was then filtered through a pat of Celite, yielding the filtrate containing NH₂OH for the later use. Meanwhile, to a solution of 4 (4.00 g, 10.57 mmol) in THF (100 mL) in a Schlenk flask were added triethylamine (2.2 mL, 15.85 mmol, 1.5 eq) and ethyl chloroformate (1.6 mL, 15.86 mmol, 1.5 eq) under an argon atmosphere and the mixture was stirred at rt for 1 h. A white precipitate formed almost immediately. The filtrate containing NH₂OH prepared earlier was added and the mixture was stirred at rt overnight. Volatiles were then removed on rotavap and water (100 mL) was added. The mixture was extracted with EtOAc (250 mL×3). The combined extracts were dried over MgSO₄ and concentrated. The residual material was chromatographed on silica gel (hexanes/EtOAc, 2:3 containing 1% AcOH) to afford 2.63 g of 5 as an orange oil (63% yield, 6.69 mmol): $^1$H NMR (DMSO) δ 1.29 (s, 9H), 1.53 (s, 9H), 1.66-1.71 (m, 2H), 1.92-2.03 (m, 2H), 2.53 (m, 1H), 2.76-2.84 (m, 2H), 7.29 (m, 2H), 7.80 (m, 2H), 8.71 (bs, 1H), 10.40 (bs, 1H): $^{13}$C NMR (DMSO-d₆) δ 27.8, 28.0, 27.9, 29.9, 37.7, 47.0, 80.1, 80.7, 129.1, 129.3, 129.6, 144.7, 165.1, 168.5, 173.5. HRMS (ESI): [M−H]− m/z 392.20771 (calcd 392.20786 for C₂₁H₃₀O₆N).

tert-Butyl 4-(5-(acetoxyamino)-2-(tert-butoxycarbonyl)-5-oxopentyl)benzoate [6]

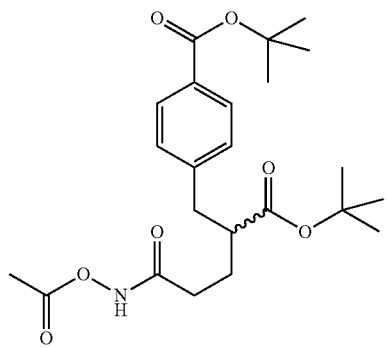 [SMILES: CC(=O)ONC(=O)CCC(Cc1ccc(C(=O)OC(C)(C)C)cc1)C(=O)OC(C)(C)C]

To a solution of 5 (6.78 g, 17.2 mmol) in anhydrous pyridine (100 mL) was dropwise (over 15 min) added acetic anhydride (1.6 mL, 17.2 mmol) was added at 0° C. The mixture was kept in cooling bath overnight. The mixture was evaporated and co-evaporated with toluene. The residual material was then chromatographed on a silica gel column in (EtOAc/hexanes, 1:1 to 3:2) to afford 5.74 g of 6 as a colorless oil (76% yield, 13.2 mmol): $^1$H NMR (DMSO) δ 1.29 (s, 9H), 1.53 (s, 9H), 1.68-1.77 (m, 2H), 2.14 (s, 3H), 2.12-2.20 (m, 2H), 2.59 (m, 1H), 2.77-2.85 (m, 2H), 7.30 (m, 2H), 7.80 (m, 2H), 11.64 (bs, 1H). $^{13}$C NMR (DMSO-d₆) δ 18.2, 27.4, 27.8, 28.0, 29.6, 37.6, 46.7, 80.2, 80.7, 129.1, 129.3, 129.6, 144.6, 165.1, 168.7, 169.2, 173.4. HRMS (ESI): [M−H]−m/z 434.21759 (calcd 434.21843 for C₂₃H₃₂O₇N).

125

4-(5-(Acetoxyamino)-2-carboxy-5-oxopentyl)benzoic acid TT171214/JV2851 [7]

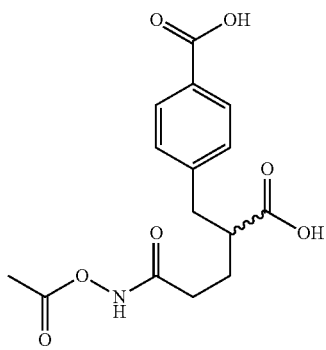 [SMILES: CC(=O)ONC(=O)CCC(Cc1ccc(C(=O)O)cc1)C(=O)O]

126

To a solution of 6 (0.90 g, 2.07 mmol) in dichloromethane (10 mL) were added TFA (5 mL) and i-Pr$_3$SiH (428 μL, 2.07 mmol) under an argon atmosphere. The mixture was stirred at rt for 1 h, when disappearance of the starting material was confirmed on TLC. Volatiles were removed on rotavap, and EtOAC (5 mL) was added to the residual material. A short sonication caused a precipitate formation. After adding hexanes (10 mL) followed by a short sonication, the mixture was filtered to give 0.57 g of 7 as a white solid (86% yield, 1.78 mmol): $^1$H NMR (DMSO) δ 1.66-1.78 (m, 2H), 2.13 (s, 3H), 2.10-2.23 (m, 2H), 2.10-2.23 (m, 2H), 2.63 (m, 1H), 2.81 (dd, J=13, 7, 6.2 Hz, 1H), 2.88 (dd, J=13.7, 8.6 Hz, 1H), 7.31 (m, 2H), 7.85 (m, 2H), 11.63 (bs, 1H), 12.57 (vbs, 2H). $^{13}$C NMR (DMSO-d6) δ 18.3, 27.1, 29.7, 37.5, 45.8, 129.0, 129.3, 129.5, 144.9, 167.5, 168.8, 169.3, 175.8. HRMS (ESI): [M−H]− m/z 322.09274 (calcd 322.09323 for C$_{15}$H$_{16}$O$_7$N).

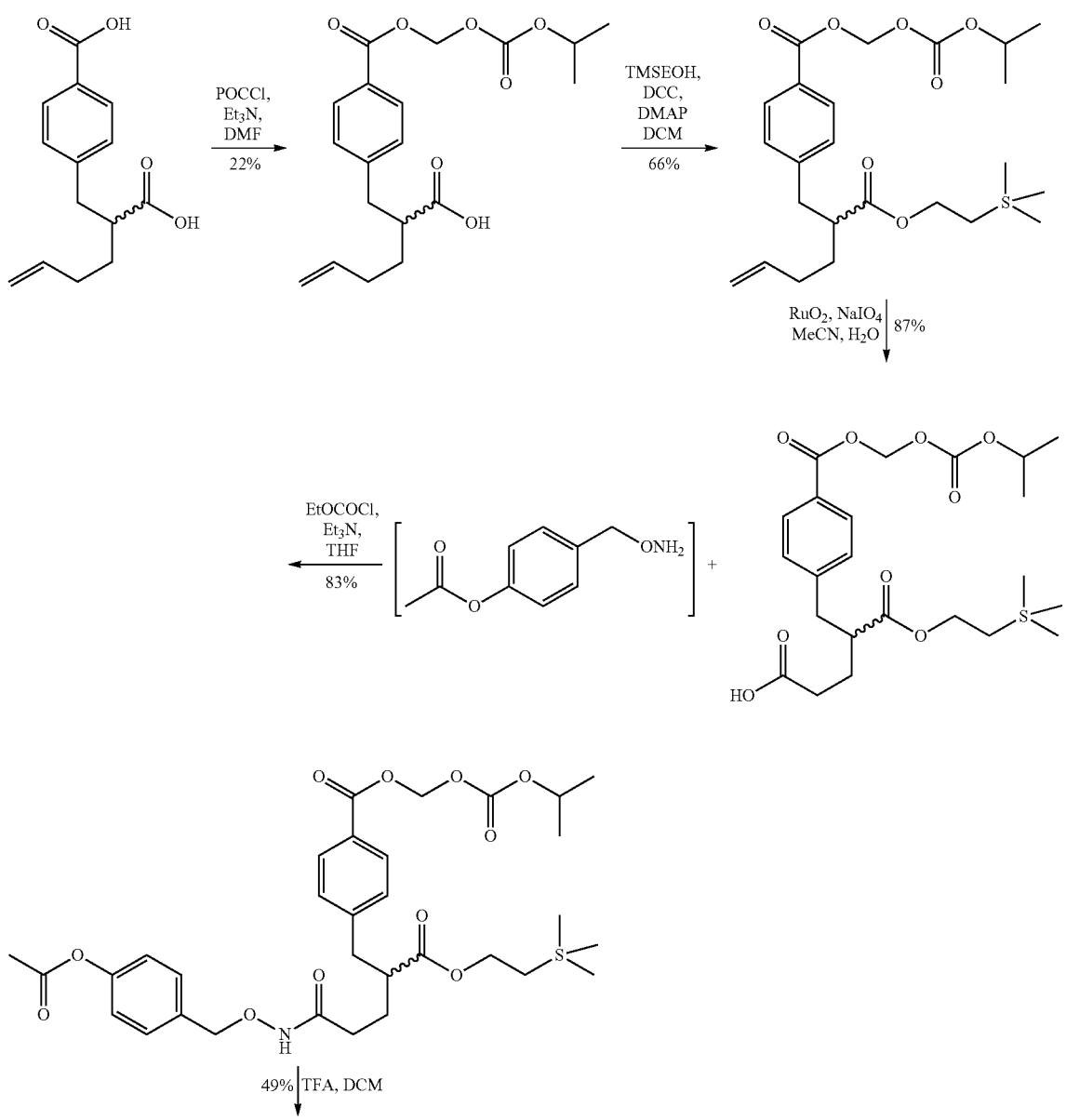

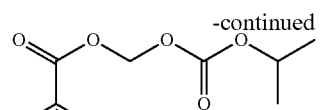
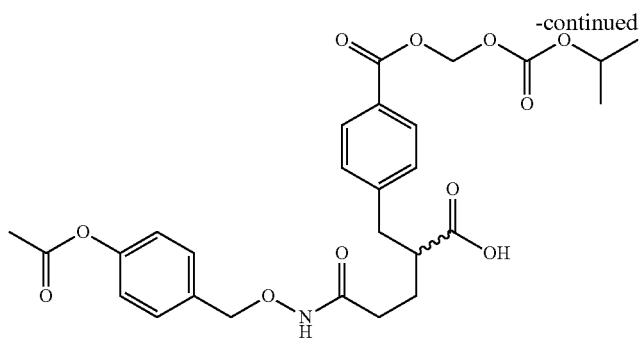

2-(4-(((((Isopropoxycarbonyl)oxy)methoxy)carbonyl)benzyl)hex-5-enoic acid [126]

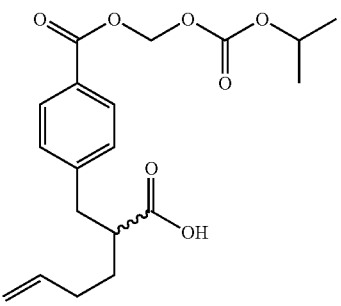 [SMILES: C=CCCC(Cc1ccc(C(=O)OCOC(=O)OC(C)C)cc1)C(=O)O]

To a solution of 2 (4.90 g, 19.74 mmol) in DMF (200 mL) was added trimethylamine (8.3 mL, 59.21 mmol) and the mixture was stirred at rt for 10 min. Chloromethyl isopropyl carbonate (8.1 mL, 59.2 mmol) was added dropwise at 0° C. over 10 min and the mixture was stirred at rt for 24 h. Volatiles were removed on rotavap and the residual material was chromatographed on a silica gel column (hexanes/acetone, 3:1) to afford 1.59 g of 26 as a yellow oil (22% yield, 4.35 mmol): $^1$H NMR (CDCl$_3$) δ 1.33 (d, J=6.3 Hz, 6H), 1.62 (m, 1H), 1.80 (m, 1H), 2.07-2.21 (m, 2H), 2.75 (m, 1H), 2.86 (dd, J=13.7, 6.6 Hz, 1H), 3.05 (dd, J=13.7, 8.2 Hz, 1H), 4.94 (sept, J=6.3 Hz, 1H), 4.97-5.05 (m, OH 2H), 5.75 (m, 1H), 5.99 (s, 2H), 7.28 (m, 2H), 8.01 (m, 2H). $^{13}$C NMR (CDCl$_3$) δ 21.6, 30.8, 31.2, 37.9, 46.1, 73.1, 82.2, 115.7, 127.2, 129.1, 130.3, 137.2, 145.3, 153.4, 164.9, 180.3. HRMS (ESI): [M−H]− m/z 363.14462 (calcd 363.14493 for C$_{19}$H$_{23}$O$_7$).

(((Isopropoxycarbonyl)oxy)methyl 4-(2-((2-(trimethylsilyl)ethoxy)carbonyl)hex-5-en-1-yl)benzoate [27]

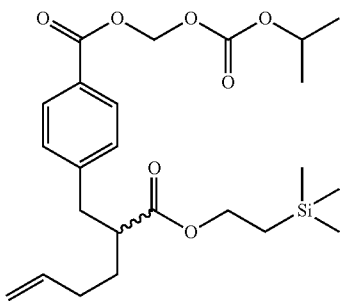 [SMILES: C=CCCC(Cc1ccc(C(=O)OCOC(=O)OC(C)C)cc1)C(=O)OCC[Si](C)(C)C]

To a solution of 26 (1.59 g, 4.35 mmol) in dichloromethane (15 mL) were added DCC (1.38 g, 6.55 mmol, 1.5 eq) and DMAP (54 mg, 0.44 mmol, 0.1 eq) under an argon atmosphere. After 15 min of stirring, 2-(trimethylsilyl)ethan-1-ol (718 µL, 4.79 mmol, 1.1 eq) was added and the mixture was stirred at rt for 16 h. Volatiles were removed on rotavap and the residual material was chromatographed on silica gel column (hexanes/EtOAc, 20:1) to afford 1.34 g of 27 as a yellow oil (66% yield, 2.89 mmol): $^1$H NMR (CDCl$_3$) δ 0.01 (s, 9H), 0.89 (m, 2H), 1.32 (d, J=6.3 Hz, 6H), 1.57 (m, 1H), 1.79 (m, 1H), 2.02-2.15 (m, 2H), 2.68 (m, 1H), 2.81 (dd, J=13.7, 6.3 Hz, 1H), 2.99 (dd, J=13.7, 8.8 Hz, 1H), 4.03-4.13 (m, 2H), 4.94 (sept, J=6.3 Hz, 1H), 4.97-5.04 (m, 2H), 5.75 (m, 1H), 5.99 (s, 2H), 7.25 (m, 2H), 7.99 (m, 2H). $^{13}$C NMR (CDCl$_3$) δ −1.6, 17.3, 21.6, 31.3, 31.4, 38.4, 46.7, 62.6, 73.1, 82.1, 115.4, 127.0, 129.1, 130.2, 137.5, 145.8, 153.4, 164.9, 175.1. HRMS (ESI): [M+Na]+ m/z 487.21217 (calcd 487.21225 for C$_{24}$H$_{36}$O$_7$NaSi).

4-(4-(((((Isopropoxycarbonyl)oxy)methoxy)carbonyl)benzyl)-5-oxo-5-(2-(trimethylsilyl)ethoxy)pentanoic acid [28]

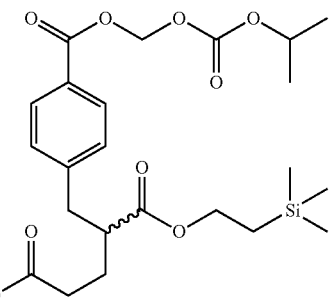

To a solution of 27 (8.48 g, 23.5 mmol) in acetonitrile (450 mL) and water (450 mL) was added RuO$_2$ hydrate (350 mg, 2.63 mmol) at once at 0° C. followed by addition of NaIO$_4$ (50.4 g, 230 mmol) portionwise (over 80 min) at 0° C. The mixture was stirred at 0° C. for 1 h and at rt for 2 h. The reaction mixture was then filtered through a pad of Celite and washed with additional acetonitrile. The volatile solvents were then removed on rotavap and brine (70 mL) was added. The mixture was extracted with EtOAc (120 mL×3). The combined organic extracts were dried over MgSO$_4$ and concentrated. The residual material was chromatographed on a silica gel column (hexanes/acetone, 7:3) to afford 7.78 g of 28 as a syrup (87% yield, 20.4 mmol): $^1$H NMR (CDCl$_3$) δ 0.01 (s, 9H), 0.88 (m, 2H), 1.33 (d, J=6.3 Hz, 6H), 1.87 (m, 1H), 1.96 (m, 1H), 2.34-2.48 (m, 2H), 2.74 (m, 1H), 2.83 (dd, J=13.7, 6.4 Hz, 1H), 3.03 (dd, J=13.7, 8.5 Hz, 1H), 4.03-4.15 (m, 2H), 4.94 (sept, J=6.3, 1H), 5.99 (s, 2H), 7.27 (m, 2H), 8.00 (m, 2H). $^{13}$C NMR (CDCl$_3$) δ −1.6, 17.3, 21.6, 26.7, 31.3, 38.4, 46.3, 63.0, 73.0, 82.1, 127.2, 129.1, 130.3, 145.2, 153.4, 164.9, 174.4, 177.3. HRMS (ESI): [M−H]− m/z 481.18949 (calcd 481.18993 for C$_{23}$H$_{33}$O$_9$Si).

((Isopropoxycarbonyl)oxy)methyl 4-(5-(((4-acetoxybenzyl)oxy)amino)-5-oxo-2-((2-(trimethylsilyl)ethoxy)carbonyl)pentyl)benzoate [29]

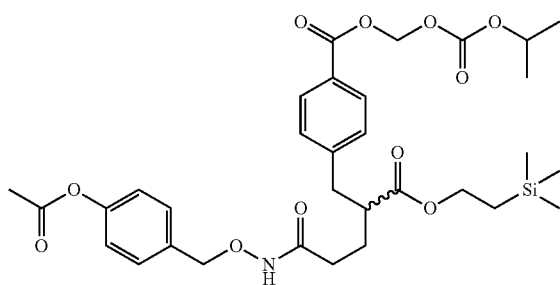 [SMILES: CC(=O)Oc1ccc(CONC(=O)CCC(Cc2ccc(C(=O)OCOC(=O)OC(C)C)cc2)C(=O)OCC[Si](C)(C)C)cc1]

A solution of 28 (583 mg, 1.21 mmol) in THF (10 mL) were added triethylamine (187 μL, 1.33 mmol) and ethyl chloroformate (131 μL, 1.33 mmol). After stirring at rt for 2 h, a 0 freshly prepared THF solution of 10 (theoretically 241 mg, 1.33 mmol) was added to the mixture. The mixture was stirred at rt for 16 h. Volatiles were removed on rotavap and the residual material was chromatographed on a silica gel column (hexanes/EtOAc, 1:1) to afford 646 mg of 29 as a colorless oil (83%, 1.00 mmol): $^1$H NMR (CDCl$_3$) δ 0.01 (s, 9H), 0.89 (m, 2H), 1.33 (d, J=6.3 Hz, 6H), 1.93 (m, 2H), 2.03, 2.13 (2×bs, 2H), 2.70 (m, 1H), 2.82 (dd, J=13.7, 6.1 Hz, 1H), 3.00 (dd, J=13.7, 8.9 Hz, 1H), 4.07 (m, 2H), 4.79, 4.88 (2×bs, 2H), 4.94 (sept, J=6.3, 1H), 5.99 (s, 2H), 7.09 (m, 2H), 7.25 (m, 2H), 7.40 (m, 2H), 7.99 (m, 2H), 8.37 (bs, 1H). $^{13}$C NMR (CDCl$_3$) δ −1.6, 17.3, 21.1, 21.6, 27.5, 30.7, 38.4, 46.5, 63.0, 73.0, 77.4, 82.1, 121.8, 127.1, 129.1, 130.2, 130.4, 133.0, 145.2, 150.9, 153.4, 164.8, 169.5, 170.0, 174.6. HRMS (ESI): [M−H]− m/z 644.25244 (calcd 644.25326 for C$_{32}$H$_{42}$O$_{11}$NSi).

5-(((4-Acetoxybenzyl)oxy)amino)-2-(4-((((isopropoxycarbonyl)oxy)methoxy)carbonyl) benzyl)-5-oxopentanoic acid TT271115/JV-3092 [30]

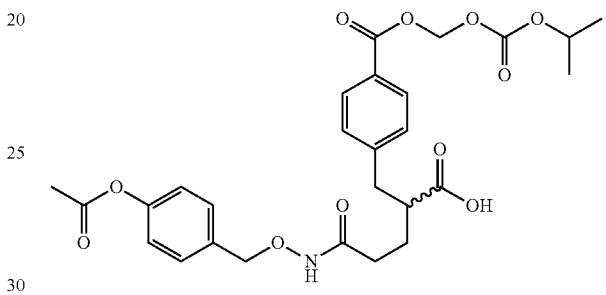

To a solution of 29 (646 mg, 1.00 mmol) in dichloromethane (5 mL) was added TFA (1.5 mL) at 0° C. under an argon atmosphere. The mixture was stirred at 0° C. for 15 min and at rt for 4 h. Volatiles were removed on rotavap and the residual TFA was removed by co-evaporating with toluene. The residual material was purified on HPLC and lyophilized to give 267 mg of 30 as a white fluffy solid (49% yield, 0.49 mmol): $^1$H NMR (CDCl$_3$) δ 1.31 (d, J=6.3 Hz, 6H), 1.78-1.92 (m, 2H), 2.00-2.14 (m, 2H), 2.31 (s, 3H), 2.69 (m, 1H), 2.77 (m, 1H), 3.02 (dd, J=13.8, 8.2 Hz, 1H), 4.73, 4.80 (2×bs, 2H), 4.93 (m, 1H), 5.97 (s, 2H), 7.04 (m, 2H), 7.25 (m, 2H), 7.36 (m, 2H), 7.98 (m, 2H), 8.86 (bs, 1H). $^{13}$C NMR (CDCl$_3$) δ 21.1, 21.6, 27.3, 30.4, 38.1, 46.0, 73.1, 77.9, 82.1, 121.7, 127.2, 129.1, 130.5, 130.9, 133.0, 145.0, 150.8, 153.4, 164.9, 170.0, 170.2, 178.3. HRMS (ESI): [M−H]− m/z 544.18144 (calcd 544.18243 for C$_{27}$H$_{30}$O$_{11}$N).

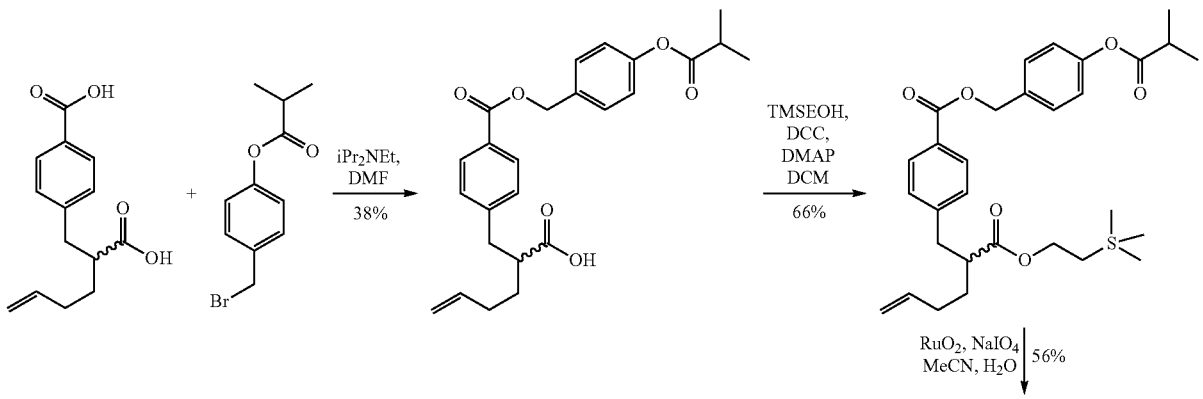

131
132
-continued
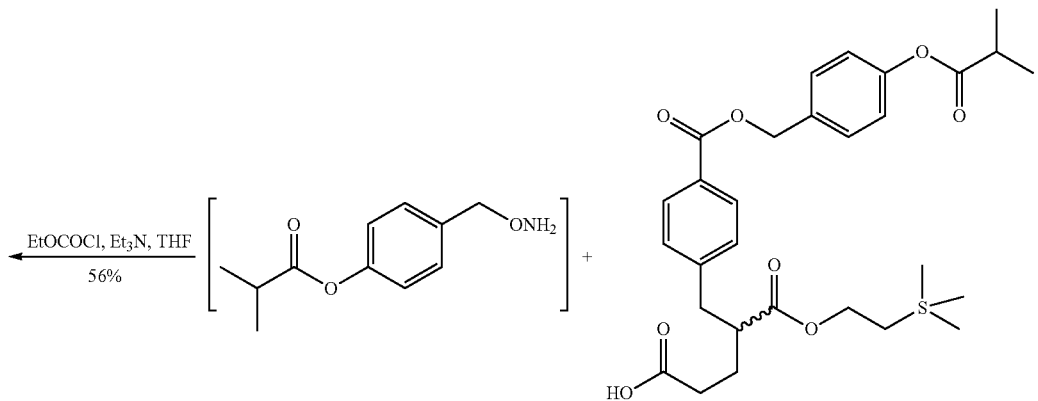
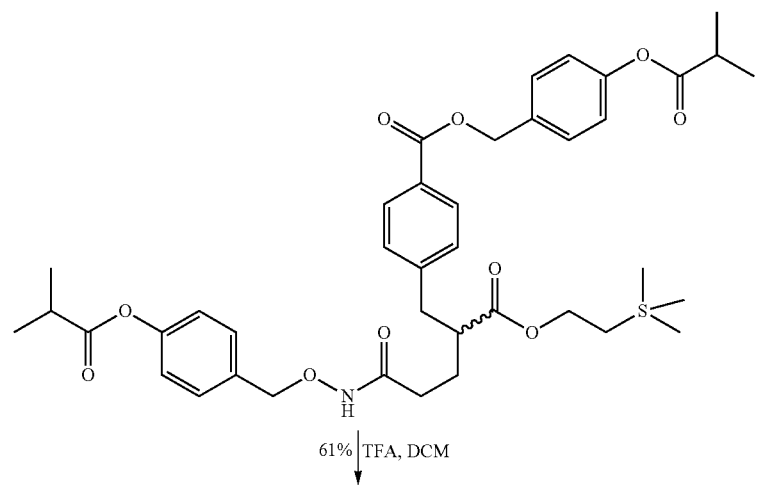
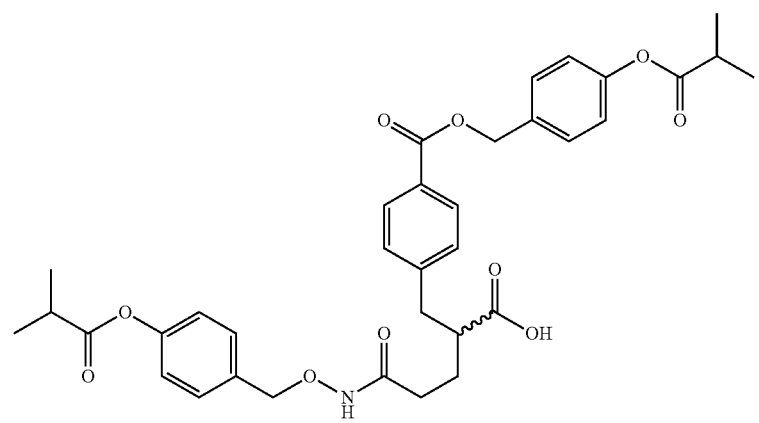

2-(4-(((4-(Isobutyryloxy)benzyl)oxy)carbonyl)benzyl)hex-5-enoic acid

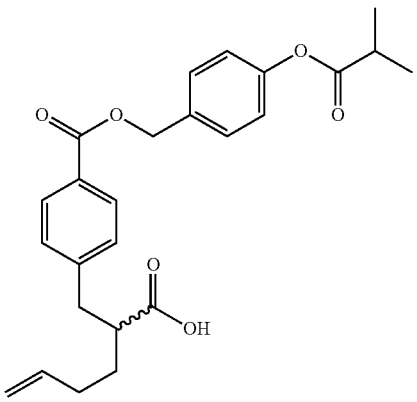 [SMILES: C=CCCC(Cc1ccc(C(=O)OCc2ccc(OC(=O)C(C)C)cc2)cc1)C(=O)O]

A solution of 4-(2-carboxyhex-5-en-1-yl)benzoic acid (4.28 g, 17.3 mmol) in anhydrous DMF (70 ml) was treated with Hunig base (3.8 ml, 21.9 mmol). The mixture was stirred 15 min and then a solution of 4-(bromomethyl)phenyl isobutyrate (5.63 g, 21.9 mmol) in DMF (150 ml) was added dropwise (15 min). The mixture was stirred overnight, then evaporated and the residue was chromatographed on a silica gel column in 20% acetone/hexane. At first, diester by-product was eluted (2.78 g, 27%), then the desired monoester (2.81 g, 38%). $^1$H NMR (400 MHz, CDCl$_3$): δ 1.33 (d, J=7.0 Hz, 6H), 1.60 (m, 1H), 1.78 (m, 1H), 2.04-2.19 (m, 2H), 2.74 (m, 1H), 1.77-2.86 (m, 2H), 3.04 (dd, J=13.7, 8.0 Hz, 1H), 4.98 (dm, J=10.2 Hz, 1H), 5.02 (dm, J=17.1 Hz, 1H), 5.34 (s, 2H), 5.74 (m, 1H), 7.10 (m, 2H), 7.26 (m, 2H), 7.46 (m, 2H), 7.99 (m, 2H), 10.4 (vbs, 1H). $^{13}$C NMR (151 MHz, CDCl$_3$): δ 18.9, 30.7, 31.2, 34.2, 37.9, 46.1, 66.0, 115.6, 121.7, 128.4, 129.0, 129.4, 129.9, 133.5, 137.2, 144.6, 150.8, 166.2, 175.5, 180.3. MS (ESI) m/z (%): 423 (100, [M−H]$^−$). HRMS (ESI): [M−H]$^−$ (C$_{25}$H$_{27}$O$_6$) calc. 423.18131, found 423.18119.

4-(Isobutyryloxy)benzyl 4-(2-((2-(trimethylsilyl)ethoxy)carbonyl)hex-5-en-1-yl)benzoate

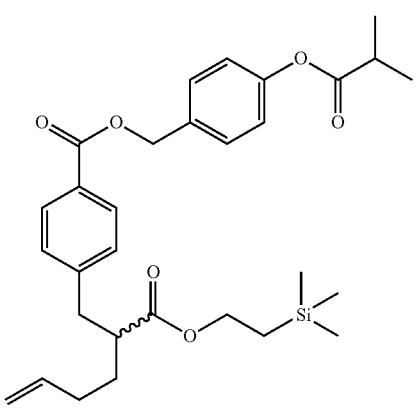 [SMILES: C=CCCC(Cc1ccc(C(=O)OCc2ccc(OC(=O)C(C)C)cc2)cc1)C(=O)OCC[Si](C)(C)C]

A mixture of 2-(4-(((4-(isobutyryloxy)benzyl)oxy) carbonyl)benzyl)hex-5-enoic acid 2.78 g (6.55 mmol), DCC (1.56 g, 7.57 mmol), DMAP (80 mg, 0.66 mmol) in dichloromethane (30 ml) was stirred 15 min at room temperature and then treated with trimethylsilylmethanol (1.5 ml, 10.5 mmol). The mixture was stirred overnight, resulting dicyclohexylurea was filtered off. The filtrate was evaporated and the residue was purified on a silica gel column in 15→25% acetone/hexane. Yield 2.40 g (70%) of syrup. $^1$H NMR (400 MHz, CDCl$_3$): δ 0.01 (s, 9H), 0.84-0.89 (m, 2H), 1.33 (d, J=7.0 Hz, 6H), 7.57 (m, 1H), 1.78 (m, 1H), 2.02-2.14 (m, 2H), 2.67 (m, 1H), 2.80 (dd, J=13.7, 6.5 Hz, 1H), 2.81 (sept, J=7.0, 1H), 2.99 (dd, J=13.7, 8.7 Hz, 1H), 4.04-4.13 (m, 2H), 4.96-5.04 (m, 2H), 5.34 (s, 2H), 5.75 (m, 1H), 7.10 (m, 2H), 7.24 (m, 2H), 7.46 (m, 2H), 7.98 (m, 2H). $^{13}$C NMR (151 MHz, CDCl$_3$): δ −1.6, 17.3, 18.9, 31.3, 31.4, 34.2, 38.4, 46.7, 62.6, 66.0, 115.3, 121.7, 128.2, 129.0, 129.4, 129.8, 133.5, 137.5, 145.1, 150.8, 166.3, 175.2, 175.5. MS (ESI) m/z (%): 547 (100, [M+Na]$^+$). HRMS (ESI): [M+Na]$^+$ (C$_{30}$H$_{40}$O$_6$NaSi) calc. 547.24864, found 547.24854.

4-(4-(((4-(Isobutyryloxy)benzyl)oxy)carbonyl)benzyl)-5-oxo-5-(2-(trimethylsilyl)ethoxy)pentanoic acid

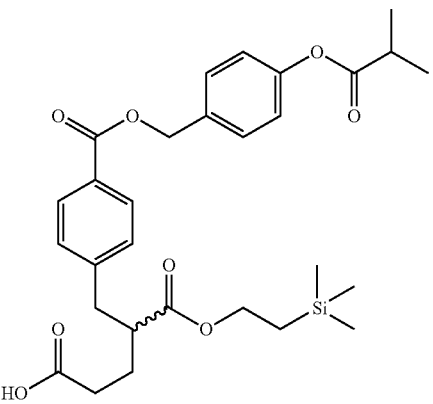 [SMILES: CC(C)C(=O)Oc1ccc(COC(=O)c2ccc(CC(CCC(=O)O)C(=O)OCC[Si](C)(C)C)cc2)cc1]

4-(Isobutyryloxy)benzyl 4-(2-((2-(trimethylsilyl)ethoxy)carbonyl)hex-5-en-1-yl)benzoate (2.34 g, 4.46 mmol) was dissolved in MeCN (30 mL) and H$_2$O (30 mL) was added. The mixture was cooled to 0° C. and RuO$_2$·xH$_2$O (60 mg) was added at once followed by portionwise (60 min) addition of NaIO$_4$ (9.54 g, 44.6 mol, 10 eq). The mixture was stirred at 0° C. for 1 h, then at room temperature for additional 2 h (cooling bath was kept to control the exothermic process). The mixture was filtered through a Celite pad washing the solid with additional MeCN. The filtrate was put on rotavap and once volatiles were removed 30 mL of brine was added and the aqueous mixture was extracted 3× with 30 mL of AcOEt. The combined organic layers were dried with MgSO$_4$, filtered and after volatiles removal the residue was chromatographed on silica (eluent hex/acetone 7:3) to afford 1.38 g (57%) of syrup. $^1$H NMR (400 MHz, CDCl$_3$): δ 0.01 (s, 9H), 0.85-0.90 (m, 2H), 1.33 (d, J=7.0 Hz, 6H), 1.87 (m, 1H), 1.95 (m, 1H), 2.36 (ddd, J=16.8, 8.6, 7.1 Hz, 1H), 2.44 (ddd, J=16.8, 9.0, 5.8 Hz, 1H), 2.73 (m, 1H), 2.78-2.85 (m, 2H), 3.02 (dd, J=13.7, 8.4 Hz, 1H), 4.05-4.13 (m, 2H), 5.34 (s, 2H), 7.10 (m, 2H), 7.25 (m, 2H), 7.46 (m, 2H), 7.98 (m, 2H), 10.8 (vbs, 1H). $^{13}$C NMR (151 MHz, CDCl$_3$): δ −1.6, 17.3, 18.9, 26.6, 31.4, 34.2, 38.3, 46.3, 63.0, 66.0, 121.7, 128.3, 129.0, 129.4, 129.9, 133.5, 144.4, 150.8, 166.2, 174.5, 175.5, 177.8. MS (ESI) m/z (%): 541 (100,

4-(((1,3-Dioxoisoindolin-2-yl)oxy)methyl)phenyl isobutyrate

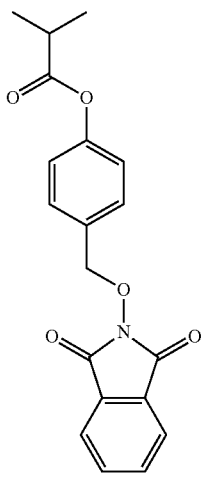 [SMILES: CC(C)C(=O)Oc1ccc(CON2C(=O)c3ccccc3C2=O)cc1]

A solution of 4-(hydroxymethyl)phenyl isobutyrate (777 mg, 4.0 mmol), N-hydroxyphthalimide (652 mg, 4.0 mmol) and PPh$_3$ (1.25 g, 4.8 mmol) in THF (20 ml) was cooled (0° C.) and treated with DIAD (945 μl, 4.8 mmol). The mixture was stirred 1 h. The solvent was evaporated and the residue was purified by chromatography on a silica gel column in 40% acetone/hexane. Product was crystallized from EtOAc-hexane; yield 1.05 g (78%). $^1$H NMR (400 MHz, CDCl$_3$): δ 1.31 (d, J=7.0 Hz, 6H), 2.79 (hept, J=7.0 Hz, 1H), 5.20 (s, 2H), 7.10 (m, 2H), 7.56 (m, 2H), 7.73 (m, 2H), 7.81 (m, 2H). $^{13}$C NMR (151 MHz, CDCl$_3$): δ 19.0, 34.3, 79.3, 121.8, 123.7, 129.0, 131.1, 131.3, 134.6, 151.8, 163.6, 175.5. MS (ESI) m/z (%): 362 (100, [M+Na]$^+$). HRMS (ESI): [M+Na]$^+$ (C$_{19}$H$_{17}$O$_5$NNa) calc. 362.09989, found 362.10013.

4-(Isobutyryloxy)benzyl 4-(5-(((4-(isobutyryloxy)benzyl)oxy)amino)-5-oxo-2-((2-(trimethylsilyl)ethoxy)carbonyl)pentyl) benzoate

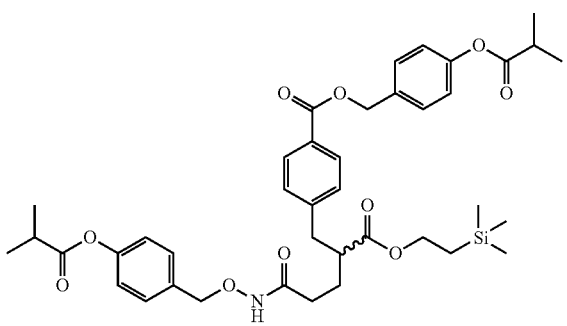 [SMILES: CC(C)C(=O)Oc1ccc(CONC(=O)CCC(Cc2ccc(C(=O)OCc3ccc(OC(=O)C(C)C)cc3)cc2)C(=O)OCC[Si](C)(C)C)cc1]

A solution of 4-(((1,3-dioxoisoindolin-2-yl)oxy)methyl) phenyl isobutyrate (733 mg, 2.16 mmol) in THF (10 ml) was treated with a solution of hydrazine in THF (1M, 2.2 ml, 2.2 mmol). Resulting precipitate was filtered off after 1.5 h and the filtrate containing 4-((aminooxy)methyl)phenyl isobutyrate was used for subsequent reaction. In the meantime, a mixture of hydroxybenzotriazole (365 mg, 2.7 mmol) and 4-(4-(((4-(isobutyryloxy)benzyl)oxy)carbonyl)benzyl)-5-oxo-5-(2-(trimethylsilyl)ethoxy) pentanoic acid (1.17 g, 2.16 mmol) in THF (6 ml) was cooled to −10° C. and a solution of EDC·HCl (518 mg, 2.7 mmol) and iPr$_2$NEt (470 μL, 2.7 mmol) in THF (16 ml) was added. Resulting mixture was stirred 30 min at −10° C., then pre-prepared solution of 4-((aminooxy)methyl)phenyl isobutyrate was added and the mixture was stirred overnight. Solvent was evaporated and the residue was partitioned between chloroform and water (80 ml, 1:1). Aqueous layer was extracted with chloroform (40 ml) again. Combined organic portions were dried (MgSO$_4$) and concentrated in vacuo. The syrupy residue was purified on a silica gel column in 25→30% acetone/hexane; yield 938 mg (56%). $^1$H NMR (400 MHz, CDCl$_3$): δ 0.00 (s, 9H), 0.83-0.86 (m, 2H), 1.32 (2×d, J=7.0 Hz, 12H), 1.92 (m, 2H), 2.01 (m, 1H), 2.11 (m, 1H), 2.70 (m, 1H), 2.77-2.85 (m, 3H), 3.00 (dd, J=13.7, 8.7 Hz, 1H), 4.03-4.10 (m, 2H), 4.75-4.91 (m, 2H), 5.33 (s, 2H), 7.08 (m, 2H), 7.10 (m, 2H), 7.23 (m, 2H), 7.39 (m, 2H), 7.46 (m, 2H), 7.97 (m, 2H), 8.14 (bs, 1H). $^{13}$C NMR (151 MHz, CDCl$_3$): δ −1.6, 17.4, 18.9, 18.9, 27.5, 30.8, 34.1, 34.1, 38.4, 46.5, 63.0, 66.0, 77.5, 121.7, 121.8, 128.3, 129.0, 129.4, 129.9, 130.3, 132.8, 133.5, 144.5, 150.8, 151.2, 166.2, 170.0, 174.6, 175.5, 175.5. MS (ESI) m/z (%): 756 (100, [M+Na]$^+$). HRMS (ESI): [M+Na]$^+$ (C$_{40}$H$_{51}$O$_{10}$NNaSi) calc. 756.31744, found 756.31756.

5-(((4-(Isobutyryloxy)benzyl)oxy)amino)-2-(4-(((4-(isobutyryloxy)benzyl)oxy)carbonyl)benzyl)-5-oxo-pentanoic acid TT200216 [45]

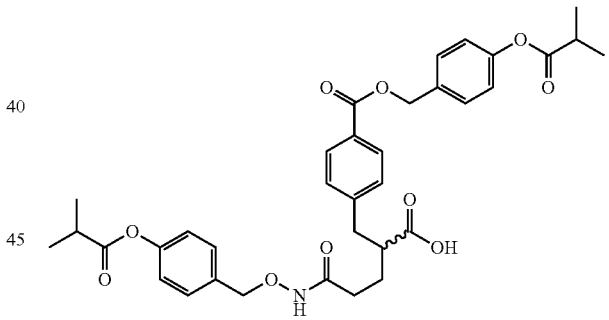

A cooled (0° C.) solution of 4-(isobutyryloxy)benzyl 4-(5-(((4-(isobutyryloxy)benzyl)oxy)amino)-5-oxo-2-((2-(trimethylsilyl)ethoxy) carbonyl)pentyl)benzoate (362 mg, 0.49 mmol) in DCM (4 mL) was treated with TFA (1.4 mL), the mixture was stirred at the temperature for 15 min and then it was let warm up to rt. After 4 h volatiles were removed on rotavap and residual TFA was removed codistillation with toluene. The residue was purified on a silica gel column in 5% MeOH+0.5% AcOH/CHCl$_3$ giving 235 mg of syrup which was crystallized from acetone-ether-hexan; yield 190 mg (61%). $^1$H NMR (400 MHz, CDCl$_3$): δ 1.30-1.33 (m, 12H), 1.86 (m, 2H), 2.08 (m, 1H), 2.26 (m, 1H), 2.70 (m, 1H), 2.74-2.85 (m, 3H), 3.02 (m, 1H), 4.70-4.84 (m, 2H), 5.32 (m, 2H), 7.04 (m, 2H), 7.09 (m, 2H), 7.24 (m, 2H), 7.35 (m, 2H), 7.44 (m, 2H), 7.97 (m, 2H), 8.69 (bm, 1H). $^{13}$C NMR (151 MHz, CDCl$_3$): δ 18.9, 18.9, 27.3, 30.4, 34.2, 34.2, 38.1, 45.9, 46.0, 66.0, 77.5, 121.7, 128.4, 129.0, 129.4, 129.9, 130.4, 132.9, 133.5, 144.3, 150.8, 151.1, 166.2, 170.1, 175.5, 176.0, 178.2. MS (ESI) m/z (%): 632 (100, [M–H]⁻). HRMS (ESI): [M–H] ($C_{35}H_{38}O_{10}N$) calc. 632.25012, found 632.24975.

Example 10

Prodrugs of a Hydroxamate-based Glutamate Carboxypeptidase II Inhibitors $IC_{50}$ Determination of Prodrugs Inhibition constants of prodrugs were determined using the radioenzymatic assay with 3HNAAG (radiolabeled at the terminal glutamate) as has been previously described (Novakova, et al., *J. Med. Chem*, 2016). Briefly, rhGCPII (30 ng/mL) was preincubated in the presence of inhibitors at varying concentrations, in 20 mM Tris, 150 mM NaCl, pH 8.0, for 15 min at 37° C. in the total volume of 80 µL. The reaction was initiated by the addition of 40 µL of the mixture of 0.31 µM NAAG (Sigma) and 15 nM 3H-NAAG (50 Ci/mmol in Tris buffer, PerkinElmer) to the total reaction volume of 120 µL. Following 20 min incubation, the reaction was terminated by addition of 120 µL of potassium phosphate (200 Mm), EDTA (50 Mm) and β-mercaptoethanol (2Mm), pH 7.4. The released glutamate was separated by ion-exchange chromatography and quantified by liquid scintillation counting. GraphPad Prism software (GraphPad Software, San Diego, CA, USA), was used for data fitting and IC50 values were calculated from the inhibition curves where applicable.

Example 11

Prodrugs of a Hydroxamate-Based Glutamate Carboxypeptidase II Inhibitors In Vitro Plasma Metabolite Identification Studies Plasma stability studies were conducted in mouse plasma as previously described. (Majer, et al., 2016) Compound 1 and prodrugs (12, 23 and 30) (10 µM) were spiked in plasma and incubated in an orbital shaker at 37° C. At zero and 60 min post incubation, 100 µL aliquots of the mixture in triplicate were removed and the reaction quenched by addition of two times the volume of ice cold acetonitrile spiked with the internal standard (losartan 5 µM). The samples were vortexed for 30 s and centrifuged at 12000 g for 10 min. Supernatant (50 µL) was diluted with 50 µL water and transferred to a 250 µL polypropylene vial sealed with a Teflon cap. Prodrug disappearance and metabolite identification were analyzed over time using an Agilent 1260 HPLC coupled to a ESITOF Agilent 6530 with Agilent Jet Stream Technology (Agilent Technologies, Santa Clara, CA). Samples were separated on a Waters 1.7 µm, C18, 100×2.1 column at a flow rate 0.3 mL/min. The concentration of mobile phase B (0.1% FA in acetonitrile) was gradually increased from 10 to 100% in mobile phase A (0.1% FA in water) over 7 min. The mass spectrometry instrument was operated in a negative or positive (for JV-2946) ion mode with a voltage of +3.00 kV applied to the capillary. The temperature, the flow rate of the nitrogen drying gas, the pressure of the nitrogen nebulizing gas, the temperature, and the flow rate of the sheath gas were set at 325° C., 10 L/min, 40 psi, 390° C., and 11/min, respectively.

Example 12

Prodrugs of a Hydroxamate-Based Glutamate Carboxypeptidase II Inhibitors Plasma Pharmacokinetic Studies in Mice All pharmacokinetic studies in mice were conducted according to protocols approved by the Animal Care and Use Committee at Johns Hopkins University (Baltimore, MD). Briefly, male CD 1 mice between 25 g and 30 g were obtained from Harlan Laboratories (Indianapolis, Indiana), and maintained on a 12-hour light-dark cycle with ad libitum access to food and water.

Compound 1 and its prodrugs were administered to male mice as a single (p.o.) dose of 10 mg/kg equivalent. Dosing solutions were prepared on the day of the experiment in 50 mM HEPES buffered saline and pH adjusted to 7.4. The mice were sacrificed by pentobarbital injection at 30 minutes post drug administration, and blood collected via cardiac puncture was placed into iced heparin-coated BD microtainers. Blood samples were spun at 2,000 g for 15 minutes, plasma was removed and stored at −80° C. until LC-MS analysis as previously described. (Novakova, et al., 2016) Briefly, chromatographic analysis was performed using an Accela™ ultra high-performance system consisting of an analytical pump, and an autosampler coupled with TSQ Vantage mass spectrometer (Thermo Fisher Scientific Inc., Waltham, MA). Separation of the analyte was achieved using Agilent Eclipse Plus column (100×2.1 mm i.d.) packed with a 1.8 µm C18 stationary phase. The mobile phase used was composed of 0.1% formic acid in acetonitrile and 0.1% formic acid in $H_2O$ with gradient elution, starting with 5% (organic) linearly increasing to 99% up to 2.5 min, maintaining at 99% (2.5-3.5 min) and reequilibrating to 5% by 4.5 min. The total run time for each analyte was 6 min. The mass transitions (M−H)− used for (1) were 279.986>203.066, 247.173; and for losartan were 421.131>156.996, 179.112.

Example 13

Prodrugs of a Hydroxamate-Based Glutamate Carboxypeptidase II Inhibitors Chronic Constrictive Injury Model of Neuropathic Pain All experimental protocols were approved by the Institutional Animal Care and Use Committee at Johns Hopkins University (Baltimore, MD) and adhered to all of the applicable institutional and governmental guidelines for the humane treatment of laboratory animals. Male Sprague-Dawley rats (200-250 g; n=10-15 per group) were subjected to peripheral neuropathy injury by constriction of the sciatic nerve performed according to methods described previously. (Novakova, et al., 2016; Bennett, et al., 1988; Attal, et al., 1990) In brief, the common sciatic nerve was exposed and 4 ligatures (4.0 chromic gut) tied loosely around it with 1 mm spacing. Wound clips were used to close wounds and animals were returned to home cages for recovery. Hyperalgesia testing was initiated 10 days post-surgery. Pain sensitivity was assessed by determining withdrawal latencies in response to a constant thermal stimulus directed to the plantar surface of the hind paw using a Basile Plantar apparatus (Ugo Basile, Vaarese, Italy) according to the method described by Hargreaves et al. (Hargreaves, et al., 1988) Apparatus was calibrated so that normal rats respond to the stimulus within 15 sec of application. Withdrawal latency (i.e., the time taken for the rat to withdraw its paw from the heat source) was measured to the nearest 0.1 sec. The "difference in score" was calculated by subtracting the average latency of the paw on the non-ligated versus ligated side. Each animal was tested during two experimental sessions per week, with three days allowed to elapse between test sessions. Test agents, prodrug 12 (3 mg/kg equivalent of 1), or gabapentin (50 mg/kg and 100 mg/kg po) as a positive control were dosed daily throughout the study via oral gavage and one hour before testing on experimental days. Statistical analysis with students t-test was used to determine differences between control and treatment group.

Example 14

Prodrugs of a Hydroxamate-Based Glutamate Carboxypeptidase II Inhibitors General Methods In Vitro Stability Studies: The stock solution for most prodrugs was prepared as a 10 mM solution in DMSO to carry out the in vitro studies. The chemical stability of prodrugs was evaluated using simulated gastric fluid (pH 1.2) and Hanks' Balanced Salt Solution (HBSS) buffer (pH 7.4). Briefly, prodrugs were spiked (10 µM) in respective solutions and incubated at 37° C. for 1 h. At predetermined time points (0, 30 and 60 min), aliquots of 100 µL were removed and diluted with 100 µL of water. Prodrug disappearance was monitored using the developed liquid chromatography and tandem mass spectrometry (LC/MS/MS) method described below.

For metabolic stability, plasma (mouse, and human) and liver microsomes (mouse and human) were used. For stability, prodrugs (10 µM) were spiked in each matrix and incubated in an orbital shaker at 37° C. At predetermined times (0, 30 and 60 min), 100 µL aliquots of the mixture in triplicate were removed and the reaction quenched by addition of three times the volume of ice cold acetonitrile spiked with the internal standard (losartan 5 µM). The samples were vortexed for 30 s and centrifuged 12000 g for 10 min. 50 µL supernatant diluted with 50 µL water was transferred to a 250 µL polypropylene vial sealed with a Teflon cap. Prodrug disappearance was monitored over time using a liquid chromatography and tandem mass spectrometry (LC/MS/MS) method as described below.

For LC/MS/MS, prodrugs were separated with Thermo Scientific Accela UPLC system coupled to Accela open autosampler on an Agilent C18 (100×2.1 mm id) UPLC column. The autosampler was temperature controlled and operating at 10° C. The mobile phase used for the chromatographic separation was composed of acetonitrile/water containing 0.1% formic acid and was run at a flow rate of 0.5 mL/minute for 4.5 minutes using gradient elution. The column effluent was monitored using TSQ Vantage triple-quadrupole mass spectrometric detector, equipped with an electrospray probe set in the positive ionization mode. Samples were introduced into the ionization source through a heated nebulized probe (350° C.).

For quantification of compound remaining, disappearance of prodrugs was measured from ratio of peak areas of analyte to IS. Percentage remaining was calculated in the following manner:

$$\frac{\text{Avg. Response} * @ 60 \min}{\text{Avg. Response} @ 0 \min} \times 100$$

Where response=[(Area of analyte)/(Area of internal standard)]

*Average response is average of two samples at each time point.

In vivo pharmacokinetics of prodrugs in rodents (Mice): Prodrugs were dosed peroral (10 mg/kg equiv.) in mice at a dosing volume of 5-10 mL/kg. Single time point studies were conducted at 30 min (N=3) following dosing. Plasma was harvested from blood by centrifugation. Mean concentration-time data was used for pharmacokinetic (PK) analysis.

Bioanalysis of parent and intact prodrug in plasma and tissues: Prior to extraction, frozen samples were thawed on ice. For plasma, 50 µL of the sample was transferred into siliconized microcentrifuge tubes. For sciatic nerves, the samples were weighed in a 1.7 mL tubes and homogenized in 5× the volume of methanol. The calibration curves were prepared using naïve plasma and sciatic nerves in a concentration range of 50-10000 pmol/g or pmol/mL. Sample preparation involved a single liquid extraction by addition of 300 µL of methanol with internal standard (losartan 200 nM in methanol), followed by vortexing for 30 s and then centrifugation at 10,000×g for 10 min. Supernatant (about 250 µL) was transferred and evaporated to dryness at 40° C. under a gentle stream of nitrogen. The residue was reconstituted with 50 µL of 30% acetonitrile and analysed by LC/MS/MS.

Chromatographic analysis was performed using an Accela™ ultra high-performance system consisting of an analytical pump, and an autosampler coupled with TSQ Vantage mass spectrometer (Thermo Fisher Scientific Inc., Waltham, MA). Separation of the analyte from potentially interfering material was achieved at ambient temperature using Agilent Eclipse Plus column (100×2.1 mm i.d.) packed with a 1.8 µm C18 stationary phase. The mobile phase used was composed of 0.1% formic acid in acetonitrile and 0.1% formic acid in $H_2O$ with gradient elution, starting with 10% (organic) linearly increasing to 99% up to 2.5 min, maintaining at 99% (2.5-3.5 min) and reequilibrating to 10% by 4.5 min. The total run time for each analyte was 4.5 min. The mass transitions (M−H)− used for Compound 50 were 280.077>175.168, 203.156; and for losartan were 420.895>127.040, 179.108.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Attal, N.; Jazat, F.; Kayser, V.; Guilbaud, G. Further evidence for 'pain-related' behaviours in a model of unilateral peripheral mononeuropathy. *Pain* 1990, 41, 235-251.

Barinka, C.; Rojas, C.; Slusher, B.; Pomper, M. Glutamate carboxypeptidase II in diagnosis and treatment of neurologic disorders and prostate cancer. *Curr. Med. Chem.* 2012, 19, 856-870.

Bennett, G. J.; Xie, Y. K. A peripheral mononeuropathy in rat that produces disorders of pain sensation like those seen in man. *Pain* 1988, 33, 87-107.

Flipo, M.; Charton, J.; Hocine, A.; Dassonneville, S.; Deprez, B.; Deprez-Poulain, R. Hydroxamates: relationships between structure and plasma stability. *J. Med. Chem* 2009, 52, 6790-802.

Hargreaves, K.; Dubner, R.; Brown, F.; Flores, C.; Joris, J. A new and sensitive method for measuring thermal nociception in cutaneous hyperalgesia. *Pain* 1988, 32, 77-88.

Jackson, P. F.; Cole, D. C.; Slusher, B. S.; Stetz, S. L.; Ross, L. E.; Donzanti, B. A.; Trainor, D. A. Design, synthesis, and biological activity of a potent inhibitor of the neuropeptidase N-acetylated alpha-linked acidic dipeptidase. *J. Med. Chem.* 1996, 39, 619-622.

Jackson, P. F.; Tays, K. L.; Maclin, K. M.; Ko, Y. S.; Li, W.; Vitharana, D.; Tsukamoto, T.; Stoermer, D.; Lu, X. C.; Wozniak, K.; Slusher, B. S. Design and pharmacological activity of phosphinic acid based NAALADase inhibitors. *J. Med. Chem.* 2001, 44, 4170-4175.

Kozikowski, A. P.; Nan, F.; Conti, P.; Zhang, J.; Ramadan, E.; Bzdega, T.; Wroblewska, B.; Neale, J. H.; Pshenichkin, S.; Wroblewski, J. T. Design of remarkably simple, yet potent urea-based inhibitors of glutamate carboxypeptidase II (NAALADase). *J. Med. Chem.* 2001, 44, 298-301.

Majer, P.; Jackson, P. F.; Delahanty, G.; Grella, B. S.; Ko, Y. S.; Li, W.; Liu, Q.; Maclin, K. M.; Polakova, J.; Shaffer, K. A.; Stoermer, D.; Vitharana, D.; Wang, E. Y.; Zakrzewski, A.; Rojas, C.; Slusher, B. S.; Wozniak, K. M.; Burak, E.; Limsakun, T.; Tsukamoto, T. Synthesis and biological evaluation of thiol-based inhibitors of glutamate carboxypeptidase II: discovery of an orally active GCP II inhibitor. *J. Med. Chem.* 2003, 46, 1989-1996.

Majer, P.; Jancarik, A.; Krecmerova, M.; Tichy, T.; Tenora, L.; Wozniak, K.; Wu, Y.; Pommier, E.; Ferraris, D.; Rais, R.; Slusher, B. S. Discovery of orally available prodrugs of the Glutamate Carboxypeptidase II (GCPII) inhibitor 2-Phosphonomethylpentanedioic Acid (2-PMPA). *J. Med. Chem.* 2016, 59, 2810-2819.

Novakova, Z.; Wozniak, K.; Jancarik, A.; Rais, R.; Wu, Y.; Pavlicek, J.; Ferraris, D.; Havlinova, B.; Ptacek, J.; Vavra, J.; Hin, N.; Rojas, C.; Majer, P.; Slusher, B. S.; Tsukamoto, T.; Barinka, C. Unprecedented binding mode of hydroxamate-based inhibitors of Glutamate Carboxypeptidase II: Structural characterization and biological activity. *J. Med. Chem.* 2016, 59, 4539-4550.

Raji, I.; Ahluwalia, K.; Oyelere, A. K. Design, synthesis and evaluation of antiproliferative activity of melanoma-targeted histone deacetylase inhibitors. *Bioorg. Med. Chem. Lett.* 2017, 27, 744-749.

Schlimme, S.; Hauser, A. T.; Carafa, V.; Heinke, R.; Kannan, S.; Stolfa, D. A.; Cellamare, S.; Carotti, A.; Altucci, L.; Jung, M.; Sippl, W. Carbamate prodrug concept for hydroxamate HDAC inhibitors. *ChemMedChem* 2011, 6, 1193-1198.

Silhar, P.; Eubanks, L. M.; Seki, H.; Pellett, S.; Javor, S.; Tepp, W. H.; Johnson, E. A.; Janda, K. D. Targeting botulinum A cellular toxicity: a prodrug approach. *J. Med. Chem.* 2013, 56, 7870-7879.

Slusher, B. S.; Rojas, C.; Coyle, J. T. Glutamate Carboxypeptidase II A2, In *Handbook of Proteolytic Enzymes*, Rawlings, Neil D. Salvesen, G., Ed. Academic Press: 2013; pp 1620-1627.

Vornov, J. J.; Hollinger, K. R.; Jackson, P. F.; Wozniak, K. M.; Farah, M. H.; Majer, P.; Rais, R.; Slusher, B. S. Still NAAG'ing after all these years: The continuing pursuit of GCPII inhibitors. *Adv. Pharmacol.* 2016, 76, 215-255.

Vornov, J. J.; Wozniak, K. M.; Wu, Y.; Rojas, C.; Rais, R.; Slusher, B. S. Pharmacokinetics and pharmacodynamics of the glutamate carboxypeptidase II inhibitor 2-MPPA show prolonged alleviation of neuropathic pain through an indirect mechanism. *J. Pharmacol. Exp. Ther.* 2013, 346, 406-413.

Wiemer, A. J.; Wiemer, D. F. Prodrugs of phosphonates and phosphates: crossing the membrane barrier. *Top. Curr. Chem.* 2015, 360, 115-160.

Yamamoto, T.; Nozaki-Taguchi, N.; Sakashita, Y. Spinal N-acetyl-alpha-linked acidic dipeptidase (NAALADase) inhibition attenuates mechanical allodynia induced by paw carrageenan injection in the rat. *Brain Res.* 2001, 909, 138-144.

Yamamoto, T.; Nozaki-Taguchi, N.; Sakashita, Y.; Inagaki, T. Inhibition of spinal Nacetylated-alpha-linked acidic dipeptidase produces an antinociceptive effect in the rat formalin test. *Neuroscience* 2001, 102, 473-479.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating neuropathic pain condition, the method comprising administering to a subject in need of treatment thereof, a compound selected from:

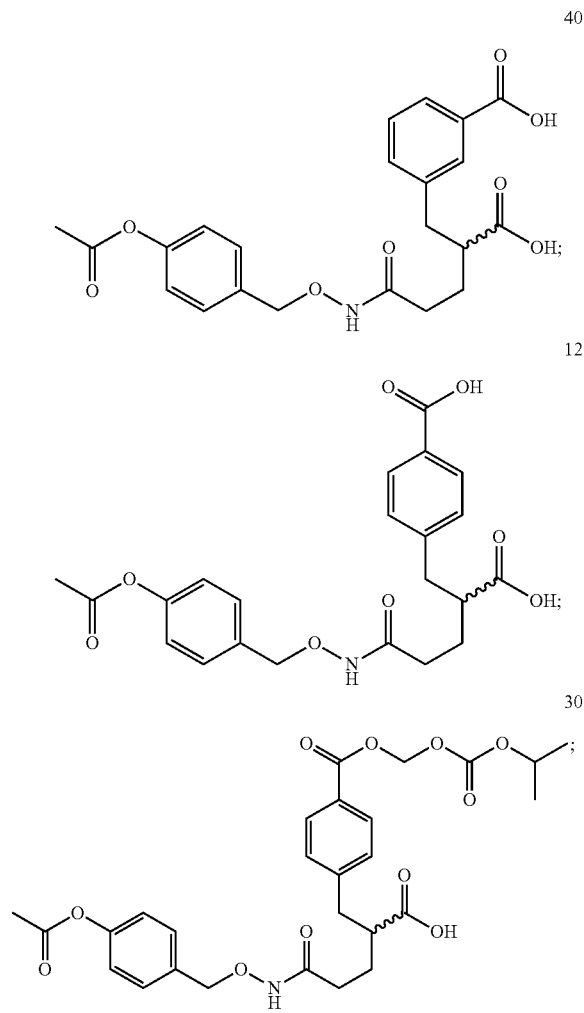

and

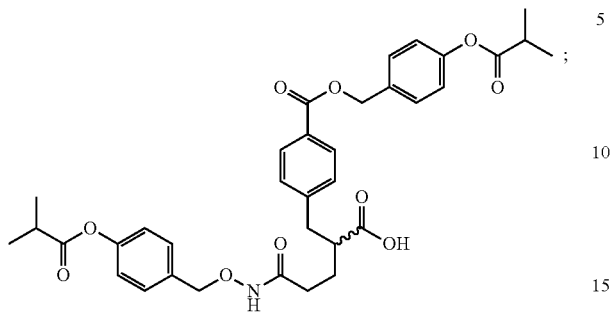

and stereoisomers and pharmaceutically acceptable salts thereof or a pharmaceutical a composition thereof, in an amount effective for treating the neuropathic pain.

2. The method of claim 1, wherein the neuropathic pain results in excess PSMA activity.

3. The method of claim 1, further comprising inhibiting the excess PSMA activity when the compound, or a pharmaceutical composition thereof, is administered.

* * * * *